(12) United States Patent
Kadereit et al.

(10) Patent No.: US 8,735,387 B2
(45) Date of Patent: May 27, 2014

(54) OXAZOLOPYRIMIDINES AS EDG-1 RECEPTOR AGONISTS

(75) Inventors: Dieter Kadereit, Frankfurt am Main (DE); Matthias Schaefer, Frankfurt am Main (DE); Werngard Czechtizky, Frankfurt am Main (DE)

(73) Assignee: Sanofi, Paris (FR)

( * ) Notice: Subject to any disclaimer, the term of this patent is extended or adjusted under 35 U.S.C. 154(b) by 473 days.

(21) Appl. No.: 13/003,125

(22) PCT Filed: Jul. 2, 2009

(86) PCT No.: PCT/EP2009/004770
§ 371 (c)(1),
(2), (4) Date: Apr. 18, 2011

(87) PCT Pub. No.: WO2010/006704
PCT Pub. Date: Jan. 21, 2010

(65) Prior Publication Data
US 2011/0190490 A1 Aug. 4, 2011

(30) Foreign Application Priority Data
Jul. 15, 2008 (EP) .................................... 08290694

(51) Int. Cl.
| | | |
|---|---|---|
| C07D 498/04 | (2006.01) | |
| A61K 31/519 | (2006.01) | |
| A61P 9/00 | (2006.01) | |
| A61P 9/10 | (2006.01) | |
| A61P 29/00 | (2006.01) | |
| A61P 25/28 | (2006.01) | |
| A61P 35/00 | (2006.01) | |

(52) U.S. Cl.
USPC ............ 514/211.15; 514/234.2; 514/260.1; 540/544; 544/117; 544/255

(58) Field of Classification Search
USPC ..................................... 544/255; 514/260.1
See application file for complete search history.

(56) References Cited

FOREIGN PATENT DOCUMENTS

| EP | 1 666 468 A1 | 6/2006 |
|---|---|---|
| WO | WO 03/061567 A2 | 7/2003 |
| WO | WO 2004/096813 A1 | 11/2004 |
| WO | WO 2005/000833 A | 1/2005 |
| WO | WO 2005/000833 A1 | 1/2005 |
| WO | WO 2005/058848 A1 | 6/2005 |
| WO | WO 2005/067546 A2 | 7/2005 |
| WO | WO 2005/069865 A2 | 8/2005 |
| WO | WO 2005/123677 A1 | 12/2005 |
| WO | WO 2006/010379 A1 | 2/2006 |
| WO | WO 2006/047195 A2 | 5/2006 |
| WO | WO 2007/061458 A2 | 5/2007 |

OTHER PUBLICATIONS

Definition for residue: http://en.wikipedia.org/wiki/Residue, downloaded Dec. 13, 2013.*
European Search Report dated Mar. 27, 2013 issued in EP 13 15 1034.
Awad, Alaa S. et al., "Selective sphingosine 1-phosphate 1 receptor activation reduces ischemia-reperfusion injury in a mouse kidney," American Journal of Physiology: Renal Physiology (2006), vol. 290, pp. F1516-1524.
Bolick, David T. et al., "Sphingosine-1-Phosphate Prevents Tumor Necrosis Factor-α-Mediated Monocyte Adhesion to Aortic Endothelium in Mice," Arteriosclerosis, Thrombosis, and Vascular Biology (2005), vol. 25, pp. 976-981.
Chae, Sung-Suk et al., "Requirement for sphingosine 1-phosphate receptor-1 in tumor angiogenesis demonstrated by in vivo RNA interference," The Journal of Clinical Investigation (2004), vol. 114, pp. 1082-1089.
Heringdorf, Dagmar Meyer zu et al., "Lysophospholipid receptors: Signalling, pharmacology and regulation by lysophospholipid metabolism," Biochimica et Biophysica Acta (2007), vol. 1768, pp. 923-940.
Holschbach, Marcus H. et al., "Synthesis and evaluation of 7-amino-2-(2(3)-furyl)-5-phenylethylamino-oxazolo[5,4-d] pyrimidines as potential $A_{2A}$ adenosine receptor antagonists for positron emission tomography (PET)," European Journal of Medicinal Chemistry (2006), vol. 41, pp. 7-15.
Igarashi, Junsuke et al., "Agonist-modulated Targeting of the EDG-1 Receptor to Plasmalemmal Caveolae," The Journal of Biological Chemistry (2000), vol. 275, pp. 32363-32370.
Jansen, A.B.A. et al., "Some 4-Substituted Oxazoles," Journal of the Chemical Society (1961), pp. 405-411.
Keul, Petra et al., "The Sphingosine-1-Phosphate Analogue FTY720 Reduces Atherosclerosis in Apolipoprotein E-Deficient Mice," Arteriosclerosis, Thrombosis, and Vascular Biology (2007), vol. 27, pp. 607-613.

(Continued)

*Primary Examiner* — Susanna Moore
(74) *Attorney, Agent, or Firm* — Scully, Scott, Murphy & Presser, P.C.

(57) ABSTRACT

The present invention relates to oxazolopyrimidine compounds of the formula I in which A, $R^1$, $R^2$ and $R^3$ are defined as indicated in the claims. The compounds of the formula I modulate the activity of the Edg-1 receptor and in particular are agonists of this receptor, and are useful for the treatment of diseases such as atherosclerosis, heart failure or peripheral arterial occlusive disease, for example. The invention furthermore relates to processes for the preparation of compounds of the formula I, their use, in particular as active ingredients in pharmaceuticals, and pharmaceutical compositions comprising them.

(I)

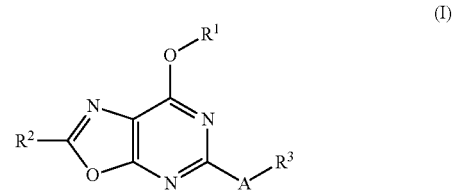

2 Claims, No Drawings

(56) References Cited

OTHER PUBLICATIONS

Kono, Mari et al., "The Sphingosine-1-phosphate Receptors $S1P_1$, $S1P_2$, and $S1P_3$ Function Coordinately during Embryonic Angiogenesis," The Journal of Biological Chemistry (2004), vol. 279, pp. 29367-29373.

Kwon, Young-Guen et al., "Sphingosine 1-Phosphate Protects Human Umbilical Vein Endothelial Cells from Serum-deprived Apoptosis by Nitric Oxide Production," The Journal of Biological Chemistry (2001), vol. 276, pp. 10627-10633.

LaMontagne, Kenneth et al., "Antagonism of Sphingosine-1-Phosphate Receptors by FTY720 Inhibits Angiogenesis and Tumor Vascularization," Cancer Research (2006), vol. 66, pp. 221-231.

Liebeskind, Lanny S. et al., "Heteroaromatic Thioether-Boronic Acid Cross-Coupling Under Neutral Reaction Conditions," Organic Letters (2002), vol. 4, pp. 979-981.

Mitsunobu, Oyo, "The Use of Diethyl Azodicarboxylate and Triphenylphosphine in Synthesis and Transformation of Natural Products," Synthesis (1981), pp. 1-28.

Nofer, Jerzy-Roch et al., "FTY720, a Synthetic Sphingosine I Phosphate Analogue, Inhibits Development of Atherosclerosis in Low-Density Lipoprotein Receptor-Deficient Mice," Circulation (2007), vol. 115, pp. 501-508.

Ozaki, Harunobu et al., "Sphingosine-1-phosphate Signaling in Endothelial Activation," Journal of Atherosclerosis and Thrombosis (2003), vol. 10, pp. 125-131.

Paik, Ji-Hye et al., "Sphingosine 1-phosphate receptor regulation of N-cadherin mediates vascular stabilization," Genes and Development (2004), vol. 18, pp. 2392-2403.

Sanchez, Teresa et al., "Induction of Vascular Permeability by the Sphingosine-1-Phosphate Receptor-2 (S1P2R) and its Downstream Effectors ROCK and PTEN," Arteriosclerosis, Thrombosis, and Vascular Biology (2007), vol. 27, pp. 1312-1318.

Schaphorst, Kane L. et al., "Role of sphingosine-1 phosphate in the enhancement of endothelial barrier integrity by platelet-released products," American Journal of Physiology: Lung Cellular and Molecular Physiology (2003), vol. 285, pp. 258-267.

Turchi, Ignatius J. et al., "A New Synthesis of Oxazolo[5,4-d]pyramid-7-ones," Synthesis (1983), pp. 837-839.

* cited by examiner

OXAZOLOPYRIMIDINES AS EDG-1 RECEPTOR AGONISTS

The present invention relates to oxazolopyrimidine compounds of the formula I,

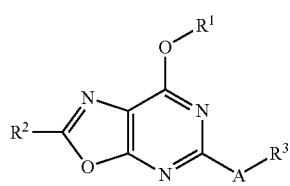

in which A, $R^1$, $R^2$ and $R^3$ are defined as indicated below. The compounds of the formula I modulate the activity of the Edg-1 receptor and in particular ace agonists of this receptor, and are useful for the treatment of diseases such as atherosclerosis, heart failure or peripheral arterial occlusive disease, for example. The invention furthermore relates to processes for the preparation of compounds of the formula I, their use, in particular as active ingredients in pharmaceuticals, and pharmaceutical compositions comprising them.

The Edg-1 receptor is a member of the endothelial differentiation gene (Edg) receptor family of currently eight identified class A GPCRs (G-protein coupled receptors). This family can be divided into subfamilies of sphingosine-1-phosphate (S1P)-activated receptors (five members) and receptors activated by lysophosphatidic acid (LPA; three members). The endogenous ligand S1P is a pluripotent lysophospholipid acting on different cell types by activating GPCRs from the Edg receptor family, namely Edg-1 (=S1P1), Edg-3 (=S1P3), Edg-5 (=S1P2), Edg-6 (=S1P4) and Edg-8 (S1P5). Although formerly S1P was also described as an intracellular messenger, there is increasing evidence in the literature that most effects of S1P are mediated Edg receptor-dependent. S1P is generated by the enzyme family of sphingosine kinases (SPHK) and degraded by different phosphatases or lyases (for an overview, see D. Meyer zu Heringdorf et al., Biochim. Biophys. Acta 1768 (2007), 923-940).

Regarding the vasculature, it is evident that the Edg-1 receptor is prominently expressed in endothelial cells, whereas it is only slightly expressed in vascular smooth muscle cells in which Edg-3 and Edg-5 are the predominant S1P receptors. Thus, the differential expression of S1P receptors in the vasculature makes specific Edg-1 receptor activation desirable, since in contrast to the endogenous ligand S1P it leads to pronounced endothelial activation without having relevant effects on vascular smooth muscle cells. Activation of Edg-1 receptor in endothelial cells was shown to be beneficial in respect to endothelial cell function in the context of atherosclerosis (for an overview, see H. Ozaki, et al., J. Atheroscler. Thromb. 10 (2003), 125-131). Edg-1 signalling was formerly shown to lead to liberation of nitric oxide (=NO) (J. Igarashi et al., J. Biol. Chem. 275 (2000), 32363-32370) and to preserve its anti-adhesive features, since it prevents from cytokine-induced cell-adhesion molecule exposure and monocyte adhesion to endothelial cells (D. T. Bolick et al., Arterioscler. Thromb. Vasc. Biol. 25 (2005), 976-981). Furthermore, Edg-1 receptor signalling promotes endothelial cell migration and endothelial cell survival (Y.-G. Kwon et al., J. Biol. Chem. 276 (2001), 10627-10633). A specific feature of Edg-1 receptor signalling is the protection of the endothelial cell barrier function by targeting reorganization of actin fibers and proteins critical for the stabilization of adherens junctions such as N-cadherin (J.-H. Paik et al., Genes Develop. 18 (2004), 2392-2403), enforcing cell-cell contacts and thus leading to decreased paracellular permeability of the endothelium (K. L. Schaphorst et al., Am. J. Physiol. Lung Cell. Mol. Physiol. 285 (2003), L258-L267). Although it has no effect on the development of vessel network itself, Edg-1 receptor signalling is essential for vascular maturation, where it promotes stabilization of nascend vessels. Edg-1 receptor knock-out mice are not viable and die from intra-uterinic hemorrhages, since signalling is non-redundant during embryonic angiogenesis (M. Kono et al., J. Biol. Chem. 279 (2004), 29367-29373). The relevance of Edg-1 signalling for vascular maturation is obvious also with respect to tumor vascularization, since pharmacological impairment of Edg-1 signalling is anti-angiogenic and critical for tumor vascularization (K. LaMontagne et al., Cancer Res. 66 (2006), 221-231), as has been demonstrated also by an in vivo siRNA approach targeting the Edg-1 receptor (S.-S. Chae et al., J. Clin. Invest. 114 (2004), 1082-1089). Recently, it was demonstrated that signalling of the Edg-5 receptor, which is also expressed in endothelial cells to a lower extent, opposes the protective Edg-1 effects regarding reduction of vascular permeability (T. Sanchez et al., Arterioscler. Thromb. Vasc. Bio. 27 (2007), 1312-1318), underlining again the need for specific Edg-1 agonists in order to improve endothelial function.

Key indications of Edg-1 receptor agonists include cardiovascular diseases, atherosclerosis, heart failure, cardio protection, peripheral arterial occlusive disease, renal diseases, inflammatory diseases, vascular permeability disorders, diabetes, respiratory diseases and cytoprotection, for example. Edg-1 agonists can also be used in higher dosages to lead to a functional impairment of Edg-1 receptor signalling due to tachyphylaxis/receptor desensitization. This offers the opportunity to use Edg-1 receptor agonists also as immunosuppressants and for the treatment of multiple sclerosis or cancer. The use for immunosuppression and for the treatment of multiple sclerosis has been investigated for the unselective Edg-1 receptor agonist FTY-720 (fingolimod) which is currently in phase III clinical studies for the treatment of multiple sclerosis. The use of FTY-720 for the prevention of atherosclerosis has been recently shown in two independent investigations (see J.-R. Nofer et al., Circulation 115 (2007), 501-508; P. Keul et al., Arterioscler. Thromb. Vasc. Biol. 27 (2007), 607-613). Edg-1 agonists can also be used in combination with other pharmacologically active compounds, for example with cytostatic agents in which case the Edg-1 agonist provides for endothelial cell protection, or with antiatherosclerotic agents such as statins or HDL (high density lipoprotein) enhancers. Additionally, Edg-1 agonists can be used in combination with pharmacologically active compounds which may generate edema as side effect, for example PPARgamma (peroxisome proliferator-activated receptor gamma) agonists, ACE/NEP (angiotensin converting enzyme/neutral endopeptidase) inhibitors or factor Xa inhibitors, or in the treatment of septic shock. Furthermore, Edg-1 agonists can be used for preventing vascular hyperpermeability as seen, for example, during cardiac surgery. Several classes of low molecular weight Edg-1 agonists have been described in the prior art, for example in WO 03/061567, WO 2005/000833, WO 2005/058848, WO 2005/123677, WO 2006/010379 and WO 2006/047195. However, there continues to be a need for further effective low molecular weight Edg-1 agonists, in particular in view of safety and Edg receptor selectivity. In addition, besides being effective as Edg-1 agonists, it is desirable that such compounds also have further advantageous properties, for example stability in plasma, liver and vascular tissue. The present invention satisfies this need by providing the oxazolopyrimidine compounds of the formula I.

Bicyclic pyrimidine derivatives which are useful for pharmaceutical applications, have already been disclosed, for example in EP 1666468, WO 2004/096813, WO 2005/067546, and WO 2005/069865. However, the oxazolo[5,4-d]pyrimidine compounds of the formula I have not yet been mentioned, and the use of such compounds as Edg-1 agonists is not suggested by the prior art.

Accordingly, a subject of the present invention is an oxazolopyrimidine compound of the formula I, in any of its stereoisomeric forms, or a mixture of stereoisomeric forms in any ratio, or a physiologically acceptable salt thereof, or a physiologically acceptable solvate of any of them,

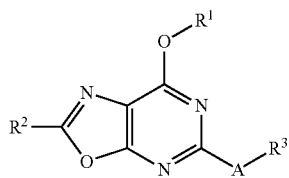

I wherein

A is —$(CR^4R^5)_a$—$CR^6R^7$—$(CR^8R^9)_b$—, wherein a and b are independently of each other chosen from 0 and 1;

$R^1$ is chosen from $(C_1-C_6)$-alkyl, $(C_2-C_6)$-alkenyl, $(C_2-C_6)$-alkynyl, $(C_3-C_7)$-cycloalkyl-$C_uH_{2u}$— and $Het^1$-$C_uH_{2u}$—, wherein u is chosen from 0, 1, 2 and 3;

$R^2$ is chosen from phenyl, naphthyl and a residue of an aromatic, 5-membered to 10-membered, monocyclic or bicyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl, naphthyl and residue of an aromatic heterocycle are optionally substituted on one or more ring carbon atoms by identical or different substituents $R^{22}$;

$R^3$ is a residue of a saturated or unsaturated, 4-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^4$, $R^5$, $R^8$ and $R^9$ are independently of each other chosen from hydrogen, fluorine and $(C_1-C_4)$-alkyl;

$R^6$ and $R^7$ are independently of each other chosen from hydrogen, fluorine and $(C_1-C_4)$-alkyl or together are $(C_2-C_8)$-alkanediyl;

$R^{21}$ is chosen from $(C_1-C_4)$-alkyl and $(C_3-C_7)$-cycloalkyl-$C_vH_{2v}$—, wherein v is chosen from 0, 1 and 2;

$R^{22}$ is chosen from halogen, hydroxy, $(C_1-C_4)$-alkyl-$S(O)_m$—, amino, nitro, cyano, hydroxycarbonyl, $(C_1-C_4)$-alkyloxycarbonyl, aminocarbonyl, aminosulfonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—;

$R^{23}$ is $(C_1-C_6)$-alkyl which is optionally substituted by one or more identical or different substituents chosen from hydroxy, $R^{25}$—S(O)$_m$—, amino, hydroxycarbonyl, $R^{25}$—O—C(O)—, aminocarbonyl, $R^{24}$, $R^{24}$—NH—, $R^{24}$—C(O)—, $R^{25}$—O—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—;

$R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_6)$-alkyl, $(C_3-C_7)$-cycloalkyl-$C_wH_{2w}$—, phenyl and $Het^2$, wherein the alkyl and cycloalkyl are optionally substituted by one or more identical or different substituents chosen from hydroxy, $(C_1-C_4)$-alkyl-$S(O)_m$—, $(C_1-C_4)$-alkylsulfonylamino, $(C_1-C_4)$-alkyloxy, amino, $(C_1-C_4)$-alkylamino, di($(C_1-C_4)$-alkyl)amino, cyano, hydroxycarbonyl, $(C_1-C_4)$-alkyloxycarbonyl, aminosulfonyl, $(C_1-C_4)$-alkylaminosulfonyl, di($(C_1-C_4)$-alkyl)aminosulfonyl, phenyl, $Het^2$ and $Het^3$, and wherein all phenyl and $Het^2$ in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, hydroxy, $(C_1-C_4)$-alkyloxy and cyano, and wherein the numbers w are independently of each other chosen from 0, 1 and 2;

$R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from hydroxy, $(C_1-C_4)$-alkyloxy, hydroxycarbonyl and $(C_1-C_4)$-alkyloxycarbonyl, and wherein x is chosen from 0, 1 and 2;

$R^{27}$ is chosen from halogen, $(C_1-C_4)$-alkyl, hydroxy-$C_yH_{2y}$—, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4;

$R^{31}$ is chosen from $(C_1-C_4)$-alkyl, phenyl-$C_qH_{2q}$—, $(C_1-C_4)$-alkylsulfonyl, $(C_1-C_4)$-alkylcarbonyl and $R^{33}$—O—C(O)—, wherein q is chosen from 1, 2 and 3, and wherein the phenyl is optionally substituted by one or more identical or different substituents chosen from halogen, $(C_1-C_4)$-alkyl, $(C_1-C_4)$-alkyloxy and cyano;

$R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-$S(O)_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, hydroxycarbonyl, $R^{34}$—O—C(O)—, aminocarbonyl, $(C_1-C_4)$-alkylaminocarbonyl, di($(C_1-C_4)$-alkyl)aminocarbonyl, aminosulfonyl, $(C_1-C_4)$-alkylaminosulfonyl, di($(C_1-C_4)$-alkyl)aminosulfonyl, phenyl-$C_rH_{2r}$— and $Het^2$-$C_rH_{2r}$—, wherein the numbers r are independently of each other chosen from 0, 1, 2 and 3, and wherein the phenyl and $Het^2$ are optionally substituted on one or more ring carbon atoms by identical or different substituents chosen from halogen, $(C_1-C_4)$-alkyl, hydroxy, $(C_1-C_4)$-alkyloxy and cyano;

$R^{33}$ and $R^{34}$ are independently of each other chosen from $(C_1-C_4)$-alkyl, $(C_3-C_7)$-cycloalkyl-$C_sH_{2s}$— and phenyl-$C_tH_{2t}$—, wherein s is chosen from 0, 1 and 2 and t is chosen from 1 and 2;

$Het^1$ is a residue of a saturated, 4-membered to 7-membered, monocyclic heterocycle which comprises 1 or 2 identical or different ring heteroatoms chosen from N, O and S and which is bonded via a ring carbon atom, wherein the residue of a heterocycle is optionally substituted by one or more identical or different substituents chosen from fluorine and $(C_1$-$C_4)$-alkyl;

$Het^2$ is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1$-$C_4)$-alkyl substituent;

$Het^3$ is a residue of a saturated, 4-membered to 7-membered, monocyclic heterocycle which comprises 1 or 2 identical or different ring heteroatoms chosen from N, O and S, wherein the residue of a heterocycle is optionally substituted by one or more identical or different substituents chosen from fluorine and $(C_1$-$C_4)$-alkyl;

m is chosen from 0, 1 and 2, wherein all numbers m are independent of each other;

wherein all cycloalkyl groups, independently of each other and independently of any other substituents, are optionally substituted by one or more identical or different substituents chosen from fluorine and $(C_1$-$C_4)$-alkyl;

wherein all alkyl, alkanediyl, $C_qH_{2q}$, $C_rH_{2r}$, $C_sH_{2s}$, $C_tH_{2t}$, $C_uH_{2u}$, $C_vH_{2v}$, $C_wH_{2w}$, $C_xH_{2x}$, $C_yH_{2y}$, alkenyl and alkynyl groups, independently of each other and independently of any other substituents, are optionally substituted by one or more fluorine substituents.

Structural elements such as groups, substituents, hetero ring members, numbers or other features, for example alkyl groups, groups like $R^{22}$, $R^{23}$, $R^{25}$ or $R^{32}$, numbers like w or y, which can occur several times in the compounds of the formula I, can all independently of one another have any of the indicated meanings and can in each case be identical to or different from one another. For example, the alkyl groups in a dialkylamino group can be identical or different.

Alkyl, alkenyl and alkynyl groups can be linear, i.e. straight-chain, or branched. This also applies when they are part of other groups, for example alkyloxy groups (=alkoxy groups, alkyl-O— groups), alkyloxycarbonyl groups or alkyl-substituted amino groups, or when they are substituted. Depending on the respective definition, the number of carbon atoms in an alkyl group can be 1, 2, 3, 4, 5 or 6, or 1, 2, 3 or 4, or 1, 2 or 3. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, and hexyl including n-hexyl, 3,3-dimethylbutyl and isohexyl. Double bonds and triple bonds in alkenyl groups and alkynyl groups can be present in any positions. In one embodiment of the invention, alkenyl groups contain one double bond and alkynyl groups contain one triple bond. In one embodiment of the invention, an alkenyl group or alkynyl group contains at least three carbon atoms and is bonded to the remainder of the molecule via a carbon atom which is not part of a double bond or triple bond. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I are sufficiently stable and is suitable for the desired purpose such as use as a drug substance, applies in general with respect to the definitions of all groups in the compounds of the formula I.

As far as applicable, the preceding explanations regarding alkyl groups apply correspondingly to divalent alkyl groups such as alkanediyl groups and the groups —$(CR^4R^6)_a$—$CR^6R^7$—$(CR^8R^9)_b$—, $C_qH_{2q}$, $C_rH_{2r}$, $C_sH_{2s}$, $C_tH_{2t}$, $C_uH_{2u}$, $C_vH_{2v}$, $C_wH_{2w}$, $C_xH_{2x}$ and $C_yH_{2y}$, which thus can likewise be linear and branched. Examples of divalent alkyl groups are —$CH_2$— (=methylene), —$CH_2$—$CH_2$—, —$CH_2$—$CH_2$—$CH_2$—, —$CH_2$—$CH_2$—$CH_2$—$CH_2$—, —$CH(CH_3)$—, —$C(CH_3)_2$—, —$CH(CH_3)$—$CH_2$—, —$CH_2$—$CH(CH_3)$—, —$C(CH_3)_2$—$CH_2$—, —$CH_2$—$C(CH_3)_2$—. If a number such as the number u in the group $C_uH_{2u}$, for example, is 0 (=zero), the two groups which are attached to the contemplated group, such as $C_uH_{2u}$, are directly connected to one another via a single bond. Similarly, if any of the numbers a and b is 0, the group $CR^6R^7$ is directly connected to the oxazolopyrimidine ring depicted in formula I and/or the group $R^3$ via a single bond.

The number of ring carbon atoms in a cycloalkyl group can be 3, 4, 5, 6 or 7. In one embodiment of the invention, the number of ring carbon atoms in a cycloalkyl group, independently of the number of ring carbon atoms in any other cycloalkyl group, is 3, 4, 5 or 6, in another embodiment 3, 4 or 5, in another embodiment 3 or 4, in another embodiment 3, in another embodiment 5, 6 or 7, in another embodiment 5 or 6, in another embodiment 6 or 7, in another embodiment 6. Examples of cycloalkyl groups are cyclopropyl, cyclobutyl, cyclopentyl, cyclohexyl and cycloheptyl. Independently of one another and independently of any other substituents, cycloalkyl groups are optionally substituted by one or more identical or different $(C_1$-$C_4)$-alkyl substituents which can be located in any positions, i.e., cycloalkyl groups can be unsubstituted by alkyl substituents or substituted by alkyl substituents, for example by 1, 2, 3 or 4, or by 1 or 2, $(C_1$-$C_4)$-alkyl substituents, for example by methyl groups. Examples of alkyl-substituted cycloalkyl groups are 4-methylcyclohexyl, 4-tert-butylcyclohexyl or 2,3-dimethylcyclopentyl. Examples of cycloalkylalkyl groups, which can represent groups such as $(C_3$-$C_7)$-cycloalkyl-$C_uH_{2u}$—, for example, are cyclopropylmethyl, cyclobutylmethyl, cyclopentylmethyl, cyclohexylmethyl, cycloheptylmethyl, 1-cyclopropylethyl, 2-cyclopropylethyl, 1-cyclobutylethyl, 2-cyclobutylethyl, 2-cyclopentylethyl, 2-cyclohexylethyl, 2-cycloheptylethyl.

Independently of one another and independently of any other substituents, alkyl groups, divalent alkyl groups, alkenyl groups, alkynyl groups and cycloalkyl groups are optionally substituted by one or more fluorine substituents which can be located in any positions, i.e., the said groups can be unsubstituted by fluorine substituents or substituted by fluorine substituents, for example by 1, 2, 3, 4, 5, 6, 7, 8, 9, 10, 11, 12 or 13, or by 1, 2, 3, 4, 5, 6, 7, 8 or 9, or by 1, 2, 3, 4, 5, 6 or 7, or by 1, 2, 3, 4 or 5, or by 1, 2 or 3, or by 1 or 2, fluorine substituents. Examples of fluorine-substituted said groups are trifluoromethyl, 2-fluoroethyl, 2,2,2-trifluoroethyl, pentafluoroethyl, 3,3,3-trifluoropropyl, 2,2,3,3,3-pentafluoropropyl, 4,4,4-trifluorobutyl, heptafluoroisopropyl, —CHF—, —$CF_2$—, —$CF_2$—$CH_2$—, —$CH_2$—$CF_2$—, —$CF_2$—$CF_2$—, —$CF(CH_3)$—, —$C(CF_3)_2$—, —$C(CH_3)_2$—$CF_2$—, —$CF_2$—$C(CH_3)_2$—, 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl. Examples of alkyloxy groups in which the alkyl moiety is fluorine-substituted, are trifluoromethoxy, 2,2,2-trifluoroethoxy, pentafluoroethoxy and 3,3,3-trifluoropropoxy. In one embodiment of the invention, the total number of fluorine substituents and $(C_1$-$C_4)$-alkyl substituents, which independently of any other substituents are optionally present on cycloalkyl groups in the compounds of the formula I, is 1, 2, 3, 4, 5, 6, 7, 8, 9, 10 or 11, in another embodiment 1, 2, 3, 4, 5, 6, 7, 8 or 9, in another embodiment 1, 2, 3, 4 or 5, in another embodiment 1, 2, 3 or 4.

Groups like phenyl, naphthyl (=naphthalenyl) and residues of aromatic heterocycles which are optionally substituted by one or more substituents, can be unsubstituted or substituted, for example by 1, 2, 3, 4 or 5, or by 1, 2, 3 or 4, or by 1, 2 or 3, or by 1 or 2, or by 1, identical or different substituents which can be located in any positions. In one embodiment of the invention the total number of nitro substituents in a compound of the formula I is not greater than two. Aromatic nitrogen heterocycles which in the parent ring system carry a hydrogen atom on a ring nitrogen atom in a 5-membered ring, such as a pyrrole, imidazole, indole or benzoimidazole ring, for example, can be substituted on ring carbon atoms and/or on such ring nitrogen atoms. In one embodiment of the invention, substituents on such ring nitrogen atoms are chosen from $(C_1-C_4)$-alkyl groups, i.e. such ring nitrogen atoms in aromatic heterocycles carry a hydrogen atom or a $(C_1-C_4)$-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent or they do not carry a hydrogen atom or substituent. Ring nitrogen atoms which carry a hydrogen atom or a substituent, occur in a nitrogen-containing aromatic 5-membered ring as is present in pyrrole, imidazole, indole or benzoimidazole, for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole, pyridine or benzoimidazole, for example, and in a non-aromatic ring in which they are bridgehead atoms or are part of a double bond, and they occur as ring nitrogen atoms via which a ring is bonded. Suitable ring nitrogen atoms in aromatic heterocycles in the compounds of the formula I, such as the ring nitrogen atom in a pyridine ring or a quinoline ring, can in general also be present as N-oxide or as quaternary salt, for example as N—$(C_1-C_4)$-alkyl salt such as N-methyl salt, wherein in one embodiment of the invention the counter anion in such quaternary salt is a physiologically acceptable anion which is derived from an acid that forms a physiologically acceptable salt. In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthyl can be 1-naphthyl (=naphthalen-1-yl) or 2-naphthyl (=naphthalen-2-yl). In monosubstituted 1-naphthyl groups, the substituent can be located in the 2-, 3-, 4-, 5-, 6-, 7- or 8-position. In monosubstituted 2-naphthyl groups, the substituent can be located in the 1-, 3-, 4-, 5-, 6-, 7- or 8-position. In disubstituted naphthyl groups, the substituents can likewise be located in any positions both in the ring via which the naphthyl group is bonded and/or in the other ring.

In residues of aromatic heterocycles representing $R^2$, $R^3$, $R^{24}$ or the group $Het^2$, which may be designated as heteroaryl groups, as well as in all other heterocyclic rings in the compounds of the formula I including the groups $Het^1$, $Het^3$ and non-aromatic heterocyclic groups representing $R^3$ and $R^{24}$, the ring heteroatoms are generally chosen from N, O and S, wherein N includes ring nitrogen atoms which carry a hydrogen atom or a substituent as well as ring nitrogen atom which do not carry a hydrogen atom or a substituent. Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms chosen from oxygen and sulfur cannot be present in adjacent ring positions of any heterocycle. Saturated rings do not contain a double bond within the ring. Unsaturated ring systems can be aromatic or partially unsaturated including partially aromatic, in which latter case one ring in a bicyclic ring system is aromatic and the ring system is bonded via an atom in the non-aromatic ring. Depending on the respective group, unsaturated rings can contain one, two, three, four or five double bonds within the ring. Aromatic groups contain a cyclic system of six or ten delocalized pi electrons in the ring. Depending on the respective group, saturated and non-aromatic unsaturated heterocyclic rings, including $Het^1$, $Het^3$ and non-aromatic groups representing $R^3$ and $R^{24}$, can be 4-membered, 5-membered, 6-membered, 7-membered, 8-membered, 9-membered or 10-membered. In one embodiment of the invention, aromatic heterocyclic rings are 5-membered or 6-membered monocyclic rings or 8-membered, 9-membered or 10-membered bicyclic rings, in another embodiment 5-membered or 6-membered monocyclic rings or 9-membered or 10-membered bicyclic rings, in another embodiment 5-membered or 6-membered monocyclic rings, wherein the 8-membered, 9-membered or 10-membered bicyclic rings are composed of two fused 5-membered rings, a 5-membered ring and a 6-membered ring which are fused to one another, and two fused 6-membered rings, respectively. In bicyclic aromatic heterocyclic groups, one or both rings can contain hetero ring members, and one or both rings can be aromatic. In general, bicyclic ring systems containing an aromatic ring and a non-aromatic ring are regarded as aromatic when they are bonded via a carbon atom in the aromatic ring, and as non-aromatic when they are bonded via a carbon atom in the non-aromatic ring. Unless stated otherwise, heterocyclic groups including aromatic heterocyclic groups can be bonded via any suitable ring carbon atom and, in the case of nitrogen heterocycles, via any suitable ring nitrogen atom. In one embodiment of the invention, an aromatic heterocyclic group in a compound of the formula I, independently of any other aromatic heterocyclic group, is bonded via a ring carbon atom, in another embodiment via a ring ntrogen atom. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 1, wherein the ring heteroatoms can be identical or different. Heterocyclic groups which are optionally substituted, can independently of any other heterocyclic group be unsubstituted or substituted by one or more identical or different substituents, for example by 1, 2, 3, 4 or 5, or by 1, 2, 3 or 4, or by 1, 2 or 3, or by 1 or 2, or by 1 substituents, which are indicated in the definition of the respective group. Substituents on heterocyclic groups can be located in any positions. For example, in a pyridin-2-yl group substituents can be located in the 3-position and/or 4-position and/or 5-position and/or 6-position, in a pyridin-3-yl group substituent can be located in the 2-position and/or 4-position and/or 5-position and/or 6-position, in a pyridin- 4-yl group substituents can be located in the 2-position and/or 3-position and/or 5-position and/or 6-position.

Examples of parent heterocycles, from which heterocyclic groups including aromatic heterocyclic groups, saturated heterocyclic groups and non-aromatic unsaturated heterocyclic groups can be derived, are azete, oxete, pyrrole, furan, thiophene, imidazole, pyrazole, [1,3]dioxole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyran, thiopyran, pyridazine, pyrimidine, pyrazine, [1,3]oxazine, [1,4]oxazine, [1,3]thiazine, [1,4]thiazine, [1,2,3]triazine, [1,3]dithiine, [1,4]dithiine, [1,2,4]triazine, [1,3,5]triazine, [1,2,4,5]tetrazine, azepine, [1,3]diazepine, [1,4]diazepine, [1,3]oxazepine, [1,4]oxazepine, [1,3]thiazepine, [1,4]thiazepine, azocine, azecine, cyclopenta[b]pyrrole, 2-azabicyclo[3.1.0]hexane, 3-azabicyclo[3.1.0]hexane, 2-oxa-5-azabicyclo[2.2.1]heptane, indole, isoindole, benzothiophene, benzofuran, [1,3]benzodioxole (=1,2-methylenedioxybenzene), [1,3]benzoxazole, [1,3]benzothiazole, benzoimidazole, thieno[3,2-c]pyridine, chromene, isochromene, [1,4]benzodioxine, [1,4]benzoxazine, [1,4]benzothiazine, quinoline, isoquinoline, cinnoline, quinazoline, quinoxaline, phthalazine, thienothiophenes, [1,8]naphthyridine and other naphthyridines, pteridine, and the respective saturated and partially saturated heterocycles in which one or more, for example one, two, three, four or all double bonds within the ring system including double bonds in aromatic ring are replaced with single bonds, such as azetidine, oxetane, pyrrolidine, tetrahydrofuran, tetrahydrothiophene, imidazolidine, oxazolidine, thiazolidine, dihydropyridine, piperidine, tetrahydropyran, piperazine, morpholine, thiomorpholine, azepane, chromane, isochromane, [1,4]benzodioxane (=1,2-ethylenedioxybenzene), 1,2,3,4-tetrahydroquinoline, 1,2,3,4-tetrahydroisoquinoline, for example.

Examples of residues of aromatic heterocycles, which can occur in the compounds of the formula I, are thiophenyl (=thienyl) including thiophen-2-yl and thiophen-3-yl, pyridinyl (=pyridyl) including pyridin-2-yl (=2-pyridyl), pyridin-3-yl (=3-pyridyl) and pyridin-4-yl (=4-pyridyl), imidazolyl including, for example, 1H-imidazol-1-yl, 1H-imidazol-2-yl, 1H-imidazol-4-yl and 1H-imidazol-5-yl, [1,2,4]triazolyl including 1H-[1,2,4]-triazol-1-yl and 4H-[1,2,4-triazol-3-yl, tetrazolyl including 1H-tetrazol-1-yl and 1H-tetrazol-5-yl, quinolinyl (=quinolyl) including quinolin-2-yl, quinolin-3-yl, quinolin-4-yl, quinolin-5-yl, quinolin-6-yl, quinolin-7-yl and quinolin-8-yl, which all are optionally substituted as indicated in the definition of the respective group. Examples of residues of saturated and non-aromatic unsaturated heterocycles, which can occur in the compounds of the formula I, are azetidinyl, pyrrolidinyl including pyrrolidin-1-yl, pyrrolidin-2-yl and pyrrolidin-3-yl, 2,5-dihydro-1H-pyrrolyl, piperidinyl including piperidin-1-yl, piperidin-2-yl, piperidin-3-yl and piperidin-4-yl, 1,2,3,4-tetrahydropyridinyl, 1,2,5,6-tetrahydropyridinyl, 1,2-dihydropyridinyl, azepanyl, azocanyl, azecanyl, octahydrocyclopenta[b]pyrrolyl, 2,3-dihydro-1H-indolyl, octahydro-1H-indolyl, 2,3-dihydro-1H-isoindolyl, octahydro-1H-isoindolyl, 1,2-dihydroquinolinyl, 1,2,3,4-tetrahydroquinolinyl, decahydroquinolinyl, 1,2-dihydroisoquinolinyl, 1,2,3,4-tetrahydroisoquinolinyl, 1,2,3,4-tetrahydroisoquinolinyl, decahydroisoquinolinyl, decahydroisoquinolinyl, 4,5,6,7-tetrahydrothieno[3,2-c]pyridinyl, pyrazolidinyl, imidazolidinyl, hexahydropyrimidinyl, 1,2-dihydropyrimidinyl, piperazinyl, [1,3]diazepanyl, [1,4]diazepanyl, oxazolidinyl, [1,3]oxazinanyl, [1,3]oxazepanyl, morpholinyl including morpholin-2-yl, morpholin-3-yl and morpholin-4-yl, [1,4]oxazepanyl, thiazolidinyl, [1,3]thiazinanyl, thiomorpholinyl including thiomorpholin-2-yl, thiomorpholin-3-yl and thiomorpholin-4-yl, 3,4-dihydro-2H-[1,4]thiazinyl, [1,3]thiazepanyl, [1,4]thiazepanyl, [1,4]thiazepanyl, oxetanyl, tetrahydrofuranyl, tetrahydrothienyl, isoxazolidinyl, isothiazolidinyl, oxazolidinyl, [1,2,4]-oxadiazolidinyl, [1,2,4]-thiadiazolidinyl, [1,2,4]triazolidinyl, [1,3,4]oxadiazolidinyl, [1,3,4]thiadiazolidinyl, [1,3,4]triazolidinyl, 2,3-dihydrofuranyl, 2,5-dihydrofuranyl, 2,3-dihydrothienyl, 2,5-dihydrothienyl, 2,3-dihydropyrrolyl, 2,3-dihydroisoxazolyl, 4,5-dihydroisoxazolyl, 2,5-dihydroisoxazolyl, 2,3-dihydroisothiazolyl, 4,5-dihydroisothiazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, tetrahydropyridazinyl, tetrahydropyrimidinyl, tetrahydropyrazinyl, tetrahydro[1,3,5]triazinyl, [1,3]dithianyl, tetrahydropyranyl, tetrahydrothiopyranyl, [1,3]dioxolanyl, 3,4,5,6-tetrahydropyridinyl, 4H-[1,3]thiazinyl, 1,1-dioxo-2,3,4,5-tetrahydrothienyl, 2-azabicyclo[3.1.0]hexyl including 2-azabicyclo[3.1.0]hex-2-yl, 3-azabicyclo[3.1.0]hexyl including 3-azabicyclo[3.1.0]hex-3-yl, 2-oxa-5-azabicyclo[2.2.1]-heptyl including 2-oxa-5-azabicyclo[2.2.1]-hept-5-yl, which all are bonded via any suitable ring carbon atom or ring nitrogen atom and are optionally substituted as indicated in the definition of the respective group.

Halogen is fluorine, chlorine, bromine or iodine. In one embodiment of the invention, any halogen in a compound of the formula I is independently of any other halogen chosen from fluorine, chlorine and bromine, in another embodiment from fluorine and chlorine.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a C(O) (=C(=O)) group. Evidently, an oxo group cannot occur as a substituent on a carbon atom in an aromatic ring such as in a phenyl group, for example. When a ring sulfur atom in a heterocyclic group can carry one or two oxo groups, it is a non-oxidized sulfur atom S in case it does not carry any oxo group, or it is an S(O) group (=sulfoxide group, S-oxide group) in case it carries one oxo group, or it is an $S(O)_2$ group (=sulfone group, S,S-dioxide group) in case it carries two oxo groups.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts. Thus, the compounds of the formula I which contain an acidic group, such as a hydroxycarbonyl group (=carboxy group =C(O)—OH group), can be present on such groups, and can be used according to the invention, as alkaline metal salts, alkaline earth metal salts or as ammonium salts, for example. More specific examples of such salts include sodium salts, potassium salts, calcium salts, magnesium salts, quaternary ammonium salts such as tetraalkylammonium salts, or acid addition salts with ammonia or organic amines such as, for example, ethylamine, ethanolamine, triethanolamine or amino acids. Compounds of the formula I which contain a basic group, i.e. a group which can be protonated such as an amino group or a nitrogen heterocycle, can be present on such groups, and can be used according to the invention, in the form of their addition salts with inorganic and organic acids. Examples for suitable acids include hydrogen chloride, hydrogen bromide, phosphoric acid, sulfuric acid, methanesulfonic acid, oxalic acid, acetic acid, trifluoroacetic acid, tartaric acid, lactic acid, benzoic acid, malonic acid, fumaric acid, maleic acid, citric acid, and other acids known to the person skilled in the art. If a compound of the formula I simultaneously contains an acidic group and a basic group in the molecule, the invention also includes, in addition to the salt forms mentioned, inner salts (=betaines, zwitterions). The salts of the compounds of the formula I can be obtained by customary methods which are known to the person skilled in the art like, for example, by contacting the compound of the formula I with an organic or inorganic acid or base in a solvent or diluent, or by anion exchange or cation exchange from another salt. The invention also includes all salts of the compounds of the formula I which, owing to low physiological compatibility of the salt-forming acid or base, are not directly suitable for use in pharmaceuticals but which can be used, for example, as intermediates for chemical reactions or for the preparation of physiologically acceptable salts.

The present invention furthermore includes all solvates of compounds of the formula I, for example hydrates or adducts with alcohols such as $(C_1-C_4)$-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

In one embodiment of the invention, A is $—(CR^4R^5)_a—CR^6R^7—$, wherein a is chosen from 0 and 1 and wherein the moiety $CR^6R^7$ is bonded to the group $R^3$, in another embodiment A is $—CR^6R^7—(CR^8R^9)_b—$, wherein b is chosen from 0 and 1 and wherein the moiety $CR^6R^7$ is bonded to the oxazolopyrimidine ring depicted in formula I, in another embodiment A is $—CR^6R^7—$, in another embodiment A is chosen from $—CH_2—$ and $—CH_2—CH_2—$, in another embodiment A is $—CH_2—$, in another embodiment A is $—CH_2—CH_2—$, in another embodiment A is $—C(CH_3)_2—$, in another embodiment A is cyclopropane-1,1-diyl, i.e., in the latter embodiment A is $—CR^6R^7—$ and $R^6$ and $R^7$ together are the divalent group $—CH_2—CH_2—$.

In one embodiment of the invention, $R^1$ is chosen from $(C_1-C_6)$-alkyl, $(C_2-C_6)$-alkenyl, $(C_3-C_7)$-cycloalkyl-$C_uH_{2u}—$ and $Het^1$-$C_uH_{2u}—$, in another embodiment from $(C_1-C_6)$-alkyl, $(C_3-C_7)$-cycloalkyl-$C_uH_{2u}—$ and $Het^1$-$C_uH_{2u}—$, in another embodiment from $(C_1-C_6)$-alkyl, $(C_2-C_6)$-alkenyl and $(C_3-C_7)$-cycloalkyl-$C_uH_{2u}—$, in another embodiment from $(C_1-C_6)$-alkyl and $(C_2-C_6)$-alkenyl, in another embodiment from $(C_1-C_6)$-alkyl and $(C_3-C_7)$-cycloalkyl-$C_uH_{2u}—$, in another embodiment from $(C_1-C_6)$-alkyl, in another embodiment from $(C_1-C_4)$-alkyl. In one embodiment, the number u is chosen from 0, 1 or 2, in another embodiment from 0 or 1, in another embodiment from 1, 2 or 3, in another embodiment from 1 or 2, in another embodiment u is 0, in another embodiment u is 1. In one embodiment, a $(C_1-C_6)$-alkyl group representing $R^1$ is $(C_2-C_6)$-alkyl, in another embodiment $(C_3-C_5)$-alkyl, in another embodiment $(C_2-C_5)$-alkyl. In one embodiment, a $(C_2-C_6)$-alkenyl group and a $(C_2-C_6)$-alkynyl group representing $R^1$ are $(C_3-C_6)$-alkenyl and $(C_3-C_6)$-alkynyl, in another embodiment $(C_3-C_4)$-alkenyl and $(C_3-C_4)$-alkynyl, respectively. In one embodiment, a $(C_3-C_7)$-cycloalkyl group present in $R^1$ is $(C_3-C_6)$-cycloalkyl, in another embodiment $(C_3-C_5)$-cycloalkyl.

In one embodiment of the invention, $R^2$ is chosen from phenyl and a residue of an aromatic, 5-membered to 6-membered monocyclic or 9-membered to 10-membered bicyclic heterocycle, in another embodiment $R^2$ is chosen from phenyl and a residue of an aromatic 5-membered to 6-membered monocyclic heterocycle, in another embodiment $R^2$ is chosen from phenyl and pyridinyl, in another embodiment $R^2$ is phenyl, in another embodiment $R^2$ is pyridinyl, in another embodiment $R^2$ is a residue of an aromatic 5-membered to 6-membered monocyclic heterocycle, in another embodiment $R^2$ is a residue of an aromatic 9-membered to 10-membered bicyclic heterocycle, wherein all groups are optionally substituted and wherein the heterocycle is defined as specified with respect to $R^2$. In one embodiment, a residue of an aromatic heterocycle representing $R^2$ can contain one or more ring nitrogen atoms which do not carry a hydrogen atom or a substituent, as occurs in a pyridine ring, for example, but $R^2$ does not contain a ring nitrogen atom which can carry a hydrogen atom or a substituent, as occurs in a pyrrole ring, for example. In one embodiment, the number of ring heteroatoms in an aromatic heterocyclic group representing $R^2$ is 1 or 2, in another embodiment it is 1. In one embodiment, a residue of an aromatic heterocyclic group representing $R^2$ is chosen from furanyl, thiophenyl, oxazolyl, thiazolyl, pyridinyl, pyridazinyl, pyrimidinyl and pyrazinyl, in another embodiment from furanyl, thiophenyl, thiazolyl, pyridinyl, pyridazinyl, pyrimidinyl and pyrazinyl, in another embodiment from furanyl, thiophenyl, pyridinyl, pyridazinyl, pyrimidinyl and pyrazinyl, in another embodiment from furanyl, thiophenyl, pyridinyl and pyrimidinyl, in another embodiment from furanyl, thiophenyl and pyridinyl, in another embodiment a residue of an aromatic heterocyclic group representing $R^2$ is a pyridinyl group, which are all optionally substituted as indicated with respect to $R^2$. In another embodiment, $R^2$ is chosen from one or more of the groups furan-2-yl, thiophen-2-yl, pyridin-3-yl, pyridin-4-yl and pyrimidin-5-yl, in another embodiment from phenyl, furan-2-yl, thiophen-2-yl, pyridin- 3-yl, pyridin-4-yl and pyrimidin-5-yl, in another embodiment from pyridin-3-yl and pyridin-4-yl, in another embodiment from phenyl, pyridin-3-yl and pyridin-4-yl, which all are optionally substituted as indicated with respect to $R^2$. In one embodiment, the number of substituents $R^{22}$ which are optionally present on ring carbon atoms in $R^2$, is 1, 2, 3, 4 or 5, in another embodiment 1, 2, 3 or 4, in another embodiment 1, 2 or 3, in another embodiment 1 or 2, in another embodiment 1. Ring carbon atoms in $R^2$ which do not carry a substituent $R^{22}$, carry a hydrogen atom.

The residue of a monocyclic or bicyclic ring representing $R^3$ can be carbocyclic or heterocyclic. In one embodiment of the invention, the number of ring heteroatoms within $R^3$ is 0, 1, 2 or 3, in another embodiment it is 0, 1 or 2, in another embodiment it is 0 or 1, in another embodiment it is 0, in another embodiment it is 1, 2, 3 or 4, in another embodiment it is 1, 2 or 3, in another embodiment it is 1 or 2, in another embodiment it is 1. In one embodiment, the ring heteroatoms in $R^3$ are chosen from N and O, in another embodiment from N and S, in another embodiment from O and S, in another embodiment they are N, wherein ring nitrogen atoms can carry a hydrogen atom or a substituent as occurs in saturated or partially saturated heterocycles or in 5-membered aromatic rings in heterocycles such as pyrrole or benzoimidazole, for example, or not carry a hydrogen atom or a substituent as occurs in aromatic heterocycles such as imidazole or pyridine, for example, or as is the case if $R^3$ is bonded via a ring nitrogen atom. In general, $R^3$ can be bonded via any suitable ring carbon atom and ring nitrogen atom. In one embodiment, $R^3$ is bonded via a ring carbon atom, in another embodiment via a ring nitrogen atom. In a residue of a heterocycle representing $R^3$ which comprises one or more ring sulfur atoms, in one embodiment one of the ring sulfur atoms is non-oxidized or carries one or two oxo groups, and any other ring sulfur atoms are non-oxidized. The residue of a monocyclic or bicyclic ring representing $R^3$ can be unsaturated and in this case contain 1, 2, 3, 4 or 5, or 1, 2, 3 or 4, or 1, 2 or 3, or 1 or 2, or 1, double bonds within the ring and can in any of the one or two rings be aromatic or non-aromatic, or saturated and in this case contain no double bonds within the ring. In one embodiment of the invention, $R^3$ is saturated or aromatic. If $R^3$ comprises ring nitrogen atoms which can carry a hydrogen atom or a substituent $R^{31}$, one of such nitrogen atoms or two of such ring nitrogen atoms can carry a substituent $R^{31}$. In one embodiment, the number of optional substituents $R^{32}$ on ring carbon atoms in $R^3$ is 1, 2, 3, 4, 5 or 6, in another embodiment 1, 2, 3, 4 or 5, in another embodiment 1, 2, 3 or 4, in another embodiment 1, 2 or 3, in another embodiment 1 or 2, in another embodiment 1. $R^3$ can be 4-membered, 5-membered, 6-membered, 7-membered, 8-membered, 9-membered or 10 membered. In one embodiment, $R^3$ is 4-membered to 9-membered, in another embodiment 4-membered to 8-membered, in another embodiment 4-membered to 7-membered, in another 5-membered to 7-membered, in another embodiment 5-membered or 6-membered, in another embodiment 6-membered, in another embodiment 8-membered to 10-membered, in another embodiment 9-membered to 10-membered. In one embodiment, $R^3$ is monocyclic, in another embodiment bicyclic. In one embodiment, a bicyclic group representing $R^3$ is at least 7-membered. Among others, the residue of a ring representing $R^3$ can be a cycloalkyl group, a phenyl group, a naphthyl group, a residue of an unsaturated, aromatic or non-aromatic heterocyclic group or a residue of a saturated heterocyclic group, which all are optionally substituted on ring carbon atoms and ring nitrogen atoms as specified with respect to $R^3$. As far as applicable, all explanations given above with respect to such groups apply correspondingly to $R^3$. Another example of groups which can represent $R^3$, are cycloalkenyl groups such as $(C_5-C_7)$-cycloalkenyl groups which can be bonded via any ring carbon atom and are optionally substituted as specified with respect to $R^3$. In one embodiment, optional substituents $R^{32}$ on a cycloalkenyl group representing $R^3$ are chosen from fluorine and $(C_1-C_4)$-alkyl. In one embodiment, cycloalkenyl groups contain one double bond within the ring which can be present in any position. Examples of cycloalkenyl are cyclopentenyl including cyclopent-1-enyl, cyclopent-2-enyl and cyclopent-3-enyl, cyclohexenyl including cyclohex-1-enyl, cyclohex-2-enyl and cyclohex-3-enyl, and cycloheptenyl including cyclohept-1-enyl, cyclohept-2-enyl, cyclopent-3-enyl and cyclohept-4-enyl. Examples of residues of rings, from any one or more of which $R^3$ can be chosen in one embodiment of the invention, are cyclobutyl, cyclopentyl, cyclohexyl, phenyl, tetrahydrofuranyl including tetrahydrofuran-3-yl, tetrahydropyranyl including tetrahydropyran-4-yl, azetidinyl including azetidin-1-yl, pyrrolidinyl including pyrrolidin-1-yl, piperidinyl including piperidin-1-yl, imidazolidinyl including imidazolidin-1-yl, piperazin-yl including piperazin-1-yl, 2-oxa-5-azabicyclo[2.2.1]heptyl including 2-oxa-5-azabicyclo[2.2.1]hept-5-yl, [1,4]oxazepanyl including [1,4]oxazepan-4-yl, thiazolidinyl including thiazolidin-3-yl, isothiazolidinyl including isothiazolidin-2-yl, morpholinyl including morpholin-4-yl, thiomorpholinyl including thiomorpholin-4-yl, pyrazolyl including pyrazol-1-yl, imidazolyl including imidazol-1-yl, [1,2,3]triazolyl including [1,2,3]triazol-1-yl, [1,2,4]triazolyl including [1,2,4]triazol-1-yl, pyridinyl including pyridin-2-yl, pyridin-3-yl and pyridin-4-yl, and benzoimidazolyl including 2,3-dihydrobenzoimidazol-1-yl, wherein in all of them, if applicable, one or two of the ring nitrogen atoms can carry a hydrogen atom or a substituent $R^{31}$, and wherein all of them are optionally substituted on one or more ring carbon atoms by identical or different substituents $R^{32}$, and wherein in all of them, if applicable, a ring sulfur atom can be non-oxidized, i.e. be present as a sulfur atom, or carry one or two oxo groups, i.e. be present in the form of a sulfoxide or sulfone.

In one embodiment, $R^3$ is chosen from phenyl and a residue of a saturated or unsaturated 4-membered to 7-membered, monocyclic ring, in another embodiment from phenyl and a residue of a saturated or unsaturated 5-membered to 7-membered, monocyclic ring, in another embodiment from phenyl, pyridinyl and a residue of a saturated 4-membered to 7-membered, monocyclic ring, in another embodiment from phenyl, pyridinyl and a residue of a saturated 5-membered to 7-membered, monocyclic ring, in another embodiment from phenyl and a residue of a saturated 4-membered to 7-membered, monocyclic ring, in another embodiment from phenyl and a residue of a saturated 5-membered to 7-membered, monocyclic ring, wherein in all these embodiments the monocyclic ring comprises 1 or 2 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the phenyl, pyridinyl and residue of a ring are optionally substituted on one or more ring carbon atoms by identical or different substituents $R^{32}$. In another embodiment, $R^3$ is chosen from any one or more of the groups phenyl, pyrrolidinyl including pyrrolidin-1-yl, piperidinyl including piperidin-1-yl, morpholinyl including morpholin-4-yl, imidazolyl including imidazol-1-yl, and pyridinyl including pyridin-2-yl, pyridin-3-yl and pyridin-4-yl, wherein in all of them, if applicable, one of the ring nitrogen atoms can carry a hydrogen atom or a substituent $R^{31}$, and wherein all of them are optionally substituted on one or more ring carbon atoms by identical or different substituents $R^{32}$. In another embodiment, $R^3$ is phenyl which is optionally substituted by one or more identical or different substituents $R^{32}$. In another embodiment, $R^3$ is chosen from pyrrolidinyl including pyrrolidin-1-yl, piperidinyl including piperidin-1-yl and morpholinyl including morpholin-4-yl, in another embodiment $R^3$ is morpholin-4-yl, wherein in all of them the ring nitrogen atoms can carry a hydrogen atom or a substituent $R^{31}$, and wherein all of them are optionally substituted on one or more ring carbon atoms by identical or different substituents $R^{32}$.

In one embodiment of the invention, $R^4$, $R^5$, $R^8$ and $R^9$ are independently of each other chosen from hydrogen, fluorine and methyl, in another embodiment from hydrogen and fluorine, in another embodiment from hydrogen and methyl, and in another embodiment $R^4$, $R^5$, $R^8$ and $R^9$ are all hydrogen. In one embodiment, $R^4$ and $R^5$ are identical. In another embodiment, $R^8$ and $R^9$ are identical.

In one embodiment of the invention, the divalent $(C_2-C_8)$-alkanediyl group which represents the two groups $R^6$ and $R^7$ together and which can be linear or branched, and which together with the carbon atom carrying $R^6$ and $R^7$ forms a cycloalkane ring which carries the group $CR^4R^5$, or the oxazolopyrimidine ring depicted in formula I, and the group $CR^8R^9$, or the group $R^3$, on the same ring carbon atom, is a $(C_2-C_5)$-alkanediyl group, in another embodiment a $(C_2-C_4)$-alkanediyl group, in another embodiment a $(C_2-C_3)$-alkanediyl group, in another embodiment a $C_2$-alkanediyl group. In one embodiment, the divalent $(C_2-C_8)$-alkanediyl group which represents the two groups $R^6$ and $R^7$ together, is bonded via two different carbon atoms to the carbon atom carrying $R^6$ and $R^7$, and in another embodiment the divalent $(C_2-C_8)$-alkanediyl group is a chain of two or more $CH_2$ groups and is bonded to the carbon atom carrying $R^6$ and $R^7$ via the terminal carbon atoms of the chain. In one embodiment, the divalent $(C_2-C_8)$-alkanediyl group which represents $R^6$ and $R^7$ together, is chosen from —$CH_2$—$CH_2$— and —$CH_2$—$CH_2$—$CH_2$— and the ring formed together with the carbon atom carrying $R^6$ and $R^7$ thus is a cyclopropane ring or a cyclobutane ring, respectively, and in another embodiment the divalent $(C_2-C_8)$-alkanediyl group which represents $R^6$ and $R^7$ together, is the group —$CH_2$—$CH_2$—. In one embodiment of the invention, $R^6$ and $R^7$ are independently of each other chosen from hydrogen, fluorine, methyl and ethyl, in another embodiment from hydrogen, fluorine and methyl, in another embodiment from hydrogen and fluorine, in another embodiment from hydrogen and methyl, in another embodiment $R^6$ and $R^7$ both are hydrogen, or in all these embodiments $R^6$ and $R^7$ together are $(C_2-C_8)$-alkanediyl. In another embodiment, $R^6$ and $R^7$ are independently of each other chosen from hydrogen, fluorine, methyl and ethyl, in another embodiment from hydrogen, fluorine and methyl, in another embodiment from hydrogen and fluorine, in another embodiment from hydrogen and methyl, in another embodiment $R^6$ and $R^7$ both are hydrogen. In another embodiment, $R^6$ and $R^7$ together are $(C_2-C_8)$-alkanediyl.

In one embodiment of the invention, the number v is chosen from 0 and 1, in another embodiment it is 0, in another embodiment it is 1. In one embodiment, a $(C_3-C_7)$-cycloalkyl group present in $R^{21}$ is $(C_3-C_6)$-cycloalkyl, in another embodiment $(C_3-C_5)$-cycloalkyl, in another embodiment cyclopropyl. In one embodiment, $R^{21}$ is chosen from $(C_1-C_4)$-alkyl, in another embodiment from $(C_1-C_3)$-alkyl, in another embodiment $R^{21}$ is methyl.

In one embodiment of the invention, the substituents $R^{22}$ which are optionally present on the group $R^2$, are chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—, in another embodiment from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—C(O)—, $R^{23}$—NH—C(O)—, $R^{23}$—N($R^{23}$)—C(O)—, $R^{24}$, $R^{24}$—O— and $R^{24}$—C(O)—, in another embodiment from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—, $R^{23}$—NH—C(O)—, $R^{23}$—N($R^{23}$)—C(O)—, $R^{24}$, $R^{24}$—O— and $R^{24}$—C(O)—, in another embodiment from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—, $R^{23}$—NH—C(O)—, $R^{23}$—N($R^{23}$)—C—(O)—, $R^{24}$ and $R^{24}$—O—, in another embodiment from halogen, hydroxy, amino, $R^{23}$, $R^{23}$—O—, $R^{23}$—NH—, $R^{23}$—N($R^{23}$)—, $R^{23}$—C(O)—, $R^{23}$—NH—C(O)—, $R^{23}$—N($R^{23}$)—C(O)— and $R^{24}$, in another embodiment from halogen, hydroxy, $(C_1-C_4)$-alkyl, $(C_1-C_4)$-alkyl-S(O)$_m$—, amino, cyano, hydroxycarbonyl, $(C_1-C_4)$-alkyloxycarbonyl, aminocarbonyl, aminosulfonyl, $R^{23}$—O— and $R^{24}$, in another embodiment from halogen, hydroxy, $(C_1-C_4)$-alkyl, $(C_1-C_4)$-alkyloxy, $(C_1-C_4)$-alkyl-S(O)$_m$—, amino, cyano, hydroxycarbonyl, $(C_1-C_4)$-alkyloxycarbonyl, aminocarbonyl, aminosulfonyl, $R^{24}$—O— and $R^{24}$, in another embodiment from halogen, hydroxy, $(C_1-C_4)$-alkyl, $(C_1-C_4)$-alkyl-S(O)$_m$—, amino, cyano, hydroxycarbonyl, $(C_1-C_4)$-alkyloxycarbonyl, aminocarbonyl and aminosulfonyl, in another embodiment from halogen, hydroxy, $(C_1-C_4)$-alkyl, $(C_1-C_4)$-alkyl-S(O)$_m$—, amino, cyano and aminosulfonyl, in another embodiment from halogen, hydroxy, $(C_1-C_4)$-alkyl, $(C_1-C_4)$-alkyl-S(O)$_m$— and amino, in another embodiment from halogen, hydroxy, amino, $R^{23}$, $R^{23}$—O—, $R^{23}$—NH—, $R^{23}$—N($R^{23}$)—, $R^{23}$—C(O)— and $R^{24}$, in another embodiment from halogen, hydroxy, $(C_1-C_4)$-alkyl, amino, $R^{23}$—O— and $R^{24}$, in another embodiment from halogen, hydroxy, $(C_1-C_4)$-alkyl, amino, $(C_1-C_4)$-alkyloxy and $R^{23}$—O—, in another embodiment from halogen, hydroxy, $(C_1-C_4)$-alkyl, amino, $(C_1-C_4)$-alkyloxy and $R^{24}$, in another embodiment from halogen, hydroxy, $(C_1-C_4)$-alkyl and $R^{23}$—O—, in another embodiment from halogen, $(C_1-C_4)$-alkyl and $R^{23}$—O—, in another embodiment from halogen and $R^{23}$, in another embodiment from halogen, $(C_1-C_4)$-alkyl and $R^{24}$, wherein in all these embodiments $R^{23}$ and $R^{24}$ are as defined.

In one embodiment, 1, 2, 3 or 4 of the substituents $R^{22}$, in another embodiment 1, 2 or 3 of the substituents $R^{22}$, in another embodiment 1 or 2 of the substituents $R^{22}$, and in another embodiment 1 of the substituents $R^{22}$, which are optionally present on the group $R^2$, are defined as in the general definition of $R^{22}$ and thus are chosen from halogen, hydroxy, $(C_1-C_4)$-alkyl-S(O)$_m$—, amino, nitro, cyano, hydroxycarbonyl, $(C_1-C_4)$-alkyloxycarbonyl, aminocarbonyl, aminosulfonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—, wherein $R^{23}$ and $R^{24}$ are as defined, and any further substituents $R^{22}$ which are optionally present on the group $R^2$, for example 1, 2 or 3 further substituents $R^{22}$, or 1 or 2 further substituents $R^{22}$, or 1 further substituent $R^{22}$, are chosen from halogen, hydroxy, $(C_1-C_4)$-alkyl-S(O)$_m$—, amino, nitro, cyano, hydroxycarbonyl, $(C_1-C_4)$-alkyloxycarbonyl, aminocarbonyl, aminosulfonyl, $(C_1-C_4)$-alkyl, $(C_1-C_4)$-alkyloxy, $(C_1-C_4)$-alkylamino, di(($C_1-C_4$)-alkyl)amino, $(C_1-C_4)$-alkyl-C (O)—NH—, $(C_1-C_4)$-alkyl-S(O)$_2$—NH—, $(C_1-C_4)$-alkyl-NH—C(O)— and di(($(C_1-C_4)$-alkyl)aminocarbonyl, wherein all alkyl groups independently of each other are optionally substituted by one or more fluorine substituents as generally applies to alkyl groups. In one embodiment, the said substituents $R^{22}$ which are optionally present on the group $R^2$ and which in the afore-mentioned embodiment are defined as in the general definition of $R^{22}$, for example 1 or 2 such substituents $R^{22}$, or 1 such substituent $R^{22}$, are chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—, in another embodiment from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—, $R^{23}$—NH—C(O)—, $R^{23}$—N($R^{23}$)—C(O)—, $R^{24}$, $R^{24}$—O— and $R^{24}$—C(O)—, in another embodiment from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—, $R^{23}$—NH—C(O)—, $R^{23}$—N($R^{23}$)—C(O)—, $R^{24}$ and $R^{24}$—O—, in another embodiment from halogen, hydroxy, amino, $R^{23}$, $R^{23}$—O—, $R^{23}$—NH—, $R^{23}$—N($R^{23}$)—, $R^{23}$—C(O)—, $R^{23}$—NH—C(O)—, $R^{23}$—N($R^{23}$)—C(O)— and $R^{24}$, in another embodiment from halogen, $R^{23}$, $R^{23}$—O— and $R^{23}$—NH—, in another embodiment from halogen, $(C_1-C_4)$-alkyl, $R^{23}$—O— and $R^{23}$—NH—, in another embodiment from halogen, hydroxy, $(C_1-C_4)$-alkyl and $R^{23}$—O—, in another embodiment from halogen, $(C_1-C_4)$-alkyl and $R^{24}$, in another embodiment from halogen, $(C_1-C_4)$-alkyl and $R^{23}$—O—, in another embodiment from halogen, $(C_1-C_4)$-alkyl and $R^{23}$—NH—, in another embodiment from halogen and $R^{23}$, in another embodiment from halogen, hydroxy, $(C_1-C_4)$-alkyl, $(C_1-C_4)$-alkyl-S(O)$_m$—, amino, cyano, hydroxycarbonyl, $(C_1-C_4)$-alkyloxycarbonyl, aminocarbonyl, aminosulfonyl, $R^{23}$—O— and $R^{24}$, in another embodiment from halogen, hydroxy, $(C_1-C_4)$-alkyl, $(C_1-C_4)$-alkyloxy, $(C_1-C_4)$-alkyl-S(O)$_m$—, amino, cyano, hydroxycarbonyl, $(C_1-C_4)$-alkyloxycarbonyl, aminocarbonyl, aminosulfonyl, $R^{24}$—O— and $R^{24}$, in another embodiment from halogen, hydroxy, $(C_1-C_4)$-alkyl, $(C_1-C_4)$-alkyloxy, $(C_1-C_4)$-alkyl-S(O)$_m$—, amino, cyano, hydroxycarbonyl, $(C_1-C_4)$-alkyloxycarbonyl, aminocarbonyl and aminosulfonyl, in another embodiment from halogen, hydroxy, $(C_1-C_4)$-alkyl, $(C_1-C_4)$-alkyloxy, $(C_1-C_4)$-alkyl-S(O)$_m$—, amino, cyano and aminosulfonyl, in another embodiment from halogen, hydroxy, $(C_1-C_4)$-alkyl, $(C_1-C_4)$-alkyloxy, $(C_1-C_4)$-alkyl-S(O)$_m$— and amino, in another embodiment from halogen, hydroxy, amino, $R^{23}$, $R^{23}$—O—, $R^{23}$—NH—, $R^{23}$—N($R^{23}$)—, $R^{23}$—C(O)— and $R^{24}$, in another embodiment from halogen, hydroxy, $(C_1-C_4)$-alkyl, amino, $R^{23}$—O— and $R^{24}$, in another embodiment from halogen, hydroxy, $(C_1-C_4)$-alkyl, amino and $R^{23}$—O—, in another embodiment from halogen, hydroxy, $(C_1-C_4)$-alkyl, amino, $(C_1-C_4)$-alkyloxy and $R^{24}$, wherein in all these embodiments $R^{23}$ and $R^{24}$ are as defined. In one embodiment, the said substituents $R^{22}$ which are optionally present on the group $R^2$ and which in the afore-mentioned embodiment are defined as in the general definition of $R^{22}$, for example 1 or 2 such substituents $R^{22}$, or 1 such substituent $R^{22}$, are not located on ring carbon atoms within the group $R^2$ which are adjacent to the atom via which the group $R^2$ is bonded to the oxazolopyrimidine ring depicted in formula I. In another embodiment, in the case of a phenyl group representing $R^2$, 1 or 2 such substituents $R^{22}$, or 1 such substituent $R^{22}$, is optionally present in any of positions 3, 4 and 5 of the phenyl group, and in another embodiment 1 such substituent $R^{22}$ is present in position 4 of the phenyl group. In one embodiment, the said further substituents $R^{22}$ which are optionally present on the group $R^2$, for example 1, 2 or 3 further substituents $R^{22}$, or 1 or 2 further substituents $R^{22}$, or 1 further substituent $R^{22}$, are chosen from halogen, hydroxy, amino, cyano, hydroxycarbonyl, $(C_1-C_4)$-alkyloxycarbonyl, aminocarbonyl, $(C_1-C_4)$-alkyloxy, $(C_1-C_4)$-alkylamino, di(($(C_1-C_4)$-alkyl)amino, $(C_1-C_4)$-alkyl-C(O)—NH—, $(C_1-C_4)$-alkyl-S(O)$_2$—NH—, $(C_1-C_4)$-alkyl-NH—C(O)— and di(($(C_1-C_4)$-alkyl)aminocarbonyl, in another embodiment from halogen, hydroxy, amino, cyano, aminocarbonyl, $(C_1-C_4)$-alkyl, $(C_1-C_4)$-alkyloxy, $(C_1-C_4)$-alkylamino, di(($(C_1-C_4)$-alkyl)amino, $(C_1-C_4)$-alkyl-C(O)—NH—, $(C_1-C_4)$-alkyl-NH—C(O)— and di(($(C_1-C_4)$-alkyl)aminocarbonyl, in another embodiment from halogen, hydroxy, amino, $(C_1-C_4)$-alkyl, $(C_1-C_4)$-alkyloxy, $(C_1-C_4)$-alkylamino and di(($(C_1-C_4)$-alkyl)amino, in another embodiment from halogen, $(C_1-C_4)$-alkyl and $(C_1-C_4)$-alkyloxy, in another embodiment from halogen and $(C_1-C_4)$-alkyl, wherein in all these embodiment all alkyl groups independently of each other are optionally substituted by one or more fluorine substituents.

In one embodiment of the invention, $R^{23}$ is $(C_1-C_4)$-alkyl, in another embodiment $(C_2-C_6)$-alkyl, in another embodiment $(C_2-C_5)$-alkyl, in another embodiment $(C_3-C_4)$-alkyl, which are all optionally substituted as indicated. In one embodiment, the number of substituents which are optionally present on the alkyl group representing $R^{23}$ is 1, 2, 3 or 4, in another embodiment 1, 2 or 3, in another embodiment 1 or 2, in another embodiment 1. In one embodiment, the optional substituents on an alkyl group representing $R^{23}$ are chosen from hydroxy, $R^{25}$—S(O)$_m$—, amino, hydroxycarbonyl, $R^{25}$—O—C(O)—, aminocarbonyl $R^{24}$, $R^{24}$—NH—, $R^{24}$—C(O)—, $R^{25}$—O—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—C(O)— and $R^{25}$—N($R^{25}$)—C(O)—, in another embodiment from hydroxy, $R^{25}$—S(O)$_m$—, amino, hydroxycarbonyl, $R^{25}$—O—C(O)—, aminocarbonyl, $R^{24}$, $R^{24}$—C(O)—, $R^{25}$—O—, $R^{25}$—NH—, $R^{25}$—N($R^{25}$)—, $R^{25}$—C(O)—NH— and $R^{25}$—NH—C(O)—, in another embodiment from hydroxy, $R^{25}$—S(O)$_m$—, amino, hydroxycarbonyl, $R^{25}$—O—C(O)—, $R^{24}$, $R^{24}$—C(O)—, $R^{25}$—NH—, $R^{25}$—N($R^{25}$)—, $R^{25}$—C(O)—NH—, and $R^{25}$—NH—C(O)—, in another embodiment from $R^{25}$—S(O)$_m$—, hydroxycarbonyl, $R^{25}$—O—C(O)—, $R^{24}$, $R^{24}$—C(O)—, $R^{25}$—NH—, $R^{25}$—N($R^{25}$)—, $R^{25}$—C(O)—NH—, and $R^{25}$—NH—C(O)—, in another embodiment from $R^{25}$—S(O)$_m$—, $R^{24}$, $R^{24}$—C(O)—, $R^{25}$—NH—, $R^{25}$—N($R^{25}$)—, $R^{25}$—C(O)—NH—, and $R^{25}$—NH—C(O)—, in another embodiment from $R^{25}$—S(O)$_m$—, $R^{24}$, $R^{24}$—C(O)—, and $R^{25}$—NH—C(O)—, in another embodiment from hydroxy, amino, hydroxycarbonyl, $(C_1-C_4)$-alkyloxycarbonyl, aminocarbonyl, $R^{24}$, $R^{24}$—C(O)—, $R^{25}$—O—, $R^{25}$—NH—, $R^{25}$—N($R^{25}$)—, $R^{25}$—C(O)—NH—, $R^{25}$—S(O)$_2$—NH—, $R^{25}$—NH—C(O)— and $R^{25}$—N($R^{25}$)—C(O)—, in another embodiment from hydroxy, amino, hydroxycarbonyl, $(C_1-C_4)$-alkyloxycarbonyl, aminocarbonyl, $R^{24}$, $R^{24}$—C(O)—, $R^{25}$—O—, $R^{25}$—NH—, $R^{25}$—N($R^{25}$)— and $R^{25}$—C(O)—NH—, in another embodiment from hydroxy, amino, hydroxycarbonyl, $(C_1-C_4)$-alkyloxycarbonyl, $R^{24}$, $R^{24}$—C(O)—, $R^{25}$—O—, $R^{25}$—NH—, $R^{25}$—N($R^{25}$)— and $R^{25}$—C(O)—NH—, in another embodiment from hydroxy, amino, $R^{24}$—C(O)—, $R^{25}$—O—, $R^{25}$—NH—, $R^{25}$—N($R^{25}$)— and $R^{25}$—C(O)—NH—.

In one embodiment of the invention, $R^{23}$ is an alkyl group as specified above which is substituted by one more, for example by 1, 2, 3 or 4, or by 1, 2 or 3, or by 1 or 2, or by 1, identical or different substituents as specified. In one embodiment, an individual carbon atom in an alkyl group representing $R^{23}$ does not carry more than one substituent chosen from hydroxy, $R^{25}$—S(O)$_m$—, amino, $R^{24}$—NH—, $R^{25}$—O—, $R^{25}$—NH—, $R^{25}$—N($R^{25}$)—, $R^{25}$—C(O)—NH—, $R^{25}$—S(O)$_2$—NH—, $R^{25}$—NH—S(O)$_2$—NH— and residues of rings $R^{24}$ which are bonded via a ring nitrogen atom, in another embodiment not more than one substituent chosen from hydroxy, (C$_1$-C$_4$)-alkyl-S(O)$_m$—, amino, $R^{24}$, $R^{25}$—O—, $R^{25}$—NH—, $R^{25}$—N($R^{25}$)—, $R^{25}$—C(O)—NH—, $R^{25}$—S(O)$_2$—NH—, $R^{25}$—NH—S(O)$_2$—NH— and residues of rings $R^{24}$ which are bonded via a ring nitrogen atom. Examples of groups, from any one or more of which $R^{23}$ can be chosen in one embodiment of the invention, are alkyl groups substituted by one or more, for example by 1, 2 or 3, or by 1 or 2, or by 1, substituents chosen from hydroxy and $R^{25}$—O—, including groups such as hydroxy-(C$_1$-C$_6$)-alkyl, dihydroxy-(C$_1$-C$_6$)-alkyl, trihydroxy-(C$_1$-C$_6$)-alkyl, (C$_1$-C$_6$)-alkyl which is substituted by a hydroxy substituent and a substituent $R^{25}$—O—, (C$_1$-C$_6$)-alkyl which is substituted by a hydroxy substituent and two identical or different substituents $R^{25}$—O—, (C$_1$-C$_6$)-alkyl which is substituted by two hydroxy substituents and a substituent $R^{25}$—O—, and (C$_1$-C$_6$)-alkyl which is substituted by one or two identical or different substituents $R^{25}$—O—, for example hydroxymethyl, 2-hydroxyethyl, 3-hydroxypropyl, 2,3-dihydroxypropyl, 2,3-dihydroxybutyl, 2,3,4-trihydroxybutyl, 2,3,4,5,6-pentahydroxyhexyl, 2-hydroxy-1-hydroxymethylethyl, 2-methoxyethyl, 2-ethoxyethyl, 2-hydroxy-3-methoxypropyl, 2-hydroxy-3-isopropoxypropyl, 2,3-dimethoxypropyl, 2-hydroxy-3-(carboxymethoxy)propyl, 2-hydroxy-3-(2-carboxyethoxy)propyl, 2-hydroxy-3-(carboxypropoxy)propyl, 2-hydroxy-3-(4-carboxybutoxy)propyl, 2,3,dihydroxy-4-methoxybutyl. Other examples of groups, from any one or more of which $R^{23}$ can be chosen in one embodiment of the invention, are alkyl groups substituted by one or more, for example by 1, 2 or 3, or by 1 or 2, or by 1, substituents chosen from hydroxy and $R^{25}$—O—, and additionally by one or more, for example by 1 or 2, or by 1, optionally substituted nitrogen substituents chosen from amino, $R^{25}$—NH—, $R^{25}$—N($R^{25}$)—, $R^{25}$—C(O)—NH—, $R^{25}$—S(O)$_2$—NH—, $R^{25}$—NH—S(O)$_2$—NH— and residues of rings $R^{24}$ which are bonded via a ring nitrogen atom, including groups such (C$_1$-C$_6$)-alkyl which is substituted by a hydroxy substituent and a said nitrogen substituent, (C$_1$-C$_6$)-alkyl which is substituted by two hydroxy substituents and a said nitrogen substituent, (C$_1$-C$_6$)-alkyl which is substituted by a hydroxy substituent, a substituent $R^{25}$—O— and a said nitrogen substituent, and (C$_1$-C$_6$)-alkyl which is substituted by a substituent $R^{25}$—O— and a said nitrogen substituent, for example 3-amino-2-hydroxypropyl, 3-methylamino-2-hydroxypropyl, 3-isopropylamino-2-hydroxypropyl, 3-cyclopropylamino-2-hydroxypropyl, 3-dimethylamino-2-hydroxypropyl, 3-(azetidin-1-yl)-2-hydroxypropyl, 2-hydroxy-3-(pyrrolidin-1-yl)propyl, 2-hydroxy-3-(piperidin-1-yl)propyl, 2-hydroxy-3-(morpholin-4-yl)propyl, 3-acetylamino-2-hydroxypropyl, 3-(2-hydroxyacetyl)amino-2-hydroxypropyl, 3-(2-aminoacetyl)amino-2-hydroxypropyl, 3-(2-carboxyacetyl)amino-2-hydroxypropyl, 3-(carboxymethylamino)-2-hydroxypropyl, 3-(2-carboxyethylamino)-2-hydroxypropyl, 3-(3-carboxypropylamino)-2-hydroxypropyl, 3-(2-carboxyazetidin-1-yl)-2-hydroxypropyl, 3-(3-carboxyazetidin-1-yl)-2-hydroxypropyl, 3-(2-carboxypyrrolidin-1-yl)-2-hydroxypropyl, 3-(3-carboxypyrrolidin-1-yl)-2-hydroxypropyl, 3-(2-carboxypiperidin-1-yl)-2-hydroxypropyl, 3-(3-carboxypiperidin-1-yl)-2-hydroxypropyl, 3-(4-carboxypiperidin-1-yl)-2-hydroxypropyl, 4-amino-2,3-dihydroxybutyl, 4-acetylamino-2,3-dihydroxybutyl, 4-(2-hydroxyacetyl) amino-2,3-dihydroxybutyl, 3-amino-2-methoxypropyl, 3-acetylamino-2-methoxypropyl, 3-(2-hydroxyacetyl) amino-2-methoxypropyl.

In one embodiment of the invention, $R^{24}$ is a residue of a monocyclic ring, in another embodiment a residue of a bicyclic ring. The residue of a ring representing $R^{24}$ can be carbocyclic or heterocyclic. In one embodiment, the residue of a monocyclic ring representing $R^{24}$ is carbocyclic, in another embodiment heterocyclic. In one embodiment, the residue of a bicyclic ring representing $R^{24}$ is carbocyclic, in another embodiment heterocyclic. In one embodiment of the invention, the number of ring heteroatoms within $R^{24}$ is 0, 1, 2 or 3, in another embodiment 0, 1 or 2, in another embodiment 0 or 1, in another embodiment 1, 2, 3 or 4, in another embodiment 1, 2 or 3, in another embodiment 1 or 2, in another embodiment 1, and in another embodiment it is 0. In one embodiment of the invention, the residue of a monocyclic ring representing $R^{24}$ is a tetrazolyl group, for example 1H-tetrazol-5-yl.

In one embodiment, the ring heteroatoms in $R^{24}$ are chosen from N and O, in another embodiment from O and S, in another embodiment they are N, wherein ring nitrogen atoms can carry a hydrogen atom or a substituent, as occurs in saturated or partially saturated heterocycles or 5-membered aromatic heterocycles such as pyrrole, for example, or do not carry a hydrogen atom or a substituent, as occurs in aromatic heterocycles such as pyridine, for example, or as is the case when $R^{24}$ is bonded via a ring nitrogen atom. In general, $R^{24}$ can be bonded via any suitable ring carbon atom and ring nitrogen atom. In case $R^{24}$ is bonded to a heteroatom, in one embodiment $R^{24}$ is bonded via a ring carbon atom. In another embodiment, $R^{24}$ is bonded via a ring carbon atom irrespective of the atom to which $R^{24}$ is bonded. In another embodiment, $R^{24}$ is bonded via a ring nitrogen atom. The residue of a ring representing $R^{24}$ can be unsaturated and in this case contain 1, 2 or 3, or 1 or 2, or 1, double bonds within the ring and be aromatic or non-aromatic, or saturated and in this case contain no double bonds within the ring. In one embodiment of the invention, $R^{24}$ is saturated or aromatic, in another embodiment $R^{24}$ is saturated, in another embodiment $R^{24}$ is aromatic. In one embodiment, $R^{24}$ is a residue of a saturated or non-aromatic unsaturated ring. If $R^{24}$ comprises ring nitrogen atoms which can carry a hydrogen atom or a substituent $R^{26}$, one of such nitrogen atoms or two of such ring nitrogen atoms can carry a substituent $R^{26}$. In one embodiment, the number of optional substituents $R^{27}$ on ring carbon atoms in $R^{24}$ is 1, 2, 3, 4 or 5, in another embodiment 1, 2, 3 or 4, in another embodiment 1, 2 or 3, in another embodiment 1 or 2, in another embodiment 1. $R^{24}$ can be 4-membered, 5-membered, 6-membered or 7-membered. In one embodiment, $R^{24}$ is 4-membered to 6-membered, in another embodiment 5-membered to 6-membered, in another embodiment 4-membered to 5-membered. Among others, the residue of a monocyclic ring representing $R^{24}$ can be a cycloalkyl group, a phenyl group, a residue of an unsaturated, aromatic or non-aromatic heterocyclic group or a residue of a saturated heterocyclic group, and the residue of a bicyclic ring representing $R^{24}$ can be a bicycloalkyl group, a residue of a bicyclic unsaturated, non-aromatic heterocyclic group or a residue of a bicyclic saturated heterocyclic group, which are all optionally substituted as specified with respect to $R^{24}$. As far as applicable, all explanations given above with respect to such groups apply correspondingly to $R^{24}$. Another example of groups which can represent $R^{24}$, are cycloalkenyl groups such as (C$_5$-C$_7$)-cycloalkenyl groups which can be bonded via any ring carbon atom and are optionally substituted as specified with respect to $R^{24}$. In one embodiment, optional substituents on a cycloalkenyl group representing $R^{24}$ are chosen from fluorine and $(C_1-C_4)$-alkyl. In one embodiment, cycloalkenyl groups contain one double bond within the ring which can be present in any position. All explanations given above with respect to cycloalkenyl groups representing $R^3$ apply correspondingly to cycloalkenyl groups representing $R^{24}$. Examples of residues of monocyclic rings, from any one or more of which $R^{24}$ can be chosen in one embodiment of the invention, are azetidin-1-yl, pyrrolidin-1-yl, piperidin-1-yl, piperidin-4-yl, morpholin-4-yl and piperazin-1-yl, which are all optionally substituted as indicated. In one embodiment, $R^{24}$ is chosen from any one or more of the residues azetidin-1-yl, pyrrolidin-1-yl, piperidin-1-yl, morpholin-4-yl and piperazin-1-yl, in another embodiment the residues azetidin-1-yl, piperidin-1-yl, morpholin-4-yl and piperazin-1-yl, in another embodiment the residues azetidin-1-yl, pyrrolidin-1-yl, and piperidin-1-yl, in another embodiment the residues pyrrolidin-1-yl, piperidin-1-yl and morpholin-4-yl, in another embodiment the residues pyrrolidin-1-yl and piperidin-1-yl, which are all optionally substituted as indicated.

In one embodiment of the invention, the number w is chosen from 0 and 1, in another embodiment from 1 and 2, in another embodiment it is 0, in another embodiment it is 1. In one embodiment, a $(C_3-C_7)$-cycloalkyl group present in $R^{25}$ is $(C_3-C_6)$-cycloalkyl, in another embodiment $(C_3-C_5)$-cycloalkyl, in another embodiment $(C_5-C_7)$-cycloalkyl, in another embodiment $(C_5-C_6)$-cycloalkyl. In one embodiment, $R^{25}$ is chosen from $(C_1-C_6)$-alkyl and $(C_3-C_7)$-cycloalkyl-$C_wH_{2w}$—, in another embodiment from $(C_1-C_6)$-alkyl, in another embodiment from $(C_1-C_4)$-alkyl, in another embodiment from $(C_1-C_3)$-alkyl, in another embodiment from $(C_1-C_6)$-alkyl, phenyl and Het$^2$, in another embodiment from $(C_3-C_7)$-cycloalkyl-$C_wH_{2w}$—, in another embodiment from phenyl and Het$^2$, in another embodiment from phenyl, in another embodiment from Het$^2$, which all are optionally substituted as indicated. In one embodiment, a group Het$^2$ representing $R^{25}$ is a residue of an aromatic 5-membered monocyclic heterocycle which comprises 1, 2 or 3 identical or different ring heteroatoms chosen from N, O and S, in another embodiment a group Het$^2$ representing $R^{25}$ is chosen from tetrazolyl, for example 1H-tetrazol-5-yl, triazolyl, for example 4H-[1,2,4]-triazolyl including 4H-[1,2,4]-triazol-3-yl, furanyl, thienyl, pyrrolyl and pyridinyl, for example pyridin-4-yl, pyridin-3-yl or pyridin-2-yl, in another embodiment a group Het$^2$ representing $R^{25}$ is chosen from tetrazolyl, for example 1H-tetrazol-5-yl and triazolyl, for example 4H-[1,2,4]-triazolyl including 4H[1,2,4]-triazol-3-yl, wherein all groups Het$^2$ representing $R^{25}$ are optionally substituted on one or more ring carbon atoms as indicated and/or one of the ring nitrogen atoms in the groups Het$^2$ can carry a hydrogen atom or a $(C_1-C_4)$-alkyl substituent.

In one embodiment, the number of optional substituents on the groups $(C_1-C_6)$-alkyl and $(C_3-C_7)$-cycloalkyl-$C_wH_{2w}$— representing $R^{25}$ is 1, 2, 3 or 4, in another embodiment 1, 2 or 3, in another embodiment 1 or 2, in another embodiment 1. In another embodiment, the groups $(C_1-C_6)$-alkyl and $(C_3-C_7)$-cycloalkyl-$C_wH_{2w}$— representing $R^{25}$ are unsubstituted. In one embodiment, the number of optional substituents on ring carbon atoms of the groups phenyl and Het$^2$ present in $R^{25}$, is 1, 2, 3 or 4, in another embodiment 1, 2 or 3, in another embodiment 1 or 2, in another embodiment 1. In another embodiment, the groups phenyl and Het$^2$ present in $R^{25}$ are unsubstituted. In one embodiment, the substituents in $(C_1-C_6)$-alkyl and $(C_3-C_7)$-cycloalkyl-$C_wH_{2w}$— groups representing $R^{25}$ are chosen from hydroxy, $(C_1-C_4)$-alkyl-$S(O)_m$—, $(C_1-C_4)$-alkylsulfonylamino, amino, $(C_1-C_4)$-alkylamino, di(($C_1-C_4$)-alkyl)amino, cyano, hydroxycarbonyl, $(C_1-C_4)$-alkyloxycarbonyl, aminosulfonyl, $(C_1-C_4)$-alkylaminosulfonyl, di(($C_1-C_4$)-alkyl)aminosulfonyl, phenyl, Het$^2$ and Het$^3$, in another embodiment from hydroxy, cyano, hydroxycarbonyl, $(C_1-C_4)$-alkyloxycarbonyl, aminosulfonyl, phenyl, Het$^2$ and Het$^3$, in another embodiment from hydroxy, $(C_1-C_4)$-alkyl-$S(O)_m$—, $(C_1-C_4)$-alkylsulfonylamino, $(C_1-C_4)$-alkyloxy, amino, $(C_1-C_4)$-alkylamino, di(($C_1-C_4$)-alkyl)amino, cyano, aminosulfonyl, $(C_1-C_4)$-alkylaminosulfonyl, di(($C_1-C_4$)-alkyl)aminosulfonyl, phenyl, Het$^2$ and Het$^3$, in another embodiment from hydroxy, $(C_1-C_4)$-alkyl-$S(O)_m$—, $(C_1-C_4)$-alkylsulfonylamino, $(C_1-C_4)$-alkyloxy, amino, $(C_1-C_4)$-alkylamino, di(($C_1-C_4$)-alkyl)amino, cyano, hydroxycarbonyl, $(C_1-C_4)$-alkyloxycarbonyl, aminosulfonyl, $(C_1-C_4)$-alkylaminosulfonyl, di(($C_1-C_4$)-alkyl)aminosulfonyl, phenyl, morpholin-4-yl, furyl and pyridyl, in another embodiment from hydroxy, $(C_1-C_4)$-alkyloxy, amino, $(C_1-C_4)$-alkylamino and di(($C_1-C_4$)-alkyl)amino, in another embodiment from hydroxy, amino, $(C_1-C_4)$-alkylamino and di(($C_1-C_4$)-alkyl)amino, in another embodiment from hydroxy and amino, in another embodiment from hydroxy, $(C_1-C_4)$-alkyloxy, di(($C_1-C_4$)-alkyl)amino, hydroxycarbonyl and $(C_1-C_4)$-alkyloxycarbonyl, in another embodiment from hydroxy, $(C_1-C_4)$-alkyloxy, hydroxycarbonyl and $(C_1-C_4)$-alkyloxycarbonyl, in another embodiment from hydroxy, hydroxycarbonyl and $(C_1-C_4)$-alkyloxycarbonyl, wherein all substituents phenyl, Het$^2$ and Het$^3$ are optionally substituted as indicated. In one embodiment, an individual carbon atom in the groups $(C_1-C_6)$-alkyl and $(C_3-C_7)$-cycloalkyl-$C_wH_{2w}$— representing $R^{25}$ does not carry more than one substituent chosen from hydroxy, $(C_1-C_4)$-alkyl-$S(O)_m$—, $(C_1-C_4)$-alkylsulfonylamino, $(C_1-C_4)$-alkyloxy, amino, $(C_1-C_4)$-alkylamino, di(($C_1-C_4$)-alkyl)amino, aminosulfonyl, $(C_1-C_4)$-alkylaminosulfonyl, di(($C_1-C_4$)-alkyl)aminosulfonyl, and heterocycles bonded via ring nitrogen atom, in another embodiment not more than one substituent chosen from hydroxy, $(C_1-C_4)$-alkyloxy, amino, $(C_1-C_4)$-alkylamino and di(($C_1-C_4$)-alkyl)amino. In one embodiment, the substituents in the groups phenyl and Het$^2$ present in $R^{25}$ are chosen from halogen, $(C_1-C_4)$-alkyl, $(C_3-C_7)$-cycloalkyl-$C_wH_{2w}$—, $(C_1-C_4)$-alkyloxy and cyano, in another embodiment from halogen, $(C_1-C_4)$-alkyl, $(C_3-C_7)$-cycloalkyl-$C_wH_{2w}$—, hydroxy and $(C_1-C_4)$-alkyloxy, in another embodiment from halogen, $(C_1-C_4)$-alkyl, $(C_3-C_7)$-cycloalkyl, hydroxy, $(C_1-C_4)$-alkyloxy and cyano, in another embodiment from halogen, $(C_1-C_4)$-alkyl, $(C_3-C_7)$-cycloalkyl, in another embodiment from halogen, $(C_1-C_4)$-alkyl, $(C_3-C_7)$-cycloalkyl, in another embodiment from $(C_1-C_4)$-alkyl and $(C_3-C_7)$-cycloalkyl, in another embodiment from halogen and $(C_1-C_4)$-alkyl, wherein the number w is as indicated. In one embodiment, a $(C_3-C_7)$-cycloalkyl group in a substituent on a phenyl or Het$^2$ group present in $R^{25}$ is a $(C_3-C_6)$-cycloalkyl, in another embodiment $(C_3-C_5)$-cycloalkyl, in another embodiment $(C_3-C_4)$-cycloalkyl, in another embodiment it is cyclopropyl.

In one embodiment of the invention, the number x is chosen from 0 and 1, in another embodiment it is 0, in another embodiment it is 1. In one embodiment, a $(C_3-C_7)$-cycloalkyl group present in $R^{26}$ is $(C_3-C_6)$-cycloalkyl, in another embodiment $(C_3-C_5)$-cycloalkyl, in another embodiment $(C_5-C_7)$-cycloalkyl, in another embodiment $(C_5-C_6)$-cycloalkyl, in another embodiment it is cyclopropyl. In one embodiment, $R^{26}$ is chosen from $(C_1-C_4)$-alkyl, in another embodiment from $(C_1-C_3)$-alkyl, which all are optionally substituted as indicated. In one embodiment, the number of substituents on the groups $(C_1-C_4)$-alkyl and $(C_3-C_7)$-cycloalkyl-$C_xH_{2x}$— representing $R^{26}$ is 1, 2, 3 or 4, in another embodiment 1, 2 or 3, in another embodiment 1 or 2, in another embodiment 1. In another embodiment, the said groups are unsubstituted. In one embodiment, the substituents in $R^{26}$ are chosen from hydroxy, hydroxycarbonyl and $(C_1-C_4)$-alkyloxycarbonyl, in another embodiment from hydroxycarbonyl and $(C_1-C_4)$-alkyloxycarbonyl. In one embodiment, an individual carbon atom in the groups $(C_1-C_4)$-alkyl and $(C_3-C_7)$-cycloalkyl-$C_xH_{2x}$— representing $R^{26}$ does not carry more than one substituent chosen from hydroxy and $(C_1-C_4)$-alkyloxy.

In one embodiment of the invention, $R^{27}$ is chosen from halogen, $(C_1-C_4)$-alkyl, hydroxy-$C_yH_{2y}$—, $(C_1-C_4)$-alkyloxy, hydroxycarbonyl-$C_yH_{2y}$—, $(C_1-C_4)$-alkyloxycarbonyl-$C_yH_{2y}$— and aminocarbonyl-$C_yH_{2y}$—, in another embodiment from halogen, $(C_1-C_4)$-alkyl, hydroxy, $(C_1-C_4)$-alkyloxy, hydroxycarbonyl-$C_yH_{2y}$—, $(C_1-C_4)$-alkyloxycarbonyl-$C_yH_{2y}$— and aminocarbonyl-$C_yH_{2y}$—, in another embodiment from fluorine, $(C_1-C_4)$-alkyl, hydroxycarbonyl-$C_yH_{2y}$—, $(C_1-C_4)$-alkyloxycarbonyl-$C_yH_{2y}$— and aminocarbonyl-$C_yH_{2y}$—, in another embodiment from fluorine, $(C_1-C_4)$-alkyl, hydroxy-$C_yH_{2y}$—, hydroxycarbonyl-$C_yH_{2y}$— and $(C_1-C_4)$-alkyloxycarbonyl-$C_yH_{2y}$—, in another embodiment from fluorine, $(C_1-C_4)$-alkyl, hydroxycarbonyl-$C_yH_{2y}$— and $(C_1-C_4)$-alkyloxycarbonyl-$C_yH_{2y}$—, in another embodiment from $(C_1-C_4)$-alkyl and hydroxycarbonyl-$C_yH_{2y}$—, in another embodiment from $(C_1-C_4)$-alkyl. In case the residue of a monocyclic ring representing $R^{24}$ contains any oxo groups as substituents $R^{27}$, in one embodiment not more than two such oxo substituents are present, and in another embodiment not more than one such oxo substituent is present. In one embodiment, the numbers y are independently of each other chosen from 0, 1, 2 and 3, in another embodiment from 0, 1 and 2, in another embodiment from 0 and 1, in another embodiment from 1 and 2, and in another embodiment y is 0, and in another embodiment y is 1.

In one embodiment of the invention $R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—C(O), $R^{24}$, $R^{24}$—O— and $R^{24}$—C(O)—; and $R^{23}$ is $(C_1-C_6)$-alkyl which is optionally substituted by one or more identical or different substituents chosen from hydroxy, $R^{25}$—S(O)$_m$—, amino, hydroxycarbonyl, $R^{25}$—O—C(O)—, aminocarbonyl, $R^{24}$, $R^{24}$C(O)—, $R^{25}$—O— and $R^{25}$—C(O)—; and $R^{24}$ is a residue of a saturated or unsaturated, 4-membered to 7-membered, monocyclic or bicyclic ring which comprises 0, 1 or 2 identical or different ring heteroatoms chosen from O and S, wherein one of the ring sulfur atoms can carry one or two oxo groups, and wherein the residue of a ring is optionally substituted on one or more ring carbon atoms by identical or different substituents $R^{27}$; and $R^{25}$ is chosen from $(C_1-C_6)$-alkyl, $(C_3-C_7)$-cycloalkyl-$C_wH_{2w}$— and phenyl, wherein the alkyl and cycloalkyl are optionally substituted by one or more identical or different substituents chosen from hydroxy, $(C_1-C_4)$-alkyl-S(O)$_m$—, $(C_1-C_4)$-alkylsulfonylamino, $(C_1-C_4)$-alkyloxy, amino, $(C_1-C_4)$-alkylamino, di($(C_1-C_4)$-alkyl)amino, hydroxycarbonyl, $(C_1-C_4)$-alkyloxycarbonyl, aminosulfonyl, $(C_1-C_4)$-alkylaminosulfonyl, di($(C_1-C_4)$-alkyl)aminosulfonyl, phenyl, Het² and Het³, and wherein all phenyl in $R^{25}$ are optionally substituted on one or more ring carbon atoms by identical or different substituents chosen from halogen, $(C_1-C_4)$-alkyl, hydroxy, $(C_1-C_4)$-alkyloxy and cyano, and wherein w is chosen from 0, 1 and 2; and $R^{27}$ is chosen from halogen, $(C_1-C_4)$-alkyl, hydroxy-$C_yH_{2y}$—, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4.

In one embodiment of the invention $R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—; and $R^{23}$ is $(C_1-C_6)$-alkyl which is optionally substituted by one or more identical or different substituents chosen from hydroxy, $R^{25}$—S(O)$_m$—, amino, aminocarbonyl, $R^{24}$, $R^{24}$—NH—, $R^{24}$—C(O)—, $R^{25}$—O—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—; and $R^{24}$ is a residue of a saturated or unsaturated, 4-membered to 7-membered, monocyclic or bicyclic ring which comprises 0, 1, 2 or 3 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$; and $R^{25}$ is chosen from $(C_1-C_6)$-alkyl, $(C_3-C_7)$-cycloalkyl-$C_wH_{2w}$—, phenyl and Het², wherein the alkyl and cycloalkyl are optionally substituted by one or more identical or different substituents chosen from hydroxy, $(C_1-C_4)$-alkyl-S(O)$_m$—, $(C_1-C_4)$-alkylsulfonylamino, $(C_1-C_4)$-alkyloxy, amino, $(C_1-C_4)$-alkylamino, di($(C_1-C_4)$-alkyl)amino, aminosulfonyl, $(C_1-C_4)$-alkylaminosulfonyl, di($(C_1-C_4)$-alkyl)aminosulfonyl, phenyl, Het² and Het³, and wherein all phenyl and Het² in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, hydroxy, $(C_1-C_4)$-alkyloxy and cyano, and wherein the numbers w are independently of each other chosen from 0, 1 and 2; and $R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from hydroxy, $(C_1-C_4)$-alkyloxy, and wherein x is chosen from 0, 1 and 2; and $R^{27}$ is chosen from halogen, $(C_1-C_4)$-alkyl, hydroxy, $(C_1-C_4)$-alkyloxy, oxo, cyano, and aminocarbonyl-$C_yH_{2y}$—, wherein the numbers y are independently of each other chosen from 0, 1, 2, 3 and 4.

In one embodiment of the invention $R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—; and $R^{23}$ is $(C_1-C_6)$-alkyl which is optionally substituted by one or more identical or different substituents chosen from hydroxy, $R^{25}$—S(O)$_m$—, amino, aminocarbonyl, $R^{24}$, $R^{24}$—NH—, $R^{24}$—C(O)—, $R^{25}$—O—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—; and $R^{24}$ is a residue of a saturated or unsaturated, 4-membered to 7-membered, monocyclic or bicyclic ring which comprises 0, 1, 2 or 3 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$; and $R^{25}$ is chosen from $(C_1-C_6)$-alkyl, $(C_3-C_7)$-cycloalkyl-$C_wH_{2w}$— and phenyl, wherein the alkyl and cycloalkyl are optionally substituted by one or more identical or different substituents chosen from hydroxy, $(C_1-C_4)$-alkyl-$S(O)_m$—, $(C_1-C_4)$-alkylsulfonylamino, $(C_1-C_4)$-alkyloxy, amino, $(C_1-C_4)$-alkylamino, di$((C_1-C_4)$-alkyl)amino, aminosulfonyl, $(C_1-C_4)$-alkylaminosulfonyl, di$((C_1-C_4)$-alkyl)aminosulfonyl, phenyl and Het³, and wherein all phenyl in $R^{25}$ are optionally substituted on one or more ring carbon atoms by identical or different substituents chosen from halogen, $(C_1-C_4)$-alkyl, hydroxy, $(C_1-C_4)$-alkyloxy and cyano, and wherein w is chosen from 0, 1 and 2; and $R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from hydroxy, $(C_1-C_4)$-alkyloxy, and wherein x is chosen from 0, 1 and 2; and $R^{27}$ is chosen from halogen, $(C_1-C_4)$-alkyl, hydroxy, $(C_1-C_4)$-alkyloxy, oxo, cyano and aminocarbonyl-$C_yH_{2y}$—, wherein the numbers y are independently of each other chosen from 0, 1, 2, 3 and 4.

In one embodiment of the invention $R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N$(R^{23})$—, $R^{23}$—C(O)—NH—, $R^{23}$—$S(O)_2$—NH—, $R^{23}$—C(O)—, $R^{23}$—NH—C(O)—, $R^{23}$—N$(R^{23})$—C(O)—, $R^{23}$—NH—$S(O)_2$—, $R^{24}$, $R^{24}$—O— and $R^{24}$—C(O)—; and $R^{23}$ is $(C_1-C_6)$-alkyl which is optionally substituted by one or more identical or different substituents chosen from hydroxy, $R^{25}$—$S(O)_m$—, hydroxycarbonyl, $R^{25}$—O—C(O)—, $R^{24}$, $R^{24}$—NH—, $R^{24}$—C(O)—, $R^{25}$—O—, $R^{25}$—NH—, $R^{25}$—N$(R^{25})$—, $R^{25}$—C(O)—, $R^{25}$—C(O)—NH—, $R^{25}$—$S(O)_2$—NH—, $R^{25}$—NH—$S(O)_2$—NH—, $R^{25}$—NH—C(O)— and $R^{25}$—N$(R^{25})$—C(O)—; and $R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$; and $R^{25}$ is chosen from $(C_1-C_6)$-alkyl, $(C_3-C_7)$-cycloalkyl-$C_wH_{2w}$—, phenyl and Het², wherein the alkyl and cycloalkyl are optionally substituted by one or more identical or different substituents chosen from hydroxy, $(C_1-C_4)$-alkyloxy, $(C_1-C_4)$-alkyl-$S(O)_m$—, $(C_1-C_4)$-alkylsulfonylamino, cyano, hydroxycarbonyl and $(C_1-C_4)$-alkyloxycarbonyl, aminosulfonyl, $(C_1-C_4)$-alkylaminosulfonyl, di$((C_1-C_4)$-alkyl)aminosulfonyl, phenyl and Het², and wherein all phenyl and Het² in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, hydroxy, $(C_1-C_4)$-alkyloxy and cyano, and wherein the numbers w are independently of each other chosen from 0, 1 and 2; and $R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from hydroxy, $(C_1-C_4)$-alkyloxy, hydroxycarbonyl and $(C_1-C_4)$-alkyloxycarbonyl, and wherein x is chosen from 0, 1 and 2; and $R^{27}$ is chosen from halogen, $(C_1-C_4)$-alkyl, hydroxy-$C_yH_{2y}$—, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4.

In one embodiment of the invention $R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N$(R^{23})$—, $R^{23}$—C(O)—NH—, $R^{23}$—$S(O)_2$—NH—, $R^{23}$—C(O)—, $R^{23}$—NH—C(O)—, $R^{23}$—N$(R^{23})$—C(O)—, $R^{23}$—NH—$S(O)_2$—, $R^{24}$, $R^{24}$—O— and $R^{24}$—C(O)—; and $R^{23}$ is $(C_1-C_6)$-alkyl which is optionally substituted by one or more identical or different substituents chosen from $R^{25}$—$S(O)_m$—, amino, hydroxycarbonyl, $R^{25}$—O—C(O)—, aminocarbonyl, $R^{24}$, $R^{24}$—NH—, $R^{24}$—C(O)—, $R^{25}$—NH—, $R^{25}$—N$(R^{25})$—, $R^{25}$—C(O)—, $R^{25}$—C(O)—NH—, $R^{25}$—$S(O)_2$—NH—, $R^{25}$—NH—$S(O)_2$—NH—, $R^{25}$—NH—C(O)— and $R^{25}$—N$(R^{25})$—C(O)—; and $R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$; and $R^{25}$ is chosen from $(C_1-C_6)$-alkyl, $(C_3-C_7)$-cycloalkyl-$C_wH_{2w}$—, phenyl and Het², wherein the alkyl and cycloalkyl are optionally substituted by one or more identical or different substituents chosen from $(C_1-C_4)$-alkyloxy, $(C_1-C_4)$-alkyl-S$(O)_m$—, $(C_1-C_4)$-alkylsulfonylamino, amino, $(C_1-C_4)$-alkylamino, di$((C_1-C_4)$-alkyl)amino, cyano, hydroxycarbonyl and $(C_1-C_4)$-alkyloxycarbonyl, aminosulfonyl, $(C_1-C_4)$-alkylaminosulfonyl, di$((C_1-C_4)$-alkyl)aminosulfonyl, phenyl, Het$^2$ and Het$^3$, and wherein all phenyl and Het$^2$ in R$^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, hydroxy, $(C_1-C_4)$-alkyloxy and cyano, and wherein the numbers w are independently of each other chosen from 0, 1 and 2; and R$^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from $(C_1-C_4)$-alkyloxy, hydroxycarbonyl and $(C_1-C_4)$-alkyloxycarbonyl, and wherein x is chosen from 0, 1 and 2; and R$^{27}$ is chosen from halogen, $(C_1-C_4)$-alkyl, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4.

In one embodiment of the invention R$^{22}$ is chosen from halogen, hydroxy, amino, cyano, hydroxycarbonyl, $(C_1-C_4)$-alkyloxycarbonyl, R$^{23}$, R$^{23}$—O—, R$^{23}$—NH—, R$^{23}$—N(R$^{23}$)—, R$^{23}$—C(O)—NH—, R$^{23}$—S(O)$_2$—NH—, R$^{23}$—C(O)—, R$^{23}$—NH—C(O)—, R$^{23}$—N(R$^{23}$)—C(O)—, R$^{23}$—NH—S(O)$_2$—, R$^{24}$, R$^{24}$—O— and R$^{24}$—C(O)—; and R$^{23}$ is $(C_1-C_6)$-alkyl which is optionally substituted by one or more identical or different substituents chosen from hydroxy, R$^{25}$—S(O)$_m$—, R$^{24}$, R$^{24}$—NH—, R$^{24}$—C(O)—, R$^{25}$—O—, R$^{25}$—NH—, R$^{25}$—N(R$^{25}$)—, R$^{25}$—C(O)—, R$^{25}$—C(O)—NH—, R$^{25}$—S(O)$_2$—NH—, R$^{25}$—NH—S(O)$_2$—NH—, R$^{25}$—NH—C(O)— and R$^{25}$—N(R$^{25}$)—C(O)—; and R$^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent R$^{26}$ and one of the ring sulfur atoms can carry one or two oxo groups, and wherein the residue of a ring is optionally substituted on one or more ring carbon atoms by identical or different substituents R$^{27}$; and R$^{25}$ is chosen from $(C_1-C_6)$-alkyl, $(C_3-C_7)$-cycloalkyl-$C_wH_{2w}$—, phenyl and Het$^2$, wherein the alkyl and cycloalkyl are optionally substituted by one or more identical or different substituents chosen from hydroxy, $(C_1-C_4)$-alkyl-S$(O)_m$—, $(C_1-C_4)$-alkylsulfonylamino, $(C_1-C_4)$-alkyloxy, cyano, aminosulfonyl, $(C_1-C_4)$-alkylaminosulfonyl, di$((C_1-C_4)$-alkyl)aminosulfonyl, phenyl, Het$^2$ and Het$^3$, and wherein all phenyl and Het$^2$ in R$^{25}$ are optionally substituted on one or more ring carbon atoms by identical or different substituents chosen from halogen, $(C_1-C_4)$-alkyl, hydroxy, $(C_1-C_4)$-alkyloxy and cyano, and wherein the numbers w are independently of each other chosen from 0, 1 and 2; and R$^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from hydroxy, $(C_1-C_4)$-alkyloxy, and wherein x is chosen from 0, 1 and 2; and R$^{27}$ is chosen from halogen, $(C_1-C_4)$-alkyl, hydroxy-$C_yH_{2y}$—, $(C_1-C_4)$-alkyloxy, oxo, cyano and aminocarbonyl-$C_yH_{2y}$—, wherein the numbers y are independently of each other chosen from 0, 1, 2, 3 and 4.

In one embodiment of the invention R$^{22}$ is chosen from halogen, hydroxy, amino, cyano, hydroxycarbonyl, $(C_1-C_4)$-alkyloxycarbonyl, R$^{23}$, R$^{23}$—O—, R$^{23}$—NH—, R$^{23}$—N(R$^{23}$)—, R$^{23}$—C(O)—NH—, R$^{23}$—S(O)$_2$—NH—, R$^{23}$—C(O)—, R$^{23}$—NH—C(O)—, R$^{23}$—N(R$^{23}$)—C(O)—, R$^{23}$—NH—S(O)$_2$—, R$^{24}$, R$^{24}$—O— and R$^{24}$—C(O)—; and R$^{23}$ is $(C_1-C_6)$-alkyl which is optionally substituted by one or more identical or different substituents chosen from R$^{25}$—S(O)$_m$—, R$^{24}$, R$^{24}$—C(O)—, R$^{24}$—NH—, R$^{25}$—O—, R$^{25}$—NH—, R$^{25}$—N(R$^{25}$)—, R$^{25}$—C(O)—, R$^{25}$—C(O)—NH—, R$^{25}$—S(O)$_2$—NH—, R$^{25}$—NH—S(O)$_2$—NH—, R$^{25}$—NH—C(O)— and R$^{25}$—N(R$^{25}$)—C(O)—; and R$^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent R$^{26}$ and one of the ring sulfur atoms can carry one or two oxo groups, and wherein the residue of a ring is optionally substituted on one or more ring carbon atoms by identical or different substituents R$^{27}$; and R$^{25}$ is chosen from $(C_1-C_4)$-alkyl, $(C_3-C_7)$-cycloalkyl-$C_wH_{2w}$—, phenyl and Het$^2$, wherein the alkyl and cycloalkyl are optionally substituted by one or more identical or different $(C_1-C_4)$-alkyloxy, $C_1-C_4)$-alkyl-S$(O)_m$—, $(C_1-C_4)$-alkylsulfonylamino, aminosulfonyl, $(C_1-C_4)$-alkylaminosulfonyl, di$((C_1-C_4)$-alkyl)aminosulfonyl, cyano, phenyl and Het$^2$, and wherein all phenyl and Het$^2$ in R$^{25}$ are optionally substituted on one or more ring carbon atoms by identical or different substituents chosen from halogen, $(C_1-C_4)$-alkyl, $(C_1-C_4)$-alkyloxy and cyano, and wherein w is chosen from 0, 1 and 2; and $R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different $(C_1-C_4)$-alkyloxy and wherein x is chosen from 0, 1 and 2; and $R^{27}$ is chosen from halogen, $(C_1-C_4)$-alkyl, $(C_1-C_4)$-alkyloxy, oxo, cyano, and aminocarbonyl-$C_yH_{2y}$—, wherein the number y is chosen from 0, 1, 2, 3 and 4.

In one embodiment of the invention $R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N$(R^{23})$—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—; and $R^{23}$ is $(C_1-C_6)$-alkyl which is optionally substituted by one or more identical or different substituents chosen from $R^{25}$—S(O)$_m$—, $R^{24}$, $R^{24}$—C(O)—, $R^{24}$—NH—, $R^{25}$—O—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—; and $R^{24}$ is a residue of a saturated or unsaturated, 4-membered to 7-membered, monocyclic or bicyclic ring which comprises 0, 1, 2 or 3 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$; and $R^{25}$ is chosen from $(C_1-C_4)$-alkyl, $(C_3-C_7)$-cycloalkyl-$C_wH_{2w}$— and phenyl, wherein the alkyl and cycloalkyl are optionally substituted by one or more identical or different substituents chosen from $(C_1-C_4)$-alkyloxy, $C_1-C_4$)-alkyl-S(O)$_m$—, $(C_1-C_4)$-alkylsulfonylamino, cyano, aminosulfonyl, $(C_1-C_4)$-alkylaminosulfonyl, di($(C_1-C_4)$-alkyl)aminosulfonyl and phenyl, and wherein all phenyl in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, $(C_1-C_4)$-alkyloxy and cyano, and wherein the numbers w are independently of each other chosen from 0, 1 and 2; and $R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different $(C_1-C_4)$-alkyloxy, and wherein x is chosen from 0, 1 and 2; and $R^{27}$ is chosen from halogen, $(C_1-C_4)$-alkyl, $(C_1-C_4)$-alkyloxy, oxo, cyano and aminocarbonyl-$C_yH_{2y}$—, wherein the number y is chosen from 0, 1, 2, 3 and 4.

In one embodiment of the invention $R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N$(R^{23})$—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—; and $R^{23}$ is $(C_1-C_6)$-alkyl which is optionally substituted by one or more identical or different substituents chosen from $R^{25}$—S(O)$_m$—, amino, aminocarbonyl, $R^{24}$, $R^{24}$—NH—, $R^{24}$—C(O)—, $R^{25}$—O—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—; and $R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$; and $R^{25}$ is chosen from $(C_1-C_4)$-alkyl, $(C_3-C_7)$-cycloalkyl-$C_wH_{2w}$—, phenyl and Het$^2$, wherein the alkyl and cycloalkyl are optionally substituted by one or more identical or different substituents chosen from $(C_1-C_4)$-alkyloxy, $(C_1-C_4)$-alkyl-S(O)$_m$—, amino, $(C_1-C_4)$-alkylamino, di($(C_1-C_4)$-alkyl)amino, aminosulfonyl, $(C_1-C_4)$-alkylaminosulfonyl, di($(C_1-C_4)$-alkyl)aminosulfonyl, phenyl, Het$^2$ and Het$^3$, and wherein all phenyl and Het$^2$ in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, hydroxy, $(C_1-C_4)$-alkyloxy and cyano, and wherein the numbers w are independently of each other chosen from 0, 1 and 2; and $R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from $(C_1-C_4)$-alkyloxy, and wherein x is chosen from 0, 1 and 2; and $R^{27}$ is chosen from halogen, $(C_1-C_4)$-alkyl, $(C_1-C_4)$-alkyloxy, oxo, cyano, and aminocarbonyl-$C_yH_{2y}$—, wherein the number y is chosen from 0, 1, 2, 3 and 4.

In one embodiment of the invention $R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N$(R^{23})$—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—; and $R^{23}$ is $(C_1-C_6)$-alkyl which is optionally substituted by one or more identical or different substituents chosen $R^{25}$—S(O)$_m$—, amino, aminocarbonyl, $R^{24}$, $R^{24}$—NH—, $R^{24}$—C(O)—, $R^{25}$—O—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—; and $R^{24}$ is a residue of a saturated or unsaturated, 4-membered to 7-membered, monocyclic or bicyclic ring which comprises 0, 1, 2 or 3 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$; and $R^{25}$ is chosen from $(C_1-C_4)$-alkyl, $(C_3-C_7)$-cycloalkyl-$C_wH_{2w}$— and phenyl, wherein the alkyl and cycloalkyl are optionally substituted by one or more identical or different substituents chosen from $(C_1-C_4)$-alkyloxy, $(C_1-C_4)$-alkyl-S(O)$_m$—, $(C_1-C_4)$-alkylsulfonylamino, amino, $(C_1-C_4)$-alkylamino, di($(C_1-C_4)$-alkyl)amino, cyano, aminosulfonyl, $(C_1-C_4)$-alkylaminosulfonyl, di($(C_1-C_4)$-alkyl)aminosulfonyl, phenyl and Het$^3$, and wherein all phenyl in $R^{25}$ are optionally substituted on one or more ring carbon atoms by identical or different substituents chosen from halogen, $(C_1-C_4)$-alkyl, hydroxy, $(C_1-C_4)$-alkyloxy and cyano, and wherein w is chosen from 0, 1 and 2; and $R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different $(C_1-C_4)$-alkyloxy, and wherein x is chosen from 0, 1 and 2; and $R^{27}$ is chosen from halogen, $(C_1-C_4)$-alkyl, $(C_1-C_4)$-alkyloxy, oxo, cyano, and aminocarbonyl-$C_yH_{2y}$—, wherein the number y is chosen from 0, 1, 2, 3 and 4.

In one embodiment of the invention $R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—; and $R^{23}$ is $(C_1-C_6)$-alkyl which is optionally substituted by one or more identical or different substituents chosen from $R^{25}$—S(O)$_m$—, hydroxycarbonyl, $R^{25}$—O—C(O)—, aminocarbonyl, $R^{24}$, $R^{24}$—NH—, $R^{24}$—C(O)—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—; and $R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$; and $R^{25}$ is chosen from $(C_1-C_4)$-alkyl, $(C_3-C_7)$-cycloalkyl-$C_wH_{2w}$—, phenyl and Het$^2$, wherein the alkyl and cycloalkyl are optionally substituted by one or more identical or different substituents chosen from $(C_1-C_4)$-alkyloxy, $(C_1-C_4)$-alkyl-S(O)$_m$—, $(C_1-C_4)$-alkylsulfonylamino, cyano, hydroxycarbonyl and $(C_1-C_4)$-alkyloxycarbonyl, aminosulfonyl, $(C_1-C_4)$-alkylaminosulfonyl, di($(C_1-C_4)$-alkyl)aminosulfonyl, phenyl and Het$^2$, and wherein all phenyl and Het$^2$ in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, $(C_1-C_4)$-alkyloxy and cyano, and wherein the numbers w are independently of each other chosen from 0, 1 and 2; and $R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from $(C_1-C_4)$-alkyloxy, hydroxycarbonyl and $(C_1-C_4)$-alkyloxycarbonyl, and wherein x is chosen from 0, 1 and 2; and $R^{27}$ is chosen from halogen, $(C_1-C_4)$-alkyl, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4.

In one embodiment of the invention $R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—; and $R^{23}$ is $(C_1-C_6)$-alkyl which is optionally substituted by one or more identical or different substituents chosen from $R^{25}$—S(O)$_m$—, hydroxycarbonyl, $R^{25}$—O—C(O)—, $R^{24}$, $R^{24}$—C(O)—, $R^{25}$—O—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—; and $R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$; and $R^{25}$ is chosen from $(C_1-C_4)$-alkyl, $(C_3-C_7)$-cycloalkyl-$C_wH_{2w}$—, phenyl and Het$^2$, wherein the alkyl and cycloalkyl are optionally substituted by one or more identical or different substituents chosen from $(C_1-C_4)$-alkyloxy, $(C_1-C_4)$-alkyl-S(O)$_m$—, $(C_1-C_4)$-alkylsulfonylamino, cyano, hydroxycarbonyl and $(C_1-C_4)$-alkyloxycarbonyl, aminosulfonyl, $(C_1-C_4)$-alkylaminosulfonyl, di($(C_1-C_4)$-alkyl)aminosulfonyl, phenyl and Het$^2$, and wherein all phenyl and Het$^2$ in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, $(C_1-C_4)$-alkyloxy and cyano, and wherein the numbers w are independently of each other chosen from 0, 1 and 2; and $R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from $(C_1-C_4)$-alkyloxy, hydroxycarbonyl and $(C_1-C_4)$-alkyloxycarbonyl, and wherein x is chosen from 0, 1 and 2; and $R^{27}$ is chosen from halogen, $(C_1-C_4)$-alkyl, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4.

In one embodiment of the invention, $R^{31}$ is chosen from $(C_1-C_4)$-alkyl, phenyl-$C_qH_{2q}$—, $(C_1-C_4)$-alkylsulfonyl and $(C_1-C_4)$-alkylcarbonyl, in another embodiment from $(C_1-C_4)$-alkyl, phenyl-$C_qH_{2q}$—, and $(C_1-C_4)$-alkylcarbonyl, in another embodiment from $(C_1-C_4)$-alkyl, phenyl-$C_qH_{2q}$— and $(C_1-C_4)$-alkylsulfonyl, in another embodiment from $(C_1-C_4)$-alkyl, $(C_1-C_4)$-alkylsulfonyl and $(C_1-C_4)$-alkylcarbonyl, in another embodiment from $(C_1-C_4)$-alkyl and $(C_1-C_4)$-alkylcarbonyl, in another embodiment from $(C_1-C_4)$-alkyl and phenyl-$C_qH_{2q}$—, in another embodiment from $(C_1-C_4)$-alkyl and $(C_1-C_4)$-alkylsulfonyl, in another embodiment from $(C_1-C_4)$-alkyl, wherein phenyl is optionally substituted as indicated and q is defined as indicated. In one embodiment, the number of substituents which are optionally present on a phenyl group present in $R^{31}$, independently of any other group, is 1, 2, 3 or 4, in another embodiment 1, 2 or 3, in another embodiment 1 or 2, in another embodiment 1, and in another embodiment a phenyl group presenting $R^{31}$ is unsubstituted. In one embodiment, the optional substituents on a phenyl group present in $R^{31}$ are, independently of any other phenyl group present in $R^{31}$, chosen from halogen, $(C_1-C_4)$-alkyl and $(C_1-C_4)$-alkyloxy, in another embodiment from halogen and $(C_1-C_4)$-alkyl. In one embodiment, the number q is chosen from 1 and 2, in another embodiment it is 1, wherein all numbers q are independent of each other.

In one embodiment of the invention, $R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminocarbonyl, $(C_1-C_4)$-alkylaminocarbonyl, di($(C_1-C_4)$-alkyl)aminocarbonyl, aminosulfonyl, $(C_1-C_4)$-alkylaminosulfonyl, di($(C_1-C_4)$-alkyl)aminosulfonyl, phenyl-$C_rH_{2r}$— and Het$^2$-$C_rH_{2r}$—, in another embodiment from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl aminosulfonyl, $(C_1-C_4)$-alkylaminosulfonyl, di($(C_1-C_4)$-alkyl)aminosulfonyl, phenyl-$C_rH_{2r}$— and Het$^2$-$C_rH_{2r}$—, in another embodiment from halogen, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, oxo, $(C_1\text{-}C_4)$-alkyl-$S(O)_m$—, amino, $(C_1\text{-}C_4)$-alkylamino, di$((C_1\text{-}C_4)$-alkyl)amino, $(C_1\text{-}C_4)$-alkylcarbonylamino, $(C_1\text{-}C_4)$-alkylsulfonylamino, cyano, $(C_1\text{-}C_4)$-alkylcarbonyl, aminosulfonyl, phenyl-$C_rH_{2r}$— and $\text{Het}^2\text{-}C_rH_{2r}$—, in another embodiment from halogen, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, oxo, $(C_1\text{-}C_4)$-alkyl-$S(O)_m$—, amino, $(C_1\text{-}C_4)$-alkylamino, di$((C_1\text{-}C_4)$-alkyl)amino, $(C_1\text{-}C_4)$-alkylcarbonylamino, $(C_1\text{-}C_4)$-alkylsulfonylamino, cyano and $(C_1\text{-}C_4)$-alkylcarbonyl, in another embodiment from halogen, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, oxo, $(C_1\text{-}C_4)$-alkyl-$S(O)_m$—, amino, $(C_1\text{-}C_4)$-alkylamino, di$((C_1\text{-}C_4)$-alkyl)amino, $(C_1\text{-}C_4)$-alkylcarbonyl, hydroxycarbonyl, $R^{34}$—O—C(O)—, phenyl-$C_rH_{2r}$— and $\text{Het}^2\text{-}C_rH_{2r}$—, in another embodiment from halogen, $(C_1\text{-}C_4)$-alkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, oxo, $(C_1\text{-}C_4)$-alkyl-$S(O)_m$—, $(C_1\text{-}C_4)$-alkylcarbonyl, hydroxycarbonyl, $R^{34}$—O—C(O)—, phenyl-$C_rH_{2r}$— and $\text{Het}^2\text{-}C_rH_{2r}$—, in another embodiment from halogen, $(C_1\text{-}C_4)$-alkyl, hydroxy-$(C_1\text{-}C_4)$-alkyl, $(C_1\text{-}C_4)$-alkyloxy-$(C_1\text{-}C_4)$-alkyl, $(C_1\text{-}C_4)$-alkyloxy, oxo, hydroxycarbonyl, $R^{34}$—O—C(O)—, phenyl-$C_rH_{2r}$— and $\text{Het}^2\text{-}C_rH_{2r}$—, in another embodiment from halogen, $(C_1\text{-}C_4)$-alkyl, hydroxy-$(C_1\text{-}C_4)$-alkyl, $(C_1\text{-}C_4)$-alkyloxy-$(C_1\text{-}C_4)$-alkyl, $(C_1\text{-}C_4)$-alkyloxy, oxo, hydroxycarbonyl and $R^{34}$—O—C(O)—, in another embodiment from halogen, $(C_1\text{-}C_4)$-alkyl, hydroxy and $(C_1\text{-}C_4)$-alkyloxy, in another embodiment from halogen, $(C_1\text{-}C_4)$-alkyl and $(C_1\text{-}C_4)$-alkyloxy, wherein in all these embodiment the phenyl and $\text{Het}^2$ are optionally substituted as indicated and the number r is defined as indicated.

In one embodiment, the optional substituents $R^{32}$ on an aromatic group representing $R^3$, for example a phenyl group, are chosen from halogen, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, $(C_1\text{-}C_4)$-alkyl-$S(O)_m$—, amino, $(C_1\text{-}C_4)$-alkylamino, di$((C_1\text{-}C_4)$-alkyl)amino, $(C_1\text{-}C_4)$-alkylcarbonylamino, $(C_1\text{-}C_4)$-alkylsulfonylamino, nitro, cyano, $(C_1\text{-}C_4)$-alkylcarbonyl, hydroxycarbonyl, $R^{34}$—O—C(O)—, aminocarbonyl, $(C_1\text{-}C_4)$-alkylaminocarbonyl, di$((C_1\text{-}C_4)$-alkyl)aminocarbonyl, aminosulfonyl, $(C_1\text{-}C_4)$-alkylaminosulfonyl, di$((C_1\text{-}C_4)$-alkyl)aminosulfonyl, phenyl-$C_rH_{2r}$— and $\text{Het}^2\text{-}C_rH_{2r}$—, in another embodiment from halogen, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, $(C_1\text{-}C_4)$-alkyl-$S(O)_m$—, amino, $(C_1\text{-}C_4)$-alkylamino, di$((C_1\text{-}C_4)$-alkyl)amino, $(C_1\text{-}C_4)$-alkylcarbonylamino, $(C_1\text{-}C_4)$-alkylsulfonylamino, nitro, cyano, $(C_1\text{-}C_4)$-alkylcarbonyl, phenyl-$C_rH_{2r}$— and $\text{Het}^2\text{-}C_rH_{2r}$—, in another embodiment from halogen, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, $(C_1\text{-}C_4)$-alkyl-$S(O)_m$—, amino, $(C_1\text{-}C_4)$-alkylamino, di$((C_1\text{-}C_4)$-alkyl)amino, $(C_1\text{-}C_4)$-alkylcarbonylamino, $(C_1\text{-}C_4)$-alkylsulfonylamino, cyano and $(C_1\text{-}C_4)$-alkylcarbonyl, in another embodiment from halogen, $(C_1\text{-}C_4)$-alkyl, hydroxy and $(C_1\text{-}C_4)$-alkyloxy, in another embodiment from halogen, $(C_1\text{-}C_4)$-alkyl and $(C_1\text{-}C_4)$-alkyloxy, in another embodiment from halogen, $(C_1\text{-}C_4)$-alkyl, $(C_3\text{-}C_7)$-cycloalkyl, $(C_1\text{-}C_4)$-alkyloxy-$(C_1\text{-}C_4)$-alkyl, hydroxy, $(C_1\text{-}C_4)$-alkyloxy, $(C_1\text{-}C_4)$-alkyl-$S(O)_m$—, amino, $(C_1\text{-}C_4)$-alkylamino, di$((C_1\text{-}C_4)$-alkyl)amino, cyano, $(C_1\text{-}C_4)$-alkylcarbonyl, hydroxycarbonyl, $R^{34}$—O—C(O)—, aminocarbonyl, $(C_1\text{-}C_4)$-alkylaminocarbonyl, di$((C_1\text{-}C_4)$-alkyl)aminocarbonyl, aminosulfonyl, $(C_1\text{-}C_4)$-alkylaminosulfonyl, di$((C_1\text{-}C_4)$-alkyl)aminosulfonyl, phenyl-$C_rH_{2r}$— and $\text{Het}^2\text{-}C_rH_{2r}$—, in another embodiment from halogen, $(C_1\text{-}C_4)$-alkyl, $(C_3\text{-}C_7)$-cycloalkyl, $(C_1\text{-}C_4)$-alkyloxy-$(C_1\text{-}C_4)$-alkyl, hydroxy, $(C_1\text{-}C_4)$-alkyloxy, $S(O)_m$—, amino, $(C_1\text{-}C_4)$-alkylamino, di$((C_1\text{-}C_4)$-alkyl)amino, cyano, phenyl-$C_rH_{2r}$— and $\text{Het}^2\text{-}C_rH_{2r}$—, wherein in all these embodiment the phenyl and $\text{Het}^2$ are optionally substituted as indicated and the number r is defined as indicated.

In one embodiment, the optional substituents $R^{32}$ on a saturated group representing $R^3$, for example a pyrrolidinyl, piperidinyl or morpholinyl group, are chosen from fluorine, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, oxo, $(C_1\text{-}C_4)$-alkyl-$S(O)_m$—, amino, $(C_1\text{-}C_4)$-alkylamino, di$((C_1\text{-}C_4)$-alkyl)amino, $(C_1\text{-}C_4)$-alkylcarbonylamino, $(C_1\text{-}C_4)$-alkylsulfonylamino, cyano, $(C_1\text{-}C_4)$-alkylcarbonyl, hydroxycarbonyl, $R^{34}$—O—C(O)—, aminocarbonyl, $(C_1\text{-}C_4)$-alkylaminocarbonyl, di$((C_1\text{-}C_4)$-alkyl)aminocarbonyl, aminosulfonyl, $(C_1\text{-}C_4)$-alkylaminosulfonyl, di$((C_1\text{-}C_4)$-alkyl)aminosulfonyl, phenyl-$C_rH_{2r}$— and $\text{Het}^2\text{-}C_rH_{2r}$—, in another embodiment from fluorine, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, alkyloxy, oxo, $(C_1\text{-}C_4)$-alkyl-$S(O)_m$—, amino, $(C_1\text{-}C_4)$-alkylamino, di$((C_1\text{-}C_4)$-alkyl)amino, $(C_1\text{-}C_4)$-alkylcarbonylamino, $(C_1\text{-}C_4)$-alkylsulfonylamino, cyano, $(C_1\text{-}C_4)$-alkylcarbonyl, phenyl-$C_rH_{2r}$— and $\text{Het}^2\text{-}C_rH_{2r}$—, in another embodiment from fluorine, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, oxo, $(C_1\text{-}C_4)$-alkyl-$S(O)_m$—, amino, $(C_1\text{-}C_4)$-alkylamino, di$((C_1\text{-}C_4)$-alkyl)amino, $(C_1\text{-}C_4)$-alkylcarbonylamino, $(C_1\text{-}C_4)$-alkylsulfonylamino, cyano and $(C_1\text{-}C_4)$-alkylcarbonyl, in another embodiment from fluorine, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy and oxo, in another embodiment from fluorine, $(C_1\text{-}C_4)$-alkyl, hydroxy-$(C_1\text{-}C_4)$-alkyl, hydroxy, $(C_1\text{-}C_4)$-alkyloxy and oxo, in another embodiment from fluorine, $(C_1\text{-}C_4)$-alkyl, hydroxy-$(C_1\text{-}C_4)$-alkyl and hydroxy, in another embodiment from fluorine and $(C_1\text{-}C_4)$-alkyl, in another embodiment from fluorine, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, oxo, $(C_1\text{-}C_4)$-alkyl-$S(O)_m$—, amino, $(C_1\text{-}C_4)$-alkylamino, di$((C_1\text{-}C_4)$-alkyl)amino, cyano, $(C_1\text{-}C_4)$-alkylcarbonyl, hydroxycarbonyl, $R^{34}$—O—C(O)—, aminocarbonyl, $(C_1\text{-}C_4)$-alkylaminocarbonyl, di$((C_1\text{-}C_4)$-alkyl)aminocarbonyl, phenyl-$C_rH_{2r}$— and $\text{Het}^2\text{-}C_rH_{2r}$—, in another embodiment from fluorine, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, oxo, amino, $(C_1\text{-}C_4)$-alkylamino, di$((C_1\text{-}C_4)$-alkyl)amino, cyano, $(C_1\text{-}C_4)$-alkylcarbonyl, hydroxycarbonyl, $R^{34}$—O—C(O)—, phenyl-$C_rH_{2r}$— and $\text{Het}^2\text{-}C_rH_{2r}$—, wherein in all these embodiment the phenyl and $\text{Het}^2$ are optionally substituted as indicated and the number r is defined as indicated.

In case the residue of a monocyclic or bicyclic ring representing $R^3$ contains any oxo groups as substituents $R^{32}$, in one embodiment not more than two such oxo substituents are present, and in another embodiment not more than one such oxo substituent is present. In one embodiment, the number of substituents which are optionally present on a phenyl group or group $\text{Het}^2$ present in $R^{32}$, independently of any other group, is 1, 2, 3 or 4, in another embodiment 1, 2 or 3, in another embodiment 1 or 2, in another embodiment 1, and in another embodiment a phenyl group or group $Het^2$ present in $R^{32}$ is unsubstituted. In one embodiment, the optional substituents on a phenyl group or group $Het^2$ present in $R^{32}$, independently of any other group, are chosen from halogen, $(C_1-C_4)$-alkyl, $(C_1-C_4)$-alkyloxy and cyano, in another embodiment from halogen, $(C_1-C_4)$-alkyl and $(C_1-C_4)$-alkyloxy, in another embodiment from halogen and $(C_1-C_4)$-alkyl. In one embodiment, the number r is chosen from 0, 1 and 2, in another embodiment from 0 and 1, in another embodiment from 1, 2 and 3, in another embodiment from 1 and 2, in another embodiment it is 0, in another embodiment it is 1, wherein all numbers r are independent of each other.

In one embodiment of the invention, $R^{33}$ and $R^{34}$ are independently of each other chosen from $(C_1-C_4)$-alkyl and $(C_3-C_7)$-cycloalkyl-$C_sH_{2s}$—, in another embodiment from $(C_1-C_4)$-alkyl and phenyl-$C_tH_{2t}$—, in another embodiment from $(C_1-C_4)$-alkyl, in another embodiment from $(C_1-C_3)$-alkyl. In one embodiment, the number s is chosen from 0 and 1, in another embodiment it is 0, in another embodiment it is 1 or 2, in another embodiment it is 1. In one embodiment, the number t is 1.

In one embodiment of the invention, the ring heteroatoms in $Het^1$ are chosen from N and O, in another embodiment from O and S, in another embodiment they are O atoms. In one embodiment, the number of ring heteroatoms in $Het^1$ is 1. In one embodiment, two ring oxygen atoms in $Het^1$ are not present in adjacent ring positions, in another embodiment two ring heteroatoms chosen from O and S are not present in adjacent ring positions, in another embodiment two ring heteroatoms are not present in adjacent ring positions. Ring nitrogen atoms in $Het^1$ carry a hydrogen atom or a substituent as specified. In one embodiment, optional substituents on ring nitrogen atoms in $Het^1$ are chosen from $(C_1-C_4)$-alkyl, and optional substituents on ring carbon atoms in $Het^1$ are chosen from fluorine and $(C_1-C_4)$-alkyl, in another embodiment optional substituents on ring nitrogen atoms and ring carbon atoms in $Het^1$ are chosen from $(C_1-C_4)$-alkyl. In one embodiment, the number of optional substituents on $Het^1$ is 1, 2, 3, 4 or 5, in another embodiment 1, 2, 3 or 4, in another embodiment 1, 2 or 3, in another embodiment 1 or 2, in another embodiment 1. $Het^1$ can be bonded via any suitable ring-carbon atom. In one embodiment, $Het^1$ is bonded via a ring carbon atom which is not adjacent to a ring heteroatom. $Het^1$ can be 4-membered, 5-membered, 6-membered or 7-membered. In one embodiment, $Het^1$ is 4-membered or 5-membered, in another embodiment 5-membered to 7-membered, in another embodiment 5-membered or 6-membered, in another embodiment 4-membered. Examples of $Het^1$, from any one or more of which $Het^1$ is chosen in one embodiment, are oxetanyl including oxetan-2-yl and oxetan-3-yl, tetrahydrofuranyl including tetrahydrofuran-2-yl and tetrahydrofuran-3-yl, tetrahydropyranyl including tetrahydropyran-2-yl, tetrahydropyran-3-yl and tetrahydropyran-4-yl, oxepanyl including oxepan-2-yl, oxepan-3-yl and oxepan-4-yl, [1,3]clioxolanyl including [1,3]dioxolan-2-yl and [1,3]dioxolan-4-yl, [1,4]dioxanyl including [1,4]dioxan-2-yl, thietanyl including thietan-2-yl and thietan-3-yl, tetrahydrothiophenyl including tetrahydrothiophen-2-yl and tetrahydrothiophen-3-yl, tetrahydrothiopyranyl including tetrahydrothiopyran-2-yl, tetrahydrothiopyran-3-yl and tetrahydrothiopyran-4-yl, [1,4]dithianyl including [1,4]dithian-2-yl, azetidinyl including azetidin-2-yl and azetidin-3-yl, pyrrolidinyl including pyrrolidinyl-2-yl and pyrrolidinyl-3-yl, piperidinyl including piperidinyl-2-yl, piperidinyl-3-yl and piperidinyl-4-yl, azepanyl including azepan-2-yl, azepan-3-yl and azepan-4-yl, oxazolidinyl including oxazolidin-2-yl, oxazolidin-4-yl and oxazolidin-5-yl, thiazolidinyl including thiazolidin-2-yl, thiazolidin-4-yl and thiazolidin-5-yl, morpholinyl including morpholin-2-yl and morpholin-3-yl, thiomorpholinyl including thiomorpholin-2-yl and thiomorpholin-3-yl, which all are optionally substituted as specified with respect to $Het^1$.

In one embodiment of the invention, the ring heteroatoms in $Het^2$ are chosen from N and S, in another embodiment from N and O, in another embodiment they are N atoms, in another embodiment they are S atoms. In one embodiment, the number of ring heteroatoms in $Het^2$ is 1, 2 or 3, in another embodiment 1 or 2, in another embodiment it is 1. $Het^2$ can be bonded via any suitable ring carbon atom. In one embodiment, $Het^2$ is 5-membered, in another embodiment 6-membered. Examples of $Het^2$, from any one or more of which $Het^2$ is chosen in one embodiment, are thiophenyl including thiophen-2-yl and thiophen-3-yl, thiazolyl including thiazol-2-yl, thiazol-4-yl and thiazol-5-yl, triazolyl such as [1,2,4]triazolyl including 4-H-[1,2,4]triazol-3-yl, tetrazolyl including 1H-tetrazol-5-yl, pyridinyl including pyridin-2-yl, pyridin-3-yl and pyridin-4-yl, pyrimidinyl including pyrimidin-2-yl, pyrimidin-4-yl and pyrimidin-5-yl, which all are optionally substituted as specified with respect to $Het^2$. In another embodiment, $Het^2$ is chosen from thiophenyl including thiophen-2-yl and thiophen-3-yl, thiazolyl including thiazol-2-yl, thiazol-4-yl and thiazol-5-yl, tetrazolyl including 1H-tetrazol-5-yl, pyridinyl including pyridin-2-yl, pyridin-3-yl and pyridin-4-yl, pyrimidinyl including pyrimidin-2-yl, pyrimidin-4-yl and pyrimidin-5-yl, in another embodiment from thiophenyl including thiophen-2-yl and thiophen-3-yl, thiazolyl including thiazol-2-yl, thiazol-4-yl and thiazol-5-yl, pyridinyl including pyridin-2-yl, pyridin-3-yl and pyridin-4-yl, pyrimidinyl including pyrimidin-2-yl, pyrimidin-4-yl and pyrimidin-5-yl, which all are optionally substituted as specified with respect to $Het^2$. In another embodiment, $Het^2$ is thiazolyl including thiazol-2-yl, thiazol-4-yl and thiazol-5-yl, which all are optionally substituted as specified with respect to $Het^2$.

In one embodiment of the invention, the ring heteroatoms in $Het^3$ are chosen from N and O, in another embodiment from O and S, in another embodiment they are N atoms. In one embodiment, the number of ring heteroatoms in $Het^3$ is 1. In one embodiment, two ring oxygen atoms in $Het^3$ are not present in adjacent ring positions, in another embodiment two ring heteroatoms chosen from O and S are not present in adjacent ring positions, in another embodiment two ring heteroatoms are not present in adjacent ring positions. Ring nitrogen atoms in $Het^3$ carry a hydrogen atom or a substituent as specified, unless the respective nitrogen atom is the ring atom via which $Het^3$ is bonded. In one embodiment, optional substituents on ring nitrogen atoms in $Het^3$ are chosen from $(C_1-C_4)$-alkyl, and optional substituents on ring carbon atoms in $Het^3$ are chosen from fluorine and $(C_1-C_4)$-alkyl, in another embodiment optional substituents on ring nitrogen atoms and ring carbon atoms in $Het^3$ are chosen from $(C_1-C_4)$-alkyl. In one embodiment, the number of optional substituents on $Het^3$ is 1, 2, 3, 4 or 5, in another embodiment 1, 2, 3 or 4, in another embodiment 1, 2 or 3, in another embodiment 1 or 2, in another embodiment 1. $Het^3$ can be bonded via any suitable ring carbon atom and ring nitrogen atom. In one embodiment, $Het^3$ is bonded via a ring nitrogen atom. In another embodiment, $Het^3$ is bonded via a ring carbon atom. In one embodiment, a group $Het^3$ which is bonded via a ring carbon atom, is bonded via a ring carbon atom which is not adjacent to a ring heteroatom. $Het^3$ can be 4-membered, 5-membered, 6-membered or 7-membered. In one embodiment, $Het^3$ is 4-membered or 5-membered, in another embodiment 5-membered to 7-membered, in another embodiment 5-membered or 6-membered, in another embodiment 4-membered, in another embodiment 5-membered, in another embodiment 6-membered. Examples of Het³, from any one or more of which Het³ is chosen in one embodiment, are oxetanyl including oxetan-2-yl and oxetan-3-yl, tetrahydrofuranyl including tetrahydrofuran-2-yl and tetrahydrofuran-3-yl, tetrahydropyranyl including tetrahydropyran-2-yl, tetrahydropyran-3-yl and tetrahydropyran-4-yl, oxepanyl including oxepan-2-yl, oxepan-3-yl and oxepan-4-yl, [1,3]dioxolanyl including [1,3]dioxolan-2-yl and [1,3]dioxolan-4-yl, [1,4]dioxanyl including [1,4]dioxan-2-yl, thietanyl including thietan-2-yl and thietan-3-yl, tetrahydrothiophenyl including tetrahydrothiophen-2-yl and tetrahydrothiophen-3-yl, tetrahydrothiopyranyl including tetrahydrothiopyran-2-yl, tetrahydrothiopyran-3-yl and tetrahydrothiopyran-4-yl, [1,4]dithianyl including [1,4]dithian-2-yl, azetidinyl including azetidin-1-yl, azetidin-2-yl and azetidin-3-yl, pyrrolidinyl including pyrrolidin-1-yl, pyrrolidinyl-2-yl and pyrrolidinyl-3-yl, piperidinyl including piperidin-1-yl, piperidinyl-2-yl, piperidinyl-3-yl and piperidinyl-4-yl, azepanyl including azepan-1-yl, azepan-2-yl, azepan-3-yl and azepan-4-yl, oxazolidinyl including oxazolidin-2-yl, oxazolidin-3-yl, oxazolidin-4-yl and oxazolidin-5-yl, thiazolidinyl including thiazolidin-2-yl, thiazolidin-3-yl, thiazolidin-4-yl and thiazolidin-5-yl, morpholinyl including morpholin-2-yl, morpholin-3-yl and morpholin-4-yl, thiomorpholinyl including thiomorpholin-2-yl, thiomorpholin-3-yl and thiomorpholin-4-yl, which all are optionally substituted as specified with respect to Het³.

A subject of the invention are all compounds of the formula I wherein any one or more structural elements such as groups, substituents and numbers are defined as in any of the specified embodiments or definitions of the elements or have any one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratio, and their physiologically acceptable salts, and the physiologically acceptable solvates of any of them, are a subject of the present invention.

Likewise, also with respect to all specific compounds disclosed herein, such as the example compounds which represent embodiments of the invention wherein the various groups and numbers in the general definition of the compounds of the formula I have the specific meanings present in the respective specific compound, it applies that they are a subject of the present invention in any of their stereoisomeric forms and or a mixture of stereoisomeric forms in any ratio, and in the form of their physiologically acceptable salts, and in the form of the physiologically acceptable solvates of any of them. Irrespective thereof whether a specific compound is disclosed herein as a free compound and/or as a specific salt, it is a subject of the invention both in the form of the free compound and in the form of all its physiologically acceptable salts, and if a specific salt is disclosed, additionally in the form of this specific salt, and in the form of the physiologically acceptable solvates of any of them. Thus, a subject of the invention also is a compound of the formula I which is chosen from any one or more of the specific compounds of the formula I disclosed herein, including the example compounds specified below, and the physiologically acceptable salts thereof, and the physiologically acceptable solvates of any of them, wherein the compound of the formula I is a subject of the invention in any of its stereoisomeric forms or a mixture of stereoisomeric forms in any ratio, if applicable. As an example mentioned is a compound of the formula I, in any of its stereoisomeric forms, or a mixture of stereoisomeric forms in any ratio, or a physiologically acceptable salt thereof, or a physiologically acceptable solvate of any of them, which is chosen from 2-(3-fluoro-phenyl)-5-morpholin-4-ylmethyl-7-propoxy-oxazolo[5,4-d]pyrimidine,
3-(5-morpholin-4-ylmethyl-7-propoxy-oxazolo[5,4-d]pyrimidin-2-yl)-phenol,
2-(2-chloro-5-fluoro-phenyl)-5-[1,4]oxazepan-4-ylmethyl-7-propoxy-oxazolo[5,4-d]pyrimidine,
2-(2-chloro-pyridin-4-yl)-5-morpholin-4-ylmethyl-7-propoxy-oxazolo[5,4-d]pyrimidine,
5-cyclohexylmethyl-7-propoxy-2-m-tolyl-oxazolo[5,4-d]pyrimidine,
5-(1-phenyl-ethyl)-7-propoxy-2-m-tolyl-oxazolo[5,4-d]pyrimidine,
3-{4-[5-(4-chloro-benzyl)-7-propoxy-oxazolo[5,4-d]pyrimidin-2-yl]-2,6-dimethyl-phenoxy}-propane-1,2-diol,
1-{4-[5-(4-chloro-benzyl)-7-ethoxy-oxazolo[5,4-d]pyrimidin-2-yl]-2,6-dimethyl-phenoxy}-3-diethylamino-propan-2-ol,
1-{4-[5-(4-chloro-benzyl)-7-ethoxy-oxazolo[5,4-d]pyrimidin-2-yl]-2,6-dimethyl-phenoxy}-3-morpholin-4-yl-propan-2-ol,
1-hydroxy-cyclopropanecarboxylic acid (3-{4-[5-(4-chloro-benzyl)-7-ethoxy-oxazolo[5,4-d]pyrimidin-2-yl]-2,6-dimethyl-phenoxy}-2-hydroxy-propyl)-amide,
N-(3-{4-[5-(4-chloro-benzyl)-7-propoxy-oxazolo[5,4-d]pyrimidin-2-yl]-2,6-dimethyl-phenoxy}-2-hydroxy-propyl)-acetamide,
4-{4-[5-(4-chloro-benzyl)-7-propoxy-oxazolo[5,4-d]pyrimidin-2-yl]-2,6-dimethyl-phenoxy}-butyric acid,
(2-{4-[5-(4-chloro-benzyl)-7-propoxy-oxazolo[5,4-d]pyrimidin-2-yl]-2,6-dimethyl-phenoxy}-acetylamino)-acetic acid,
3-(3-{4-[5-(4-chloro-benzyl)-7-propoxy-oxazolo[5,4-d]pyrimidin-2-yl]-2,6-dimethyl-phenoxy}-2-hydroxy-propylamino)-propionic acid,
(S)-1-(2-{4-[5-(4-chloro-benzyl)-7-propoxy-oxazolo[5,4-d]pyrimidin-2-yl]-2,6-dimethyl-phenoxy}-acetyl)-pyrrolidine-2-carboxylic acid,
1-(5-tert-butyl-4H-[1,2,4]triazole-3-sulfonyl)-3-{4-[5-(4-chloro-benzyl)-7-ethoxy-oxazolo[5,4-d]pyrimidin-2-yl]-2,6-dimethyl-phenoxy}-propan-2-ol, and
4-[5-(4-chloro-benzyl)-7-ethoxy-oxazolo[5,4-d]pyrimidin-2-yl]-2-fluoro-phenol.

An example of compounds of the invention which with respect to any structural elements are defined as in specified embodiments of the invention or definitions of such elements, and which are a subject of the invention, are compounds of the formula I, wherein A is —CR⁶R⁷—;
R¹ is chosen from (C₁-C₆)-alkyl and (C₃-C₇)-cycloalkyl-C$_u$H$_{2u}$—, wherein u is chosen from 0, 1, 2 and 3;
R² is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent R²¹, and wherein the phenyl and residue of an aromatic heterocycle are optionally substituted on one or more ring carbon atoms by identical or different substituents R²²;
R³ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and $(C_1-C_4)$-alkyl or together are $(C_2-C_8)$-alkanediyl;

$R^{21}$ is $(C_1-C_4)$-alkyl;

$R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—C(O), $R^{24}$, $R^{24}$—O— and $R^{24}$—C(O)—;

$R^{23}$ is $(C_1-C_6)$-alkyl which is optionally substituted by one or more identical or different substituents chosen from hydroxy, $R^{25}$—S(O)$_m$—, amino, hydroxycarbonyl, $R^{25}$—O—C(O)—, aminocarbonyl, $R^{24}$, $R^{24}$—C(O)—, $R^{25}$—O— and $R^{25}$—C(O)—;

$R^{24}$ is a residue of a saturated or unsaturated, 4-membered to 7-membered, monocyclic or bicyclic ring which comprises 0, 1 or 2 identical or different ring heteroatoms chosen from O and S, wherein one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_6)$-alkyl, $(C_3-C_7)$-cycloalkyl-$C_wH_{2w}$— and phenyl, wherein the alkyl and cycloalkyl are optionally substituted by one or more identical or different substituents chosen from hydroxy, $(C_1-C_4)$-alkyl-S(O)$_m$—, $(C_1-C_4)$-alkylsulfonylamino, $(C_1-C_4)$-alkyloxy, amino, $(C_1-C_4)$-alkylamino, di$((C_1-C_4)$-alkyl)amino, hydroxycarbonyl, $(C_1-C_4)$-alkyloxycarbonyl, aminosulfonyl, $(C_1-C_4)$-alkylaminosulfonyl, di$((C_1-C_4)$-alkyl)aminosulfonyl, phenyl, Het$^2$ and Het$^3$, and wherein all phenyl in $R^{26}$ are optionally substituted on one or more ring carbon atoms by identical or different substituents chosen from halogen, $(C_1-C_4)$-alkyl, hydroxy, $(C_1-C_4)$-alkyloxy and cyano, and wherein w is chosen from 0, 1 and 2;

$R^{27}$ is chosen from halogen, $(C_1-C_4)$-alkyl, hydroxy-$C_yH_{2y}$—, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4;

$R^{31}$ is chosen from $(C_1-C_4)$-alkyl and phenyl-$C_qH_{2q}$—, wherein q is chosen from 1 and 2;

$R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S(O)$_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, phenyl-$C_rH_{2r}$— and Het$^2$-$C_rH_{2r}$—, wherein the numbers r are independently of each other chosen from 0, 1 and 2, and wherein the phenyl and Het$^2$ are optionally substituted on one or more ring carbon atoms by identical or different substituents chosen from halogen, $(C_1-C_4)$-alkyl, hydroxy, $(C_1-C_4)$-alkyloxy and cyano;

Het$^2$ is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1-C_4)$-alkyl substituent;

Het$^3$ is a residue of a saturated, 4-membered to 7-membered, monocyclic heterocycle which comprises 1 or 2 identical or different ring heteroatoms chosen from N, O and S, wherein the residue of a heterocycle is optionally substituted by one or more identical or different substituents chosen from fluorine and $(C_1-C_4)$-alkyl;

m is chosen from 0, 1 and 2, wherein all numbers m are independent of each other.

Another such example are compounds of the formula I, wherein

A is —CR$^6$R$^7$—;

$R^1$ is chosen from $(C_1-C_6)$-alkyl and $(C_3-C_7)$-cycloalkyl-$C_uH_{2u}$—, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and $(C_1-C_4)$-alkyl or together are $(C_2-C_8)$-alkanediyl;

$R^{21}$ is $(C_1-C_4)$-alkyl;

$R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N(R$^{23}$)—, $R^{23}$—C(O)—NH—, $R^{23}$—S(O)$_2$—NH—, $R^{23}$—C(O)—, $R^{23}$—NH—C(O)—, $R^{23}$—N(R$^{23}$)—C(O)—, $R^{23}$—NH—S(O)$_2$—, $R^{24}$, $R^{24}$—O— and $R^{24}$—C(O)—;

$R^{23}$ is $(C_1-C_6)$-alkyl which is optionally substituted by one or more identical or different substituents chosen from hydroxy, $R^{25}$—S(O)$_m$—, amino, aminocarbonyl, $R^{24}$, $R^{24}$—NH—, $R^{24}$—C(O)—, $R^{25}$—O—, $R^{25}$—NH—, $R^{25}$—N(R$^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N(R$^{25}$)—C(O)—;

$R^{24}$ is a residue of a saturated or unsaturated, 4-membered to 7-membered, monocyclic or bicyclic ring which comprises 0, 1, 2 or 3 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$, $R^{25}$ is chosen from $(C_1-C_6)$-alkyl, $(C_3-C_7)$-cycloalkyl-$C_wH_{2w}$—, phenyl and Het$^2$, wherein the alkyl and cycloalkyl are optionally substituted by one or more identical or different substituents chosen from hydroxy, $(C_1-C_4)$-alkyl-S(O)$_m$—, $(C_1-C_4)$-alkylsulfonylamino, $(C_1-C_4)$-alkyloxy, amino, $(C_1-C_4)$-alkylamino, di$((C_1-C_4)$-alkyl)amino, aminosulfonyl, $(C_1-C_4)$-alkylaminosulfonyl, di$((C_1-C_4)$-alkyl)aminosulfonyl, phenyl, Het$^2$ and Het$^3$, and wherein all phenyl and Het$^2$ in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, hydroxy, $(C_1-C_4)$-alkyloxy and cyano, and wherein the numbers w are independently of each other chosen from 0, 1 and 2;

$R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from hydroxy, $(C_1-C_4)$-alkyloxy, and wherein x is chosen from 0, 1 and 2;

$R^{27}$ is chosen from halogen, $(C_1$-$C_4)$-alkyl, hydroxy, $(C_1$-$C_4)$-alkyloxy, oxo, cyano, and aminocarbonyl-$C_yH_{2y}$—, wherein the numbers y are independently of each other chosen from 0, 1, 2, 3 and 4;

$R^{31}$ is chosen from $(C_1$-$C_4)$-alkyl and phenyl-$C_qH_{2q}$—, wherein q is chosen from 1 and 2;

$R^{32}$ is chosen from halogen, $(C_1$-$C_4)$-alkyl, $(C_3$-$C_7)$-cycloalkyl, hydroxy-$(C_1$-$C_4)$-alkyl, $(C_1$-$C_4)$-alkyloxy-$(C_1$-$C_4)$-alkyl, hydroxy, $(C_1$-$C_4)$-alkyloxy, oxo, $(C_1$-$C_4)$-alkyl-$S(O)_m$—, amino, $(C_1$-$C_4)$-alkylamino, di$((C_1$-$C_4)$-alkyl)amino, $(C_1$-$C_4)$-alkylcarbonylamino, $(C_1$-$C_4)$-alkylsulfonylamino, cyano, phenyl-$C_rH_{2r}$— and Het$^2$-$C_rH_{2r}$—, wherein the numbers r are independently of each other chosen from 0, 1 and 2, and wherein the phenyl and Het$^2$ are optionally substituted on one or more ring carbon atoms by identical or different substituents chosen from halogen, $(C_1$-$C_4)$-alkyl, hydroxy, $(C_1$-$C_4)$-alkyloxy and cyano;

Het$^2$ is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1$-$C_4)$-alkyl substituent;

Het$^3$ is a residue of a saturated, 4-membered to 7-membered, monocyclic heterocycle which comprises 1 or 2 identical or different ring heteroatoms chosen from N, O and S, wherein the residue of a heterocycle is optionally substituted by one or more identical or different substituents chosen from fluorine and $(C_1$-$C_4)$-alkyl;

m is chosen from 0, 1 and 2, wherein all numbers m are independent of each other.

Another such example are compounds of the formula I, wherein

A is —CR$^6$R$^7$—;

$R^1$ is chosen from $(C_1$-$C_6)$-alkyl and $(C_3$-$C_7)$-cycloalkyl-$C_uH_{2u}$—, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and $(C_1$-$C_4)$-alkyl or together are $(C_2$-$C_8)$-alkanediyl;

$R^{21}$ is $(C_1$-$C_4)$-alkyl;

$R^{22}$ is chosen from halogen, hydroxy, amino, cyano, hydroxycarbonyl, $(C_1$-$C_4)$-alkyloxycarbonyl, $R^{23}$, $R^{23}$—O—, $R^{23}$—NH—, $R^{23}$—N$(R^{23})$—, $R^{23}$—C(O)—NH—, $R^{23}$—S(O)$_2$—NH—, $R^{23}$—C(O)—, $R^{23}$—NH—C(O)—, $R^{23}$—N$(R^{23})$—C(O)—, $R^{23}$—NH—S(O)$_2$—, $R^{24}$, $R^{24}$—O— and $R^{24}$—C(O)—;

$R^{23}$ is $(C_1$-$C_6)$-alkyl which is optionally substituted by one or more identical or different substituents chosen from hydroxy, $R^{25}$—S(O)$_m$—, amino, aminocarbonyl, $R^{24}$, $R^{24}$—NH—, $R^{24}$—C(O)—, $R^{25}$—O—, $R^{25}$—NH—, $R^{25}$—N$(R^{25})$—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N$(R^{25})$—C(O)—;

$R^{24}$ is a residue of a saturated or unsaturated, 4-membered to 7-membered, monocyclic or bicyclic ring which comprises 0, 1, 2 or 3 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1$-$C_6)$-alkyl, $(C_3$-$C_7)$-cycloalkyl-$C_wH_{2w}$— and phenyl, wherein the alkyl and cycloalkyl are optionally substituted by one or more identical or different substituents chosen from hydroxy, $(C_1$-$C_4)$-alkyl-$S(O)_m$—, $(C_1$-$C_4)$-alkylsulfonylamino, $(C_1$-$C_4)$-alkyloxy, amino, $(C_1$-$C_4)$-alkylamino, di$((C_1$-$C_4)$-alkyl)amino, aminosulfonyl, $(C_1$-$C_4)$-alkylaminosulfonyl, di$((C_1$-$C_4)$-alkyl)aminosulfonyl, phenyl and Het$^3$, and wherein all phenyl in $R^{25}$ are optionally substituted on one or more ring carbon atoms by identical or different substituents chosen from halogen, $(C_1$-$C_4)$-alkyl, hydroxy, $(C_1$-$C_4)$-alkyloxy and cyano, and wherein w is chosen from 0, 1 and 2;

$R^{26}$ is chosen from $(C_1$-$C_4)$-alkyl and $(C_3$-$C_7)$-cycloalkyl-$C_xH_{2x}$—, wherein the alkyl and cycloalkyl are optionally substituted by one or more identical or different substituents chosen from hydroxy, $(C_1$-$C_4)$-alkyloxy, and wherein x is chosen from 0, 1 and 2;

$R^{27}$ is chosen from halogen, $(C_1$-$C_4)$-alkyl, hydroxy, $(C_1$-$C_4)$-alkyloxy, oxo, cyano and aminocarbonyl-$C_yH_{2y}$—, wherein the numbers y are independently of each other chosen from 0, 1, 2, 3 and 4;

$R^{31}$ is chosen from $(C_1$-$C_4)$-alkyl and phenyl-$C_qH_{2q}$—, wherein q is chosen from 1 and 2;

$R^{32}$ is chosen from halogen, $(C_1$-$C_4)$-alkyl, $(C_3$-$C_7)$-cycloalkyl, hydroxy-$(C_1$-$C_4)$-alkyl, $(C_1$-$C_4)$-alkyloxy-$(C_1$-$C_4)$-alkyl, hydroxy, $(C_1$-$C_4)$-alkyloxy, oxo, $(C_1$-$C_4)$-alkyl-$S(O)_m$—, amino, $(C_1$-$C_4)$-alkylamino, di$((C_1$-$C_4)$-alkyl)amino, $(C_1$-$C_4)$-alkylcarbonylamino, $(C_1$-$C_4)$-alkylsulfonylamino, cyano, phenyl-$C_rH_{2r}$— and Het$^2$-$C_rH_{2r}$—, wherein the numbers r are independently of each other chosen from 0, 1 and 2, and wherein the phenyl and Het$^2$ are optionally substituted on one or more ring carbon atoms by identical or different substituents chosen from halogen, $(C_1$-$C_4)$-alkyl, hydroxy, $(C_1$-$C_4)$-alkyloxy and cyano;

Het$^2$ is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1$-$C_4)$-alkyl substituent;

Het$^3$ is a residue of a saturated, 4-membered to 7-membered, monocyclic heterocycle which comprises 1 or 2 identical or different ring heteroatoms chosen from N, O and S, wherein the residue of a heterocycle is optionally substituted by one or more identical or different substituents chosen from fluorine and $(C_1$-$C_4)$-alkyl;

m is chosen from 0, 1 and 2, wherein all numbers m are independent of each other.

Another such example are compounds of the formula I, wherein

A is —CR$^6$R$^7$—;

$R^1$ is chosen from $(C_1$-$C_6)$-alkyl and $(C_3$-$C_7)$-cycloalkyl-$C_uH_{2u}$—, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and $(C_1-C_4)$-alkyl or together are $(C_2-C_8)$-alkanediyl;

$R^{21}$ is $(C_1-C_4)$-alkyl;

$R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—;

$R^{23}$ is $(C_1-C_6)$-alkyl which is optionally substituted by one or more identical or different substituents chosen from hydroxy, $R^{26}$—S(O)$_m$—, hydroxycarbonyl, $R^{25}$—O—C(O)—, $R^{24}$, $R^{24}$—NH—, $R^{24}$—C(O)—, $R^{25}$—O—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—;

$R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_6)$-alkyl, $(C_3-C_7)$-cycloalkyl-$C_wH_{2w}$—, phenyl and Het$^2$, wherein the alkyl and cycloalkyl are optionally substituted by one or more identical or different substituents chosen from hydroxy, $(C_1-C_4)$-alkyloxy, $(C_1-C_4)$-alkyl-S(O)$_m$—, $(C_1-C_4)$-alkylsulfonylamino, cyano, hydroxycarbonyl and $(C_1-C_4)$-alkyloxycarbonyl, aminosulfonyl, $(C_1-C_4)$-alkylaminosulfonyl, di(($C_1-C_4$)-alkyl)aminosulfonyl, phenyl and Het$^2$, and wherein all phenyl and Het$^2$ in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, hydroxy, $(C_1-C_4)$-alkyloxy and cyano, and wherein the numbers w are independently of each other chosen from 0, 1 and 2;

$R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from hydroxy, $(C_1-C_4)$-alkyloxy, hydroxycarbonyl and $(C_1-C_4)$-alkyloxycarbonyl, and wherein x is chosen from 0, 1 and 2;

$R^{27}$ is chosen from halogen, $(C_1-C_4)$-alkyl, hydroxy-$C_yH_{2y}$—, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4;

$R^{31}$ is chosen from $(C_1-C_4)$-alkyl and phenyl-$C_qH_{2q}$—, wherein q is chosen from 1 and 2;

$R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S(O)$_m$—, amino, $(C_1-C_4)$-alkylamino, di(($C_1-C_4$)-alkyl)amino, $(C_1-C_4)$-alkylcarbonylamino, $(C_1-C_4)$-alkylsulfonylamino, cyano, phenyl-$C_rH_{2r}$— and Het$^2$-$C_rH_{2r}$—, wherein the numbers r are independently of each other chosen from 0, 1 and 2, and wherein the phenyl and Het$^2$ are optionally substituted on one or more ring carbon atoms by identical or different substituents chosen from halogen, $(C_1-C_4)$-alkyl, hydroxy, $(C_1-C_4)$-alkyloxy and cyano;

Het$^2$ is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1-C_4)$-alkyl substituent;

m is chosen from 0, 1 and 2, wherein all numbers m are independent of each other.

Another such example are compounds of the formula I, wherein

A is —$CR^6R^7$—;

$R^1$ is chosen from $(C_1-C_6)$-alkyl and $(C_3-C_7)$-cycloalkyl-$C_uH_{2u}$—, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and $(C_1-C_4)$-alkyl or together are $(C_2-C_8)$-alkanediyl;

$R^{21}$ is —$(C_1-C_4)$-alkyl;

$R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—;

$R^{23}$ is $(C_1-C_6)$-alkyl which is optionally substituted by one or more identical or different substituents chosen from hydroxy, $R^{26}$—S(O)$_m$—, hydroxycarbonyl, $R^{26}$—O—C(O)—, $R^{24}$, $R^{24}$—C(O)—, $R^{25}$—O—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—;

$R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_6)$-alkyl, $(C_3-C_7)$-cycloalkyl-$C_wH_{2w}$—, phenyl and Het$^2$, wherein the alkyl and cycloalkyl are optionally substituted by one or more identical or different substituents chosen from hydroxy, $(C_1-C_4)$-alkyloxy, $(C_1-C_4)$-alkyl-S(O)$_m$—, $(C_1-C_4)$-alkylsulfonylamino, hydroxycarbonyl and $(C_1-C_4)$-alkyloxycarbonyl, cyano, aminosulfonyl, $(C_1-C_4)$-alkylaminosulfonyl, di$((C_1-C_4)$-alkyl)aminosulfonyl, phenyl and Het$^2$, and wherein all phenyl and Het$^2$ in R$^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, hydroxy, $(C_1-C_4)$-alkyloxy and cyano, and wherein the numbers w are independently of each other chosen from 0, 1 and 2;

R$^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from hydroxy, $(C_1-C_4)$-alkyloxy, hydroxycarbonyl and $(C_1-C_4)$-alkyloxycarbonyl, and wherein x is chosen from 0, 1 and 2;

R$^{27}$ is chosen from halogen, $(C_1-C_4)$-alkyl, hydroxy-$C_yH_{2y}$—, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4;

R$^{31}$ is chosen from $(C_1-C_4)$-alkyl and phenyl-$C_qH_{2q}$—, wherein q is chosen from 1 and 2;

R$^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S(O)$_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, phenyl-$C_rH_{2r}$— and Het$^2$-$C_rH_{2r}$—, wherein the numbers r are independently of each other chosen from 0, 1 and 2, and wherein the phenyl and Het$^2$ are optionally substituted on one or more ring carbon atoms by identical or different substituents chosen from halogen, $(C_1-C_4)$-alkyl, hydroxy, $(C_1-C_4)$-alkyloxy and cyano;

Het$^2$ is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1-C_4)$-alkyl substituent;

m is chosen from 0, 1 and 2, wherein all numbers m are independent of each other.

Another such example are compounds of the formula I, wherein

A is —CR$^6$R$^7$—;

R$^1$ is chosen from $(C_1-C_6)$-alkyl and $(C_3-C_7)$-cycloalkyl-$C_uH_{2u}$—, wherein u is chosen from 0, 1, 2 and 3;

R$^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent R$^{21}$, and wherein the phenyl and residue of an aromatic heterocycle are optionally substituted on one or more ring carbon atoms by identical or different substituents R$^{22}$;

R$^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent R$^{31}$ and one or two of the ring sulfur atoms can carry one or two oxo groups, and wherein the residue of a ring is optionally substituted on one or more ring carbon atoms by identical or different substituents R$^{32}$;

R$^6$ and R$^7$ are independently of each other chosen from hydrogen, fluorine and $(C_1-C_4)$-alkyl or together are $(C_2-C_8)$-alkanediyl;

R$^{21}$ is $(C_1-C_4)$-alkyl;

R$^{22}$ is chosen from halogen, hydroxy, amino, cyano, hydroxycarbonyl, $(C_1-C_4)$-alkyloxycarbonyl, R$^{23}$, R$^{23}$—O—, R$^{23}$—NH—, R$^{23}$—N(R$^{23}$)—, R$^{23}$—C(O)—NH—, R$^{23}$—S(O)$_2$—NH—, R$^{23}$—C(O)—, R$^{23}$—NH—C(O)—, R$^{23}$—N(R$^{23}$)—C(O)—, R$^{23}$—NH—S(O)$_2$—, R$^{24}$, R$^{24}$—O— and R$^{24}$—C(O)—;

R$^{23}$ is $(C_1-C_6)$-alkyl which is optionally substituted by one or more identical or different substituents chosen from R$^{25}$—S(O)$_m$—, amino, hydroxycarbonyl, R$^{25}$—O—C(O)—, aminocarbonyl, R$^{24}$, R$^{24}$—NH—, R$^{24}$—C(O)—, R$^{25}$—O—, R$^{25}$—NH—, R$^{25}$—N(R$^{25}$)—, R$^{25}$—C(O)—, R$^{25}$—C(O)—NH—, R$^{25}$—S(O)$_2$—NH—, R$^{25}$—NH—S(O)$_2$—NH—, R$^{25}$—NH—C(O)— and R$^{25}$—N(R$^{25}$)—C(O)—;

R$^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent R$^{26}$ and one of the ring sulfur atoms can carry one or two oxo groups, and wherein the residue of a ring is optionally substituted on one or more ring carbon atoms by identical or different substituents R$^{27}$;

R$^{25}$ is chosen from $(C_1-C_6)$-alkyl, $(C_3-C_7)$-cycloalkyl-$C_wH_{2w}$—, phenyl and Het$^2$, wherein the alkyl and cycloalkyl are optionally substituted by one or more identical or different substituents chosen from $(C_1-C_4)$-alkyloxy, $(C_1-C_4)$-alkyl-S(O)$_m$—, $(C_1-C_4)$-alkylsulfonylamino, amino, $(C_1-C_4)$-alkylamino, di$((C_1-C_4)$-alkyl)amino, cyano, hydroxycarbonyl and $(C_1-C_4)$-alkyloxycarbonyl, aminosulfonyl, $(C_1-C_4)$-alkylaminosulfonyl, di$((C_1-C_4)$-alkyl)aminosulfonyl, phenyl, Het$^2$ and Het$^3$, and wherein all phenyl and Het$^2$ in R$^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, hydroxy, $(C_1-C_4)$-alkyloxy and cyano, and wherein the numbers w are independently of each other chosen from 0, 1 and 2;

R$^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from $(C_1-C_4)$-alkyloxy, hydroxycarbonyl and $(C_1-C_4)$-alkyloxycarbonyl, and wherein x is chosen from 0, 1 and 2;

R$^{27}$ is chosen from halogen, $(C_1-C_4)$-alkyl, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4;

R$^{31}$ is chosen from $(C_1-C_4)$-alkyl and phenyl-$C_qH_{2q}$—, wherein q is chosen from 1 and 2;

R$^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S(O)$_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, phenyl-$C_rH_{2r}$— and Het$^2$-$C_rH_{2r}$—, wherein the numbers r are independently of each other chosen from 0, 1 and 2, and wherein the phenyl and Het$^2$ are optionally substituted on one or more ring carbon atoms by identical or different substituents chosen from halogen, $(C_1-C_4)$-alkyl, hydroxy, $(C_1-C_4)$-alkyloxy and cyano;

Het$^2$ is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1-C_4)$-alkyl substituent;

Het$^3$ is a residue of a saturated, 4-membered to 7-membered, monocyclic heterocycle which comprises 1 or 2 identical or different ring heteroatoms chosen from N, O and S, wherein the residue of a heterocycle is optionally substituted by one or more identical or different substituents chosen from fluorine and $(C_1-C_4)$-alkyl;

m is chosen from 0, 1 and 2, wherein all numbers m are independent of each other.

Another such example are compounds of the formula I, wherein

A is $—CR^6R^7—$;

$R^1$ is chosen from $(C_1-C_6)$-alkyl and $(C_3-C_7)$-cycloalkyl-$C_uH_{2u}—$, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and $(C_1-C_4)$-alkyl or together are $(C_2-C_8)$-alkanediyl;

$R^{21}$ is $(C_1-C_4)$-alkyl;

$R^{22}$ is chosen from halogen, hydroxy, amino, cyano, hydroxycarbonyl, $(C_1-C_4)$-alkyloxycarbonyl, $R^{23}$, $R^{23}—O—$, $R^{23}—NH—$, $R^{23}—N(R^{23})—$, $R^{23}—C(O)—NH—$, $R^{23}—S(O)_2—NH—$, $R^{23}—C(O)—$, $R^{23}—NH—C(O)—$, $R^{23}—N(R^{23})—C(O)—$, $R^{23}—NH—S(O)_2—$, $R^{24}$, $R^{24}—O—$ and $R^{24}—C(O)—$;

$R^{23}$ is $(C_1-C_6)$-alkyl which is optionally substituted by one or more identical or different substituents chosen from hydroxy, $R^{25}—S(O)_m—$, $R^{24}$, $R^{24}—NH—$, $R^{24}—C(O)—$, $R^{25}—O—$, $R^{25}—NH—$, $R^{25}—N(R^{25})—$, $R^{25}—C(O)—$, $R^{25}—C(O)—NH—$, $R^{25}—S(O)_2—NH—$, $R^{25}—NH—S(O)_2—NH—$, $R^{25}—NH—C(O)—$ and $R^{25}—N(R^{25})—C(O)—$;

$R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_6)$-alkyl, $(C_3-C_7)$-cycloalkyl-$C_wH_{2w}—$, phenyl and $Het^2$, wherein the alkyl and cycloalkyl are optionally substituted by one or more identical or different substituents chosen from hydroxy, $(C_1-C_4)$-alkyl-$S(O)_m—$, $(C_1-C_4)$-alkylsulfonylamino, $(C_1-C_4)$-alkyloxy, cyano, aminosulfonyl, $(C_1-C_4)$-alkylaminosulfonyl, di$((C_1-C_4)$-alkyl)aminosulfonyl, phenyl, $Het^2$ and $Het^3$, and wherein all phenyl and $Het^2$ in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}—$, hydroxy, $(C_1-C_4)$-alkyloxy and cyano, and wherein the numbers w are independently of each other chosen from 0, 1 and 2;

$R^{26}$ is chosen from $(C_1-C_4)$-alkyl and $(C_3-C_7)$-cycloalkyl-$C_xH_{2x}—$, wherein the alkyl and cycloalkyl are optionally substituted by one or more identical or different substituents chosen from hydroxy, $(C_1-C_4)$-alkyloxy, and wherein x is chosen from 0, 1 and 2;

$R^{27}$ is chosen from halogen, $(C_1-C_4)$-alkyl, hydroxy-$C_yH_{2y}—$, $(C_1-C_4)$-alkyloxy, oxo, cyano and aminocarbonyl-$C_yH_{2y}—$, wherein the numbers y are independently of each other chosen from 0, 1, 2, 3 and 4;

$R^{31}$ is chosen from $(C_1-C_4)$-alkyl and phenyl-$C_qH_{2q}—$, wherein q is chosen from 1 and 2;

$R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-$S(O)_m—$, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, phenyl-$C_rH_{2r}—$ and $Het^2-C_rH_{2r}—$, wherein the numbers r are independently of each other chosen from 0, 1 and 2, and wherein the phenyl and $Het^2$ are optionally substituted on one or more ring carbon atoms by identical or different substituents chosen from halogen, $(C_1-C_4)$-alkyl, hydroxy, $(C_1-C_4)$-alkyloxy and cyano;

$Het^2$ is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1-C_4)$-alkyl substituent;

$Het^3$ is a residue of a saturated, 4-membered to 7-membered, monocyclic heterocycle which comprises 1 or 2 identical or different ring heteroatoms chosen from N, O and S, wherein the residue of a heterocycle is optionally substituted by one or more identical or different substituents chosen from fluorine and $(C_1-C_4)$-alkyl;

m is chosen from 0, 1 and 2, wherein all numbers m are independent of each other.

Another such example are compounds of the formula I, wherein

A is $—CR^6R^7—$;

$R^1$ is chosen from $(C_1-C_6)$-alkyl and $(C_3-C_7)$-cycloalkyl-$C_uH_{2u}—$, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and $(C_1-C_4)$-alkyl or together are $(C_2-C_8)$-alkanediyl;

$R^{21}$ is $(C_1-C_4)$-alkyl;

$R^{22}$ is chosen from halogen, hydroxy, amino, cyano, hydroxycarbonyl, $(C_1-C_4)$-alkyloxycarbonyl, $R^{23}$, $R^{23}—O—$, $R^{23}—NH—$, $R^{23}—N(R^{23})—$, $R^{23}—C(O)—NH—$, $R^{23}—S(O)_2—NH—$, $R^{23}—C(O)—$, $R^{23}—NH—C(O)—$, $R^{23}—N(R^{23})—C(O)—$, $R^{23}—NH—S(O)_2—$, $R^{24}$, $R^{24}—O—$ and $R^{24}—C(O)—$;

$R^{23}$ is $(C_1-C_6)$-alkyl which is optionally substituted by one or more identical or different substituents chosen from hydroxy, $R^{25}$—S(O)$_m$—, $R^{24}$, $R^{24}$—NH—, $R^{24}$—C(O)—, $R^{25}$—O—,
$R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{26}$—N($R^{25}$)—C(O)—;

$R^{24}$ is a residue of a saturated or unsaturated, 4-membered to 7-membered, monocyclic or bicyclic ring which comprises 0, 1, 2 or 3 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_6)$-alkyl, $(C_3-C_7)$-cycloalkyl-$C_wH_{2w}$—, phenyl, wherein the alkyl and cycloalkyl are optionally substituted by one or more identical or different substituents chosen from hydroxy, $(C_1-C_4)$-alkyl-S(O)$_m$—, $(C_1-C_4)$-alkylsulfonylamino, $(C_1-C_4)$-alkyloxy, aminosulfonyl, cyano, $(C_1-C_4)$-alkylaminosulfonyl, di($(C_1-C_4)$-alkyl)aminosulfonyl and phenyl, and wherein all phenyl in $R^{25}$ are optionally substituted on one or more ring carbon atoms by identical or different substituents chosen from halogen, $(C_1-C_4)$-alkyl, hydroxy, $(C_1-C_4)$-alkyloxy and cyano, and wherein w is chosen from 0, 1 and 2;

$R^{26}$ is chosen from $(C_1-C_4)$-alkyl and $(C_3-C_7)$-cycloalkyl-$C_xH_{2x}$— and, wherein the alkyl and cycloalkyl are optionally substituted by one or more identical or different substituents chosen from hydroxy, $(C_1-C_4)$-alkyloxy, and wherein x is chosen from 0, 1 and 2;

$R^{27}$ is chosen from halogen, $(C_1-C_4)$-alkyl, hydroxy-$C_yH_{2y}$—, $(C_1-C_4)$-alkyloxy, oxo, cyano and aminocarbonyl-$C_yH_{2y}$—, wherein the numbers y are independently of each other chosen from 0, 1, 2, 3 and 4;

$R^{31}$ is chosen from $(C_1-C_4)$-alkyl and phenyl-$C_qH_{2q}$—, wherein q is chosen from 1 and 2;

$R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, cyano, phenyl-$C_rH_{2r}$— and Het$^2$-$C_rH_{2r}$—, wherein the numbers r are independently of each other chosen from 0, 1 and 2, and wherein the phenyl and Het$^2$ are optionally substituted on one or more ring carbon atoms by identical or different substituents chosen from halogen, $(C_1-C_4)$-alkyl, hydroxy, $(C_1-C_4)$-alkyloxy and cyano;

Het$^2$ is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1-C_4)$-alkyl substituent;

m is chosen from 0, 1 and 2, wherein all numbers m are independent of each other.

Another such example are compounds of the formula I, wherein

A is —CR$^6$R$^7$—;

$R^1$ is chosen from $(C_1-C_6)$-alkyl and $(C_3-C_7)$-cycloalkyl-$C_uH_{2u}$—, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and $(C_1-C_4)$-alkyl or together are $(C_2-C_5)$-alkanediyl;

$R^{21}$ is $(C_1-C_4)$-alkyl;

$R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—;

$R^{23}$ is $(C_1-C_6)$-alkyl which is optionally substituted by one or more identical or different substituents chosen from $R^{25}$—S(O)$_m$—, $R^{24}$, $R^{24}$—C(O)—, $R^{24}$—NH—, $R^{25}$—O—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—;

$R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_4)$-alkyl, $(C_3-C_7)$-cycloalkyl-$C_wH_{2w}$—, phenyl and Het$^2$, wherein the alkyl and cycloalkyl are optionally substituted by one or more identical or different $(C_1-C_4)$-alkyloxy, $C_1-C_4)$-alkyl-S(O)$_m$—, $(C_1-C_4)$-alkylsulfonylamino, aminosulfonyl, $(C_1-C_4)$-alkylaminosulfonyl, di($(C_1-C_4)$-alkyl)aminosulfonyl, cyano, phenyl and Het$^2$, and wherein all phenyl and Het$^2$ in $R^{25}$ are optionally substituted on one or more ring carbon atoms by identical or different substituents chosen from halogen, $(C_1-C_4)$-alkyl, $(C_1-C_4)$-alkyloxy and cyano, and wherein w is chosen from 0, 1 and 2;

$R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different $(C_1-C_4)$-alkyloxy and wherein x is chosen from 0, 1 and 2;

$R^{27}$ is chosen from halogen, $(C_1-C_4)$-alkyl, $(C_1-C_4)$-alkyloxy, oxo, cyano, and aminocarbonyl-$C_yH_{2y}$—, wherein the number y is chosen from 0, 1, 2, 3 and 4;

$R^{31}$ is chosen from $(C_1-C_4)$-alkyl and phenyl-$C_qH_{2q}$—, wherein q is chosen from 1 and 2;

$R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, cyano, phenyl-$C_rH_{2r}$— and Het$^2$-$C_rH_{2r}$—, wherein the numbers r are independently of each other chosen from 0, 1 and 2, and wherein the phenyl and Het$^2$ are optionally substituted on one or more ring carbon atoms by identical or different substituents chosen from halogen, $(C_1-C_4)$-alkyl, hydroxy, $(C_1-C_4)$-alkyloxy and cyano;

Het² is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a ($C_1$-$C_4$)-alkyl substituent;

m is chosen from 0, 1 and 2, wherein all numbers m are independent of each other.

Another such example are compounds of the formula I, wherein

A is —$CR^6R^7$—;

$R^1$ is chosen from ($C_1$-$C_6$)-alkyl and ($C_3$-$C_7$)-cycloalkyl-$C_uH_{2u}$—, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and ($C_1$-$C_4$)-alkyl or together are ($C_2$-$C_5$)-alkanediyl;

$R^{21}$ is ($C_1$-$C_4$)-alkyl;

$R^{22}$ is chosen from halogen, hydroxy, amino, cyano, hydroxycarbonyl, ($C_1$-$C_4$)-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—;

$R^{23}$ is ($C_1$-$C_6$)-alkyl which is optionally substituted by one or more identical or different substituents chosen from $R^{25}$—S(O)$_m$—, $R^{24}$, $R^{24}$—C(O)—, $R^{24}$—NH—, $R^{25}$—O—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—;

$R^{24}$ is a residue of a saturated or unsaturated, 4-membered to 7-membered, monocyclic or bicyclic ring which comprises 0, 1, 2 or 3 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from ($C_1$-$C_4$)-alkyl, ($C_3$-$C_7$)-cycloalkyl-$C_wH_{2w}$— and phenyl, wherein the alkyl and cycloalkyl are optionally substituted by one or more identical or different substituents chosen from ($C_1$-$C_4$)-alkyloxy, $C_1$-$C_4$-alkyl-S(O)$_m$—, ($C_1$-$C_4$)-alkylsulfonylamino, cyano, aminosulfonyl, ($C_1$-$C_4$)-alkylaminosulfonyl, di(($C_1$-$C_4$)-alkyl)aminosulfonyl and phenyl, and wherein all phenyl in $R^{25}$ are optionally substituted on one or more ring carbon atoms by identical or different substituents chosen from halogen, ($C_1$-$C_4$)-alkyl, ($C_3$-$C_7$)-cycloalkyl-$C_wH_{2w}$—, ($C_1$-$C_4$)-alkyloxy and cyano, and wherein the numbers w are independently of each other chosen from 0, 1 and 2;

$R^{26}$ is chosen from ($C_1$-$C_4$)-alkyl and ($C_3$-$C_7$)-cycloalkyl-$C_xH_{2x}$—, wherein the alkyl and cycloalkyl are optionally substituted by one or more identical or different ($C_1$-$C_4$)-alkyloxy, and wherein x is chosen from 0, 1 and 2;

$R^{27}$ is chosen from halogen, ($C_1$-$C_4$)-alkyl, ($C_1$-$C_4$)-alkyloxy, oxo, cyano and aminocarbonyl-$C_yH_{2y}$—, wherein the number y is chosen from 0, 1, 2, 3 and 4;

$R^{31}$ is chosen from ($C_1$-$C_4$)-alkyl and phenyl-$C_qH_{2q}$—, wherein q is chosen from 1 and 2;

$R^{32}$ is chosen from halogen, ($C_1$-$C_4$)-alkyl, ($C_3$-$C_7$)-cycloalkyl, hydroxy-($C_1$-$C_4$)-alkyl, ($C_1$-$C_4$)-alkyloxy-($C_1$-$C_4$)-alkyl, hydroxy, ($C_1$-$C_4$)-alkyloxy, oxo, ($C_1$-$C_4$)-alkyl-S(O)$_m$—, amino, ($C_1$-$C_4$)-alkylamino, di(($C_1$-$C_4$)-alkyl)amino, ($C_1$-$C_4$)-alkylcarbonylamino, ($C_1$-$C_4$)-alkylsulfonylamino, cyano, phenyl-$C_rH_{2r}$— and Het²-$C_rH_{2r}$—, wherein the numbers r are independently of each other chosen from 0, 1 and 2, and wherein the phenyl and Het² are optionally substituted on one or more ring carbon atoms by identical or different substituents chosen from halogen, ($C_1$-$C_4$)-alkyl, hydroxy, ($C_1$-$C_4$)-alkyloxy and cyano;

Het² is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a ($C_1$-$C_4$)-alkyl substituent;

m is chosen from 0, 1 and 2, wherein all numbers m are independent of each other.

Another such example are compounds of the formula I, wherein

A is —$CR^6R^7$—;

$R^1$ is chosen from ($C_1$-$C_6$)-alkyl and ($C_3$-$C_7$)-cycloalkyl-$C_uH_{2u}$—, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and ($C_1$-$C_4$)-alkyl or together are ($C_2$-$C_8$)-alkanediyl;

$R^{21}$ is ($C_1$-$C_4$)-alkyl;

$R^{22}$ is chosen from halogen, hydroxy, amino, cyano, hydroxycarbonyl, ($C_1$-$C_4$)-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—;

$R^{23}$ is ($C_1$-$C_6$)-alkyl which is optionally substituted by one or more identical or different substituents chosen from $R^{25}$—S(O)$_m$—, amino, aminocarbonyl, $R^{24}$, $R^{24}$—NH—, $R^{24}$—C(O)—, $R^{25}$—O—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—;

$R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_4)$-alkyl, $(C_3-C_7)$-cycloalkyl-$C_wH_{2w}$—, phenyl and $Het^2$, wherein the alkyl and cycloalkyl are optionally substituted by one or more identical or different substituents chosen from $(C_1-C_4)$-alkyloxy, $(C_1-C_4)$-alkyl-S$(O)_m$—, amino, $(C_1-C_4)$-alkylamino, di$((C_1-C_4)$-alkyl)amino, aminosulfonyl, $(C_1-C_4)$-alkylaminosulfonyl, di$((C_1-C_4)$-alkyl)aminosulfonyl, phenyl, $Het^2$ and $Het^3$, and wherein all phenyl and $Het^2$ in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, hydroxy, $(C_1-C_4)$-alkyloxy and cyano, and wherein the numbers w are independently of each other chosen from 0, 1 and 2;

$R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from $(C_1-C_4)$-alkyloxy, and wherein x is chosen from 0, 1 and 2;

$R^{27}$ is chosen from halogen, $(C_1-C_4)$-alkyl, $(C_1-C_4)$-alkyloxy, oxo, cyano, and aminocarbonyl-$C_yH_{2y}$—, wherein the number y is chosen from 0, 1, 2, 3 and 4;

$R^{31}$ is chosen from $(C_1-C_4)$-alkyl and phenyl-$C_qH_{2q}$—, wherein q is chosen from 1 and 2;

$R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S$(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, phenyl-$C_rH_{2r}$— and $Het^2$-$C_rH_{2r}$—, wherein the numbers r are independently of each other chosen from 0, 1 and 2, and wherein the phenyl and $Het^2$ are optionally substituted on one or more ring carbon atoms by identical or different substituents chosen from halogen, $(C_1-C_4)$-alkyl, hydroxy, $(C_1-C_4)$-alkyloxy and cyano;

$Het^2$ is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1-C_4)$-alkyl substituent;

$Het^3$ is a residue of a saturated, 4-membered to 7-membered, monocyclic heterocycle which comprises 1 or 2 identical or different ring heteroatoms chosen from N, O and S, wherein the residue of a heterocycle is optionally substituted by one or more identical or different substituents chosen from fluorine and $(C_1-C_4)$-alkyl;

m is chosen from 0, 1 and 2, wherein all numbers m are independent of each other.

Another such example are compounds of the formula I, wherein

A is —$CR^6R^7$—;

$R^1$ is chosen from $(C_1-C_6)$-alkyl and $(C_3-C_7)$-cycloalkyl-$C_uH_{2u}$—, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and $(C_1-C_4)$-alkyl or together are $(C_2-C_8)$-alkanediyl;

$R^{21}$ is $(C_1-C_4)$-alkyl;

$R^{22}$ are chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—;

$R^{23}$ is $(C_1-C_6)$-alkyl which is optionally substituted by one or more identical or different substituents chosen $R^{26}$—S$(O)_m$—, amino, aminocarbonyl, $R^{24}$, $R^{24}$—NH—, $R^{24}$—C$(O)$—, $R^{25}$—O—, $R^{25}$—NH—, $R^{25}$—N($R^{25}$)—, $R^{25}$—C$(O)$—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—;

$R^{24}$ is a residue of a saturated or unsaturated, 4-membered to 7-membered, monocyclic or bicyclic ring which comprises 0, 1, 2 or 3 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_4)$-alkyl, $(C_3-C_7)$-cycloalkyl-$C_wH_{2w}$— and phenyl, wherein the alkyl and cycloalkyl are optionally substituted by one or more identical or different substituents chosen from $(C_1-C_4)$-alkyloxy, $(C_1-C_4)$-alkyl-S$(O)_m$—, $(C_1-C_4)$-alkylsulfonylamino, amino, $(C_1-C_4)$-alkylamino, di$((C_1-C_4)$-alkyl)amino, cyano, aminosulfonyl, $(C_1-C_4)$-alkylaminosulfonyl, di$((C_1-C_4)$-alkyl)aminosulfonyl, phenyl and $Het^3$, and wherein all phenyl in $R^{25}$ are optionally substituted on one or more ring carbon atoms by identical or different substituents chosen from halogen, $(C_1-C_4)$-alkyl, hydroxy, $(C_1-C_4)$-alkyloxy and cyano, and wherein w is chosen from 0, 1 and 2;

$R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different $(C_1-C_4)$-alkyloxy, and wherein x is chosen from 0, 1 and 2;

$R^{27}$ is chosen from halogen, $(C_1-C_4)$-alkyl, $(C_1-C_4)$-alkyloxy, oxo, cyano, and aminocarbonyl-$C_yH_{2y}$—, wherein the number y is chosen from 0, 1, 2, 3 and 4;

$R^{31}$ is chosen from $(C_1-C_4)$-alkyl and phenyl-$C_qH_{2q}$—, wherein q is chosen from 1 and 2;

$R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, phenyl-$C_rH_{2r}$— and $Het^2$-$C_rH_{2r}$—, wherein the numbers r are independently of each other chosen from 0, 1 and 2, and wherein the phenyl and $Het^2$ are optionally substituted on one or more ring carbon atoms by identical or different substituents chosen from halogen, $(C_1-C_4)$-alkyl, hydroxy, $(C_1-C_4)$-alkyloxy and cyano;

Het² is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1-C_4)$-alkyl substituent;

Het³ is a residue of a saturated, 4-membered to 7-membered, monocyclic heterocycle which comprises 1 or 2 identical or different ring heteroatoms chosen from N, O and S, wherein the residue of a heterocycle is optionally substituted by one or more identical or different substituents chosen from fluorine and $(C_1-C_4)$-alkyl;

m is chosen from 0, 1 and 2, wherein all numbers m are independent of each other.

Another such example are compounds of the formula I, wherein

A is —$CR^6R^7$—;

$R^1$ is chosen from $(C_1-C_6)$-alkyl and $(C_3-C_7)$-cycloalkyl-$C_uH_{2u}$—, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and $(C_1-C_4)$-alkyl or together are $(C_2-C_8)$-alkanediyl;

$R^{21}$ is $(C_1-C_4)$-alkyl;

$R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, $R^{23}$—S(O)$_2$—NH—, $R^{23}$—C(O)—, $R^{23}$—NH—C(O)—, $R^{23}$—N($R^{23}$)—C(O)—, $R^{23}$—NH—S(O)$_2$—, $R^{24}$, $R^{24}$—O— and $R^{24}$—C(O)—;

$R^{23}$ is $(C_1-C_6)$-alkyl which is optionally substituted by one or more identical or different substituents chosen from $R^{25}$—S(O)$_m$—, hydroxycarbonyl, $R^{25}$—O—C(O)—, aminocarbonyl, $R^{24}$, $R^{24}$—NH—, $R^{24}$—C(O)—, $R^{25}$—NH—, $R^{25}$—N($R^{25}$)—, $R^{25}$—C(O)—, $R^{25}$—C(O)—NH—, $R^{25}$—S(O)$_2$—NH—, $R^{25}$—NH—S(O)$_2$—NH—, $R^{25}$—NH—C(O)— and $R^{25}$—N($R^{25}$)—C(O)—;

$R^{24}$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_4)$-alkyl, $(C_3-C_7)$-cycloalkyl-$C_wH_{2w}$—, phenyl and Het², wherein the alkyl and cycloalkyl are optionally substituted by one or more identical or different substituents chosen from $(C_1-C_4)$-alkyloxy, $(C_1-C_4)$-alkyl-S(O)$_m$—, $(C_1-C_4)$-alkylsulfonylamino, cyano, hydroxycarbonyl and $(C_1-C_4)$-alkyloxycarbonyl, aminosulfonyl, $(C_1-C_4)$-alkylaminosulfonyl, di($(C_1-C_4)$-alkyl)aminosulfonyl, phenyl and Het², and wherein all phenyl and Het² in $R^{25}$ are optionally substituted on one or more ring carbon atoms by identical or different substituents chosen from halogen, $(C_1-C_4)$-alkyl, $(C_3-C_7)$-cycloalkyl-$C_wH_{2w}$—, $(C_1-C_4)$-alkyloxy and cyano, and wherein the numbers w are independently of each other chosen from 0, 1 and 2;

$R^{26}$ is chosen from $(C_1-C_4)$-alkyl and $(C_3-C_7)$-cycloalkyl-$C_wH_{2w}$—, wherein the alkyl and cycloalkyl are optionally substituted by one or more identical or different substituents chosen from $(C_1-C_4)$-alkyloxy, hydroxycarbonyl and $(C_1-C_4)$-alkyloxycarbonyl, and wherein x is chosen from 0, 1 and 2;

$R^{27}$ is chosen from halogen, $(C_1-C_4)$-alkyl, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4;

$R^{31}$ is chosen from $(C_1-C_4)$-alkyl and phenyl-$C_qH_{2q}$—, wherein q is chosen from 1 and 2;

$R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, cyano, phenyl-$C_rH_{2r}$— and Het²-$C_rH_{2r}$—, wherein the numbers r are independently of each other chosen from 0, 1 and 2, and wherein the phenyl and Het² are optionally substituted on one or more ring carbon atoms by identical or different substituents chosen from halogen, $(C_1-C_4)$-alkyl, hydroxy, $(C_1-C_4)$-alkyloxy and cyano;

Het² is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a $(C_1-C_4)$-alkyl substituent;

m is chosen from 0, 1 and 2, wherein all numbers m are independent of each other.

Another such example are compounds of the formula I, wherein

A is —$CR^6R^7$—;

$R^1$ is chosen from $(C_1-C_6)$-alkyl and $(C_3-C_7)$-cycloalkyl-$C_uH_{2u}$—, wherein u is chosen from 0, 1, 2 and 3;

$R^2$ is chosen from phenyl and a residue of an aromatic, 5-membered or 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is a residue of a saturated or unsaturated, 4-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^6$ and $R^7$ are independently of each other chosen from hydrogen, fluorine and $(C_1-C_4)$-alkyl or together are $(C_2-C_8)$-alkanediyl;

$R^{21}$ is $(C_1-C_4)$-alkyl;

$R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N($R^{23}$)—, $R^{23}$—C(O)—NH—, R²³—S(O)₂—NH—, R²³—C(O)—, R²³—NH—C(O)—, R²³—N(R²³)—C(O)—, R²³—NH—S(O)₂—, R²⁴, R²⁴—O— and R²⁴—C(O)—;

R²³ is (C₁-C₆)-alkyl which is optionally substituted by one or more identical or different substituents chosen from R²⁵—S(O)ₘ—, hydroxycarbonyl, R²⁵—O—C(O)—, R²⁴, R²⁴—C(O)—, R²⁵—O—, R²⁵—C(O)—, R²⁵—C(O)—NH—, R²⁵—S(O)₂—NH—, R²⁵—NH—S(O)₂—NH—, R²⁵—NH—C(O)— and R²⁵—N(R²⁵)—C(O)—;

R²⁴ is a residue of a saturated or unsaturated, 4-membered to 7-membered, monocyclic or bicyclic ring which comprises 0, 1, 2, 3 or 4 identical or different ring heteroatoms chosen from N, O and S, wherein one of the ring nitrogen atoms can carry a hydrogen atom or a substituent R²⁶ and one of the ring sulfur atoms can carry one or two oxo groups, and wherein the residue of a ring is optionally substituted on one or more ring carbon atoms by identical or different substituents R²⁷;

R²⁵ is chosen from (C₁-C₄)-alkyl, (C₃-C₇)-cycloalkyl-C_wH_{2w}—, phenyl and Het², wherein the alkyl and cycloalkyl are optionally substituted by one or more identical or different substituents chosen from (C₁-C₄)-alkyloxy, (C₁-C₄)-alkyl-S(O)ₘ—, (C₁-C₄)-alkylsulfonylamino, cyano, hydroxycarbonyl and (C₁-C₄)-alkyloxycarbonyl, aminosulfonyl, (C₁-C₄)-alkylaminosulfonyl, di((C₁-C₄)-alkyl)aminosulfonyl, phenyl and Het², and wherein all phenyl and Het² in R²⁵ are optionally substituted on one or more ring carbon atoms by identical or different substituents chosen from halogen, (C₁-C₄)-alkyl, (C₃-C₇)-cycloalkyl-C_wH_{2w}—, (C₁-C₄)-alkyloxy and cyano, and wherein the numbers w are independently of each other chosen from 0, 1 and 2;

R²⁶ is chosen from (C₁-C₄)-alkyl and (C₃-C₇)-cycloalkyl-C_xH_{2x}—, wherein the alkyl and cycloalkyl are optionally substituted by one or more identical or different substituents chosen from (C₁-C₄)-alkyloxy, hydroxycarbonyl and (C₁-C₄)-alkyloxycarbonyl, and wherein x is chosen from 0, 1 and 2;

R²⁷ is chosen from halogen, (C₁-C₄)-alkyl, (C₁-C₄)-alkyloxy, oxo, cyano, hydroxycarbonyl-C_yH_{2y}—, (C₁-C₄)-alkyloxycarbonyl-C_yH_{2y}— and aminocarbonyl-C_yH_{2y}—, wherein the numbers y are independently of each other chosen from 0, 1, 2, 3 and 4;

R³¹ is chosen from (C₁-C₄)-alkyl and phenyl-C_qH_{2q}—, wherein q is chosen from 1 and 2;

R³² is chosen from halogen, (C₁-C₄)-alkyl, (C₃-C₇)-cycloalkyl, hydroxy-(C₁-C₄)-alkyl, (C₁-C₄)-alkyloxy-(C₁-C₄)-alkyl, hydroxy, (C₁-C₄)-alkyloxy, oxo, (C₁-C₄)-alkyl-S(O)ₘ—, amino, (C₁-C₄)-alkylamino, di((C₁-C₄)-alkyl)amino, (C₁-C₄)-alkylcarbonylamino, (C₁-C₄)-alkylsulfonylamino, cyano, phenyl-C_rH_{2r}— and Het²-C_rH_{2r}—, wherein the numbers r are independently of each other chosen from 0, 1 and 2, and wherein the phenyl and Het² are optionally substituted on one or more ring carbon atoms by identical or different substituents chosen from halogen, (C₁-C₄)-alkyl, hydroxy, (C₁-C₄)-alkyloxy and cyano;

Het² is a residue of an aromatic, 5-membered or 6-membered, monocyclic heterocycle which comprises 1, 2, 3 or 4 identical or different ring heteroatoms chosen from N, O and S, wherein one of the ring nitrogen atoms can carry a hydrogen atom or a (C₁-C₄)-alkyl substituent;

m is chosen from 0, 1 and 2, wherein all numbers m are independent of each other.

With respect to all these examples of compounds defined above, it applies that all other structural elements are defined as in the general definition of the compounds of the formula I or in any embodiment specified herein, or have any one or more of the specific meanings mentioned herein as examples of the structural elements, and that the compounds are a subject of the invention in any of their stereoisomeric forms, or a mixture of stereoisomeric forms in any ratio, and in the form of the physiologically acceptable salts thereof, and in the form of the physiologically acceptable solvates of any of them.

Another such example of compounds of the invention which with respect to any structural elements are defined as in specified embodiments of the invention or definitions of such elements, and which are a subject of the invention, are the compounds of the formulae Ia-1 to Ia-6, Ib-1 to Ib-18, Ic-1 to Ic-18, Id-1 to Id-18, Ie-1 to Ie-18, If-1 to If-18, Ig-1 to Ig-18, Ih-1 to Ih-18, Ik-1 to Ik-18, Im-1 to Im-18, In-1 to In-18, Ip-1 to Ip-18, Iq-1 to Iq-18, Ir-1 to Ir-18, in any of their stereoisomeric forms or a mixture of stereoisomeric forms in any ratio, and their physiologically acceptable salts, and the physiologically acceptable solvates of any of them, which are defined in the following and in which "oxapyr" represents the group of the formula

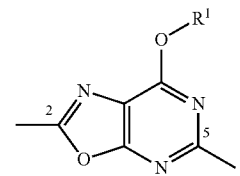

wherein the line starting at the 2-position of the oxazolopyrimidine ring represents the free bond via which the oxazolopyrimidine ring is bonded to the phenyl, furan-2-yl, pyridin-3-yl, pyridin-4-yl, thiophen-2-yl or pyrimidin-5-yl group representing R² in formula I and the line starting at the 5-position of the oxazolopyrimidine ring represents the free bond via which the oxazolopyrimidine ring is bonded to the group A in formula I or the CH₂ group representing A:

| | |
|---|---|
| Ia-1 | phenyl-oxapyr-CH₂-R³ |
| Ia-2 | furan-2-yl-oxapyr-CH₂-R³ |
| Ia-3 | pyridin-3-yl-oxapyr-CH₂-R³ |
| Ia-4 | pyridinyl-4-yl-oxapyr-CH₂-R³ |
| Ia-5 | thiophen-2-yl-oxapyr-CH₂-R³ |
| Ia-6 | pyrimidin-5-yl-oxapyr-CH₂-R³ |
| Ib-1 | R²-oxapyr-CH₂-phenyl |
| Ib-2 | R²-oxapyr-CH₂-morpholin-4-yl |
| Ib-3 | R²-oxapyr-CH₂-piperidin-1-yl |
| Ib-4 | R²-oxapyr-CH₂-[1,4]oxazepan-4-yl |
| Ib-5 | R²-oxapyr-CH₂-[1,2,3]triazol-1-yl |
| Ib-6 | R²-oxapyr-CH₂-[1,2,4]triazol-1-yl |
| Ib-7 | R²-oxapyr-CH₂-thiomorpholin-4-yl |
| Ib-8 | R²-oxapyr-CH₂-imidazol-1-yl |
| Ib-9 | R²-oxapyr-CH₂-2-oxa-5-azabicyclo[2.2.1]hept-5-yl |
| Ib-10 | R²-oxapyr-CH₂-azetidin-1-yl |
| Ib-11 | R²-oxapyr-CH₂-imidazolidin-1-yl |
| Ib-12 | R²-oxapyr-CH₂-piperazin-1-yl |
| Ib-13 | R²-oxapyr-CH₂-pyrazol-1-yl |
| Ib-14 | R²-oxapyr-CH₂-thiazolidin-3-yl |
| Ib-15 | R²-oxapyr-CH₂-pyrrolidin-1-yl |
| Ib-16 | R²-oxapyr-CH₂-pyridin-2-yl |
| Ib-17 | R²-oxapyr-CH₂-pyridin-3-yl |
| Ib-18 | R²-oxapyr-CH₂-pyridin-4-yl |
| Ic-1 | phenyl-oxapyr-A-phenyl |
| Ic-2 | phenyl-oxapyr-A-morpholin-4-yl |
| Ic-3 | phenyl-oxapyr-A-piperidin-1-yl |
| Ic-4 | phenyl-oxapyr-A-[1,4]oxazepan-4-yl |
| Ic-5 | phenyl-oxapyr-A-[1,2,3]triazol-1-yl |
| Ic-6 | phenyl-oxapyr-A-[1,2,4]triazol-1yl |
| Ic-7 | phenyl-oxapyr-A-thiomorpholin-4-yl |
| Ic-8 | phenyl-oxapyr-A-imidazol-1-yl |
| Ic-9 | phenyl-oxapyr-A-2-oxa-5-azabicyclo[2.2.1]hept-5-yl |
| Ic-10 | phenyl-oxapyr-A-azetidin-1-yl |

| | |
|---|---|
| lc-11 | phenyl-oxapyr-A-imidazolidin-1-yl |
| lc-12 | phenyl-oxapyr-A-piperazin-1-yl |
| lc-13 | phenyl-oxapyr-A-pyrazol-1-yl |
| lc-14 | phenyl-oxapyr-A-thiazolidin-3-yl |
| lc-15 | phenyl-oxapyr-A-pyrrolidin-1-yl |
| lc-16 | phenyl-oxapyr-A-pyridin-2-yl |
| lc-17 | phenyl-oxapyr-A-pyridin-3-yl |
| lc-18 | phenyl-oxapyr-A-pyridin-4-yl |
| ld-1 | furan-2-yl-oxapyr-A-phenyl |
| ld-2 | furan-2-yl-oxapyr-A-morpholin-4-yl |
| ld-3 | furan-2-yl-oxapyr-A-piperidin-1-yl |
| ld-4 | furan-2-yl-oxapyr-A-[1,4]oxazepan-4-yl |
| ld-5 | furan-2-yl-oxapyr-A-[1,2,3]triazol-1-yl |
| ld-6 | furan-2-yl-oxapyr-A-[1,2,4]triazol-1-yl |
| ld-7 | furan-2-yl-oxapyr-A-thiomorpholin-4-yl |
| ld-8 | furan-2-yl-oxapyr-A-imidazol-1-yl |
| ld-9 | furan-2-yl-oxapyr-A-2-oxa-5-azabicyclo[2.2.1]hept-5-yl |
| ld-10 | furan-2-yl-oxapyr-A-azetidin-1-yl |
| ld-11 | furan-2-yl-oxapyr-A-imidazolidin-1-yl |
| ld-12 | furan-2-yl-oxapyr-A-piperazin-1-yl |
| ld-13 | furan-2-yl-oxapyr-A-pyrazol-1-yl |
| ld-14 | furan-2-yl-oxapyr-A-thiazolidin-3-yl |
| ld-15 | furan-2-yl-oxapyr-A-pyrrolidin-1-yl |
| ld-16 | furan-2-yl-oxapyr-A-pyridin-2-yl |
| ld-17 | furan-2-yl-oxapyr-A-pyridin-3-yl |
| ld-18 | furan-2-yl-oxapyr-A-pyridin-4-yl |
| le-1 | pyridin-3-yl-oxapyr-A-phenyl |
| le-2 | pyridin-3-yl-oxapyr-A-morpholin-4-yl |
| le-3 | pyridin-3-yl-oxapyr-A-piperidin-1-yl |
| le-4 | pyridin-3-yl-oxapyr-A-[1,4]oxazepan-4-yl |
| le-5 | pyridin-3-yl-oxapyr-A-[1,2,3]triazol-1-yl |
| le-6 | pyridin-3-yl-oxapyr-A-[1,2,4]triazol-1-yl |
| le-7 | pyridin-3-yl-oxapyr-A-thiomorpholin-4-yl |
| le-8 | pyridin-3-yl-oxapyr-A-imidazol-1-yl |
| le-9 | pyridin-3-yl-oxapyr-A-2-oxa-5-azabicyclo[2.2.1]hept-5-yl |
| le-10 | pyridin-3-yl-oxapyr-A-azetidin-1-yl |
| le-11 | pyridin-3-yl-oxapyr-A-imidazolidin-1-yl |
| le-12 | pyridin-3-yl-oxapyr-A-piperazin-1-yl |
| le-13 | pyridin-3-yl-oxapyr-A-pyrazol-1-yl |
| le-14 | pyridin-3-yl-oxapyr-A-thiazolidin-3-yl |
| le-15 | pyridin-3-yl-oxapyr-A-pyrrolidin-1-yl |
| le-16 | pyridin-3-yl-oxapyr-A-pyridin-2-yl |
| le-17 | pyridin-3-yl-oxapyr-A-pyridin-3-yl |
| le-18 | pyridin-3-yl-oxapyr-A-pyridin-4-yl |
| lf-1 | pyridin-4-yl-oxapyr-A-phenyl |
| lf-2 | pyridin-4-yl-oxapyr-A-morpholin-4-yl |
| lf-3 | pyridin-4-yl-oxapyr-A-piperidin-1-yl |
| lf-4 | pyridin-4-yl-oxapyr-A-[1,4]oxazepan-4-yl |
| lf-5 | pyridin-4-yl-oxapyr-A-[1,2,3]triazol-1-yl |
| lf-6 | pyridin-4-yl-oxapyr-A-[1,2,4]triazol-1-yl |
| lf-7 | pyridin-4-yl-oxapyr-A-thiomorpholin-4-yl |
| lf-8 | pyridin-4-yl-oxapyr-A-imidazol-1-yl |
| lf-9 | pyridin-4-yl-oxapyr-A-2-oxa-5-azabicyclo[2.2.1]hept-5-yl |
| lf-10 | pyridin-4-yl-oxapyr-A-azetidin-1-yl |
| lf-11 | pyridin-4-yl-oxapyr-A-imidazolidin-1-yl |
| lf-12 | pyridin-4-yl-oxapyr-A-piperazin-1-yl |
| lf-13 | pyridin-4-yl-oxapyr-A-pyrazol-1-yl |
| lf-14 | pyridin-4-yl-oxapyr-A-thiazolidin-3-yl |
| lf-15 | pyridin-4-yl-oxapyr-A-pyrrolidin-1-yl |
| lf-16 | pyridin-4-yl-oxapyr-A-pyridin-2-yl |
| lf-17 | pyridin-4-yl-oxapyr-A-pyridin-3-yl |
| lf-18 | pyridin-4-yl-oxapyr-A-pyridin-4-yl |
| lg-1 | thiophen-2-yl-oxapyr-A-phenyl |
| lg-2 | thiophen-2-yl-oxapyr-A-morpholin-4-yl |
| lg-3 | thiophen-2-yl-oxapyr-A-piperidin-1-yl |
| lg-4 | thiophen-2-yl-oxapyr-A-[1,4]oxazepan-4-yl |
| lg-5 | thiophen-2-yl-oxapyr-A-[1,2,3]triazol-1-yl |
| lg-6 | thiophen-2-yl-oxapyr-A-[1,2,4]triazol-1-yl |
| lg-7 | thiophen-2-yl-oxapyr-A-thiomorpholin-4-yl |
| lg-8 | thiophen-2-yl-oxapyr-A-imidazol-1-yl |
| lg-9 | thiophen-2-yl-oxapyr-A-2-oxa-5-azabicyclo[2.2.1]hept-5-yl |
| lg-10 | thiophen-2-yl-oxapyr-A-azetidin-1-yl |
| lg-11 | thiophen-2-yl-oxapyr-A-imidazolidin-1-yl |
| lg-12 | thiophen-2-yl-oxapyr-A-piperazin-1-yl |
| lg-13 | thiophen-2-yl-oxapyr-A-pyrazol-1-yl |
| lg-14 | thiophen-2-yl-oxapyr-A-thiazolidin-3-yl |
| lg-15 | thiophen-2-yl-oxapyr-A-pyrrolidin-1-yl |
| lg-16 | thiophen-2-yl-oxapyr-A-pyridin-2-yl |
| lg-17 | thiophen-2-yl-oxapyr-A-pyridin-3-yl |
| lg-18 | thiophen-2-yl-oxapyr-A-pyridin-4-yl |
| lh-1 | pyrimidin-5-yl-oxapyr-A-phenyl |
| lh-2 | pyrimidin-5-yl-oxapyr-A-morpholin-4-yl |
| lh-3 | pyrimidin-5-yl-oxapyr-A-piperidin-1-yl |
| lh-4 | pyrimidin-5-yl-oxapyr-A-[1,4]oxazepan-4-yl |
| lh-5 | pyrimidin-5-yl-oxapyr-A-[1,2,3]triazol-1-yl |
| lh-6 | pyrimidin-5-yl-oxapyr-A-[1,2,4]triazol-1-yl |
| lh-7 | pyrimidin-5-yl-oxapyr-A-thiomorpholin-4-yl |
| lh-8 | pyrimidin-5-yl-oxapyr-A-imidazol-1-yl |
| lh-9 | pyrimidin-5-yl-oxapyr-A-2-oxa-5-azabicyclo[2.2.1]hept-5-yl |
| lh-10 | pyrimidin-5-yl-oxapyr-A-azetidin-1-yl |
| lh-11 | pyrimidin-5-yl-oxapyr-A-imidazolidin-1-yl |
| lh-12 | pyrimidin-5-yl-oxapyr-A-piperazin-1-yl |
| lh-13 | pyrimidin-5-yl-oxapyr-A-pyrazol-1-yl |
| lh-14 | pyrimidin-5-yl-oxapyr-A-thiazolidin-3-yl |
| lh-15 | pyrimidin-5-yl-oxapyr-A-pyrrolidin-1-yl |
| lh-16 | pyrimidin-5-yl-oxapyr-A-pyridin-2-yl |
| lh-17 | pyrimidin-5-yl-oxapyr-A-pyridin-3-yl |
| lh-18 | pyrimidin-5-yl-oxapyr-A-pyridin-4-yl |
| lk-1 | phenyl-oxapyr-$CH_2$-phenyl |
| lk-2 | phenyl-oxapyr-$CH_2$-morpholin-4-yl |
| lk-3 | phenyl-oxapyr-$CH_2$-piperidin-1-yl |
| lk-4 | phenyl-oxapyr-$CH_2$-[1,4]oxazepan-4-yl |
| lk-5 | phenyl-oxapyr-$CH_2$-[1,2,3]triazol-1-yl |
| lk-6 | phenyl-oxapyr-$CH_2$-[1,2,4]triazol-1-yl |
| lk-7 | phenyl-oxapyr-$CH_2$-thiomorpholin-4-yl |
| lk-8 | phenyl-oxapyr-$CH_2$-imidazol-1-yl |
| lk-9 | phenyl-oxapyr-$CH_2$-2-oxa-5-azabicyclo[2.2.1]hept-5-yl |
| lk-10 | phenyl-oxapyr-$CH_2$-azetidin-1-yl |
| lk-11 | phenyl-oxapyr-$CH_2$-imidazolidin-1-yl |
| lk-12 | phenyl-oxapyr-$CH_2$-piperazin-1-yl |
| lk-13 | phenyl-oxapyr-$CH_2$-pyrazol-1-yl |
| lk-14 | phenyl-oxapyr-$CH_2$-thiazolidin-3-yl |
| lk-15 | phenyl-oxapyr-$CH_2$-pyrrolidin-1-yl |
| lk-16 | phenyl-oxapyr-$CH_2$-pyridin-2-yl |
| lk-17 | phenyl-oxapyr-$CH_2$-pyridin-3-yl |
| lk-18 | phenyl-oxapyr-$CH_2$-pyridin-4-yl |
| lm-1 | furan-2-yl-oxapyr-$CH_2$-phenyl |
| lm-2 | furan-2-yl-oxapyr-$CH_2$-morpholin-4-yl |
| lm-3 | furan-2-yl-oxapyr-$CH_2$-piperidin-1-yl |
| lm-4 | furan-2-yl-oxapyr-$CH_2$-[1,4]oxazepan-4-yl |
| lm-5 | furan-2-yl-oxapyr-$CH_2$-[1,2,3]triazol-1-yl |
| lm-6 | furan-2-yl-oxapyr-$CH_2$-[1,2,4]triazol-1-yl |
| lm-7 | furan-2-yl-oxapyr-$CH_2$-thiomorpholin-4-yl |
| lm-8 | furan-2-yl-oxapyr-$CH_2$-imidazol-1-yl |
| lm-9 | furan-2-yl-oxapyr-$CH_2$-2-oxa-5-azabicyclo[2.2.1]hept-5-yl |
| lm-10 | furan-2-yl-oxapyr-$CH_2$-azetidin-1-yl |
| lm-11 | furan-2-yl-oxapyr-$CH_2$-imidazolidin-1-yl |
| lm-12 | furan-2-yl-oxapyr-$CH_2$-piperazin-1-yl |
| lm-13 | furan-2-yl-oxapyr-$CH_2$-pyrazol-1-yl |
| lm-14 | furan-2-yl-oxapyr-$CH_2$-thiazolidin-3-yl |
| lm-15 | furan-2-yl-oxapyr-$CH_2$-pyrrolidin-1-yl |
| lm-16 | furan-2-yl-oxapyr-$CH_2$-pyridin-2-yl |
| lm-17 | furan-2-yl-oxapyr-$CH_2$-pyridin-3-yl |
| lm-18 | furan-2-yl-oxapyr-$CH_2$-pyridin-4-yl |
| ln-1 | pyridin-4-yl-oxapyr-$CH_2$-phenyl |
| ln-2 | pyridin-4-yl-oxapyr-$CH_2$-morpholin-4-yl |
| ln-3 | pyridin-4-yl-oxapyr-$CH_2$-piperidin-1-yl |
| ln-4 | pyridin-4-yl-oxapyr-$CH_2$-[1,4]oxazepan-4-yl |
| ln-5 | pyridin-4-yl-oxapyr-$CH_2$-[1,2,3]triazol-1-yl |
| ln-6 | pyridin-4-yl-oxapyr-$CH_2$-[1,2,4]triazol-1-yl |
| ln-7 | pyridin-4-yl-oxapyr-$CH_2$-thiomorpholin-4-yl |
| ln-8 | pyridin-4-yl-oxapyr-$CH_2$-imidazol-1-yl |
| ln-9 | pyridin-4-yl-oxapyr-$CH_2$-2-oxa-5-azabicyclo[2.2.1]hept-5-yl |
| ln-10 | pyridin-4-yl-oxapyr-$CH_2$-azetidin-1-yl |
| ln-11 | pyridin-4-yl-oxapyr-$CH_2$-imidazolidin-1-yl |
| ln-12 | pyridin-4-yl-oxapyr-$CH_2$-piperazin-1-yl |
| ln-13 | pyridin-4-yl-oxapyr-$CH_2$-pyrazol-1-yl |
| ln-14 | pyridin-4-yl-oxapyr-$CH_2$-thiazolidin-3-yl |
| ln-15 | pyridin-4-yl-oxapyr-$CH_2$-pyrrolidin-1-yl |
| ln-16 | pyridin-4-yl-oxapyr-$CH_2$-pyridin-2-yl |
| ln-17 | pyridin-4-yl-oxapyr-$CH_2$-pyridin-3-yl |
| ln-18 | pyridin-4-yl-oxapyr-$CH_2$-pyridin-4-yl |
| lp-1 | pyridin-3-yl-oxapyr-$CH_2$-phenyl |
| lp-2 | pyridin-3-yl-oxapyr-$CH_2$-morpholin-4-yl |
| lp-3 | pyridin-3-yl-oxapyr-$CH_2$-piperidin-1-yl |
| lp-4 | pyridin-3-yl-oxapyr-$CH_2$-[1,4]oxazepan-4-yl |
| lp-5 | pyridin-3-yl-oxapyr-$CH_2$-[1,2,3]triazol-1-yl |
| lp-6 | pyridin-3-yl-oxapyr-$CH_2$-[1,2,4]triazol-1-yl |
| lp-7 | pyridin-3-yl-oxapyr-$CH_2$-thiomorpholin-4-yl |
| lp-8 | pyridin-3-yl-oxapyr-$CH_2$-imidazol-1-yl |

-continued

| | |
|---|---|
| lp-9 | pyridin-3-yl-oxapyr-$CH_2$-2-oxa-5-azabicyclo[2.2.1]hept-5-yl |
| lp-10 | pyridin-3-yl-oxapyr-$CH_2$-azetidin-1-yl |
| lp-11 | pyridin-3-yl-oxapyr-$CH_2$-imidazolidin-1-yl |
| lp-12 | pyridin-3-yl-oxapyr-$CH_2$-piperazin-1-yl |
| lp-13 | pyridin-3-yl-oxapyr-$CH_2$-pyrazol-1-yl |
| lp-14 | pyridin-3-yl-oxapyr-$CH_2$-thiazolidin-3-yl |
| lp-15 | pyridin-3-yl-oxapyr-$CH_2$-pyrrolidin-1-yl |
| lp-16 | pyridin-3-yl-oxapyr-$CH_2$-pyridin-2-yl |
| lp-17 | pyridin-3-yl-oxapyr-$CH_2$-pyridin-3-yl |
| lp-18 | pyridin-3-yl-oxapyr-$CH_2$-pyridin-4-yl |
| lq-1 | thiophen-2-yl-oxapyr-$CH_2$-phenyl |
| lq-2 | thiophen-2-yl-oxapyr-$CH_2$-morpholin-4-yl |
| lq-3 | thiophen-2-yl-oxapyr-$CH_2$-piperidin-1-yl |
| lq-4 | thiophen-2-yl-oxapyr-$CH_2$-[1,4]oxazepan-4-yl |
| lq-5 | thiophen-2-yl-oxapyr-$CH_2$-[1,2,3]triazol-1-yl |
| lq-6 | thiophen-2-yl-oxapyr-$CH_2$-[1,2,4]triazol-1-yl |
| lq-7 | thiophen-2-yl-oxapyr-$CH_2$-thiomorpholin-4-yl |
| lq-8 | thiophen-2-yl-oxapyr-$CH_2$-imidazol-1-yl |
| lq-9 | thiophen-2-yl-oxapyr-$CH_2$-2-oxa-5-azabicyclo[2.2.1]hept-5-yl |
| lq-10 | thiophen-2-yl-oxapyr-$CH_2$-azetidin-1-yl |
| lq-11 | thiophen-2-yl-oxapyr-$CH_2$-imidazolidin-1-yl |
| lq-12 | thiophen-2-yl-oxapyr-$CH_2$-piperazin-1-yl |
| lq-13 | thiophen-2-yl-oxapyr-$CH_2$-pyrazol-1-yl |
| lq-14 | thiophen-2-yl-oxapyr-$CH_2$-thiazolidin-3-yl |
| lq-15 | thiophen-2-yl-oxapyr-$CH_2$-pyrrolidin-1-yl |
| lq-16 | thiophen-2-yl-oxapyr-$CH_2$-pyridin-2-yl |
| lq-17 | thiophen-2-yl-oxapyr-$CH_2$-pyridin-3-yl |
| lq-18 | thiophen-2-yl-oxapyr-$CH_2$-pyridin-4-yl |
| lr-1 | pyrimidin-5-yl-oxapyr-$CH_2$-phenyl |
| lr-2 | pyrimidin-5-yl-oxapyr-$CH_2$-morpholin-4-yl |
| lr-3 | pyrimidin-5-yl-oxapyr-$CH_2$-piperidin-1-yl |
| lr-4 | pyrimidin-5-yl-oxapyr-$CH_2$-[1,4]oxazepan-4-yl |
| lr-5 | pyrimidin-5-yl-oxapyr-$CH_2$-[1,2,3]triazol-1-yl |
| lr-6 | pyrimidin-5-yl-oxapyr-$CH_2$-[1,2,4]triazol-1-yl |
| lr-7 | pyrimidin-5-yl-oxapyr-$CH_2$-thiomorpholin-4-yl |
| lr-8 | pyrimidin-5-yl-oxapyr-$CH_2$-imidazol-1-yl |
| lr-9 | pyrimidin-5-yl-oxapyr-$CH_2$-2-oxa-5-azabicyclo[2.2.1]hept-5-yl |
| lr-10 | pyrimidin-5-yl-oxapyr-$CH_2$-azetidin-1-yl |
| lr-11 | pyrimidin-5-yl-oxapyr-$CH_2$-imidazolidin-1-yl |
| lr-12 | pyrimidin-5-yl-oxapyr-$CH_2$-piperazin-1-yl |
| lr-13 | pyrimidin-5-yl-oxapyr-$CH_2$-pyrazol-1-yl |
| lr-14 | pyrimidin-5-yl-oxapyr-$CH_2$-thiazolidin-3-yl |
| lr-15 | pyrimidin-5-yl-oxapyr-$CH_2$-pyrrolidin-1-yl |
| lr-16 | pyrimidin-5-yl-oxapyr-$CH_2$-pyridin-2-yl |
| lr-17 | pyrimidin-5-yl-oxapyr-$CH_2$-pyridin-3-yl |
| lr-18 | pyrimidin-5-yl-oxapyr-$CH_2$-pyridin-4-yl | wherein in the compounds of the formulae Ia-1 to Ia-6, Ib-1 to Ib-18, Ic-1 to Ic-18, Id-1 to Id-18, Ie-1 to Ie-18, If-1 to If-18, Ig-1 to Ig-18, Ih-1 to Ih-18, Ik-1 to Ik-18, Im-1 to Im-18, In-1 to In-18, Ip-1 to Ip-18, Iq-1 to Iq-18, Ir-1 to Ir-18 the groups A, $R^1$, $R^2$ and $R^3$ are defined as in the compounds of the formula I or in any embodiment specified herein, and the groups phenyl, furan-2-yl, pyridin-3-yl, pyridin-4-yl, thiophen-2-yl and pyrimidin-5-yl group representing $R^2$ in formula I are optionally substituted on one or more ring carbon atoms by identical or different substituents $R^{22}$, and the groups phenyl, morpholin-4-yl, piperidin-1-yl, [1,4]oxazepan-4-yl, [1,2,3]triazol-1-yl, [1,2,4]triazol-1-yl, thiomorpholin-4-yl, imidazol-1-yl, 2-oxa-5-azabicyclo[2.2.1]hept-5-yl, azetidin-1-yl, imidazolidin-1-yl, piperazin-1-yl, pyrazol-1-yl, thiazolidin-3-yl, pyrrolidin-1-yl, pyridin-2-yl, pyridin-3-yl, pyridin-4-yl bonded to the group A or the $CH_2$ group representing A in formula I, which groups represent the group $R^3$ in formula I, are optionally substituted on one or more ring carbon atoms by identical or different substituents $R^{32}$ and, in the case of the groups imidazolidin-1-yl and piperazin-1-yl, one of the ring nitrogen atoms can carry a hydrogen atom or a substituent $R^{31}$ and, in the case of the groups thiomorpholin-4-yl and thiazolidin-3-yl, the ring sulfur atom can carry one or two oxo groups.

Another such example are compounds of the formula I, wherein

A is —$(CR^4R^6)_a$—$CR^6R^7$—$(CR^8R^9)_b$—, wherein a and b are independently of each other chosen from 0 and 1;

$R^1$ is chosen from $(C_1-C_6)$-alkyl, $(C_2-C_6)$-alkenyl, $(C_2-C_6)$-alkynyl, $(C_3-C_7)$-cycloalkyl-$C_uH_{2u}$— and $Het^1$-$C_uH_{2u}$—, wherein u is chosen from 0, 1, 2 and 3;

$R^2$ is chosen from phenyl, naphthyl and a residue of an aromatic, 5-membered to 10-membered, monocyclic or bicyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl, naphthyl and residue of an aromatic heterocycle are optionally substituted on one or more ring carbon atoms by identical or different substituents $R^{22}$;

$R^3$ is a residue of a saturated or unsaturated, 4-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^4$, $R^5$, $R^8$ and $R^9$ are independently of each other chosen from hydrogen, fluorine and $(C_1-C_4)$-alkyl;

$R^6$ and $R^7$ are independently of each other chosen from hydrogen, fluorine and $(C_1-C_4)$-alkyl or together are $(C_2-C_8)$-alkanediyl;

$R^{21}$ is chosen from $(C_1-C_4)$-alkyl and $(C_3-C_7)$-cycloalkyl-$C_vH_{2v}$—, wherein v is chosen from 0, 1 and 2;

$R^{22}$ is chosen from halogen, hydroxy, $(C_1-C_4)$-alkyl-$S(O)_m$—, amino, nitro, cyano, hydroxycarbonyl, $(C_1-C_4)$-alkyloxycarbonyl, aminocarbonyl, aminosulfonyl, $R^{23}$, $R^{23}$—O—, $R^{23}$—NH—, $R^{23}$—$N(R^{23})$—, $R^{23}$—C(O)—NH—, $R^{23}$—$S(O)_2$—NH—, $R^{23}$—C(O)—, $R^{23}$—NH—C(O)—, $R^{23}$—$N(R^{23})$—C(O)—, $R^{23}$—NH—$S(O)_2$—, $R^{24}$, $R^{24}$—O— and $R^{24}$—C(O)—;

$R^{23}$ is $(C_1-C_6)$-alkyl which is optionally substituted by one or more identical or different substituents chosen from hydroxy, $(C_1-C_4)$-alkyl-$S(O)_m$—, amino, hydroxycarbonyl, $(C_1-C_4)$-alkyloxycarbonyl, aminocarbonyl, $R^{24}$, $R^{24}$—C(O)—, $R^{25}$—O—, $R^{25}$—NH—, $R^{25}$—$N(R^{25})$—, $R^{25}$—C(O)—NH—, $R^{25}$—$S(O)_2$—NH—, $R^{25}$—NH—$S(O)_2$—NH—, $R^{25}$—NH—C(O)— and $R^{25}$—$N(R^{25})$—C(O)—;

$R^{24}$ is a residue of a saturated or unsaturated, 4-membered to 7-membered, monocyclic ring which comprises 0, 1, 2 or 3 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_6)$-alkyl and $(C_3-C_7)$-cycloalkyl-$C_wH_{2w}$—, wherein the alkyl and cycloalkyl are optionally substituted by one or more identical or different substituents chosen from hydroxy, $(C_1-C_4)$-alkyloxy, amino, $(C_1-C_4)$-alkylamino, di$((C_1-C_4)$-alkyl)amino, hydroxycarbonyl and $(C_1-C_4)$-alkyloxycarbonyl, and wherein w is chosen from 0, 1 and 2;

$R^{26}$ is chosen from $(C_1-C_4)$-alkyl and $(C_3-C_7)$-cycloalkyl-$C_xH_{2x}$—, wherein the alkyl and cycloalkyl are optionally substituted by one or more identical or different substituents chosen from hydroxy, $(C_1-C_4)$-alkyloxy, hydroxycarbonyl and $(C_1-C_4)$-alkyloxycarbonyl, and wherein x is chosen from 0, 1 and 2;

$R^{27}$ is chosen from halogen, $(C_1-C_4)$-alkyl, hydroxy, $(C_1-C_4)$-alkyloxy, oxo, cyano, hydroxycarbonyl-$C_yH_{2y}$—, $(C_1-C_4)$-alkyloxycarbonyl-$C_yH_{2y}$— and aminocarbonyl-$C_yH_{2y}$—, wherein the numbers y are independently of each other chosen from 0, 1, 2, 3 and 4;

$R^{31}$ is chosen from $(C_1-C_4)$-alkyl, phenyl-$C_qH_{2q}$—, $(C_1-C_4)$-alkylsulfonyl, $(C_1-C_4)$-alkylcarbonyl and $R^{33}$—O—C(O)—, wherein q is chosen from 1, 2 and 3, and wherein the phenyl is optionally substituted by one or more identical or different substituents chosen from halogen, $(C_1-C_4)$-alkyl, $(C_1-C_4)$-alkyloxy and cyano;

$R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, hydroxycarbonyl, $R^{34}$—O—C(O)—, aminocarbonyl, $(C_1-C_4)$-alkylaminocarbonyl, di($(C_1-C_4)$-alkyl)aminocarbonyl, aminosulfonyl, $(C_1-C_4)$-alkylaminosulfonyl, di($(C_1-C_4)$-alkyl)aminosulfonyl, phenyl-$C_rH_{2r}$— and Het$^2$-$C_rH_{2r}$—, wherein the numbers r are independently of each other chosen from 0, 1, 2 and 3, and wherein the phenyl and Het$^2$ are optionally substituted on one or more ring carbon atoms by identical or different substituents chosen from halogen, $(C_1-C_4)$-alkyl, $(C_1-C_4)$-alkyloxy and cyano;

$R^{33}$ and $R^{34}$ are independently of each other chosen from $(C_1-C_4)$-alkyl, $(C_3-C_7)$-cycloalkyl-$C_sH_{2s}$— and phenyl-$C_tH_{2t}$—, wherein s is chosen from 0, 1 and 2 and t is chosen from 1 and 2;

Het$^1$ is a residue of a saturated, 4-membered to 7-membered, monocyclic heterocycle which comprises 1 to 2 identical or different ring heteroatoms chosen from N, O and S and which is bonded via a ring carbon atom, wherein the residue of a heterocycle is optionally substituted by one or more identical or different substituents chosen from fluorine and $(C_1-C_4)$-alkyl;

Het$^2$ is a residue of an aromatic, 5-membered or 6-membered, monocyclic heterocycle which comprises 1, 2 or 3 identical or different ring heteroatoms chosen from N, O and S, wherein one of the ring nitrogen atoms can carry a hydrogen atom or a $(C_1-C_4)$-alkyl substituent;

m is chosen from 0, 1 and 2, wherein all numbers m are independent of each other;

wherein all cycloalkyl groups, independently of each other and independently of any other substituents, are optionally substituted by one or more identical or different substituents chosen from fluorine and $(C_1-C_4)$-alkyl;

wherein all alkyl, alkanediyl, $C_qH_{2q}$, $C_rH_{2r}$, $C_sH_{2s}$, $C_tH_{2t}$, $C_uH_{2u}$, $C_vH_{2v}$, $C_wH_{2w}$, $C_xH_{2x}$, $C_yH_{2y}$, alkenyl and alkynyl groups, independently of each other and independently of any other substituents, are optionally substituted by one or more fluorine substituents;

in any of their stereoisomeric forms, or a mixture of stereoisomeric forms in any ratio, and the physiologically acceptable salts thereof, and the physiologically acceptable solvates of any of them.

Another such example are the compounds of the formula I, wherein

A is —(CR$^4$R$^5$)$_a$—CR$^6$R$^7$—, wherein a is chosen from 0 and 1;

$R^1$ is chosen from $(C_1-C_6)$-alkyl, $(C_3-C_7)$-cycloalkyl-$C_uH_{2u}$— and Het$^1$-$C_uH_{2u}$—, wherein u is chosen from 0, 1 and 2;

$R^2$ is chosen from phenyl and a residue of an aromatic, 5-membered to 6-membered, monocyclic heterocycle which comprises 1 or 2 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^3$ is chosen from phenyl and a residue of a saturated or unsaturated, 4-membered to 7-membered, monocyclic ring which comprises 1 or 2 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the residue of a ring is optionally substituted on one or more ring carbon atoms by identical or different substituents $R^{32}$;

$R^4$, $R^5$, $R^8$ and $R^9$ are independently of each other chosen from hydrogen and $(C_1-C_4)$-alkyl;

$R^6$ and $R^7$ are independently of each other chosen from hydrogen and $(C_1-C_4)$-alkyl or together are $(C_2-C_5)$-alkanediyl;

$R^{21}$ is chosen from $(C_1-C_4)$-alkyl;

$R^{22}$ is chosen from halogen, hydroxy, amino, cyano, hydroxycarbonyl, $(C_1-C_4)$-alkyloxycarbonyl, $R^{23}$, $R^{23}$—O—, $R^{23}$—NH—, $R^{23}$—N(R$^{23}$)—, $R^{23}$—C(O)—NH—, $R^{23}$—C(O)—, $R^{23}$—NH—C(O)—, $R^{23}$—N(R$^{23}$)—C(O)—, $R^{24}$, $R^{24}$—O— and $R^{24}$—C(O)—;

$R^{23}$ is $(C_1-C_6)$-alkyl which is optionally substituted by one or more identical or different substituents chosen from hydroxy, amino, hydroxycarbonyl, $(C_1-C_4)$-alkyloxycarbonyl, $R^{24}$, $R^{24}$—C(O)—, $R^{25}$—O—, $R^{25}$—NH—, $R^{25}$—N(R$^{25}$)— and $R^{25}$—C(O)—NH—;

$R^{24}$ is a residue of a saturated or unsaturated, 4-membered to 7-membered, monocyclic ring which comprises 0, 1 or 2 identical or different ring heteroatoms chosen from N, O and S, wherein one or two of the ring nitrogen atoms can carry a hydrogen atom or a substituent $R^{26}$ and one of the ring sulfur atoms can carry one or two oxo groups, and wherein the residue of a ring is optionally substituted on one or more ring carbon atoms by identical or different substituents $R^{27}$;

$R^{25}$ is chosen from $(C_1-C_6)$-alkyl, wherein the alkyl is optionally substituted by one or more identical or different substituents chosen from hydroxy, $(C_1-C_4)$-alkyloxy, di(($C_1-C_4$)-alkyl)amino, hydroxycarbonyl and $(C_1-C_4)$-alkyloxycarbonyl;

$R^{26}$ is chosen from $(C_1-C_4)$-alkyl, wherein the alkyl is optionally substituted by one or more identical or different substituents chosen from hydroxy, hydroxycarbonyl and $(C_1-C_4)$-alkyloxycarbonyl;

$R^{27}$ is chosen from fluorine, $(C_1-C_4)$-alkyl, hydroxycarbonyl-$C_yH_{2y}$— and $(C_1-C_4)$-alkyloxycarbonyl-$C_yH_{2y}$—, wherein the numbers y are independently of each other chosen from 0, 1 and 2;

$R^{31}$ is chosen from $(C_1-C_4)$-alkyl, phenyl-$C_qH_{2q}$— and $(C_1-C_4)$-alkylsulfonyl, wherein q is chosen from 1 and 2, and wherein the phenyl is optionally substituted by one or more identical or different substituents chosen from halogen, $(C_1-C_4)$-alkyl, $(C_1-C_4)$-alkyloxy and cyano;

$R^{32}$ is chosen from halogen, $(C_1-C_4)$-alkyl, $(C_3-C_7)$-cycloalkyl, hydroxy-$(C_1-C_4)$-alkyl, $(C_1-C_4)$-alkyloxy-$(C_1-C_4)$-alkyl, hydroxy, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonyl, hydroxycarbonyl, $R^{34}$—O—C(O)—, phenyl-$C_rH_{2r}$— and Het$^2$-$C_rH_{2r}$—, wherein the numbers r are independently of each other chosen from 0, 1 and 2, and wherein the phenyl and Het$^2$ are optionally substituted on one or more ring carbon atoms by identical or different substituents chosen from halogen, $(C_1-C_4)$-alkyl, $(C_1-C_4)$-alkyloxy and cyano;

$R^{34}$ is chosen from $(C_1\text{-}C_4)$-alkyl;

Het$^1$ is a residue of a saturated, 4-membered to 7-membered, monocyclic heterocycle which comprises 1 heteroatom chosen from N, O and S and which is bonded via a ring carbon atom, wherein the residue of a heterocycle is optionally substituted by one or more identical or different substituents chosen from fluorine and $(C_1\text{-}C_4)$-alkyl;

Het$^2$ is a residue of an aromatic, 5-membered or 6-membered, monocyclic heterocycle which comprises 1 or 2 identical or different ring heteroatoms chosen from N, O and S, wherein one of the ring nitrogen atoms can carry a hydrogen atom or a $(C_1\text{-}C_4)$-alkyl substituent;

m is chosen from 0, 1 and 2, wherein all numbers m are independent of each other;

wherein all cycloalkyl groups, independently of each other and independently of any other substituents, are optionally substituted by one or more identical or different substituents chosen from fluorine and $(C_1\text{-}C_4)$-alkyl;

wherein all alkyl, alkanediyl, $C_qH_{2q}$, $C_rH_{2r}$, $C_uH_{2u}$ and $C_yH_{2y}$ groups, independently of each other and independently of any other substituents, are optionally substituted by one or more fluorine substituents, in any of their stereoisomeric forms, or a mixture of stereoisomeric forms in any ratio, and the physiologically acceptable salts thereof, and the physiologically acceptable solvates of any of them.

Another such example are the compounds of the formula I, wherein

A is —CH$_2$—;

$R^1$ is chosen from $(C_1\text{-}C_6)$-alkyl;

$R^3$ is chosen from phenyl and a residue of a saturated or unsaturated 5-membered to 7-membered, monocyclic ring which comprises 1 or 2 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the phenyl and residue of a ring are optionally substituted on one or more ring carbon atoms by identical or different substituents $R^{32}$;

and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

Another such example are the compounds of the formula I, wherein

A is —CH$_2$—;

$R^1$ is chosen from $(C_1\text{-}C_6)$-alkyl;

$R^2$ is chosen from phenyl which is optionally substituted by one or more identical or different substituents $R^{22}$;

$R^3$ is chosen from phenyl and a residue of a saturated or unsaturated 5-membered to 7-membered, monocyclic ring which comprises 1 or 2 identical or different ring heteroatoms chosen from N, O and S, wherein one or two of the ring nitrogen atoms can carry a hydrogen atom or a substituent $R^{31}$ and one or two of the ring sulfur atoms can carry one or two oxo groups, and wherein the phenyl and residue of a ring are optionally substituted on one or more ring carbon atoms by identical or different substituents $R^{32}$;

and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

Another such example are compounds of the formula I, wherein $R^{31}$ is chosen from $(C_1\text{-}C_4)$-alkyl, phenyl-$C_qH_{2q}$—, $(C_1\text{-}C_4)$-alkylsulfonyl and $(C_1\text{-}C_4)$-alkylcarbonyl, wherein q is chosen from 1, 2 and 3, and wherein the phenyl is optionally substituted by one or more identical or different substituents chosen from halogen, $(C_1\text{-}C_4)$-alkyl, $(C_1\text{-}C_4)$-alkyloxy and cyano;

$R^{32}$ is chosen from halogen, $(C_1\text{-}C_4)$-alkyl, $(C_3\text{-}C_7)$-cycloalkyl, hydroxy-$(C_1\text{-}C_4)$-alkyl, $(C_1\text{-}C_4)$-alkyloxy-$(C_1\text{-}C_4)$-alkyl, hydroxy, $(C_1\text{-}C_4)$-alkyloxy, oxo, $(C_1\text{-}C_4)$-alkyl-S(O)$_m$—, amino, $(C_1\text{-}C_4)$-alkylamino, di($(C_1\text{-}C_4)$-alkyl)amino, $(C_1\text{-}C_4)$-alkylcarbonylamino, $(C_1\text{-}C_4)$-alkylsulfonylamino, nitro, cyano, $(C_1\text{-}C_4)$-alkylcarbonyl, aminocarbonyl, $(C_1\text{-}C_4)$-alkylaminocarbonyl, di($(C_1\text{-}C_4)$-alkyl)aminocarbonyl, aminosulfonyl, $(C_1\text{-}C_4)$-alkylaminosulfonyl, di($(C_1\text{-}C_4)$-alkyl)aminosulfonyl, phenyl-$C_rH_{2r}$— and Het$^2$-$C_rH_{2r}$—, wherein the numbers r are independently of each other chosen from 0, 1, 2 and 3, and wherein the phenyl and Het$^2$ are optionally substituted on one or more ring carbon atoms by identical or different substituents chosen from halogen, $(C_1\text{-}C_4)$-alkyl, hydroxy, $(C_1\text{-}C_4)$-alkyloxy and cyano;

and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

Another subject of the present invention are processes for the preparation of the compounds of the formula I and their salts and solvates, by which the compounds are obtainable and which are outlined in the following. In one process, a compound of the formula II is reacted with a compound of the formula III to give a compound of the formula I,

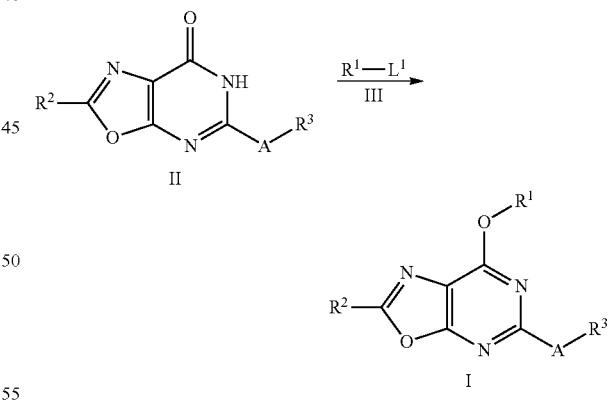

wherein the groups A, $R^1$, $R^2$ and $R^3$ in the compounds of the formulae II and III are defined as in the compounds of the formula I and additionally functional groups can be present in protected form or in the form of a precursor group which is later converted into the final group. The group $L^1$ in the compounds of the formula III is a nucleophilically substitutable leaving group, for example a halogen atom, such as chlorine, bromine or iodine, or a sulfonyloxy group like arylsulfonyloxy or alkylsulfonyloxy, such as benzenesulfonyloxy, 4-nitrobenzenesulfonyloxy, 4-methylbenzenesulfonyloxy (=tosyloxy), methanesulfonyloxy or trifluoromethanesulfonyloxy. The compounds of the formula II may also present in another tautomeric form, for example the form of the respective 7-hydroxy-oxazolo[5,4-d]pyrimidine derivatives in which the mobile hydrogen atom, which in formula II is bonded to the ring nitrogen atom in the 6-position of the oxazolopyrimidine ring system, is bonded to the oxygen atom attached to the ring carbon atom in the 7-position. As far as applicable, it applies to all compounds occurring in the preparation of the compounds of the formula I that they can be present in any other tautomeric form than the one represented in their formulae.

The reaction of the compounds of the formulae II and III is a nucleophilic substitution reaction at the carbon atom in the group $R^1$ carrying the group $L^1$ and can be carried out under standard conditions for such reactions which are well known to a person skilled in the art. Generally the reaction is carried out in an inert solvent, for example a hydrocarbon or chlorinated hydrocarbon such as benzene, toluene, xylene, chlorobenzene, dichloromethane, chloroform or dichloroethane, an ether such as tetrahydrofuran (THF), dioxane, dibutyl ether, diisopropyl ether or 1,2-dimethoxyethane (DME), an alcohol such as methanol, ethanol or isopropanol, a ketone such as acetone or butan-2-one, an ester such as ethyl acetate or butyl acetate, a nitrile such acetonitrile, an amide such as N,N-dimethylformamide (DMF) or N-methylpyrrolidin-2-one (NMP), or a mixture of solvents, at temperatures from about 20° C. to about 100° C., for example at temperatures from about 40° C. to about 80° C., depending on the particulars of the specific case. Generally it is favorable for enhancing the nucleophilicity of the compound of the formula II and/or binding an acid which is liberated during the reaction, to add a base, for example a tertiary amine, such as triethylamine, ethyldiisopropylamine or N-methylmorpholine, or an inorganic base such as an alkaline metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide. A compound of the formula II can also be treated with a base and converted into a salt separately before the reaction with the compound of the formula III. Besides by reaction with a compound of the formula III, a compound of the formula II can also be converted into a compound of the formula I by reaction with the respective alcohol of the formula $R^1$—OH, wherein $R^1$ is defined as in the compounds of the formula I and additionally functional groups can be present in protected form or in the form of a precursor group, under the conditions of the Mitsunobu reaction in the presence of an azodicarboxylate such as diethyl azodicarboxylate or diisopropyl azodicarboxylate and a phosphine such as triphenylphosphine or tributylphosphine in an inert aprotic solvent, for example an ether such as THF or dioxane (cf. 0. Mitsunobu, Synthesis (1981), 1-28).

The compounds of the formula II can be obtained by reacting an aminomalonic acid ester of the formula IV with an activated carboxylic acid derivative of the formula V to give a compound of the formula VI, reacting the latter compound with an amidine of the formula VII to give a compound of the formula VIII, and cyclizing the latter compound with formation of the oxazolo[5,4-d]pyrimidine ring system to give the compound of the formula II.

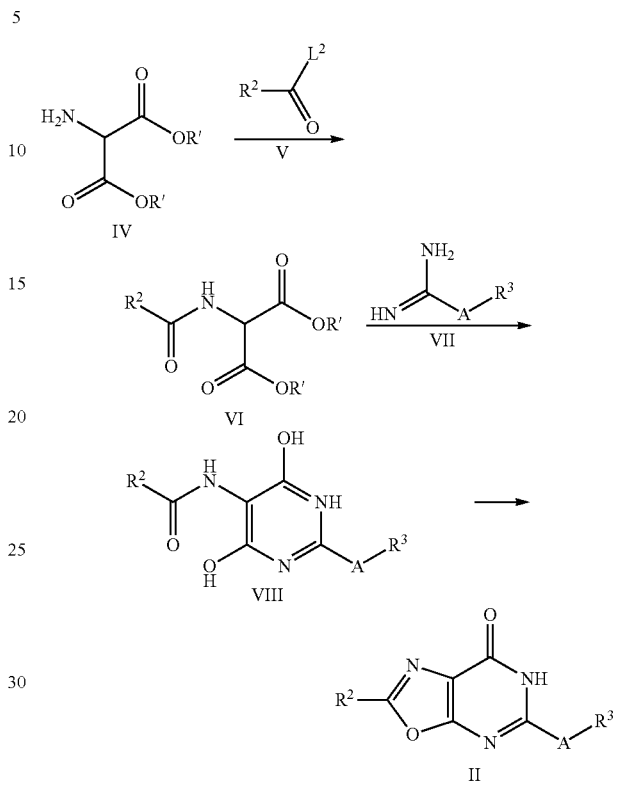

The groups A, $R^2$ and $R^3$ in the compounds of the formulae V, VI, VII and VIII are defined as in the compounds of the formula I and additionally functional groups can be present in protected form or in the form of a precursor group which is later converted into the final group. The group R' in the compounds of the formulae IV and VI can be alkyl like $(C_1$-$C_3)$-alkyl, for example, such as methyl or ethyl. The group $L^2$ in the compounds of the formula V is a nucleophilically substitutable leaving group and can in particular be a halogen atom, such as chlorine or bromine, and the compound of the formula V can thus be a carboxylic acid halide. $L^2$ can also be a group of the formula $R^2$—C(O)—O and the compound of the formula V can thus be a carboxylic acid anhydride, for example. In the reactions of this process, as in all other reactions carried out in the preparation of the compounds of the formula I, starting compounds can also be employed and/or products obtained in the form of a salt. For example, compounds of the formulae IV and VII can be employed in the form of an acid addition salt such as the hydrochloride.

The reaction of the compounds of the formulae IV and V can be carried out under standard conditions for the acylation of an amine with an activated carboxylic acid derivative like an acid halide or anhydride. Generally the reaction is carried out in an inert solvent, for example a hydrocarbon or chlorinated hydrocarbon such as benzene, toluene, xylene, chlorobenzene, dichloromethane, chloroform or dichloroethane, an ether such as THF, dioxane, dibutyl ether, diisopropyl ether or DME, a ketone such as acetone or butan-2-one, an ester such as ethyl acetate or butyl acetate, or water, or a mixture of solvents, at temperatures from about −10° C. to about 40° C., for example at temperatures from about 0° C. to about 30° C. Generally the reaction is carried out with addition of a base, for example a tertiary amine, such as triethylamine, ethyldiisopropylamine or N-methylmorpholine, or an inorganic base such as an alkaline metal hydroxide, carbonate or hydrogencarbonate like sodium hydroxide, potassium hydroxide, sodium carbonate, potassium carbonate or sodium hydrogencarbonate. The reaction of the compounds of the formulae VI and VII is generally carried out in an inert solvent, for example an alcohol such as methanol, ethanol or isopropanol, or an ether such as THF, dioxane or DME, or a mixture of solvents, at temperatures from about 20° C. to about 80° C., for example temperatures from about 40° C. to about 80° C., in the presence of a base, for example an alkoxide such as sodium methoxide, sodium ethoxide, potassium methoxide or potassium tert-butoxide. The cyclization of the compound of the formula VIII to the compound of the formula II can favorably be carried out in the presence of a phosphorus halide, such as phosphorus pentachloride or phosphorus oxychloride or a mixture thereof, in an inert solvent, for example a hydrocarbon or chlorinated hydrocarbon such as benzene, toluene, xylene, chlorobenzene, dichloromethane, chloroform or dichloroethane, at temperatures from about 20° C. to about 100° C., for example temperatures from about 50° C. to about 80° C.

In another process for the preparation of compounds of the formula I, a compound of the formula VI is reacted with an amidine of the formula IX instead of with an amidine of the formula VII, the obtained compound of the formula X is cyclized to a compound of the formula XI which is then reacted with a compound of the formula III to give a compound of the formula XII, and the latter compound is brominated in the group -A-H to give a bromo intermediate of the formula XIII which can be converted into compounds of the formula I by reaction with a compound of the formula XIV in case the group $R^3$ in the compound of the formula I is bonded via a ring nitrogen atom, i.e. the hydrogen atom depicted in formula XIV is bonded to a ring nitrogen atom, or by reaction with other compounds as outlined below.

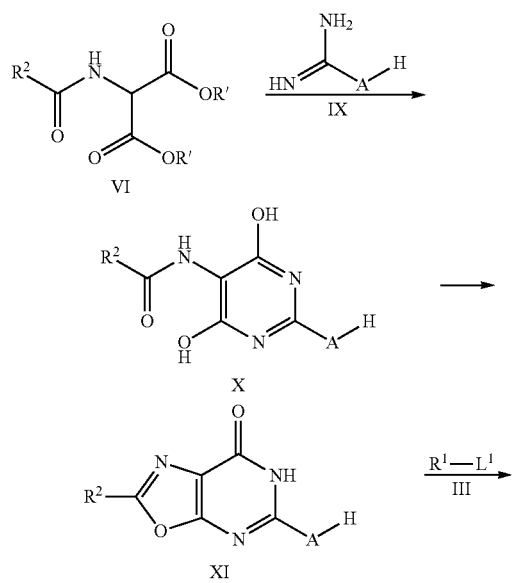

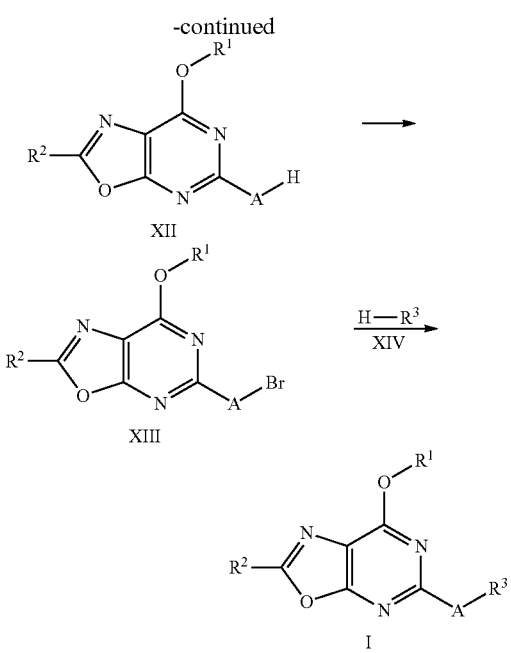

The groups $R^1$, $R^2$ and $R^3$ in the compounds of the formulae IX, X, XI, XII and XIII are defined as in the compounds of the formula I and additionally functional groups can be present in protected form or in the form of a precursor group which is later converted into the final group. The group $R^3$ in the compounds of the formula XIV is defined as in the compounds of the formula I and additionally functional groups can be present in protected form or in the form of a precursor group which is later converted into the final group, provided that $R^3$ comprises at least one ring nitrogen atom which carries a hydrogen atom. The group A in the compounds of the formulae IX, X, XI, XII and XIII is a group —$CR^6R^7$— wherein $R^6$ and $R^7$ are defined as in the compounds of the formula I. In one embodiment of the invention, by this process compounds of the formula I and respective bromo intermediates of the formula XIII are obtained in which the group A is the group —$CH_2$—.

The explanations given above with respect to the reaction of the compounds of the formulae VI and VII, the cyclization of the compound of the formula VIII to the compound of the formula II and the reaction of the compounds of the formulae II and III apply correspondingly to the reaction of the compounds of the formulae VI and IX, the cyclization of the compound of the formula X to the compound of the formula XI and the reaction of the compounds of the formulae XI and III, respectively. The bromination of the compound of the formula XII to the compound of the formula XIII can be carried out by means of N-bromosuccinimide (NBS), for example. Such a bromination by means of NBS is generally carried out in an inert solvent, for example a chlorinated hydrocarbon such as tetrachloromethane, in the presence of a radical starter, for example azobisisobutyronitrile (AIBN), at temperatures from about 60° C. to about 100° C., for example at about 80° C. Besides the mono-brominated compound of the formula XIII, such a bromination of the compound of the formula XII may lead to a compound in which additional hydrogen atoms are replaced with bromine atoms, in particular to a dibrominated compound in which in the group A, besides the hydrogen atom depicted in formula XII, another hydrogen atom, which represents $R^6$ or $R^7$, is replaced with a bromine atom. For example, in case the group -A-H in the compound of the formula XII is the group —$CH_3$, such a bromination may lead to the compound of the formula XIII in which the group -A-Br is the group —$CH_2Br$, and the respective compound which contains the group —CHBr$_2$ instead of the group —CH$_2$Br. Such di-brominated compounds containing the group —CHBr$_2$, both in isolated form and in the form of a mixture with the mono-brominated compound, can be converted into the desired mono-brominated compounds of the formula XIII by treatment with a suitable reducing agent like a dialkyl phosphite, for example a di((C$_1$-C$_4$)-alkyl)phosphite such as diethyl phosphite. Such a conversion by means of a dialkyl phosphite is generally carried out in an inert solvent, for example an ether such as THF or dioxane or DME, at temperatures from about −10° C. to about 30° C., for example at about 0° C., in the presence of base, for example a tertiary amine such as ethyldiisopropylamine or triethylamine. The reaction of a compound of the formula XIV, which contains a ring nitrogen atom via which the group R$^3$ is bonded to the group A in the resulting compound of the formula I and to which the hydrogen atom depicted in formula XIV is bonded, with a compound of the formula XIII, which is a nucleophilic substitution reaction like the reaction of the compounds of the formulae II and III, is generally carried out in an inert solvent, for example a hydrocarbon or chlorinated hydrocarbon such as benzene, toluene, xylene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone or butan-2-one, an ester such as ethyl acetate or butyl acetate, a nitrile such acetonitrile, an amide such as DMF or NMP, or a mixture of solvents, at temperatures from about 0° C. to about 100° C., for example at temperatures from about 0° C. to about 40° C., favorably with addition of a base, for example a tertiary amine, such as triethylamine, ethyldiisopropylamine or N-methylmorpholine, or an inorganic base such as an alkaline metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide, wherein the compound of the formula XIV can also be treated with a base and converted into a salt separately before the reaction with the compound of the formula XIII.

By reaction of the bromo-intermediate of the formula XIII with a boronic acid or boronic acid derivative of the formula XV compounds of the formula I can be prepared in which the group R$^3$ in the compound of the formula I is bonded via a ring carbon atom.

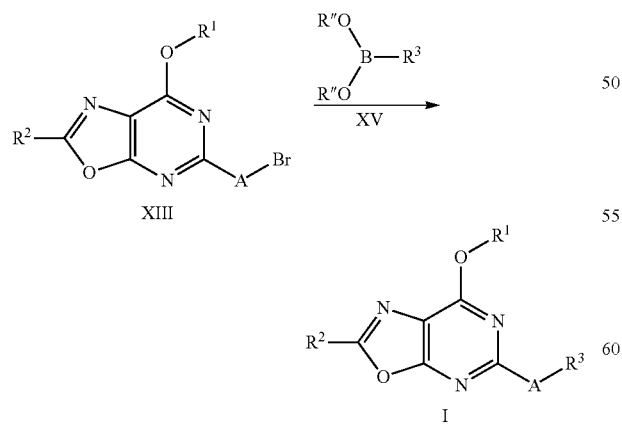

XIII

XV

I

The group R$^3$ in the compounds of the formula XV is defined as in the compounds of the formula I and additionally functional groups can be present in protected form or in the form of a precursor group which is later converted into the final group. The group R" in the compounds of the formula XV can be hydrogen, i.e. the compound of the formula XV can be a boronic acid, or R" can be alkyl like (C$_1$-C$_4$)-alkyl, i.e. the compound of the formula XV can be a boronic acid ester, for example. The reaction of the compound of the formula XV, which can be an optionally substituted cycloalkylboronic acid, arylboronic acid including phenylboronic acid, or heteroarylboronic acid or derivative thereof, for example, with a compound of the formula XIII is generally carried out in the presence of catalytic palladium compound, for example a palladium(II) salt such as palladium(II)acetate, which can be employed in the presence of a phosphine such as tricyclohexylphosphine or triphenylphosphine, or a palladium complex such as tetrakis(triphenylphosphine)palladium(0) or bis(triphenylphosphine)palladium(II) chloride, and a base, for example an alkaline metal carbonate or phosphate such as sodium carbonate or tripotassium phosphate, in an inert solvent, for example a hydrocarbon, such as benzene, toluene or xylene, or an ether, such as THF, dioxane or DME, or water, or a mixture of solvents, at temperatures from about 60° C. to about 140° C., for example at temperatures from about 80° C. to about 120° C.

In another process for the preparation of the compounds of the formula I, a compound of the formula VI is reacted with thiourea, the obtained compound of the formula XVI is alkylated at the sulfur atom, for example methylated with iodomethane to give a compound of the formula XVII, the compound of the formula XVII is cyclized to a compound of the formula XVIII which is then reacted with a compound of the formula III to give a compound of the formula XIX, and the latter compound is oxidized to a compound of the formula XX which can be converted into a compound of the formula I by reaction with an organometallic compound of the formula XXI.

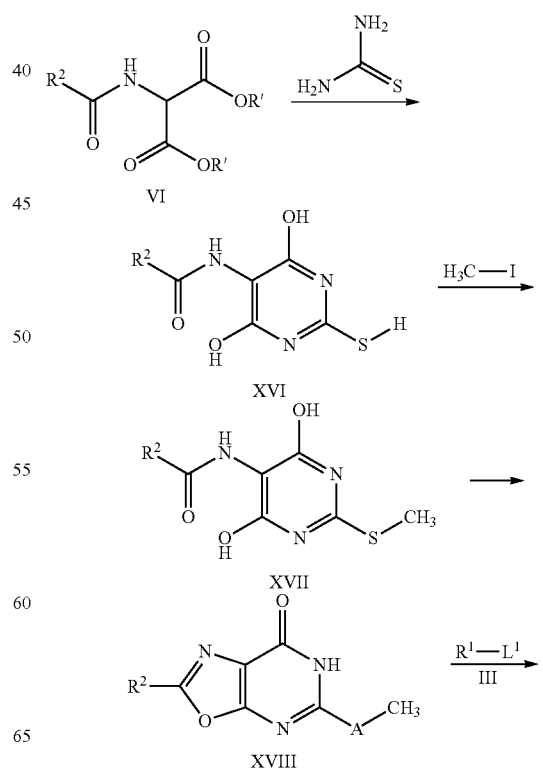

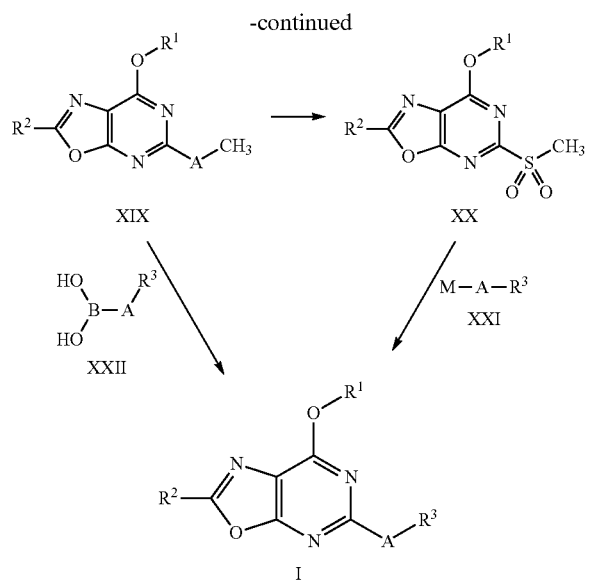

The groups A, $R^1$, $R^2$ and $R^3$ in the compounds of the formulae XVI, XVII, XVIII, XIX, XX and XXI are defined as in the compounds of the formula I and additionally functional groups can be present in protected form or in the form of a precursor group which is later converted into the final group. The group M in the compounds of the formulae XXI is a magnesium halide group Mg-Hal, wherein Hal is chlorine, bromine or iodine, i.e. the compound of the formula XXI is a Grignard compound, or lithium, i.e. the compound of the formula XXI is an organolithium compound, for example.

The reaction of a compound of the formula VI with thiourea is carried out in an inert solvent, for example an alcohol like a ($C_1$-$C_3$)-alkanol such as ethanol, at temperatures from about 50° C. to about 80° C., for example at about 60° C., in the presence of a base, for example an alkaline metal alkoxide such as sodium methoxide, sodium ethoxide, potassium methoxide or potassium tert-butoxide. The methylation of the compound of the formula XVI with iodomethane is favorably carried out with addition of a base, for example an alkaline metal hydroxide or alkoxide such as sodium hydroxide, potassium hydroxide, sodium methoxide, sodium ethoxide or potassium methoxide, in an inert solvent, for example an ether such as THF, dioxane or DME, an alcohol such as methanol, ethanol or isopropanol, an amide such as DMF or NMP, or a mixture of solvents, at temperatures from about 0° C. to about 40° C., for example at temperatures from about 0° C. to about 30° C. The sequence of steps in the preparation of the compounds of the formula XVII can also be changed and first an aminomalonic acid ester of the formula IV such as the diethyl ester reacted with thiourea in the presence of an alkaline metal alkoxide such as sodium ethoxide, then the sulfur atom alkylated, for example methylated with iodomethane, and the obtained product acylated with a compound of the formula V (cf. M. H. Holschbach et al., Eur. J. Med. Chem. 41 (2006), 7-15). The explanations given above with respect to the cyclization of the compound of the formula VIII to the compound of the formula II and the reaction of the compounds of the formulae II and III apply correspondingly to the cyclization of the compound of the formula XVII to the compound of the formula XVIII and the reaction of the compounds of the formulae XVIII and III, respectively. The oxidation of the $CH_3$—S— group in a compound of the formula XIX to the sulfone of the formula XX can be carried out by means of hydrogen peroxide or a peracid such as 3-chloroperbenzoic acid or monoperoxyphthalic acid in an inert solvent, for example a chlorinated hydrocarbon such as dichloromethane or chloroform or an ester such as ethyl acetate or butyl acetate, at temperatures from about 0° C. to about 40° C., for example at about 20° C. The reaction of the compound of the formula XX with the organometallic compound of the formula XXI is carried out in an inert solvent, for example a hydrocarbon such as benzene or hexane or an ether such as THF, dioxane, dibutyl ether, diisopropyl ether or DME, or a mixture of solvents, either without or with addition of a salt, for example a lithium halide such as lithium chloride, at temperatures from about −70° C. to about 80° C., for example at temperatures from about 0° C. to about 40° C., depending on the circumstances of the specific case. Compounds of the formula I can also be obtained directly from compounds of the formula XIX, without oxidation of the $CH_3$—S— group, in a Liebeskind-like reaction with a boronic acid of the formula XXII (cf. L. S. Liebeskind et al., Org. Lett. 4 (2002), 979-981). The groups A and $R^3$ in the compounds of the formulae XXII are defined as in the compounds of the formula I and additionally functional groups can be present in protected form or in the form of a precursor group which is later converted into the final group.

In another process for the preparation of the compounds of the formula I, an aminomalonic acid ester of the formula IV is reacted with an amidine of the formula VII to give a compound of the formula XXIII which is then reacted with a compound of the formula III to give a compound of the formula XXIV, the compound of the formula XXIV is reacted with thiophosgene to give a compound of the formula XXV, the latter compound is alkylated at the sulfur atom, for example methylated with iodomethane to give a compound of the formula XXVI, and the compound of the formula XXVI is converted into a compound of the formula I by reaction with a boronic acid of the formula XXVII.

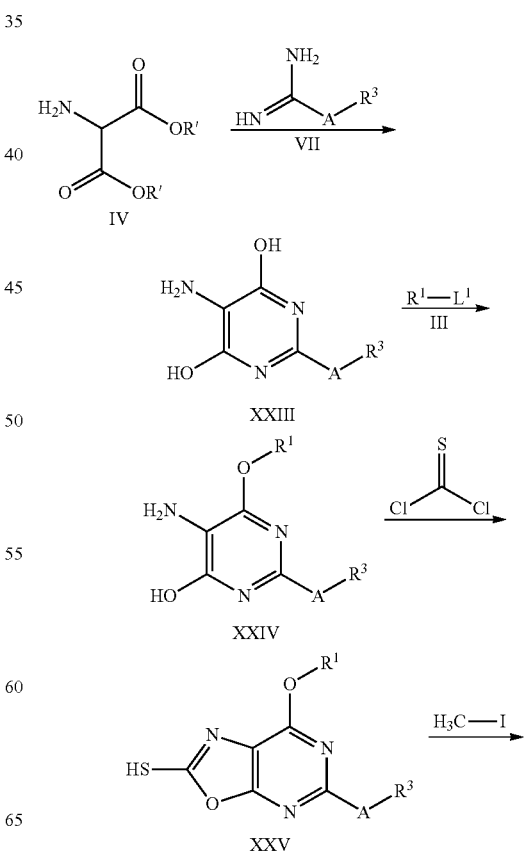

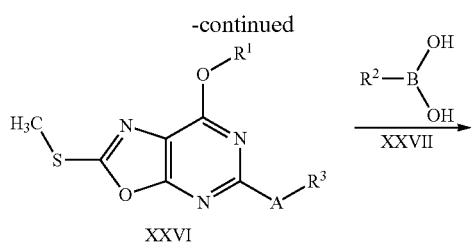

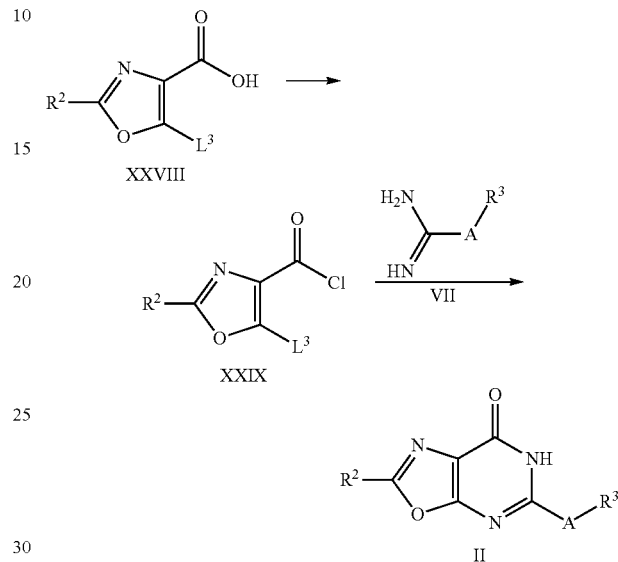

The groups A, $R^1$, $R^2$ and $R^3$ in the compounds of the formulae XXIII, XXIV, XXV, XXVI and XXVII are defined as in the compounds of the formula I and additionally functional groups can be present in protected form or in the form of a precursor group which is later converted into the final group. The explanations given above with respect to the reactions carried out in other processes apply correspondingly to the reactions of the respective type carried out in this process. The reaction of the compounds of the formula XXIII with thiophosgene can be carried out in an inert solvent, for example a hydrocarbon or chlorinated hydrocarbon such as benzene, toluene, chlorobenzene, dichloromethane, chloroform or dichloroethane, an ether such as THF, dioxane or DME, or an amide such as DMF or NMP, or a mixture of solvents, either without or with addition of a base, for example an alkaline metal carbonate such as sodium carbonate, potassium carbonate or cesium carbonate or a tertiary amine such as triethylamine, ethyldiisopropylamine or N-methylmorpholine, at temperatures from about −10° C. to about 80° C., for example at temperatures from about 0° C. to about 60° C. The reaction of the compounds of the formulae XXVI and XXVII to give a compound of the formula I can be carried out under the conditions of the Liebeskind reaction (cf. L. S. Liebeskind et al., Org. Lett. 4 (2002), 979-981) in the presence of a palladium compound such as tris(dibenzylideneacetone)dipalladium(0), which can be employed in the presence of a phosphine such as tri(furan-2-yl)phosphine or triphenylphosphine, or a palladium complex such as tetrakis(triphenylphosphine)palladium(0) or bis(triphenylphosphine)palladium(II) chloride, and a copper compound such as a copper(I) salt like copper(I)thiophene-2-carboxylate, in an inert solvent, for example a hydrocarbon such as benzene, toluene or xylene, or an ether such as THF, dioxane or DME, or water, or a mixture of solvents, either without or with addition of a Lewis acid, for example zinc acetate, at temperatures from about 30° C. to about 100° C., for example at temperatures from about 40° C. to about 80° C.

Compounds of the formula I can also be obtained from a compound of the formula XXVI by oxidizing the group $CH_3$—S— to the sulfone and reacting the obtained compound containing the group $CH_3$—$S(O)_2$— instead of the group $CH_3$—S— with an organometallic compound of the formula $R^2$-M, wherein M is defined as in the compounds of the formula XXI, analogously as outlined above with respect to the oxidation of the compound of the formula XIX to the compound of the formula XX and the reaction of the compounds of the formulae XX and XXI.

In another process for the preparation of the compounds of the formula I, an oxazole-4-carboxylic acid of the formula XXVIII is activated, for example by conversion into the carboxylic acid chloride of the formula XXIX, and then reacted with an amidine of the formula VII to give a compound of the formula II which can then be converted into a compound of the formula I as outlined above.

The group $R^2$ in the compounds of the formulae XXVIII and XXIX is defined as in the compounds of the formula I and additionally functional groups can be present in protected form or in the form of a precursor group which is later converted into the final group. The group $L^3$ in the compounds of the formulae XXVIII and XXIX is a leaving group, for example an ethoxy group or chlorine. The conversion of the carboxylic acid of the formula XXVIII to the acid chloride of the formula XXIX can be carried out under standard conditions, for example by means of thionyl chloride of oxalyl chloride. The reaction of the compounds of the formulae XXIX and VII to give a compound of the formula II can be carried out by first acylating the amidine in the presence of a base, for example an alkaline metal hydroxide such as sodium hydroxide, in an inert solvent, for example a chlorinated hydrocarbon such as dichloromethane, an ether such as THF, dioxane or DME, or water, or a mixture of solvents, at temperatures from about 0° C. to about 40° C., for example at temperatures from about 0° C. to about 30° C., heating the obtained compound in toluene under reflux and subsequently treating it with a base, for example an alkaline metal hydroxide such sodium hydroxide or potassium in an inert solvent, for example an alcohol like a ($C_1$-$C_3$)-alkanol such as ethanol at temperatures from about 10° C. to about 40° C., for example at about 20° C., analogously as described in I. J. Turchi et al., Synthesis (1983), 837-839. In a similar approach for the formation of the oxazolo[5,4-d]pyrimidine ring system, a 5-amido-4-cyano-oxazole can be cyclized by treatment with hydrogen peroxide and an alkaline metal hydroxide such as sodium hydroxide or potassium hydroxide in water at about 100° C. analogously as described in A. B. A. Jansen et al., J. Chem. Soc. (1961), 405-411, for example a 5-acetamido-4-cyano-oxazole such as 5-acetamido-4-cyano-2-phenyl-oxazole which can be cyclized to give the compound of the formula XI in which A is —CH$_2$— and R$^2$ is phenyl which can then be converted in compounds of the formula I as outlined above.

Further compounds of the formula I can be obtained from suitable compounds prepared according to the above-described processes by functionalization or modification of contained functional groups according to standard procedures, for example by esterification, amidation, hydrolysis, etherification, alkylation, acylation, sulfonylation, reduction, oxidation, conversion into salts, and others. For example, a hydroxy group, which may be liberated from an ether group by ether cleavage, for example by means of boron tribromide, or from a protected hydroxy group by deprotection, can be esterified to give a carboxylic acid ester or a sulfonic acid ester, or etherified. Etherifications of hydroxy groups can favorably be performed by alkylation with the respective halogen compound, for example a bromide or iodide, in the presence of a base, for example an alkaline metal carbonate such potassium carbonate or cesium carbonate in an inert solvent, for example an amide like DMF or NMP or a ketone like acetone or butan-2-one, or with the respective alcohol under the conditions of the Mitsunobu reaction referred to above. A hydroxy group can be converted into a halide by treatment with a halogenating agent. A halogen atom can be replaced with a variety of groups in a substitution reaction which may also be a transition-metal catalyzed reaction. A nitro group can be reduced to an amino group, for example by catalytic hydrogenation. An amino group can be modified under standard conditions for alkylation, for example by reaction with a halogen compound or by reductive amination of a carbonyl compound, or for acylation or sulfonylation, for example by reaction with a reactive carboxylic acid derivative, like an acid chloride or anhydride or a sulfonic acid chloride, or with an activated carboxylic acid which may be obtained from the carboxylic acid by treatment with a coupling agent like N,N'-carbonyldiimidazole (CDI), a carbodiimide such as 1,3-dicyclohexylcarbodiimide (DCC) or 1-(3-dimethylaminopropyl)-3-ethylcarbodiimide hydrochloride (EDC), O-(7-azabenzotriazol-1-yl)-N,N,N',N'-tetramethyluronium hexafluorophosphate (HATU), 0-(cyano(ethoxycarbonyl)methyleneamino)-N,N,N',N'-tetramethyluronium tetrafluoroborate (TOTU), or [(benzotriazol-1-yloxy)-dimethylamino-methylene]-dimethyl-ammonium tetrafluoroborate (TBTU), for example. A carboxylic ester group can be hydrolyzed under acidic or basic conditions to give a carboxylic acid. A carboxylic acid group can be activated or converted into a reactive derivative as mentioned afore and reacted with an alcohol or an amine or ammonia to give an ester or amide. A primary amide can be dehydrated to give a nitrile. A sulfur atom, for example in an alkyl-S— group or in a heterocyclic ring, can be oxidized with a peroxide like hydrogen peroxide or a peracid to give a sulfoxide moiety S(O) or a sulfone moiety S(O)$_2$. A carboxylic acid group, carboxylic acid ester group and a ketone group can be reduced to an alcohol, for example by means of a complex hydride such as lithium aluminium hydride, lithium borohydride or sodium borohydride.

All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. If desired, the obtained compounds of the formula I, as well as any intermediate compounds, can be purified by customary purification procedures, for example by recrystallization or chromatography. As already mentioned, all starting compounds and intermediates employed into the above-described syntheses which contain an acidic or basic group, can also be employed in the form of salts, and all intermediates and final target compounds can also be obtained in the form of salts. As likewise mentioned above, depending on the circumstances of the specific case, in order to avoid an unwanted course of a reaction or side reactions during the synthesis of a compound it can generally be necessary or advantageous to temporarily block functional groups by introducing protective groups and deprotect them at a later stage of the synthesis, or to introduce functional groups in the form of precursor groups which later are converted into the desired functional groups. As examples of protecting groups amino-protecting groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protecting groups of carboxylic acid groups which can be protected as ester groups, such as tert-butyl esters which can be deprotected by treatment with trifluoroacetic acid, or benzyl esters which can be deprotected by catalytic hydrogenation. As an example of a precursor group the nitro group may be mentioned which can be converted into an amino group by reduction, for example by catalytic hydrogenation. Such synthesis strategies, and protective groups and precursor groups which are suitable in a specific case, are known to the skilled person.

Another subject of the present invention are the novel starting compounds and intermediates occurring in the synthesis of the compounds of the formula I, including the compounds of the formulae II, III, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII and XXIX, wherein A, R$^1$, R$^2$, R$^3$, R', R", L$^1$, L$^2$, L$^3$ and M are defined as above, in any of their stereoisomeric forms or a mixture of stereoisomeric forms in any ratio, and their salts, and solvates of any of them, and their use as intermediates. The invention also includes all tautomeric forms of the said intermediates and starting compounds. All explanations given above and embodiments specified above with respect to the compounds of the formula I apply correspondingly to the said intermediates and starting compounds. A subject of the invention are in particular the novel specific starting compounds and intermediates disclosed herein. Independently thereof whether they are disclosed as a free compound and/or as a specific salt, they are a subject of the invention both in the form of the free compounds and in the form of their salts, and if a specific salt is disclosed, additionally in the form of this specific salt, and in the form of solvates of any of them.

The compounds of the formula I are useful pharmacologically active compounds which modulate the Edg-1 receptor and more specifically act as efficacious Edg-1 agonists, and which can be employed as pharmaceuticals, or as active ingredients of pharmaceutical compositions or medicaments, and used for the treatment of various diseases. The Edg-1 agonistic action also includes the possibility of a functional impairment of Edg-1 receptor signaling due to tachyphylaxis or receptor desensitization which is desirable in the treatment of certain diseases. The efficacy of the compounds of the formula I can be demonstrated in the pharmacological test described below and other tests which are known to a person skilled in the art, for example in the mouse model of renoprotection after ischemia-reperfusion described in A. S. Awad et al., Am. J. Physiol. Renal Physiol. 290 (2006), F1516-F1524, or in the mouse model of atherosclerosis described in J.-R. Nofer et al., Circulation 115 (2007), 501-508. In the context of the present invention, treatment of diseases is understood as comprising both therapy, including alleviation and cure, of diseases or disease symptoms and prevention or prophylaxis of diseases or disease symptoms. For example, in patients who on account of their disease history are susceptible to myocardial infarction, or to asthmatic attacks, by means of a preventive or prophylactic medicinal treatment the occurrence or re-occurrence of a myocardial infarction, or of asthmatic disease symptoms, respectively, can be prevented or their extent or sequelae decreased. The diseases or disease symptoms can be acute or chronic. Diseases which can be treated with the compounds of the formula I, include cardiovascular diseases, coronary heart disease, coronary artery disease, stable and unstable angina pectoris, Prinzmetal angina (spasm), acute coronary syndrome, myocardial infarction, cardiac ischemia and/or reperfusion injury including cardiac ischemia and/or reperfusion injury during cardiac surgery or transplantation, cardiac insufficiency, heart failure including systolic heart failure, diastolic heart failure and heart failure with preserved ejection fraction (=HF-PEF), cardiomyopathy, stroke, thrombosis, atherosclerosis, endothelial dysfunction, peripheral arterial occlusive disease (=PAOD=peripheral arterial disease=PAD), restenosis, vasculopathy including transplant vasculopathy, endothelial damage after PTCA (=percutaneous transluminal coronary angioplasty), hypertension including systolic hypertension, pulmonary hypertension and portal hypertension, vascular remodeling, vascular permeability disorders, and edema including edema formation after surgery or due to drug treatment, for example. The compounds of the formula I can also be used in the treatment, including therapy and prevention, of diabetes, diabetic complications, diabetic cardiomyopathy, diabetic vasculopathy, retinopathy, renal diseases, nephropathy, renal failure including acute renal failure, renal ischemia and/or renal reperfusion injury, respiratory diseases, asthma bronchiale, pulmonary edema, wound healing disorders, inflammatory diseases, rheumatoid arthritis, sepsis, autoimmune diseases, multiple sclerosis, neurodegenerative diseases, CNS injury, spinal chord injury, pain, and cancer, for example. The compounds of the formula I can further be used for modulating angiogenesis, arteriogenesis, vasculogenesis, lymphangiogenesis and vascular maturation, for modulating lymphocyte homing, for modulating stem cell and progenitor cell mobilization, migration, differentiation and homing, for example by treating stem or progenitor cells ex vivo with a compound of the formula I, and for modulating immunosuppression including immunosuppression after transplantation, for example. Additionally, the compounds of the formula I can be used for vascular stabilization, for neuronal repair, for cytoprotection, for example in combination with a chemotherapy or after radiation, for renoprotection and for cardioprotection, for example. Other uses of the compounds of the formula I are the improvement of cell cultures, for example as a growth factor or survival factor surrogate for supplementing or replacing serum such as fetal calf serum, for example, and the use in regenerative medicine and cell-based therapy, including the use in stem cell or progenitor cell culture, cellular assays, preparation of primary cells including stem cells, tissue culture and the preservation of cells, tissues and organs and their viability, for example for improving cell-based repair, stem cell or progenitor cell therapy, or tissue or organ transplantation.

Another subject of the present invention thus is a compound of the formula I, in any of its stereoisomeric forms, or a mixture of stereoisomeric forms in any ratio, or a physiologically acceptable salt thereof, or a physiologically acceptable solvate of any of them, for use as a pharmaceutical. Another subject is a pharmaceutical composition, or a medicament, comprising at least one compound of the formula I, in any of its stereoisomeric forms, or a mixture of stereoisomeric forms in any ratio, and/or a physiologically acceptable salt thereof, or a physiologically acceptable solvate of any of them, and a pharmaceutically acceptable carrier, i.e. one or more pharmaceutically acceptable carrier substances and/or additives. A subject of the invention also is a compound of the formula I, in any of its stereoisomeric forms, or a mixture of stereoisomeric forms in any ratio, or a physiologically acceptable salt thereof, or a physiologically acceptable solvate of any of them, for use in the treatment of a disease associated with the Edg-1 receptor, in particular a disease which can be treated by an agonistic action on the Edg-1 receptor or in which an agonistic action on the Edg-1 receptor is desired, for example cardiovascular diseases, atherosclerosis, heart failure, peripheral arterial occlusive disease, renal diseases, inflammatory diseases, vascular permeability disorders, diabetes, respiratory diseases, autoimmune diseases, multiple sclerosis, cancer, or any other disease mentioned above or below herein, or for use in cardioprotection, renoprotection or cytoprotection or for any other use mentioned above or below herein. A subject of the invention also is the use of a compound of the formula I in any of its stereoisomeric forms, or a mixture of stereoisomeric forms in any ratio, or a physiologically acceptable salt thereof, or a physiologically acceptable solvate of any of them, for the manufacture of a medicament for the treatment of a disease associated with the Edg-1 receptor, in particular a disease which can be treated by an agonistic action on the Edg-1 receptor or in which an agonistic action on the Edg-1 receptor is desired, for example cardiovascular diseases, atherosclerosis, heart failure, peripheral arterial occlusive disease, renal diseases, inflammatory diseases, vascular permeability disorders, diabetes, respiratory diseases, autoimmune diseases, multiple sclerosis, cancer, or any other disease mentioned above or below herein, or for cardioprotection, renoprotection or cytoprotection or for any other use mentioned above or below herein. A subject of the invention also is a method for the treatment of a disease associated with the Edg-1 receptor, in particular a disease which can be treated by an agonistic action on the Edg-1 receptor or in which an agonistic action on the Edg-1 receptor is desired, for example cardiovascular diseases, atherosclerosis, heart failure, peripheral arterial occlusive disease, renal diseases, inflammatory diseases, vascular permeability disorders, diabetes, respiratory diseases, autoimmune diseases, multiple sclerosis, cancer, or any other disease mentioned above or below herein, or for cardioprotection, renoprotection or cytoprotection or for any other use mentioned above or below herein, comprising administering to a patient in need thereof a pharmacologically effective dose of compound of the formula I in any of its stereoisomeric forms, or a mixture of stereoisomeric forms in any ratio, or a physiologically acceptable salt thereof, or a physiologically acceptable solvate of any of them. A subject of the present invention also is the use of a compound of the formula I in any of its stereoisomeric forms, or a mixture of stereoisomeric forms in any ratio, or a physiologically acceptable salt thereof, or a physiologically acceptable solvate of any of them, as an additive in the culture, the handling or the preservation of cells, tissues or organs, for example during organ transport for transplantation purposes, or in stem cell or progenitor cell culture, or in scientific experiments including assays and pharmacological tests in which human or animal cells, tissues or organs are used.

The compounds of the formula I can also be used in combination with other pharmacologically active compounds, or pharmaceuticals, in particular with compounds which are able to enhance the favorable physiological effect of the compounds according to formula I, or with compounds which cause any undesired side effect which can be prevented or attenuated by the compounds of the formula I. Examples of such other compounds include statins, HDL (high density lipoprotein) enhancer, cytostatics, PPAR gamma (peroxisome proliferator-activated receptor subtype gamma) agonists, ACE/NEP (angiotensin converting enzyme/neutral endopeptidase) inhibitors and factor Xa inhibitors.

The compounds of the formula I, optionally in combination with other pharmacologically active compounds, can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions. Other suitable administration forms are, for example, percutaneous or topical administration, for example in the form of ointments, creams, tinctures, sprays, powders or transdermal therapeutic systems, or inhalative administration, for example in the form of nasal sprays or aerosol mixtures, or forms such as microcapsules, implants or rods. The compounds of the formula I can additionally be used in modes of local drug delivery, for example in coated stents for preventing or reducing in-stent restenosis or by applying them locally by means of a catheter. The appropriate administration form depends, among others, on the disease to be treated and on its severity.

The amount of a compound of the formula I and/or its physiologically acceptable salts and/or solvates present in the pharmaceutical compositions normally ranges from about 0.2 to about 800 mg, for example from about 0.5 to about 500 mg, for example from about 1 to about 200 mg, per unit dose, but depending on the type of the pharmaceutical composition it may also be higher. The pharmaceutical compositions usually comprise from about 0.5 to about 90 percent by weight of the compound of the formula I and/or its physiologically acceptable salts and/or solvates. The production of the pharmaceutical compositions can be carried out in a manner known per se. To this end, one or more compounds of the formula I and/or their physiologically acceptable salts and/or solvates together with one or more solid or liquid pharmaceutical carrier substances, or vehicles, and/or additives, or auxiliary substances, and, if a combination medicament is desired, other pharmacologically active compounds having therapeutic or prophylactic action are brought into a suitable form for administration and dosage which can be used in human or veterinary medicine. As carrier substances and additives, suitable organic and inorganic substances can be used which do not react in an undesired manner with the compounds of the formula I or their physiologically acceptable salts or solvates. As examples of types of additives which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of carrier substances and additives are water, physiologically sodium chloride solution, vegetable oils, waxes, alcohols such as ethanol, isopropanol, 1,2-propanediol, benzyl alcohols or glycerol, polyols, mannitol, polyethylene glycols, polypropylene glycols, glycerol triacetate, polyvinylpyrrolidone, gelatin, cellulose, carbohydrates such as lactose, glucose, saccharose or starch like corn starch, stearic acid and its salts such as magnesium stearate, talc, lanolin, petroleum jelly, or mixtures thereof, for example mixtures of water with one or more organic solvents such as mixtures of water with alcohols. The compounds of the formula I and their physiologically acceptable salts and solvates can also be lyophilized and the obtained lyophilisates used for the production of injectable compositions, for example. For example for topical application, also liposomal compositions are suitable.

The dosage of a compound of the formula I and/or a physiologically acceptable salt and/or solvate thereof to be administered depends on the specific case and, as is usual, has to be adapted by the physician according to the customary rules and procedures to the individual circumstances in order to achieve an optimum effect. It depends, for example, on the nature and the severity of the disorder to be treated, the sex, age, weight and individual responsiveness of the human or animal patient, on the efficacy and duration of action of the compound used, on whether the treatment is for the therapy of a acute or chronic disease or prophylactic, or on whether other active compounds are administered in addition to a compound of the formula I. In general, a daily dose from about 0.01 mg/kg to about 100 mg/kg, or from about 0.1 mg/kg to about 10 mg/kg, or from about 0.3 mg/kg to about 5 mg/kg (in each case mg per kg of bodyweight), for example, is appropriate for administration to an adult weighing about 75 kg in order to obtain the desired results. The daily dose can be administered in a single dose or, in particular when larger amounts are administered, divided into several, for example two, three or four, individual doses. The administration can also be carried out continuously, for example by continuous infusion or injection. Depending on the individual behavior in a specific case, it may be necessary to deviate upward or downward from the indicated dosages.

The compounds of the formula I can also be used for other purposes than those indicated in the foregoing. Non-limiting examples include the use as diagnostics, for example the use in methods for determining the activity of Edg-1 receptors in biological samples, the use as biochemical tools, and the use as intermediates for the preparation of further compounds, for example further pharmacologically active compounds.

The following examples illustrate the invention.

When example compounds containing a basic group were purified by preparative high pressure liquid chromatography (HPLC) on reversed phase (RP) column material and, as customary, the eluent was a gradient mixture of water and acetonitrile containing trifluoroacetic acid (TFA), they were in part obtained in the form of their acid addition salt with trifluoroacetic acid, depending on the details of the workup such as evaporation or lyophilization conditions. In the names of the example compounds and their structural formulae any such contained trifluoroacetic acid is not specified.

Preparative HPLC was performed according to the following methods.

Method HPLC1

Column: Agilent Prep C-18, 10μ, 30×250 mm; flow: 75 ml/min; eluent A: water+0.1% TFA; eluent B: acetonitrile;

gradient: 97% A+3% B for 5 min, then from 97% A+3% B to 10% A+90% B in 7.5 min, then 10% A+90% B for 2.5 min
Method HPLC2

Column: Agilent Prep C-18, 10μ, 30×250 mm; flow: 75 ml/min; eluent A: water+0.1% TFA; eluent B: acetonitrile; gradient: from 90% A+10% B to 10% A+90% B in 8 min, then 10% A+90% B for 7 min Silica gel chromatography according to the following method was performed using a FlashMaster® device.
Method SC1

Column: 20 g pre-packed silica gel cartridges, flow: 10 ml/min; eluent A: heptane; eluent B: ethyl acetate; gradient: 100% A for 5 min, then from 100% A to 90% A+10% B in 2 min, then 90% A+10% B for 10 min, then from 90% A+10% B to 80% A+20% B in 3 min, then 80% A+20% B for 10 min, then from 80% A+20% B to 70% A+30% B in 3 min, then 70% A+30% B for 10 min The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. In the NMR characterization, the chemical shift δ (in ppm), the number of hydrogen atoms and the multiplicity (s=singlet, d=doublet, dd=double doublet, t=triplet, dt=double triplet, q=quartet, m=multiplet; br=broad) of the peaks is given. In the MS characterization, in general the mass number (m/z) of the peak of the molecular ion M, e.g. $M^+$, or of a related ion such as the ion M+1, e.g. $[M+1]^+$, i.e. the protonated molecular ion $[M+H]^+$, which was formed depending on the ionization method used, is given. Generally, the ionization method was electrospray ionization (ESI). The LC/MS conditions used were as follows.
Method LC1

Column: YMC-Pack J'sphere H80, 33×2.1 mm i.d., S-4 μm, 8 nm; flow: 1.0 ml/min; eluent A: acetonitrile+0.05% TFA; eluent B: water+0.05% TFA; gradient: from 5% A+95% B to 95% A+5% B in 2.5 min, then 95% A+5% B for 0.5 min; MS ionization method: $ESI^+$
Method LC2

Column: YMC-Pack J'sphere H80, 33×2.1 mm i.d., S-4 μm, 8 nm; flow: 1.0 ml/min; eluent A: acetonitrile+0.05% TFA; eluent B: water+0.05% TFA; gradient: from 5% A+95% B to 95% A+5% B in 3.4 min, then 95% A+5% B for 1.0 min; MS ionization method: $ESI^+$
Method LC3

Column: YMC-Pack J'sphere H80, 33×2.1 mm i.d., S-4 μm, 8 nm; flow: 1.3 ml/min; eluent A: acetonitrile+0.08% formic acid; eluent B: water+0.1% formic acid; gradient: from 5% A+95% B to 95% A+5% B in 2.5 min, then 95% A+5% B for 0.5 min; MS ionization method: $ESI^+$
Method LC4

Column: YMC-Pack J'sphere ODS H80, 20×2.1 mm i.d., S-4 μm; flow: 1.0 ml/min; eluent A: acetonitrile; eluent B: water+0.05% TFA; gradient: from 4% A+96% B to 95% A+5% B in 2 min, then 95% A+5% B for 0.4 min; MS ionization method: $ESI^+$
Method LC5

Column: YMC-Pack J'sphere H80, 33×2.1 mm i.d., S-4 μm, 8 nm; flow: 1.3 ml/min; eluent A: acetonitrile+0.08% formic acid; eluent B: water+0.1% formic acid; gradient: from 5% A+95% B to 95% A+5% B in 2.5 min; MS ionization method: $ESI^+$
Method LC6

Column: YMC-Pack J'sphere H80, 33×2.1 mm i.d., S-4 μm, 8 nm; flow: 1.0 ml/min; eluent A: acetonitrile+0.05% TFA; eluent B: water+0.05% TEA; gradient: from 2% A+98% B to 95% A+5% B in 5 min, then 95% A+5% B for 1.25 min; MS ionization method: $ESI^+$
Method LC7

Column: YMC-Pack J'sphere H80, 33×2.1 mm i.d., S-4 μm, 8 nm; flow: 1 ml/min; eluent A: acetonitrile+0.05% formic acid; eluent B: water+0.05% formic acid; gradient: from 5% A+95% B to 95% A+5% B in 2.5 min, then 95% A+5% B for 0.5 min; MS ionization method: $ESI^+$
Method LC8

Column: YMC-Pack J'sphere H80, 33×2.1 mm i.d., S-4 μm, 8 nm; flow: 1 ml/min; eluent A: acetonitrile+0.05% formic acid; eluent B: water+0.05% formic acid; gradient: 5% A+95% B for 0.5 min, then from 5% A+95% B to 95% A+5% B in 3 min, then 95% A+5% B for 0.5 min; MS ionization method: $ESI^+$
Method LC9

Column: Waters XBridge C18, 50×4.6 mm, 2.5 μm; flow: 1.3 ml/min; eluent A: acetonitrile+0.08% formic acid; eluent B: water+0.1% formic acid; gradient: from 3% A+97% B to 60% A+40% B in 3.5 min, then from 60% A+40% B to 98% A+2% B in 0.5 min, then 98% A+2% B for 1 min; MS ionization method: $ESI^+$
Method LC10

Column: Waters XBridge C18, 50×4.6 mm, 2.5 μm; flow: 1 ml/min; eluent A: acetonitrile+0.05% TFA; eluent B: water+0.05% TFA; gradient: 5% A+95% B for 0.3 min, then from 5% A+95% B to 95% A+5% B in 3.2 min, then 95% A+5% B for 0.5 min; MS ionization method: $ESI^+$
Method LC11

Column: YMC-Pack J'sphere H80, 33×2.1 mm i.d., S-4 μm, 8 nm; flow: 1.3 ml/min; eluent A: acetonitrile+0.05% TFA; eluent B: water+0.05% TFA; gradient: from 5% A+95% B to 95% A+5% B in 3.5 min, then 95% A+5% B for 0.5 min; MS ionization method: $ESI^+$
Method LC12

Column: YMC-Pack J'sphere H80, 33×2.1 mm i.d., S-4 μm, 8 nm; flow: 1.0 ml/min; eluent A: acetonitrile+0.05% TFA; eluent B: water+0.05% TFA; gradient: from 5% A+95% B to 95% A+5% B in 3.7 min; MS ionization method: $ESI^+$
Method LC13

Column: YMC-Pack J'sphere H80, 33×2.1 mm i.d., S-4 μm, 8 nm; flow: 1.3 ml/min; eluent A: acetonitrile+0.05% TFA; eluent B: water+0.05% TFA; gradient: from 5% A+95% B to 95% A+5% B in 2.5 min, then 95% A+5% B for 0.7 min; MS ionization method: $ESI^+$
Method LC14

Column: Waters XBridge C18, 50×4.6 mm, 2.5 μm; flow: 1.7 ml/min; eluent A: acetonitrile+0.05% TFA; eluent B: water+0.05% TFA; gradient: 5% A+95% B for 0.2 min, then from 5% A+95% B to 95% A+5% B in 2.2 min, then 95% A+5% B for 1 min; MS ionization method: $ESI^+$
Method LC15

Column: Waters XBridge C18, 50×4.6 mm, 2.5 μm; flow: 1.7 ml/min; eluent A: acetonitrile+0.05% TFA; eluent B: water+0.05% TFA; gradient: 5% A+95% B for 0.2 min, then from 5% A+95% B to 95% A+5% B in 2.2 min, then 95% A+5% B for 1.1 min; MS ionization method: $ESI^+$
Method LC16

Column: Waters XBridge C18, 50×4.6 mm, 2.5 μm; flow: 1.7 ml/min; eluent A: acetonitrile+0.05% TFA; eluent B: water+0.05% TFA; gradient: 5% A+95% B to 95% A+5% B in 2.6 min, then 95% A+5% B for 0.4 min; MS ionization method: $ESI^+$
Method LC17

Column: Waters XBridge C18, 50×4.6 mm, 2.5 μm; flow: 1.7 ml/min; eluent A: acetonitrile+0.05% TFA; eluent B:

water+0.05% TFA; gradient: 5% A+95% B to 95% A+5% B in 3.3 min, then 95% A+5% B for 0.55 min; MS ionization method: ESI⁺

Method LC18

Column: YMC-Pack J'sphere H80, 33×2.1 mm i.d., S-4 µm, 8 nm; flow: 1.0 ml/min; eluent A: acetonitrile+0.05% TFA; eluent B: water+0.05% TFA; gradient: 2% A+98% B for 1 min, then from 2% A+98% B to 95% A+5% B in 4 min, then 95% A+5% B for 1.25 min; MS ionization method: ESI⁺

Method LC19

Column: Merck Chromolith FastGradient RP-18e, 50×2 mm; flow: 2.0 ml/min; eluent A: acetonitrile+0.05% TFA; eluent B: water+0.05% TFA; gradient: 2% A+98% B for 0.2 min, then from 2% A+98% B to 98% A+2% B in 2.2 min, then 98% A+2% B for 0.8 min; MS ionization method: ESI⁺

Method LC20

Column: Merck Chromolith FastGradient RP-18e, 50×2 mm; flow: 2.4 ml/min; eluent A: acetonitrile+0.05% TFA; eluent B: water+0.05% TFA; gradient: 2% A+98% B for 0.2 min, then from 2% A+98% B to 98% A+2% B in 2.2 min, then 98% A+2% B for 0.8 min; MS ionization method: ESI⁺

Method LC21

Column: Waters HPLC BEH XBridge C18, 50×2.1 mm, 1.7 µm; flow: 0.9 ml/min; eluent A: acetonitrile+0.08% formic acid; eluent B: water+0.1% formic acid; gradient: from 5% A+95% B to 95% A+5% B in 1.1 min, then 95% A+5% B for 0.6 min; MS ionization method: ESI⁺

Method LC22

Column: Waters HPLC BEH XBridge C18, 50×2.1 mm, 1.7 µm; flow: 0.9 ml/min; eluent A: acetonitrile+0.035% formic acid; eluent B: water+0.5% formic acid; gradient: from 5% A+95% B to 60% A+40% B in 2.1 min, then from 60% A+40% B to 95% A+5% B in 0.5 min, then 95% A+5% B for 0.6 min; MS ionization method: ESI⁺

EXAMPLE 1

2-(2-Chloro-5-fluoro-phenyl)-5-morpholin-4-ylmethyl-7-propoxy-oxazolo[5,4-d]pyrimidine

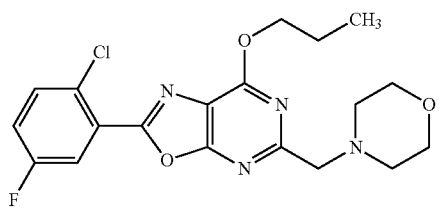 [SMILES: CCCOc1nc(CN2CCOCC2)nc2oc(-c3cc(F)ccc3Cl)nc12]

(a) 2-(2-Chloro-5-fluoro-benzoylamino)malonic acid diethyl ester

A solution of 24.4 g of 2-chloro-5-fluoro-benzoyl chloride in 100 ml of dichloromethane was added dropwise to a solution of 26.8 g of aminomalonic acid diethyl ester hydrochloride and 38.6 ml of triethylamine in 50 ml of dichloromethane with cooling in an ice bath. The reaction mixture was stirred for 2 h while the temperature was maintained at 0-5° C. Then 100 ml of water were added slowly. The phases were separated, and the aqueous phase was extracted twice with 100 ml of dichloromethane. The combined organic phases were dried with sodium sulfate, filtered and evaporated to give 39.3 g of the crude title compound.

(b) 2-Chloro-5-fluoro-N-(4,6-dihydroxy-2-methylpyrimidin-5-yl)-benzamide 1.5 equivalents of sodium methoxide (30% in methanol) were added to a suspension of 13.4 g of acetamidine hydrochloride in 150 ml of ethanol. The precipitate was filtered off and washed with 100 ml of ethanol. Additional 1.5 equivalents of sodium methoxide (30% in methanol) were added to the filtrate. Then a solution of 39.3 g of 2-(2-chloro-5-fluoro-benzoylamino)malonic acid diethyl ester in 100 ml of ethanol was added dropwise. The reaction mixture was stirred at 60° C. for 2 h. After cooling to 0° C. for 30 min, the precipitate was filtered off with suction, washed with 100 ml of a solution of hydrogen chloride in isopropanol and dried to give 35.7 g of the title compound.

(c) 2-(2-Chloro-5-fluoro-phenyl)-5-methyl-6H-oxazolo[5,4-d]pyrimidin-7-one 22.2 g of phosphorus pentachloride were added to a suspension of the product obtained in step (b) in 300 ml of dry chloroform. The reaction mixture was stirred at room temperature for 3 h. Then another 22.2 g of phosphorus pentachloride were added and the reaction mixture was stirred at 60° C. for 4 h. After cooling to room temperature, the precipitate was filtered off, washed with a little dichloromethane and dried to give 30.2 g of the crude title compound.

(d) 2-(2-Chloro-5-fluoro-phenyl)-5-methyl-7-propoxy-oxazolo[5,4-d]pyrimidine 26.2 g of potassium carbonate and 6.4 g of 1-bromo-propane were added to a solution of 15 g of 2-(2-chloro-5-fluoro-phenyl)-5-methyl-6H-oxazolo[5,4-d]pyrimidin-7-one in 150 ml of dimethylformamide. The suspension was stirred at 60° C. for 72 h. After cooling, the mixture was poured onto 300 ml of water. The precipitate was filtered off by suction. The obtained mixture of regioisomers was separated by silica gel chromatography (method SC1). Besides 3.3 g of 2-(2-chloro-5-fluoro-phenyl)-5-methyl-6-propyl-6H-oxazolo[5,4-d]pyrimidin-7-one, 3.2 g of the title compound were obtained.

LC/MS (method LC1): Rt=2.26 min; m/z=322.01 [M+H]⁺

(e) 5-Bromomethyl-2-(2-chloro-5-fluoro-phenyl)-7-propoxy-oxazolo[5,4-d]pyrimidine A mixture of 1 g of 2-(2-chloro-5-fluoro-phenyl)-5-methyl-7-propoxy-oxazolo[5,4-d]pyrimidine, 609 mg of N-bromosuccinimide and 25 mg of azobisisobutyronitrile in 30 ml of tetrachloromethane was heated to reflux for 72 h. After evaporation to dryness and purification by silica gel chromatography (method SC1), 1.65 g of a mixture of the 5-bromomethyl compound and the 5-dibromomethyl compound were obtained.

3.1 g of diethyl phosphite and 2.9 g of ethyldiisopropylamine were added to a solution of 1.5 g of the obtained mixture in 50 ml of tetrahydrofuran at 0° C. The reaction mixture was stirred at 0° C. for 2 h. Then 20 ml of a half-saturated solution of sodium hydrogencarbonate were added and the mixture was extracted twice with 30 ml each of diethyl ether. The combined organic phases were dried with sodium sulfate, filtered and evaporated in vacuo. Silica gel chromatography (method SC1) of the residue yielded 400 mg of the title compound.

LC/MS (method LC1): Rt=2.39 min; m/z=399.95 [M+H]⁺

(f) 2-(2-Chloro-5-fluoro-phenyl)-5-morpholin-4-ylmethyl-7-propoxy-oxazolo[5,4-d]pyrimidine A mixture of 130 mg of 5-bromomethyl-2-(2-chloro-5-fluoro-phenyl)-7-propoxy-oxazolo[5,4-d]pyrimidine, 33.9 mg of morpholine and 135 mg of potassium carbonate in 3 ml of dimethylformamide was stirred at room temperature for 4 h. Then 50 ml water and 50 ml of dichloromethane were added. The phases were separated and the aqueous layer was extracted with 50 ml of dichloromethane. The combined organic layers were dried with sodium sulfate, filtered, and evaporated in vacuo. The residue was purified by preparative HPLC (Method HPLC1) to give 72 mg of the title compound in the form of 2-(2-chloro-5-fluoro-phenyl)-5-morpholin-4-ylmethyl-7-propoxy-oxazolo[5,4-d]pyrimidine trifluoroacetic acid salt.

LC/MS (method LC1): Rt=1.35 min; m/z=407.14 [M+H]$^+$

EXAMPLE 2

2-Furan-2-yl-5-morpholin-4-ylmethyl-7-propoxy-oxazolo[5,4-d]pyrimidine

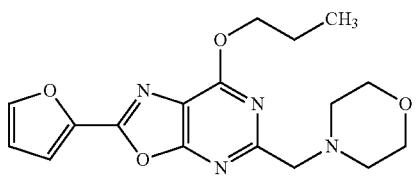 [SMILES: CCCOc1nc(CN2CCOCC2)nc2oc(-c3ccco3)nc12]

(a) 5-Bromomethyl-2-furan-2-yl-7-propoxy-oxazolo[5,4-d]pyrimidine and 2-(5-bromo-furan-2-yl)-5-bromomethyl-7-propoxy-oxazolo[5,4-d]pyrimidine A mixture of 5.4 g of 2-furan-2-yl-5-methyl-7-propoxy-oxazolo[5,4-d]pyrimidine (prepared in analogy to the procedures described in example 1, steps (a) to (d)), 4.1 g of N-bromosuccinimide and 171 mg of azobisisobutyronitrile in 75 ml of tetrachloromethane was heated under reflux for 3 h. Then additional 6.2 g of N-bromosuccinimide and 257 mg of azobisisobutyronitrile were added, and the reaction mixture was heated under reflux for 3 days. After cooling, the precipitate was filtered off and washed with tetrachloromethane. 10.4 g of a mixture of the 5-bromomethyl compound and the 5-dibromomethyl compound, in which the furanyl groups had in part been brominated in position 5, were obtained.

19.3 ml of diethyl phosphite and 25.6 g of ethyldiisopropylamine were added at 0° C. to a solution of 10.4 g of the obtained mixture in 200 ml of tetrahydrofuran. The reaction mixture was stirred at 0° C. for 2 h and then at room temperature for 16 h. Then 200 ml of a half-saturated solution of sodium hydrogencarbonate were added, and the mixture was extracted twice with 100 ml each of diethyl ether. The combined organic layers were dried with sodium sulfate, filtered and evaporated in vacuo. Chromatography of the residue (silica gel, ethyl acetate/n-heptane, 8:2) yielded 8.3 g of a mixture of 5-bromomethyl-2-furan-2-yl-7-propoxy-oxazolo[5,4-d]pyrimidine and 2-(5-bromo-furan-2-yl)-5-bromomethyl-7-propoxy-oxazolo[5,4-d]pyrimidine as a light yellow solid.

(b) 2-Furan-2-yl-5-morpholin-4-ylmethyl-7-propoxy-oxazolo[5,4-d]pyrimidine 91.5 mg of morpholine and 207 mg of potassium carbonate were added to a solution of 169 mg of the mixture of 5-bromomethyl-2-furan-2-yl-7-propoxy-oxazolo[5,4-d]pyrimidine and 2-(5-bromo-furan-2-yl)-5-bromomethyl-7-propoxy-oxazolo[5,4-d]pyrimidine obtained in step (a) in 3 ml of dimethylformamide. The reaction mixture was stirred at room temperature for 48 h. Then 50 ml each of water and ethyl acetate were added, the mixture was filtered through a Varian ChemElut cartridge, the cartridge washed with 10 ml of ethyl acetate, and the combined filtrates were evaporated to dryness in vacuo. Preparative HPLC (method HPLC1) of the residue yielded 41 mg of 2-(5-bromo-furan-2-yl)-5-morpholin-4-ylmethyl-7-propoxy-oxazolo[5,4-d]pyrimidine (example 3) and 25 mg of the title compound in the form of 2-furan-2-yl-5-morpholin-4-ylmethyl-7-propoxy-oxazolo[5,4-d]pyrimidine trifluoroacetic acid salt.

LC/MS (method LC1): Rt=1.06 min; m/z=345.11 [M+H]$^+$

EXAMPLE 3

2-(5-Bromo-furan-2-yl)-5-morpholin-4-ylmethyl-7-propoxy-oxazolo[5,4-d]pyrimidine

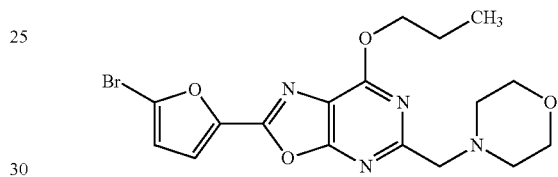

The title compound was prepared as described in example 2 and obtained in the form of 2-(5-bromo-furan-2-yl)-5-morpholin-4-ylmethyl-7-propoxy-oxazolo[5,4-d]pyrimidine trifluoroacetic acid salt. Yield: 41 mg.

LC/MS (method LC1): Rt=1.26 min; m/z=423.03 [M+H]$^+$

EXAMPLE 4

3-(5-Morpholin-4-ylmethyl-7-propoxy-oxazolo[5,4-d]pyrimidin-2-yl)-phenol

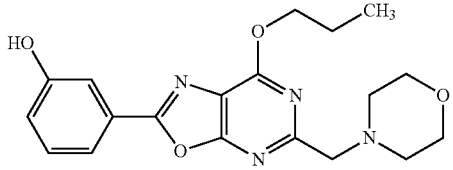 [SMILES: CCCOc1nc(CN2CCOCC2)nc2oc(-c3cccc(O)c3)nc12]

1.25 ml of a 1 M solution of boron tribromide in dichloromethane were slowly added to a solution of 160 mg of 2-(3-methoxy-phenyl)-5-morpholin-4-ylmethyl-7-propoxy-oxazolo[5,4-d]pyrimidine in 5 ml of dichloromethane at 0° C. The reaction mixture was stirred at 0° C. for 2 h and at room temperature for 1 h. The mixture was cautiously neutralized with a saturated solution of sodium hydrogencarbonate. The organic layer was separated and the aqueous layer extracted two times with dichloromethane. The combined organic layers were dried with sodium sulfate, filtered and evaporated in vacuo. The residue was purified by preparative HPLC (method HPLC1) to give 23 mg of the title compound in the form of 3-(5-morpholin-4-ylmethyl-7-propoxy-oxazolo[5,4-d]pyrimidin-2-yl)phenol trifluoroacetic acid salt.

LC/MS (method LC2): Rt=1.17 min; m/z=371.18 [M+H]$^+$

EXAMPLE 5

5-(4-Chloro-benzyl)-2-(3-fluoro-phenyl)-7-propoxy-oxazolo[5,4-d]pyrimidine

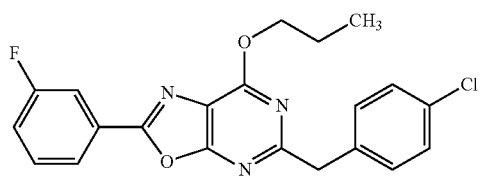 [SMILES: CCCOc1nc(Cc2ccc(Cl)cc2)nc2oc(-c3cccc(F)c3)nc12]

(a) 2-(3-Fluoro-benzoylamino)-malonic acid diethyl ester 36.1 ml of triethylamine were added to a solution of 25 g of aminomalonic acid diethyl ester hydrochloride in 200 ml of dichloromethane with cooling in an ice bath. Then a solution of 18.7 g of 3-fluoro-benzoyl chloride in 100 ml of dichloromethane was added dropwise. After stirring for 2 h at 0° C., 100 ml of water were added dropwise. The layers were separated, and the aqueous layer was extracted with 100 ml of dichloromethane. The combined organic layers were dried with magnesium sulfate, filtered and evaporated to give 33.2 g of the crude title compound.

(b) N-[2-(4-Chloro-benzyl)-4,6-dihydroxy-pyrimidin-5-yl]-3-fluoro-benzamide hydrochloride 2.25 g of sodium were dissolved in 140 ml of ethanol at 60° C. to give a solution of sodium ethoxide. 6.9 g of 2-(4-chloro-phenyl)acetamidine hydrochloride were added while the temperature was maintained at 60° C. The mixture was stirred for 10 min, and then a solution of 10 g of 2-(3-fluoro-benzoylamino)-malonic acid diethyl ester in 20 ml of ethanol was added. The reaction mixture was stirred at 60° C. for 3 h and then evaporated to dryness. The residue was dissolved in the minimum amount of water, and the pH was adjusted to 1-2 by addition of concentrated aqueous hydrochloric acid. The precipitate was filtered off and dried in an infrared dryer until constant weight. 8.9 g of the title compound were obtained.

(c) 5-(4-Chloro-benzyl)-2-(3-fluoro-phenyl)-6H-oxazolo[5,4-d]pyrimidin-7-one 7.4 g of phosphorus pentachloride were added at 60° C. to a suspension of 8.9 g of N-[2-(4-chloro-benzyl)-4,6-dihydroxy-pyrimidin-5-yl]-3-fluoro-benzamide hydrochloride in 100 ml of dry chloroform. After heating at 60° C. for several hours, 5.5 g of phosphorus oxychloride were added and the reaction mixture was stirred at 75° C. for 20 h. After cooling to room temperature, the precipitate was filtered off and purified by silica gel chromatography (gradient from ethyl acetate to dichloromethane to dichloromethane/methanol 3:1). The product fractions were evaporated and the residue washed with chloroform and water and dried in an infrared dryer until constant weight to give 0.47 g of the title compound.

(d) 5-(4-Chloro-benzyl)-2-(3-fluoro-phenyl)-7-propoxy-oxazolo[5,4-d]pyrimidine 28 mg of potassium carbonate and 21 mg of 1-bromopropane were added to a solution of 60 mg of 5-(4-chloro-benzyl)-2-(3-fluoro-phenyl)-6H-oxazolo[5,4-d]pyrimidin-7-one in 3 ml of dimethylformamide, and the reaction mixture was stirred at 60° C. for 16 h. After cooling, the mixture was subjected to chromatography (silica gel, gradient from heptane to heptane/ethyl acetate 3:1). 15 mg of the title compound were obtained.

LC/MS (method LC1): Rt=2.62 min; m/z=398.21 [M+H]$^+$

Analogously to the preparation of the compound of example 5, the example compounds of the formula Iu listed in Table 1 were prepared. They can be referred to as 2-($R^2$)-5-[2-($R^3$)-ethyl]-7-($R^1$-oxy)-oxazolo[5,4-d]pyrimidine, allowing for necessary adaptations in view of the rules of nomenclature, for example as 5-[2-(4-methoxy-phenyl)-ethyl]-2-(3-methyl-phenyl)-7-propoxy-oxazolo[5,4-d]pyrimidine in the case of the compound of example 8.

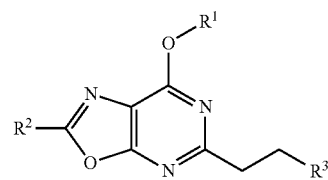

TABLE 1

Example compounds of the formula Iu

| Example | $R^1$ | $R^2$ | $R^3$ | LC/MS | Rt [min] | m/z [M + H]$^+$ |
|---|---|---|---|---|---|---|
| 6 | n-propyl | 3-fluoro-phenyl | 4-chloro-phenyl | LC1 | 2.75 | 412.12 |
| 7 | cyclopropyl-methyl | 3-fluoro-phenyl | 4-chloro-phenyl | LC1 | 2.72 | 424.1 |
| 8 | n-propyl | 3-methyl-phenyl | 4-methoxy-phenyl | LC9 | 5.52 | 404.22 |

EXAMPLE 9

7-Cyclopropylmethoxy-5-(2-methyl-2-phenyl-propyl)-2-(3-methyl-phenyl)-oxazolo[5,4-d]pyrimidine

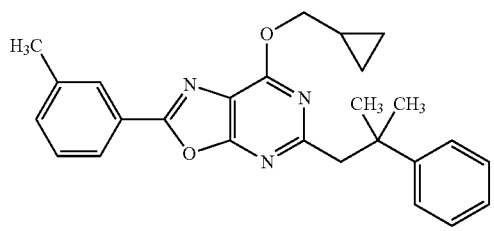 [SMILES: Cc1cccc(-c2nc3c(OCC4CC4)nc(CC(C)(C)c4ccccc4)nc3o2)c1]

The title compound was prepared analogously to the preparation of the compound of example 5.

LC/MS (method LC9): Rt=5.70 min; m/z=414.3 [M+H]$^+$

EXAMPLE 10

5-[1-(4-Chloro-phenyl]-cyclopropyl]-7-propoxy-2-(3-methyl-phenyl)-oxazolo[5,4-d]pyrimidine

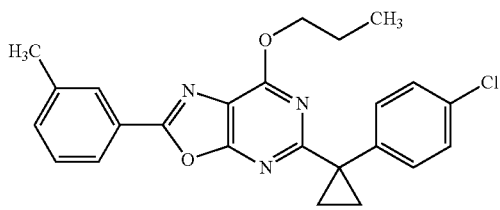 [SMILES: CCCOc1nc(C2(c3ccc(Cl)cc3)CC2)nc2oc(-c3cccc(C)c3)nc12]

The title compound was prepared analogously to the preparation of the compound of example 5.
LC/MS (method LC9): Rt=5.90 min; m/z=420.22 [M+H]$^+$

EXAMPLE 11

5-(3,4-Dichloro-benzyl)-7-propoxy-2-(3-methyl-phenyl)-oxazolo[5,4-d]pyrimidine

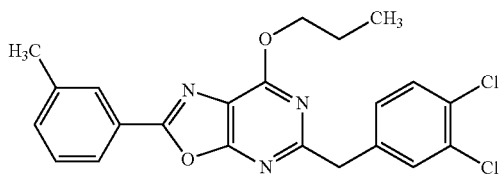 [SMILES: CCCOc1nc(Cc2ccc(Cl)c(Cl)c2)nc2oc(-c3cccc(C)c3)nc12]

(a) 2-(3-Methyl-benzoylamino)malonic acid diethyl ester 41.1 g of aminomalonic acid diethyl ester hydrochloride were dissolved in 200 ml of dichloromethane, and 80.7 ml of triethylamine were added with cooling in an ice bath. A solution of 30 g of 3-methyl-benzoyl chloride in 200 ml of dichloromethane was slowly added dropwise. After 2 h at 0° C., 100 ml of water were added dropwise. The phases were separated, and the aqueous phase was extracted with 100 ml of dichloromethane. The combined organic phases were dried with sodium sulfate, filtered and evaporated to give 54 g of the crude title compound.

(b) N-(4,6-Dihydroxy-2-mercapto-pyrimidin-5-yl)-3-methyl-benzamide 1.5 equivalents of sodium methoxide (30% in methanol) were added to 7.79 g of thiourea in 150 ml of absolute ethanol. A solution of 30 g of 2-(3-methyl-benzoylamino)malonic acid diethyl ester in 100 ml of absolute ethanol was added dropwise, and the reaction mixture was stirred at 60° C. for 2 h. Then the mixture was cooled to 0° C. for 30 min, and the precipitate was filtered off with suction, washed and dried. 28.6 g of the crude title compound were obtained.

(c) N-(4,6-Dihydroxy-2-methylsulfanyl-pyrimidin-5-yl)-3-methyl-benzamide 28.6 g of N-(4,6-dihydroxy-2-mercapto-pyrimidin-5-yl)-3-methyl-benzamide in 280 ml of water were cooled to 0° C. With cooling, 10.3 g of sodium hydroxide were added, and the mixture was stirred at 0° C. for 30 min. Then a solution of 6.4 ml of iodomethane in 108 ml of N-methylpyrrolidin-2-one was added. After completion of the reaction (6 h), the mixture was acidified with 6 N hydrochloric acid, and the precipitate filtered off and dried. 21.3 g of the title compound were obtained.

(d) 5-Methylsulfanyl-2-(3-methyl-phenyl)-oxazolo[5,4-d]pyrimidin-7-ol 21 g of N-(4,6-dihydroxy-2-methylsulfanyl-pyrimidin-5-yl)-3-methyl-benzamide in 100 ml of phosphorus oxychloride were heated to 70° C. for 3 h. After cooling, the mixture was poured into 500 ml of diethyl ether. The precipitate was filtered off and washed with diethyl ether. 7.6 g of the title compound were obtained.
LC/MS (method LC1): Rt=1.62 min; m/z=274.10 [M+H]$^+$

(e) 5-Methylsulfanyl-7-propoxy-2-(3-methyl-phenyl)-oxazolo[5,4-d]pyrimidine 7.1 g of 5-methylsulfanyl-2-(3-methyl-phenyl)-oxazolo[5,4-d]pyrimidin-7-ol were dissolved in 50 ml of dimethylformamide, and 14.4 g of potassium carbonate and then 3.2 g of 1-bromo-propane were added. The suspension was stirred at 60° C. for 5 h and then, after cooling, poured onto 150 ml of water. The precipitate was filtered off with suction. The obtained mixture of regioisomers was separated by silica gel chromatography (method SC1). Besides 2.3 g of 5-methylsulfanyl-6-propyl-2-(3-methyl-phenyl)-6H-oxazolo[5,4-d]pyrimidin-7-one (LC/MS (method LC1): Rt=2.16 min; m/z=316.14 [M+H]$^+$), 3.4 g of the title compound were obtained.
LC/MS (method LC1): Rt=2.54 min; m/z=316.14 [M+H]$^+$

(f) 5-Methanesulfonyl-7-propoxy-2-(3-methyl-phenyl)-oxazolo[5,4-d]pyrimidine 3.9 g of 5-methylsulfanyl-7-propoxy-2-(3-methyl-phenyl)-oxazolo[5,4-d]pyrimidine were dissolved in 100 ml of dichloromethane, 6.4 g of 3-chloroperbenzoic acid were added, and the reaction mixture was stirred at room temperature for 2 h. The precipitate was filtered off and washed with dichloromethane. The combined filtrates were washed two times with 100 ml each of an aqueous 0.1 N sodium hydroxide solution, dried over sodium sulfate, filtered and evaporated in vacuo. 4.1 g of the title compound were obtained.
LC/MS (method LC1): Rt=1.96 min; m/z=348.07 [M+H]$^+$

(g) 5-(3,4-Dichloro-benzyl)-7-propoxy-2-(3-methyl-phenyl)-oxazolo[5,4-d]pyrimidine 100 mg of 3,4-dichloro-benzyl bromide were dissolved in 5 ml of diethyl ether, 11 mg of magnesium turnings were added, and the mixture was stirred at room temperature for 16 h. Then the solution was decanted from the solids and added to a solution of 100 mg of 5-methanesulfonyl-7-propoxy-2-(3-methyl-phenyl)-oxazolo[5,4-d]pyrimidine in 3 ml of dioxane. The reaction mixture was heated to 30° C. for 4 h. After cooling, the mixture was evaporated. The residue was purified by silica gel chromatography (method SC1) and subsequently by preparative HPLC (method HPLC2). 17 mg of the title compound were obtained.
LC/MS (method LC2): Rt=3.67 min; m/z=428.26 [M+H]$^+$

EXAMPLE 12

2-(3-Fluoro-phenyl)-7-propoxy-5-(4-trifluoromethyl-benzyl)-oxazolo[5,4-d]pyrimidine

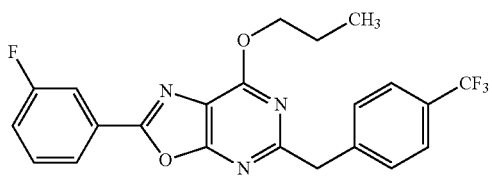 [SMILES: CCCOc1nc(Cc2ccc(C(F)(F)F)cc2)nc2oc(-c3cccc(F)c3)nc12]

146.5 mg of 5-bromomethyl-2-(3-fluoro-phenyl)-7-propoxy-oxazolo[5,4-d]pyrimidine and 114 mg of 4-trifluoromethyl-benzeneboronic acid were dissolved in 3 ml of toluene. 170 mg of tripotassium phosphate and 11.2 mg of tricyclohexylphosphine were added, and argon was bubbled through the mixture for 10 min. Then 4.5 mg of palladium(II) acetate were added, and the reaction mixture was heated to reflux for 8 h under argon. After cooling, ethyl acetate and water were added. The mixture was filtered through a ChemElut cartridge and the cartridge washed with ethyl acetate. The combined filtrates were evaporated in vacuo and the residue purified by preparative HPLC (method HPLC2). 23 mg of the title compound were obtained.

LC/MS (method LC1): Rt=2.67 min; m/z=432.20 [M+H]$^+$

EXAMPLE 13

5-(1-Phenyl-ethyl)-7-propoxy-2-(3-methyl-phenyl)-oxazolo[5,4-d]pyrimidine

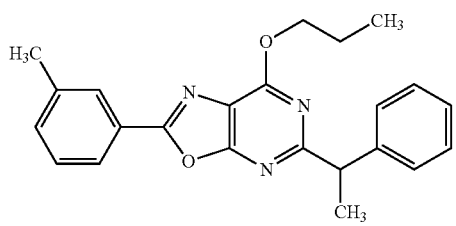 [SMILES: CCCOc1nc(C(C)c2ccccc2)nc2oc(-c3cccc(C)c3)nc12]

(a) 5-(1-Phenyl-vinyl)-7-propoxy-2-(3-methyl-phenyl)-oxazolo[5,4-d]pyrimidine 298 mg of 1-phenyl-vinylmagnesium bromide were added to a solution of 500 mg of 5-methanesulfonyl-7-propoxy-2-(3-methyl-phenyl)-oxazolo[5,4-d]pyrimidine (example 5, step (f)) and 61 mg of lithium chloride in 20 ml of tetrahydrofuran. The reaction mixture was stirred for 1 h. Then 100 ml of ethyl acetate were added. The solution was extracted with 1 N hydrochloric acid, dried over sodium sulfate, filtered and evaporated in vacuo to give the crude title compound.

(b) 5-(1-Phenyl-ethyl)-7-propoxy-2-(3-methyl-phenyl)-oxazolo[5,4-d]pyrimidine

The 5-(1-phenyl-vinyl)-7-propoxy-2-(3-methyl-phenyl)-oxazolo[5,4-d]pyrimidine obtained in step (a) was dissolved in 20 ml of methanol. 10% palladium on charcoal was added and the mixture was hydrogenated under a hydrogen pressure of about 1 bar. After 5 h the catalyst was filtered off and the solvents were removed in vacuo. Preparative HPLC (method HPLC2) of the residue yielded 125 mg of the title compound.

LC/MS (method LC6): Rt=4.94 min; m/z=374.22 [M+H]$^+$

Analogously to the preparation of the compound of example 13, the example compounds of the formula Iv listed in Table 2 were prepared. They can be referred to as 2-(R$^2$)-5-[1-(R$^3$)-ethyl]-7-(R$^1$-oxy)-oxazolo[5,4-d]pyrimidine, allowing for necessary adaptations in view of the rules of nomenclature, for example as 7-ethoxy-2-(3-fluoro-phenyl)-5-(1-phenyl-ethyl)-oxazolo[5,4-d]pyrimidine in the case of the compound of example 15.

Iv

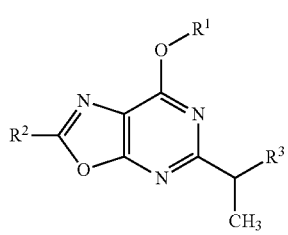

TABLE 2

Example compounds of the formula Iv

| Example | R$^1$ | R$^2$ | R$^3$ | LC/MS | Rt [min] | m/z [M + H]$^+$ |
|---|---|---|---|---|---|---|
| 14 | n-propyl | 3-fluoro-phenyl | phenyl | LC6 | 4.85 | 378.2 |
| 15 | ethyl | 3-fluoro-phenyl | phenyl | LC9 | 5.38 | 364.2 |
| 16 | cyclopropyl-methyl | 3-methyl-phenyl | phenyl | LC9 | 5.55 | 386.3 |

EXAMPLE 17

4-[5-(4-Chloro-benzyl)-7-propoxy-oxazolo[5,4-d]pyrimidin-2-yl]-2,6-dimethyl-phenol

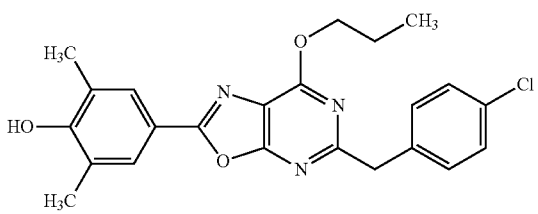 [SMILES: CCCOc1nc(Cc2ccc(Cl)cc2)nc2oc(-c3cc(C)c(O)c(C)c3)nc12]

20 ml of a 1 M solution of boron tribromide in dichloromethane was added to 435 mg of 5-(4-chloro-benzyl)-2-(4-methoxy-3,5-dimethyl-phenyl)-7-propoxy-oxazolo[5,4-d]pyrimidine (example 168, prepared analogously to the preparation of the compound of example 5). The reaction mixture was stirred at room temperature for 30 min. Upon completion of the reaction the solution was cooled with ice and a saturated sodium hydrogencarbonate solution was added until the pH was adjusted to 7. Filtration of the precipitate yielded the crude product which was purified by preparative HPLC (method HPLC2) to give 263 mg of the title compound.

LC/MS (method LC6): Rt=4.73 min; m/z=424.2 [M+H]$^+$

EXAMPLE 18

3-{4-[5-(4-Chloro-benzyl)-7-propoxy-oxazolo[5,4-d]pyrimidin-2-yl]-2,6-dimethyl-phenoxy}-propane-1,2-diol

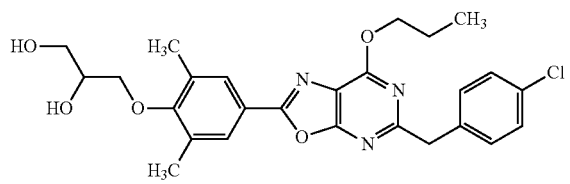 [SMILES: CCCOc1nc(Cc2ccc(Cl)cc2)nc2oc(-c3cc(C)c(OCC(O)CO)c(C)c3)nc12]

(a) 5-(4-Chloro-benzyl)-2-[4-(2,2-dimethyl-[1,3]dioxolan-4-ylmethoxy)-3,5-dimethyl-phenyl]-7-propoxy-oxazolo[5,4-d]pyrimidine A suspension of 0.736 mmol of polystyrene-bound triphenylphosphine (Argonaut) and 128 mg of diethyl azodicarboxylate in 10 ml of tetrahydrofuran was stirred for 15 min at 0° C. Then 260 mg of 4-[5-(4-chloro-benzyl)-7-propoxy-oxazolo[5,4-d]pyrimidin-2-yl]-2,6-dimethyl-phenol, 81 mg of (2,2-dimethyl-[1,3]dioxolan-4-yl)-methanol and 85 µl of triethylamine were added. The reaction mixture was stirred at room temperature for 3 h. Then another 81 mg of (2,2-dimethyl-[1,3]dioxolan-4-yl)-methanol, 0.736 mmol of polystyrene-bound triphenylphosphine and 128 mg of diethyl azodicarboxylate were added and the reaction mixture was stirred for 18 h. The polymer was filtered off and washed thoroughly with tetrahydrofuran. The solvent was removed in vacuo and the title compound isolated by silica gel chromatography (method SC1) and then by preparative HPLC (method HPLC2).

(b) 3-{-4-[5-(4-Chloro-benzyl)-7-propoxy-oxazolo[5,4-d]pyrimidin-2-yl]-2,6-dimethyl-phenoxy}-propane-1,2-diol The 5-(4-chloro-benzyl)-2-[4-(2,2-dimethyl-[1,3]dioxolan-4-ylmethoxy)-3,5-dimethyl-phenyl]-7-propoxy-oxazolo[5,4-d]pyrimidine obtained in step (a) was dissolved in 6 ml of dichloromethane and 2 ml of trifluoroacetic acid. The reaction mixture was stirred for 2 h at room temperature. Then the solvents were removed in vacuo and the residue was purified by preparative HPLC (method HPLC1). 4.1 mg of the title compound were obtained.

LC/MS (method LC9): Rt=5.01 min; m/z=498.25 [M+H]$^+$

EXAMPLE 19

2-{4-[5-(4-Chloro-benzyl)-7-propoxy-oxazolo[5,4-d]pyrimidin-2-yl]-2,6-dimethyl-phenoxy}-ethanol

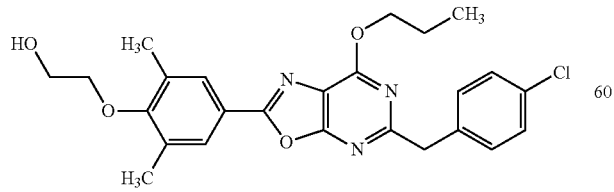

130 mg of potassium carbonate and 32.4 mg of 2-bromoethanol were added to a solution of 100 mg of 4-[5-(4-chlorobenzyl)-7-propoxy-oxazolo[5,4-d]pyrimidin-2-yl]2,6-dimethyl-phenol in 3 ml of dimethylformamide. The reaction mixture was heated to 60° C. for 3 h. After filtration, the solvent was removed in vacuo. Preparative HPLC (method HPLC1) of the residue yielded 5.4 mg of the title compound.

LC/MS (method LC9): Rt=5.14 min; m/z=468.37 [M+H]$^+$

EXAMPLE 20

1-Amino-3-{4-[5-(4-chloro-benzyl)-7-propoxy-oxazolo[5,4-d]pyrimidin-2-yl]-2,6-dimethyl-phenoxy}-propan-2-ol

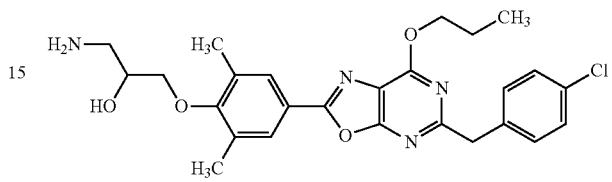

(a) 5-(4-Chloro-benzyl)-2-(3,5-dimethyl-4-oxiranylmethoxy-phenyl)-7-propoxy-oxazolo[5,4-d]pyrimidine A mixture of 218.5 µl of epichlorohydrine and 370 mg of 4-[5-(4-chloro-benzyl)-7-propoxy-oxazolo[5,4-d]pyrimidin-2-yl]-2,6-dimethyl-phenol in 4.4 ml of isopropanol and 1.2 ml of an aqueous 3 N sodium hydroxide solution was heated to 50° C. for 8 h. Then ethyl acetate and water were added and the layers were separated. The organic layer was extracted with water, dried over sodium sulfate, filtered and evaporated in vacuo to give 410 mg of the crude title compound which was used in the next step without further purification.

(b) 1-Amino-3-{4-[5-(4-chloro-benzyl)-7-propoxy-oxazolo[5,4-d]pyrimidin-2-yl]-2,6-dimethyl-phenoxy}-propan-2-ol 5 ml of a 7 N solution of ammonia in methanol were added to 100 mg of crude 5-(4-chloro-benzyl)-2-(3,5-dimethyl-4-oxiranylmethoxy-phenyl)-7-propoxy-oxazolo[5,4-d]pyrimidine. The mixture was heated to 60° C. for 6 h. Then the solvent was removed in vacuo and the residue was purified by silica gel chromatography (method SC1) to give 44 mg of the title compound.

LC/MS (method LC10): Rt=3.54 min; m/z=497.11 [M+H]$^+$

EXAMPLE 21

3-[5-(4-Chloro-benzyl)-7-propoxy-oxazolo[5,4-d]pyrimidin-2-yl]-phenylamine

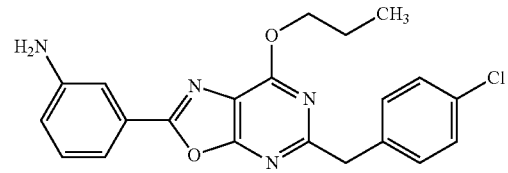 [SMILES: CCCOc1nc(Cc2ccc(Cl)cc2)nc2oc(-c3cccc(N)c3)nc12]

(a) 5-Amino-2-(4-chloro-benzyl)-pyrimidine-4,6-diol 18.75 ml of a solution of sodium methoxide (30% in methanol) were added to a suspension of 8.43 g of 4-chlorophenyl-acetamidine hydrochloride in 25 ml of ethanol. The precipitate was filtered off and washed with 25 ml of ethanol. The resulting solution was added dropwise to 13.76 g of aminomalonic acid diethylester hydrochloride and 18.75 ml of a solution of sodium methoxide (30% in methanol) in 50 ml of ethanol. The reaction mixture was stirred for 2 h at 60° C. After cooling to room temperature the precipitate was filtered off. The filtrate was evaporated under reduced pressure to give 12.5 g of the title compound as a light brown solid which was used without further purification.

LC/MS (method LC4): Rt=0.66 min; m/z=251.9 [M+H]$^+$ (b) 5-(4-Chloro-benzyl)-2-methylsulfanyl-oxazolo[5,4-d]pyrimidin-7-ol 3 ml of thiophosgene were added slowly to a suspension of 9.65 g of 5-amino-2-(4-chloro-benzyl)-pyrimidine-4,6-diol and 5.3 g of potassium carbonate in 75 ml of N-methyl-pyrrolidin-2-one (NMP) while maintaining the temperature below 10° C. The reaction mixture was stirred for 2 h at 0-10° C. Then 300 ml of water were added and the resulting solution was extracted three times with 200 ml of dichloromethane and three times with 200 ml of a mixture of dichloromethane and isopropanol (3:1). The combined organic phases were dried over sodium sulfate and filtered. The solvents were removed in vacuo to yield approximately 7 g of 5-(4-chloro-benzyl)-2-mercapto-oxazolo[5,4-d]pyrimidin-7-ol as a solution in NMP. 45 ml of NMP and a solution of 2.38 g of sodium hydroxide in 64 ml of water were added at 0° C., and the mixture was stirred for 30 min at 0° C. while the color changed to brown. Then a solution of 1.5 ml of iodomethane in 1.5 ml of NMP was added dropwise. After stirring at 0° C. for 90 min the reaction was complete. The solution was extracted twice with 80 ml of ethyl acetate, and the combined organic phases were dried over sodium sulfate and filtered. The solvents were removed in vacuo to yield 2.2 g of the title compound as a brown solid.

LC/MS (method LC4): Rt=1.36 min; m/z=307.9 [M+H]$^+$ (c) 5-(4-Chloro-benzyl)-2-methylsulfanyl-7-propoxy-oxazolo[5,4-d]pyrimidine A suspension of 8.7 mmol of polystyrene-bound triphenylphosphine (Argonaut) and 1.5 g of diethyl azodicarboxylate (DEAD) in 55 ml of tetrahydrofuran was stirred for 15 min at 0° C. Then 2.2 g of 5-(4-chloro-benzyl)-2-methylsulfanyl-oxazolo[5,4-d]pyrimidin-7-ol, 0.65 ml of propan-1-ol and 1 ml of triethylamine were added. The reaction mixture was stirred at room temperature for 3 h. The polymer was filtered off and washed thoroughly with tetrahydrofuran. The solvent was removed in vacuo and the title compound isolated by silica gel chromatography (method SC1).

LC/MS (method LC4): Rt=2.06 min; m/z=349.9 [M+H]$^+$ (d) 3-[5-(4-Chloro-benzyl)-7-propoxy-oxazolo[5,4-d]pyrimidin-2-yl]-phenylamine Under argon atmosphere, 13.1 mg of tris(dibenzylideneacetone)dipalladium and 13.3 mg of tri(furan-2-yl)phosphine were added to a solution of 125 mg of 5-(4-chloro-benzyl)-2-methylsulfanyl-7-propoxy-oxazolo[5,4-d]pyrimidine, 81.7 mg of copper(I)thiophene-2-carboxylate and 58.7 mg of 3-amino-benzeneboronic acid in 3.5 ml of tetrahydrofuran. The mixture was heated to 80° C. for 2 h in a microwave reactor (CEM Discover). After cooling, 3 ml of water and 3 ml of ethyl acetate were added. The mixture was filtered through a ChemElut cartridge and the cartridge washed with ethyl acetate. The combined filtrates were evaporated in vacuo. Preparative HPLC (method HPLC1) of the residue yielded 44 mg of the title compound in the form of the 3-[5-(4-chloro-benzyl)-7-propoxy-oxazolo[5,4-d]pyrimidin-2-yl]-phenylamine trifluoroacetic acid salt.

LC/MS (method LC8): Rt=2.71 min; m/z=436.16 [M+CH$_3$CN+H]$^+$

Analogously to the preparation of the compounds of the above examples, the example compounds of the formula Iw listed in Table 3 were prepared. They can be referred to as 2-(R$^2$)-5-(R$^3$-methyl)-7-(R$^1$-oxy)-oxazolo[5,4-d]pyrimidine, allowing for necessary adaptations in view of the rules of nomenclature, for example as 5-(4-chloro-benzyl)-7-cyclopropylmethoxy-2-(3-methyl-phenyl)-oxazolo[5,4-d]pyrimidine in the case of the compound of example 105. In part, they were obtained in the form of their trifluoroacetic acid salt.

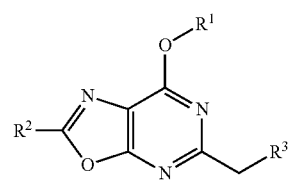

Iw

TABLE 3

Example compounds of the formula Iw

| Example | R$^1$ | R$^2$ | R$^3$ | LC/MS | Rt [min] | m/z [M + H]$^+$ |
|---|---|---|---|---|---|---|
| 22 | n-propyl | 2-chloro-5-fluoro-phenyl | 4,4-difluoro-piperidin-1-yl | LC1 | 1.47 | 441.13 |
| 23 | n-propyl | 2-chloro-5-fluoro-phenyl | [1,4]oxazepan-4-yl | LC1 | 1.35 | 421.19 |
| 24 | n-propyl | 3,5-difluoro-phenyl | morpholin-4-yl | LC1 | 1.27 | 391.05 |
| 25 | n-propyl | 3,5-difluoro-phenyl | 4,4-difluoro-piperidin-1-yl | LC1 | 1.38 | 425.00 |
| 26 | n-propyl | 3,5-difluoro-phenyl | [1,4]oxazepan-4-yl | LC1 | 1.31 | 405.05 |
| 27 | n-propyl | 3-chloro-phenyl | morpholin-4-yl | LC1 | 1.40 | 389.04 |
| 28 | n-propyl | 3-chloro-phenyl | 4,4-difluoro-piperidin-1-yl | LC1 | 1.48 | 423.00 |
| 29 | n-propyl | 3-chloro-phenyl | [1,4]oxazepan-4-yl | LC1 | 1.36 | 403.04 |
| 30 | n-propyl | 3-fluoro-phenyl | morpholin-4-yl | LC1 | 1.40 | 373.06 |

TABLE 3-continued

Example compounds of the formula Iw

| Example | R¹ | R² | R³ | LC/MS | Rt [min] | m/z [M + H]⁺ |
|---|---|---|---|---|---|---|
| 31 | 3-fluoro-propyl | 3-fluoro-phenyl | morpholin-4-yl | LC2 | 1.95 | 391.30 |
| 32 | 2-fluoro-ethyl | 3-fluoro-phenyl | morpholin-4-yl | LC2 | 2.23 | 377.21 |
| 33 | n-propyl | 3-fluoro-phenyl | 4,4-difluoro-piperidin-1-yl | LC1 | 1.41 | 407.15 |
| 34 | n-propyl | 3-fluoro-phenyl | [1,4]oxazepan-4-yl | LC1 | 1.30 | 387.18 |
| 35 | n-propyl | 3-methoxy-phenyl | morpholin-4-yl | LC1 | 1.31 | 385.04 |
| 36 | n-propyl | 3-methoxy-phenyl | 4,4-difluoro-piperidin-1-yl | LC1 | 1.46 | 419.11 |
| 37 | n-propyl | 3-methoxy-phenyl | [1,4]oxazepan-4-yl | LC1 | 1.32 | 399.15 |
| 38 | n-propyl | 3-methyl-phenyl | morpholin-4-yl | LC1 | 1.36 | 369.08 |
| 39 | n-propyl | 5-fluoro-pyridin-3-yl | morpholin-4-yl | LC1 | 1.13 | 374.16 |
| 40 | n-propyl | 5-fluoro-pyridin-3-yl | 4,4-difluoro-piperidin-1-yl | LC1 | 1.20 | 408.16 |
| 41 | n-propyl | phenyl | morpholin-4-yl | LC1 | 1.23 | 355.20 |
| 42 | n-propyl | phenyl | 4,4-difluoro-piperidin-1-yl | LC1 | 1.37 | 389.20 |
| 43 | n-propyl | phenyl | [1,4]oxazepan-4-yl | LC1 | 1.22 | 369.09 |
| 44 | n-propyl | 3-fluoro-phenyl | [1,2,3]triazol-1-yl | LC3 | 2.13 | 396.46 (1) |
| 45 | n-propyl | 3-fluoro-phenyl | 1,1-dioxo-thiomorpholin-4-yl | LC1 | 1.66 | 421.16 |
| 46 | n-propyl | 3-fluoro-phenyl | 1-oxo-thiomorpholin-4-yl | LC1 | 1.23 | 405.15 |
| 47 | n-propyl | 3-fluoro-phenyl | 2,6-dimethyl-morpholin-4-yl | LC1 | 1.68 | 401.08 |
| 48 | n-propyl | 3-fluoro-phenyl | 2-methyl-imidazol-1-yl | LC1 | 1.39 | 368.04 |
| 49 | n-propyl | 3-fluoro-phenyl | 2-oxa-5-azabicyclo[2.2.1]-hept-5-yl | LC1 | 1.28 | 385.17 |
| 50 | n-propyl | 3-fluoro-phenyl | 3,3-difluoro-piperidin-1-yl | LC1 | 1.46 | 407.32 |
| 51 | n-propyl | 3-fluoro-phenyl | 3-hydroxycarbonyl-azetidin-1-yl | LC2 | 1.28 | 387.30 |
| 52 | n-propyl | 3-fluoro-phenyl | 3-methoxycarbonyl-azetidin-1-yl | LC1 | 1.39 | 401.21 |
| 53 | n-propyl | 3-fluoro-phenyl | 3-methyl-2,5-dioxo-imidazolidin-1-yl | LC1 | 1.73 | 400.14 |
| 54 | n-propyl | 3-fluoro-phenyl | 4-hydroxymethyl-imidazol-1-yl | LC3 | 1.48 | 384.44 |
| 55 | n-propyl | 3-fluoro-phenyl | 4-methanesulfonyl-piperazin-1-yl | LC1 | 1.41 | 450.38 |
| 56 | n-propyl | 3-fluoro-phenyl | 4-methoxycarbonyl-imidazol-1-yl | LC1 | 1.53 | 412.01 |
| 57 | n-propyl | 3-fluoro-phenyl | 4-methyl-imidazol-1-yl | LC1 | 1.43 | 368.03 |
| 58 | n-propyl | 3-fluoro-phenyl | 4-methyl-pyrazol-1-yl | LC1 | 2.01 | 368.16 |
| 59 | n-propyl | 3-fluoro-phenyl | 4-phenyl-imidazol-1-yl | LC1 | 1.62 | 430.39 |
| 60 | n-propyl | 3-fluoro-phenyl | 5-methoxycarbonyl-imidazol-1-yl | LC1 | 1.53 | 412.01 |
| 61 | n-propyl | 3-fluoro-phenyl | imidazol-1-yl | LC1 | 1.39 | 354.14 |
| 62 | n-propyl | 3-fluoro-phenyl | 3,5-dioxo-morpholin-4-yl | LC1 | 1.92 | 401.06 |
| 63 | n-propyl | 3-fluoro-phenyl | 2,6-dioxo-piperidin-1-yl | LC1 | 1.87 | 399.15 |
| 64 | n-propyl | 3-fluoro-phenyl | thiazolidin-3-yl | LC1 | 1.73 | 375.02 |
| 65 | n-propyl | 3-fluoro-phenyl | thiomorpholin-4-yl | LC1 | 1.40 | 389.16 |
| 66 | n-propyl | 3,4-difluoro-phenyl | morpholin-4-yl | LC1 | 1.33 | 391.05 |
| 67 | n-propyl | 3,4-difluoro-phenyl | [1,4]oxazepan-4-yl | LC1 | 1.35 | 405.04 |
| 68 | n-propyl | 3,4-difluoro-phenyl | 4,4-difluoro-piperidin-1-yl | LC1 | 1.47 | 425.04 |
| 69 | n-propyl | 3-fluoro-phenyl | 3-fluoro-piperidin-1-yl | LC2 | 1.49 | 389.09 |

TABLE 3-continued

Example compounds of the formula Iw

| Example | R¹ | R² | R³ | LC/MS | Rt [min] | m/z [M + H]⁺ |
|---|---|---|---|---|---|---|
| 70 | n-propyl | 3-fluoro-phenyl | 4-fluoro-piperidin-1-yl | LC1 | 1.37 | 389.14 |
| 71 | n-propyl | 2-chloro-pyridin-4-yl | morpholin-4-yl | LC2 | 1.32 | 390.21 |
| 72 | n-propyl | 3-trifluoromethyl-phenyl | morpholin-4-yl | LC1 | 1.45 | 423.13 |
| 73 | n-propyl | 3-trifluoromethyl-phenyl | 4,4-difluoro-piperidin-1-yl | LC1 | 1.57 | 457.10 |
| 74 | n-propyl | 3-chloro-6-methoxy-phenyl | [1,4]oxazepan-4-yl | LC2 | 1.52 | 433.27 |
| 75 | n-propyl | 3-chloro-6-methoxy-phenyl | morpholin-4-yl | LC1 | 1.35 | 419.10 |
| 76 | n-propyl | 3-chloro-6-methoxy-phenyl | 4,4-difluoro-piperidin-1-yl | LC2 | 1.68 | 453.30 |
| 77 | n-propyl | 3,4-dichloro-phenyl | morpholin-4-yl | LC1 | 1.51 | 423.09 |
| 78 | n-propyl | 3,4-dichloro-phenyl | [1,4]oxazepan-4-yl | LC1 | 1.51 | 437.10 |
| 79 | n-propyl | 3,4-dichloro-phenyl | 4,4-difluoro-piperidin-1-yl | LC1 | 1.61 | 457.08 |
| 80 | n-propyl | 2,5-dimethoxy-phenyl | [1,4]oxazepan-4-yl | LC1 | 1.25 | 429.18 |
| 81 | n-propyl | 2,5-dimethoxy-phenyl | 4,4-difluoro-piperidin-1-yl | LC1 | 1.36 | 449.17 |
| 82 | n-propyl | 2,3,6-trifluoro-phenyl | morpholin-4-yl | LC1 | 1.28 | 409.08 |
| 83 | n-propyl | 2,3,6-trifluoro-phenyl | 4,4-difluoro-piperidin-1-yl | LC2 | 1.57 | 443.11 |
| 84 | n-propyl | 2-chloro-4,5-difluoro-phenyl | morpholin-4-yl | LC3 | 1.49 | 425.28 |
| 85 | n-propyl | 2-chloro-4,5-difluoro-phenyl | [1,4]oxazepan-4-yl | LC1 | 1.38 | 439.15 |
| 86 | n-propyl | 2,3,6-trifluoro-phenyl | [1,4]oxazepan-4-yl | LC1 | 1.30 | 423.17 |
| 87 | n-propyl | 2-chloro-4,5-difluoro-phenyl | 4,4-difluoro-piperidin-1-yl | LC2 | 1.50 | 459.13 |
| 88 | n-propyl | 3-fluoro-4-methoxy-phenyl | morpholin-4-yl | LC1 | 1.32 | 403.22 |
| 89 | n-propyl | 4-chloro-3-fluoro-phenyl | morpholin-4-yl | LC1 | 1.45 | 407.20 |
| 90 | n-propyl | 4-chloro-3-fluoro-phenyl | 4,4-difluoro-piperidin-1-yl | LC1 | 1.57 | 441.19 |
| 91 | n-propyl | 4-chloro-3-fluoro-phenyl | [1,4]oxazepan-4-yl | LC1 | 1.46 | 421.19 |
| 92 | n-propyl | 3-fluoro-4-methoxy-phenyl | [1,4]oxazepan-4-yl | LC1 | 1.30 | 417.20 |
| 93 | n-propyl | 3-fluoro-4-methoxy-phenyl | 4,4-difluoro-piperidin-1-yl | LC1 | 1.46 | 437.22 |
| 94 | n-propyl | 3-fluoro-phenyl | 4-trifluoromethyl-piperidin-1-yl | LC1 | 1.50 | 439.13 |
| 95 | n-propyl | 3-fluoro-phenyl | 2,2-difluoro-pyrrolidin-1-yl | LC1 | 1.51 | 393.09 |
| 96 | n-propyl | furan-2-yl | 4,4-difluoro-piperidin-1-yl | LC1 | 1.26 | 379.11 |
| 97 | n-propyl | furan-2-yl | [1,4]oxazepan-4-yl | LC1 | 1.11 | 359.15 |
| 98 | n-propyl | 5-bromo-furan-2-yl | 4,4-difluoro-piperidin-1-yl | LC1 | 1.38 | 457.05 |
| 99 | n-propyl | 5-bromo-furan-2-yl | [1,4]oxazepan-4-yl | LC1 | 1.28 | 437.07 |
| 100 | n-propyl | 4-methyl-phenyl | 4-chloro-phenyl | LC1 | 2.73 | 394.24 |
| 101 | n-propyl | 3-methyl-phenyl | 4-chloro-phenyl | LC1 | 2.75 | 394.23 |
| 102 | n-propyl | furan-2-yl | 4-chloro-phenyl | LC1 | 2.31 | 370.19 |
| 103 | n-propyl | thiophen-2-yl | 4-chloro-phenyl | LC1 | 2.50 | 386.18 |
| 104 | cyclopropyl-methyl | 3-fluoro-phenyl | 4-chloro-phenyl | LC2 | 3.46 | 410.06 |
| 105 | cyclopropyl-methyl | 3-methyl-phenyl | 4-chloro-phenyl | LC2 | 3.67 | 406.07 |
| 106 | 3-methyl-butyl | 3-methyl-phenyl | 4-chloro-phenyl | LC2 | 3.96 | 422.13 |
| 107 | cyclopentyl | 3-methyl-phenyl | 4-chloro-phenyl | LC2 | 3.74 | 420.15 |
| 108 | n-butyl | 3-methyl-phenyl | 4-chloro-phenyl | LC2 | 3.71 | 408.18 |
| 109 | propargyl | 3-methyl-phenyl | 4-chloro-phenyl | LC2 | 3.25 | 390.16 |
| 110 | cyclopentyl | furan-2-yl | 4-chloro-phenyl | LC2 | 3.27 | 396.11 |
| 111 | n-butyl | furan-2-yl | 4-chloro-phenyl | LC2 | 3.25 | 384.17 |

TABLE 3-continued

Example compounds of the formula Iw

| Example | R¹ | R² | R³ | LC/MS | Rt [min] | m/z [M + H]⁺ |
|---|---|---|---|---|---|---|
| 112 | cyclopentyl | 3-fluoro-phenyl | 4-chloro-phenyl | LC2 | 3.60 | 424.18 |
| 113 | cyclopentyl | 4-methyl-phenyl | 4-chloro-phenyl | LC2 | 3.72 | 420.15 |
| 114 | cyclopentyl | thiophen-2-yl | 4-chloro-phenyl | LC2 | 3.48 | 412.09 |
| 115 | n-butyl | thiophen-2-yl | 4-chloro-phenyl | LC2 | 3.47 | 400.14 |
| 116 | allyl | 3-methyl-phenyl | 4-chloro-phenyl | LC1 | 2.70 | 392.11 |
| 117 | ethyl | 3-methyl-phenyl | 4-chloro-phenyl | LC1 | 2.68 | 380.09 |
| 118 | 2-fluoro-ethyl | 3-methyl-phenyl | 4-chloro-phenyl | LC1 | 2.48 | 398.12 |
| 119 | 2-methyl-allyl | 3-methyl-phenyl | 4-chloro-phenyl | LC1 | 2.80 | 406.11 |
| 120 | 3-fluoro-propyl | 3-methyl-phenyl | 4-chloro-phenyl | LC1 | 2.57 | 412.11 |
| 121 | but-3-enyl | 3-methyl-phenyl | 4-chloro-phenyl | LC1 | 2.80 | 406.11 |
| 122 | n-propyl | pyridin-3-yl | 4-chloro-phenyl | LC1 | 2.17 | 381.08 |
| 123 | propargyl | pyridin-3-yl | 4-chloro-phenyl | LC1 | 1.94 | 377.05 |
| 124 | 2-methyl-allyl | pyridin-3-yl | 4-chloro-phenyl | LC1 | 2.19 | 393.06 |
| 125 | 3-fluoro-propyl | pyridin-3-yl | 4-chloro-phenyl | LC1 | 1.97 | 399.06 |
| 126 | 3-fluoro-propyl | pyridin-3-yl | 4-chloro-phenyl | LC1 | 1.97 | 399.06 |
| 127 | allyl | pyridin-3-yl | 4-chloro-phenyl | LC1 | 2.08 | 379.06 |
| 128 | ethyl | pyridin-3-yl | 4-chloro-phenyl | LC1 | 2.02 | 367.11 |
| 129 | n-propyl | 3-methoxy-phenyl | 4-chloro-phenyl | LC1 | 2.69 | 410.1 |
| 130 | n-propyl | 3-chloro-phenyl | 4-chloro-phenyl | LC1 | 2.80 | 414.02 |
| 131 | n-propyl | 2,5-difluoro-phenyl | 4-chloro-phenyl | LC1 | 2.59 | 416.09 |
| 132 | n-propyl | 3,4-difluoro-phenyl | 4-chloro-phenyl | LC1 | 2.62 | 416.06 |
| 133 | n-propyl | 3-fluoro-phenyl | 2-oxo-3-methyl-benzoimidazol-1-yl | LC2 | 2.64 | 434.13 |
| 134 | n-propyl | 3-fluoro-phenyl | 4-oxo-3-methoxycarbonyl-piperidin-1-yl | LC5 | 1.44 | 443.13 |
| 135 | n-propyl | 3-amino-6-fluoro-phenyl | 4-chloro-phenyl | LC8 | 2.75 | 413.13 |
| 136 | n-propyl | 3-fluoro-phenyl | 4-methyl-phenyl | LC5 | 2.61 | 378.13 |
| 137 | n-propyl | 3-dimethylamino-phenyl | 4-chloro-phenyl | LC7 | 2.84 | 464.07 |
| 138 | n-propyl | 3,5-bis(trifluoro-methyl)-phenyl | 4-chloro-phenyl | LC7 | 2.91 | 516.07 |
| 139 | cyclopropyl-methyl | 6-morpholin-4-yl-pyridin-3-yl | 4-chloro-phenyl | LC5 | 2.28 | 478.17 |
| 140 | n-propyl | 3-fluoro-phenyl | 2-methoxymethyl-pyrrolidin-1-yl | LC5 | 1.44 | 401.32 |
| 141 | allyl | 3-fluoro-phenyl | 3,4-dichloro-phenyl | LC5 | 2.68 | 430.05 |
| 142 | n-propyl | 3-fluoro-phenyl | 2,6-dioxo-4,4-dimethyl-piperidin-1-yl | LC2 | 2.65 | 427.14 |
| 143 | n-propyl | 3-fluoro-phenyl | 2-benzyl-pyrrolidin-1-yl | LC5 | 1.64 | 447.15 |
| 144 | n-propyl | 3-methyl-phenyl | cyclohexyl | LC6 | 5.37 | 366.12 |
| 145 | n-propyl | 3-fluoro-phenyl | 4-methoxy-piperidin-1-yl | LC5 | 1.35 | 401.14 |
| 146 | n-propyl | 3-fluoro-phenyl | 3-benzyl-2,4-dioxo-imidazolidin-1-yl | LC2 | 2.67 | 476.16 |
| 147 | n-propyl | 3-fluoro-phenyl | 2-thiazol-2-yl-piperidin-1-yl | LC5 | 1.50 | 454.11 |
| 148 | n-propyl | 6-morpholin-4-yl-pyridin-3-yl | 4-chloro-phenyl | LC5 | 2.24 | 466.23 |
| 149 | n-propyl | 3,5-dimethyl-phenyl | 4-chloro-phenyl | LC7 | 2.89 | 408.13 |
| 150 | n-propyl | 3-fluoro-pyridin-4-yl | 4-chloro-phenyl | LC7 | 2.59 | 440.14 (1) |
| 151 | n-propyl | 6-methoxy-pyridin-3-yl | 4-chloro-phenyl | LC8 | 3.32 | 411.13 |
| 152 | n-propyl | 3-fluoro-4-hydroxy-phenyl | 4-chloro-phenyl | LC8 | 3.04 | 414.10 |
| 153 | n-propyl | 5-methyl-pyridin-3-yl | 4-chloro-phenyl | LC8 | 2.83 | 395.11 |

TABLE 3-continued

Example compounds of the formula Iw

| Example | R¹ | R² | R³ | LC/MS | Rt [min] | m/z [M + H]⁺ |
|---|---|---|---|---|---|---|
| 154 | n-propyl | 3-fluoro-phenyl | 3-methyl-[1,2,4]triazol-1-yl | LC2 | 1.97 | 369.2 |
| 155 | n-propyl | 3-fluoro-phenyl | 5-methyl-[1,2,4]triazol-1-yl | LC2 | 1.99 | 369.26 |
| 156 | cyclopropyl-methyl | 3-methyl-phenyl | cyclohexyl | LC6 | 5.29 | 378.16 |
| 157 | n-propyl | 3-fluoro-phenyl | cyclohexyl | LC6 | 4.77 | 370.12 |
| 158 | cyclopropyl-methyl | 3-fluoro-phenyl | cyclohexyl | LC6 | 4.75 | 382.13 |
| 159 | n-propyl | 3-methyl-phenyl | tetrahydro-pyran-4-yl | LC10 | 4.12 | 368.25 |
| 160 | n-propyl | 3-fluoro-phenyl | tetrahydro-pyran-4-yl | LC6 | 4.22 | 372.12 |
| 161 | cyclopropyl-methyl | 3-fluoro-phenyl | tetrahydro-pyran-4-yl | LC6 | 4.22 | 384.10 |
| 162 | n-propyl | 3-methyl-phenyl | cyclobutyl | LC6 | 5.10 | 338.10 |
| 163 | ethyl | 3-methyl-phenyl | cyclobutyl | LC9 | 5.64 | 324.23 |
| 164 | ethyl | 2-chloro-5-fluoro-phenyl | cyclobutyl | LC10 | 5.32 | 362.27 |
| 165 | cyclopropyl-methyl | 3-methyl-phenyl | cyclobutyl | LC9 | 5.74 | 350.24 |
| 166 | n-propyl | 3-methyl-phenyl | 3,5-dimethoxy-phenyl | LC6 | 4.65 | 420.28 |
| 167 | n-propyl | 2-fluoro-5-methyl-phenyl | 4-chloro-phenyl | LC6 | 4.87 | 412.2 |
| 168 | n-propyl | 4-methoxy-3,5-dimethyl-phenyl | 4-chloro-phenyl | LC6 | 5.12 | 438.2 |
| 169 | n-propyl | 4-chloro-3-methyl-phenyl | 4-chloro-phenyl | LC6 | 5.28 | 428.2 |
| 170 | n-propyl | 2,3-dimethyl-phenyl | 4-chloro-phenyl | LC9 | 5.69 | 408.2 |
| 171 | n-propyl | 2-fluoro-3-methyl-phenyl | 4-chloro-phenyl | LC10 | 5.39 | 412.2 |
| 172 | n-propyl | 4-fluoro-3-methyl-phenyl | 4-chloro-phenyl | LC10 | 5.49 | 412.2 |
| 173 | n-propyl | 2-(4-methyl-piperazin-1-yl)-pyrimidin-5-yl | 4-chloro-phenyl | LC6 | 3.27 | 480.3 |
| 174 | n-propyl | pyrimidin-5-yl | 4-chloro-phenyl | LC6 | 4.12 | 382.2 |
| 175 | n-propyl | 5-acetyl-thiophen-2-yl | 4-chloro-phenyl | LC6 | 4.57 | 428.1 |
| 176 | n-propyl | 4-methoxy-3-methyl-phenyl | 4-chloro-phenyl | LC6 | 5.04 | 424.22 |
| 177 | n-propyl | 5-chloro-2-methoxy-pyridin-4-yl | 4-chloro-phenyl | LC9 | 5.57 | 445.1 |
| 178 | n-propyl | 4-dimethylamino-3-methyl-phenyl | 4-chloro-phenyl | LC10 | 3.87 | 437.07 |
| 179 | n-propyl | 3-fluoro-phenyl | (S)-3-hydroxy-piperidin-1-yl | LC10 | 2.70 | 387.09 |
| 180 | n-propyl | 3-fluoro-phenyl | 3-carboxy-1,1-dioxoisothiazolidin-2-yl | LC6 | 3.55 | 451.1 |
| 181 | n-propyl | 3-fluoro-phenyl | (R)-3-hydroxy-pyrrolidin-1-yl | LC10 | 2.69 | 373.07 |
| 182 | n-propyl | 3-fluoro-phenyl | piperidin-1-yl | LC9 | 3.50 | 371.37 |
| 183 | n-propyl | 3-fluoro-phenyl | pyrrolidin-1-yl | LC10 | 2.88 | 357.18 |
| 184 | n-propyl | 3-fluoro-phenyl | (S)-3-methyl-morpholin-4-yl | LC10 | 2.89 | 387.1 |
| 185 | n-propyl | 3-fluoro-phenyl | (S)-3-hydroxymethyl-morpholin-4-yl | LC10 | 2.78 | 403.1 |
| 186 | isopropyl | 3-methyl-phenyl | morpholin-4-yl | LC10 | 2.79 | 369.22 |
| 187 | oxetan-3-yl | 3-methyl-phenyl | morpholin-4-yl | LC10 | 2.58 | 383.17 |
| 188 | n-propyl | 4-methoxy-3,5-dimethyl-phenyl | phenyl | LC9 | 5.60 | 404.22 |
| 189 | isobutyl | 3-methoxy-phenyl | phenyl | LC9 | 5.28 | 390.31 |
| 190 | ethyl | 4-methoxy-3,5-dimethyl-phenyl | 4-chloro-phenyl | LC9 | 5.41 | 424.23 |
| 191 | ethyl | 4-hydroxy-3,5-dimethyl-phenyl | 4-chloro-phenyl | LC10 | 4.14 | 410.09 |

TABLE 3-continued

Example compounds of the formula Iw

| Example | R¹ | R² | R³ | LC/MS | Rt [min] | m/z [M + H]⁺ |
|---|---|---|---|---|---|---|
| 192 | n-propyl | 4-(3-dimethylamino-2-hydroxy propoxy)-3,5-dimethyl-phenyl | 4-chloro-phenyl | LC10 | 3.63 | 525.12 |
| 193 | n-propyl | 4-(2-hydroxy-3-morpholin-4-yl-propoxy)-3,5-dimethyl-phenyl | 4-chloro-phenyl | LC10 | 3.65 | 567.11 |
| 194 | isopropyl | 4-(2-hydroxy-3-morpholin-4-yl-propoxy)-3,5-dimethyl-phenyl | 4-chloro-phenyl | LC10 | 3.51 | 567.12 |

(1) [M + CH₃CN + H]⁺

EXAMPLE 195

N-(3-{4-[5-(4-Chloro-benzyl)-7-propoxy-oxazolo[5,4-d]pyrimidin-2-yl]-2,6-dimethyl-phenoxy}-2-hydroxy-propyl)-benzamide

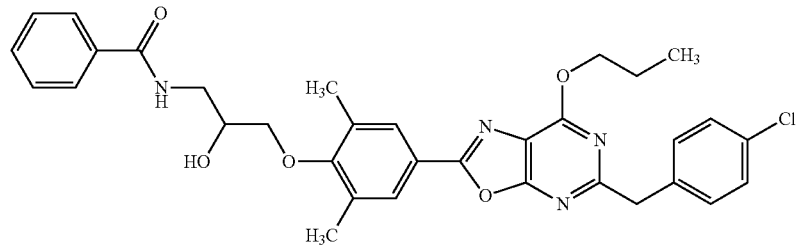 [SMILES: CCCOc1nc(Cc2ccc(Cl)cc2)nc2oc(-c3cc(C)c(OCC(O)CNC(=O)c4ccccc4)c(C)c3)nc12]

A mixture of 37 mg of benzoic acid, 110 mg of [(benzotriazol-1-yloxy)-dimethylamino-methylene]-dimethyl-ammonium tetrafluoroborate (TBTU), 100 mg of 1-amino-3-{4-[5-(4-chloro-benzyl)-7-propoxy-oxazolo[5,4-d]pyrimidin-2-yl]-2,6-dimethyl-phenoxy}-propan-2-ol (example 20) and 104 mg of ethyldiisopropylamine in 2 ml of dimethylformamide was stirred for 16 h at room temperature. After removal of the solvent the product was isolated via preparative HPLC (method HPLC2) to yield 11 mg of the title compound.

LC/MS (method LC6): Rt=4.59 min; m/z=601.09 [M+H]⁺

EXAMPLE 196

1-{4-[5-(4-Chloro-benzyl)-7-ethoxy-oxazolo[5,4-d]pyrimidin-2-yl]-2,6-dimethyl-phenoxy}-3-(5-isopropyl-4H-[1,2,4]triazol-3-ylsulfanyl)-propan-2-ol

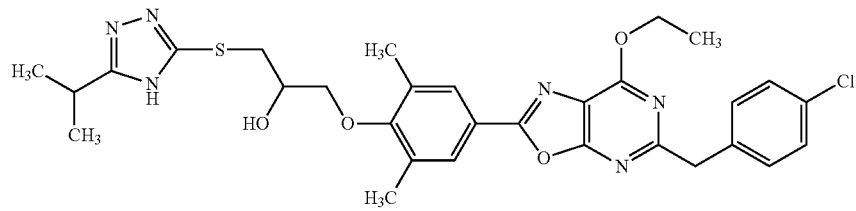 [SMILES: CCOc1nc(Cc2ccc(Cl)cc2)nc2oc(-c3cc(C)c(OCC(O)CSc4nnc(C(C)C)[nH]4)c(C)c3)nc12]

A solution of 300 mg of 5-(4-chloro-benzyl)-2-(3,5-dimethyl-4-oxiranylmethoxy-phenyl)-7-ethoxy-oxazolo[5,4-d]pyrimidine (prepared analogously as described in example 20, step (a)) and 92 mg of 5-isopropyl-4H-[1,2,4]triazole-3-thiol in 3 ml of dimethylformamide was heated for 2 h to 130° C. in a microwave reactor. After removal of the solvent the product was isolated by preparative HPLC (method HPLC1) to yield 89 mg of the title compound.

LC/MS (method LC19): Rt=2.02 min; m/z=609.18 [M+H]$^+$

EXAMPLE 197

1-{4-[5-(4-Chloro-benzyl)-7-ethoxy-oxazolo[5,4-d]pyrimidin-2-yl]-2,6-dimethyl-phenoxy}-3-(5-isopropyl-4H-[1,2,4]triazole-3-sulfonyl)-propan-2-ol

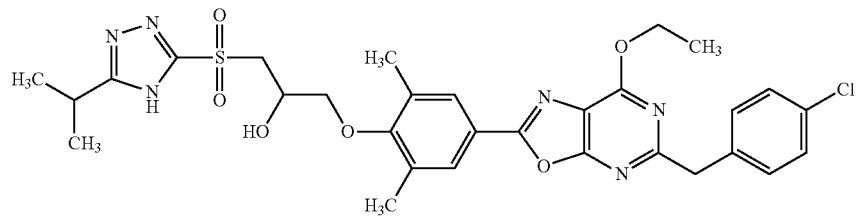 [SMILES: CCOc1nc(Cc2ccc(Cl)cc2)nc2oc(-c3cc(C)c(OCC(O)CS(=O)(=O)c4nnc(C(C)C)[nH]4)c(C)c3)nc12]

A solution of 250 mg of 4-[5-(4-chloro-benzyl)-7-ethoxy-oxazolo[5,4-d]pyrimidin-2-yl]-2,6-dimethyl-phenoxy}-3-(5-isopropyl-4H-[1,2,4]triazol-3-ylsulfanyl)-propan-2-ol (example 196) in 20 ml of dichloromethane was cooled to 0° C., and 177 mg of 3-chloroperbenzoic acid were added portionwise over a period of 15 min. After stirring for additional 30 min, 100 ml of ethyl acetate were added. The organic phase was separated, extracted twice with a 1 N solution of sodium hydroxide, dried with sodium sulfate, filtered and evaporated in vacuo. The crude product (300 mg) was purified by silica gel chromatography to yield 125 mg of the title compound.

LC/MS (method LC21): Rt=1.36 min; m/z=641.29 [M+H]$^+$

EXAMPLE 198

{4-[5-(4-Chloro-benzyl)-7-propoxy-oxazolo[5,4-d]pyrimidin-2-yl]-2,6-dimethyl-phenoxy}-acetic acid

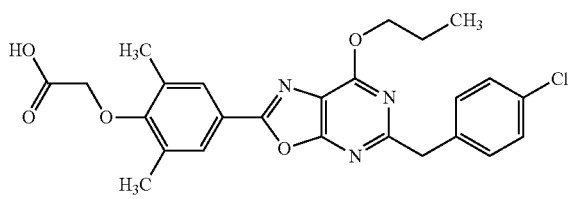 [SMILES: CCCOc1nc(Cc2ccc(Cl)cc2)nc2oc(-c3cc(C)c(OCC(=O)O)c(C)c3)nc12]

(a) {4-[5-(4-Chloro-benzyl)-7-propoxy-oxazolo[5,4-d]pyrimidin-2-yl]-2,6-dimethyl-phenoxy}-acetic acid tert-butyl ester A mixture of 1.5 g of 4-[5-(4-chloro-benzyl)-7-propoxy-oxazolo[5,4-d]pyrimidin-2-yl]-2,6-dimethyl-phenol (example 17), 690 mg of tert-butyl bromoacetate and 1.96 g of potassium carbonate in 50 ml of dimethylformamide was heated to 60° C. for 1 h. After cooling to room temperature, the solids were removed by filtration. The solvent was distilled off in vacuo and the residue was used without further purification in the next step.

(b) {4-[5-(4-Chloro-benzyl)-7-propoxy-oxazolo[5,4-d]pyrimidin-2-yl]-2,6-dimethyl-phenoxy}-acetic acid The crude {4-[5-(4-chloro-benzyl)-7-propoxy-oxazolo[5,4-d]pyrimidin-2-yl]-2,6-dimethyl-phenoxy}-acetic acid tert-butyl ester obtained in step (a) was dissolved in trifluoroacetic acid and stirred for 3 h at room temperature. After addition of water the precipitate was isolated by filtration to yield 1.3 g of the crude title compound. 500 mg thereof were purified by preparative HPLC (method HPLC1) to yield 260 mg of the pure title compound.

LC/MS (method LC15): Rt=2.92 min; m/z=482.17 [M+H]$^+$

EXAMPLE 199

(2-{4-[5-(4-Chloro-benzyl)-7-propoxy-oxazolo[5,4-d]pyrimidin-2-yl]-2,6-dimethyl-phenoxy}-acetylamino)-acetic acid

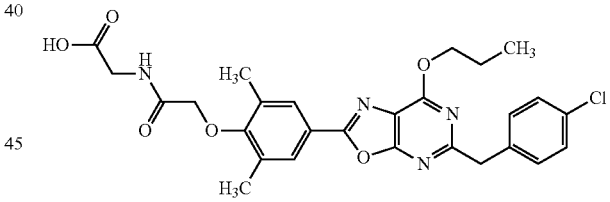

(a) {4-[5-(4-Chloro-benzyl)-7-propoxy-oxazolo[5,4-d]pyrimidin-2-yl]-2,6-dimethyl-phenoxy}-acetyl chloride 2 g of {-4-[5-(4-chloro-benzyl)-7-propoxy-oxazolo[5,4-d]pyrimidin-2-yl]-2,6-dimethyl-phenoxy}-acetic acid (example 198), 1.6 ml of thionyl chloride and 60 ml of tetrahydrofuran were stirred at room temperature for 16 h. Then toluene was added and the solvents were distilled off in vacuo to yield 2.05 g of the acid chloride, which was used in the next step without further purification.

(b) (2-{4-[5-(4-Chloro-benzyl)-7-propoxy-oxazolo[5,4-d]pyrimidin-2-yl]-2,6-dimethyl-phenoxy}-acetylamino)-acetic acid tert-butyl ester 200 mg of {4-[5-(4-chloro-benzyl)-7-propoxy-oxazolo[5,4-d]pyrimidin-2-yl]-2,6-dimethyl-phenoxy}-acetyl chloride were dissolved in 2 ml of dichloromethane, and the solution was slowly added to a solution of 67 mg of glycine tert-butyl ester hydrochloride and 121 mg of triethylamine in 3 ml of dichloromethane. The mixture was stirred for 18 h at room temperature. Then the solvent was distilled off in vacuo and the product was isolated via preparative HPLC (method HPLC2) to yield 53 mg of the title compound.

(c) (2-{4-[5-(4-Chloro-benzyl)-7-propoxy-oxazolo[5,4-d]pyrimidin-2-yl]-2,6-dimethyl-phenoxy}-acetylamino)-acetic acid 50 mg of (2-{4-[5-(4-chloro-benzyl)-7-propoxy-oxazolo[5,4-d]pyrimidin-2-yl]-2,6-dimethyl-phenoxy}-acetylamino)-acetic acid tert-butyl ester were dissolved in 1 ml of trifluoroacetic acid and the mixture was stirred for 30 min. Then the solvent was removed in vacuo to yield 37 mg of the title compound.
LC/MS (method LC6): Rt=4.15 min; m/z=539.02 [M+H]$^+$

EXAMPLE 200

5-(4-Chloro-benzyl)-2-[3,5-dimethyl-4-(3-morpholin-4-yl-propoxy)-phenyl]-7-propoxy-oxazolo[5,4-d]pyrimidine

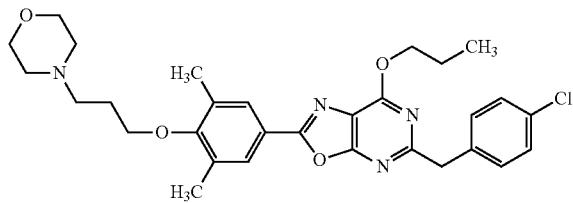 [SMILES: CCCOc1nc(Cc2ccc(Cl)cc2)nc2oc(-c3cc(C)c(OCCCN4CCOCC4)c(C)c3)nc12]

(a) 2-[4-(3-Bromo-propoxy)-3,5-dimethyl-phenyl]-5-(4-chloro-benzyl)-7-propoxy-oxazolo[5,4-d]pyrimidine A mixture of 300 mg of 4-[5-(4-chloro-benzyl)-7-propoxy-oxazolo[5,4-d]pyrimidin-2-yl]-2,6-dimethyl-phenol (example 17), 286 mg of 1,3-dibromopropane and 98 mg of potassium carbonate in 10 ml of dimethylformamide was heated to 60° C. for 3 h. After cooling to room temperature, the solids were removed by filtration. The solvent was distilled off in vacuo and the residue was purified by chromatography (method SC1) to yield 230 mg of the title compound.

(b) 5-(4-Chloro-benzyl)-2-[3,5-dimethyl-4-(3-morpholin-4-yl-propoxy)-phenyl]-7-propoxy-oxazolo[5,4-d]pyrimidine A mixture of 230 mg of 2-[4-(3-bromo-propoxy)-3,5-dimethyl-phenyl]-5-(4-chloro-benzyl)-7-propoxy-oxazolo[5,4-d]pyrimidine, 74 mg of morpholine and 233 mg of potassium carbonate in 5 ml of dimethylformamide was heated to 60° C. for 3 h. After cooling to room temperature, the solids were removed by filtration. The solvent was distilled off in vacuo and the residue was purified by preparative HPLC to yield 137 mg of the title compound in the form of the 5-(4-chloro-benzyl)-2-[3,5-dimethyl-4-(3-morpholin-4-yl-propoxy)-phenyl]-7-propoxy-oxazolo[5,4-d]pyrimidine trifluoroacetic acid salt.
LC/MS (method LC9): Rt=4.41 min; m/z=551.06 [M+H]$^+$ Analogously to the preparation of the compounds described above, the example compounds of the formula Iw listed in Table 4 were prepared. They can be referred to as 2-(R$^2$)-5-(R$^3$-methyl)-7-(R$^1$-oxy)-oxazolo[5,4-d]pyrimidine, allowing for necessary adaptations in view of the rules of nomenclature, for example as (2-{4-[5-(4-chloro-benzyl)-7-ethoxy-oxazolo[5,4-d]pyrimidin-2-yl]-2,6-dimethyl-phenoxy}-acetylamino)-acetic acid in the case of the compound of example 240. In part, they were obtained in the form of their trifluoroacetic acid salt.

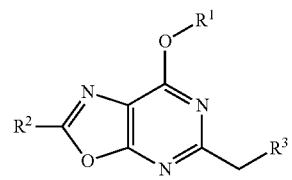

Iw

TABLE 4

Example compounds of the formula Iw

| Example | R$^1$ | R$^2$ | R$^3$ | LC/MS | Rt [min] | m/z [M + H]$^+$ |
|---|---|---|---|---|---|---|
| 201 | n-propyl | 6-chloro-pyridin-3-yl | 4-chloro-phenyl | LC11 | 3.35 | 415.11 |
| 202 | n-propyl | 3-fluoro-phenyl | (S)-3-fluoro-pyrrolidin-1-yl | LC12 | 1.52 | 375.26 |
| 203 | n-propyl | 3-fluoro-phenyl | 3-cyano-[1,2,4]triazol-1-yl | LC12 | 2.5 | 380.24 |
| 204 | n-propyl | 3-fluoro-phenyl | [1,2,4]triazol-1-yl | LC12 | 2.05 | 355.23 |
| 205 | isopropyl | 3-fluoro-phenyl | morpholin-4-yl | LC13 | 1.33 | 373.12 |
| 206 | n-propyl | 4-[2-hydroxy-3-(1-isobutyl-piperidin-4-ylamino)-propoxy]-3,5-dimethyl-phenyl | 4-chloro-phenyl | LC14 | 2.31 | 636.2 |
| 207 | n-propyl | 4-(3-amino-2-hydroxy-propoxy)-3-chloro-phenyl | 4-chloro-phenyl | LC14 | 2.46 | 503.09 |

TABLE 4-continued

Example compounds of the formula Iw

| Example | R¹ | R² | R³ | LC/MS | Rt [min] | m/z [M + H]⁺ |
|---|---|---|---|---|---|---|
| 208 | ethyl | 4-(3-acetylamino-2-hydroxy-propoxy)-3,5-dimethyl-phenyl | 4-chloro-phenyl | LC14 | 2.63 | 525.16 |
| 209 | n-propyl | 4-(3-benzylamino-2-hydroxy-propoxy)-3,5-dimethyl-phenyl | 4-chloro-phenyl | LC14 | 2.63 | 587.16 |
| 210 | n-propyl | 4-(3-benzylamino-2-hydroxy-propoxy)-3-chloro-phenyl | 4-chloro-phenyl | LC14 | 2.64 | 593.12 |
| 211 | n-propyl | 3-chloro-4-(3-cyclohexylamino-2-hydroxy-propoxy)-phenyl | 4-chloro-phenyl | LC14 | 2.66 | 585.14 |
| 212 | n-propyl | 4-[2-hydroxy-3-(2-hydroxy-acetyl-amino)-propoxy]-3,5-dimethyl-phenyl | 4-chloro-phenyl | LC14 | 2.68 | 555.14 |
| 213 | n-propyl | 3-(2-hydroxy-ethoxy)-phenyl | phenyl | LC14 | 2.73 | 406.12 |
| 214 | n-propyl | 4-(3-acetylamino-2-hydroxy-propoxy)-3,5-dimethyl-phenyl | 4-chloro-phenyl | LC14 | 2.75 | 539.16 |
| 215 | n-propyl | 3-hydroxy-phenyl | phenyl | LC14 | 2.75 | 362.1 |
| 216 | ethyl | 4-(3-butyrylamino-2-hydroxy-propoxy)-3,5-dimethyl-phenyl | 4-chloro-phenyl | LC14 | 2.78 | 553.17 |
| 217 | ethyl | 4-[2-hydroxy-3-(3-methyl-butyryl-amino)-propoxy]-3,5-dimethyl-phenyl | 4-chloro-phenyl | LC14 | 2.84 | 567.18 |
| 218 | n-propyl | 3-chloro-4-methoxy-phenyl | 4-chloro-phenyl | LC14 | 2.89 | 444.08 |
| 219 | n-propyl | 4-carboxymethoxy-3-chloro-phenyl | 4-chloro-phenyl | LC14 | 2.92 | 488.06 |
| 220 | n-propyl | 4-[2-hydroxy-3-(3-methyl-butyryl-amino)-propoxy]-3,5-dimethyl-phenyl | 4-chloro-phenyl | LC14 | 2.96 | 581.2 |
| 221 | ethyl | 4-[3-(2-dimethyl-amino-2-pyridin-3-yl-ethylamino)-2-hydroxy-propoxy]-3,5-dimethyl-phenyl | 4-chloro-phenyl | LC14 | 2.19 | 631.24 |
| 222 | ethyl | 4-[2-hydroxy-3-((S)-3-hydroxy-pyrrolidin-1-yl)-propoxy]-3,5-dimethyl-benzyl | 4-chloro-phenyl | LC15 | 2.38 | 553.27 |
| 223 | n-propyl | 3,5-dimethyl-4-[3-(2-sulfamoyl-ethylamino)-propoxy]-phenyl | 4-chloro-phenyl | LC15 | 2.53 | 588.32 |
| 224 | n-propyl | 4-[3-(2-carboxy-ethylamino)-propoxy]-3,5-dimethyl-phenyl | 4-chloro-phenyl | LC15 | 2.54 | 553.31 |
| 225 | n-propyl | 4-[3-(2-hydroxy-ethylamino)-propoxy]-3,5-dimethyl-phenyl | 4-chloro-phenyl | LC15 | 2.54 | 525.33 |
| 226 | ethyl | 4-[((S)-1-carboxy-2-hydroxy-ethyl-carbamoyl)-methoxy]-3,5-dimethyl-phenyl | 4-chloro-phenyl | LC15 | 2.59 | 555.26 |

TABLE 4-continued

Example compounds of the formula Iw

| Example | R¹ | R² | R³ | LC/MS | Rt [min] | m/z [M + H]⁺ |
|---|---|---|---|---|---|---|
| 227 | n-propyl | 3,5-dimethyl-4-{3-[(1H-tetrazol-5-ylmethyl)-amino]-propoxy}-phenyl | 4-chloro-phenyl | LC15 | 2.6 | 563.31 |
| 228 | ethyl | 4-[2-(3-carboxy-azetidin-1-yl)-2-oxo-ethoxy]-3,5-dimethyl-phenyl | 4-chloro-phenyl | LC15 | 2.65 | 551.26 |
| 229 | n-propyl | 4-[3-((S)-1-methoxycarbonyl-3-methylsulfanyl-propylamino)-propoxy]-3,5-dimethyl-phenyl | 4-chloro-phenyl | LC15 | 2.69 | 627.28 |
| 230 | n-propyl | 4-[3-(2-tert-butoxycarbonyl-ethylamino)-propoxy]-3,5-dimethyl-phenyl | 4-chloro-phenyl | LC15 | 2.74 | 609.32 |
| 231 | n-propyl | 4-[2-((S)-3-hydroxy-pyrrolidin-1-yl)-2-oxo-ethoxy]-3,5-dimethyl-phenyl | 4-chloro-phenyl | LC15 | 2.75 | 551.28 |
| 232 | n-propyl | 4-[2-((R)-3-hydroxy-pyrrolidin-1-yl)-2-oxo-ethoxy]-3,5-dimethyl-phenyl | 4-chloro-phenyl | LC15 | 2.75 | 551.28 |
| 233 | n-propyl | 4-ethoxycarbonyl-methoxy-3,5-dimethyl-phenyl | 4-chloro-phenyl | LC15 | 3.31 | 510.16 |
| 234 | ethyl | 3,5-dimethyl-4-[(2-morpholin-4-yl-ethylcarbamoyl)-methoxy]-phenyl | 4-chloro-phenyl | LC15 | 2.41 | 580.25 |
| 235 | n-propyl | 4-[2-(3,5-dimethyl-isoxazol-4-yl)-ethoxy]-3,5-dimethyl-phenyl | 4-chloro-phenyl | LC15 | 3.41 | 547.13 |
| 236 | ethyl | 4-(2-hydroxy-3-(morpholin-4-yl)-propoxy)-3,5-dimethyl-phenyl | 4-chloro-phenyl | LC15 | 2.42 | 553.31 |
| 237 | n-propyl | 4-[3-(2-carboxy-ethylamino)-2-hydroxy-propoxy]-3,5-dimethyl-phenyl | 4-chloro-phenyl | LC15 | 2.47 | 569.13 |
| 238 | ethyl | 4-(3-diethylamino-2-hydroxy-propoxy)-3,5-dimethyl-phenyl | 4-chloro-phenyl | LC15 | 2.49 | 539.28 |
| 239 | ethyl | 4-[2-(3-carboxy-pyrrolidin-1-yl)-2-oxo-ethoxy]-3,5-dimethyl-phenyl | 4-chloro-phenyl | LC15 | 2.65 | 565.28 |
| 240 | ethyl | 4-[(carboxymethyl-carbamoyl)-methoxy]-3,5-dimethyl-phenyl | 4-chloro-phenyl | LC15 | 2.67 | 525.22 |
| 241 | n-propyl | 4-[(2-carboxy-ethylcarbamoyl)-methoxy]-3,5-dimethyl-phenyl | 4-chloro-phenyl | LC15 | 2.76 | 553.07 |
| 242 | n-propyl | 4-[2-(3-carboxy-azetidin-1-yl)-2-oxo-ethoxy]-3,5-dimethyl-phenyl | 4-chloro-phenyl | LC15 | 2.76 | 565.09 |
| 243 | n-propyl | 4-[2-(3-carboxy-pyrrolidin-1-yl)-2-oxo-ethoxy]-3,5-dimethyl-phenyl | 4-chloro-phenyl | LC15 | 2.76 | 579.11 |

TABLE 4-continued

Example compounds of the formula Iw

| Example | R¹ | R² | R³ | LC/MS | Rt [min] | m/z [M + H]⁺ |
|---|---|---|---|---|---|---|
| 244 | n-propyl | 4-[(2-hydroxy-ethylcarbamoyl)-methoxy]-3,5-dimethyl-phenyl | 4-chloro-phenyl | LC15 | 2.77 | 525.19 |
| 245 | n-propyl | 4-[2-((S)-2-carboxy-pyrrolidin-1-yl)-2-oxo-ethoxy]-3,5-dimethyl-phenyl | 4-chloro-phenyl | LC15 | 2.82 | 579.32 |
| 246 | ethyl | 4-[2-(3-methoxy-carbonyl-azetidin-1-yl)-2-oxo-ethoxy]-3,5-dimethyl-phenyl | 4-chloro-phenyl | LC15 | 2.84 | 565.25 |
| 247 | n-propyl | 4-carboxymethoxycarbonyl-methoxy-3,5-di-methyl-phenyl | 4-chloro-phenyl | LC15 | 2.91 | 540.07 |
| 248 | n-propyl | 4-methoxycarbonylmethoxy-3,5-dimethyl-phenyl | 4-chloro-phenyl | LC15 | 3.2 | 496.11 |
| 249 | ethyl | 4-[(2-dimethyl-amino-ethylcarbamoyl)-methoxy]-3,5-dimethyl-phenyl | 4-chloro-phenyl | LC15 | 2.4 | 538.3 |
| 250 | ethyl | 4-[(tert-butoxycarbonylmethyl-carbamoyl)-methoxy]-3,5-dimethyl-phenyl | 4-chloro-phenyl | LC15 | 3.06 | 581.26 |
| 251 | n-propyl | 4-(3-carboxy-propoxy)-3,5-dimethyl-phenyl | 4-chloro-phenyl | LC15 | 3.07 | 510.12 |
| 252 | n-propyl | 4-{[(furan-2-yl-methyl)-carbamoyl]-methoxy}-3,5-dimethyl-phenyl | 4-chloro-phenyl | LC15 | 3.07 | 561.16 |
| 253 | ethyl | 4-carboxymethoxy-3,5-di-methyl-phenyl | 4-chloro-phenyl | LC15 | 2.8 | 468.22 |
| 254 | n-propyl | 4-[(cyclopropyl-methyl-carbamoyl)-methoxy]-3,5-dimethyl-phenyl | 4-chloro-phenyl | LC15 | 3.09 | 535.19 |
| 255 | ethyl | 4-[(2-tert-butoxy-carbonyl-ethyl-carbamoyl)-methoxy]-3,5-dimethyl-phenyl | 4-chloro-phenyl | LC15 | 3.12 | 595.35 |
| 256 | n-propyl | 4-[(tert-butoxycarbonylmethyl-carbamoyl)-methoxy]-3,5-dimethyl-phenyl | 4-chloro-phenyl | LC15 | 3.21 | 595.09 |
| 257 | ethyl | 4-(3-benzylamino-2-hydroxy-propoxy)-3,5-dimethyl-phenyl | 4-chloro-phenyl | LC16 | 2.61 | 573.14 |
| 258 | ethyl | 4-[2-hydroxy-3-(2-hydroxy-acetyl-amino)-propoxy]-3,5-dimethyl-phenyl | 4-chloro-phenyl | LC16 | 2.62 | 541.14 |
| 259 | ethyl | 4-(3-diisopropyl-amino-2-hydroxy-propoxy)-3,5-dimethyl-phenyl | 4-chloro-phenyl | LC16 | 2.65 | 567.19 |
| 260 | ethyl | 4-{2-hydroxy-3-[(1-hydroxy-cyclopropanecarbonyl)-amino]-propoxy}-3,5-dimethyl-phenyl | 4-chloro-phenyl | LC16 | 2.72 | 567.18 |

TABLE 4-continued

Example compounds of the formula Iw

| Example | R¹ | R² | R³ | LC/MS | Rt [min] | m/z [M + H]⁺ |
|---|---|---|---|---|---|---|
| 261 | ethyl | 4-[2-hydroxy-3-(4-trifluoromethyl-cyclohexylamino)-propoxy]-3,5-dimethyl-phenyl | 4-chloro-phenyl | LC16 | 2.7 | 633.19 |
| 262 | ethyl | 4-[2-hydroxy-3-(1-isobutyl-piperidin-4-ylamino)-propoxy]-3,5-dimethyl-phenyl | 4-chloro-phenyl | LC16 | 2.21 | 622.23 |
| 263 | ethyl | 4-(3-amino-2-hydroxy-propoxy)-3,5-dimethyl-phenyl | 4-chloro-phenyl | LC17 | 2.82 | 483.12 |
| 264 | ethyl | 4-(3-dimethylamino-2-hydroxy-propoxy)-3,5-dimethyl-phenyl | 4-chloro-phenyl | LC17 | 2.91 | 511.15 |
| 265 | ethyl | 4-[2-hydroxy-3-(4-methyl-cyclohexylamino)-propoxy]-3,5-dimethyl-phenyl | 4-chloro-phenyl | LC17 | 3.24 | 579.16 |
| 266 | ethyl | 3-[(2-morpholin-4-yl-ethylcarbamoyl)-methoxy]-phenyl | 4-chloro-phenyl | LC18 | 3.22 | 552.37 |
| 267 | ethyl | 3-[(carboxymethyl-carbamoyl)-methoxy]-phenyl | 4-chloro-phenyl | LC18 | 3.74 | 497.2 |
| 268 | ethyl | 3-[((S)-1-carboxy-ethylcarbamoyl)-methoxy]-phenyl | 4-chloro-phenyl | LC18 | 3.82 | 511.22 |
| 269 | ethyl | 3-[2-((R)-2-carboxy-pyrrolidin-1-yl)-2-oxo-ethoxy]-phenyl | 4-chloro-phenyl | LC18 | 3.84 | 537.3 |
| 270 | ethyl | 3-[2-((S)-2-carboxy-pyrrolidin-1-yl)-2-oxo-ethoxy]-phenyl | 4-chloro-phenyl | LC18 | 3.89 | 537.22 |
| 271 | ethyl | 3-[(1-carboxy-1-methyl-ethylcarbamoyl)-methoxy]-phenyl | 4-chloro-phenyl | LC18 | 3.99 | 525.27 |
| 272 | ethyl | 4-[2-hydroxy-3-(5-methyl-4H-[1,2,4]triazole-3-sulfonyl)-propoxy]-3,5-dimethyl-phenyl | 4-chloro-phenyl | LC18 | 4.02 | 613.32 |
| 273 | ethyl | 3-fluoro-4-hydroxy-phenyl | 4-chloro-phenyl | LC18 | 4.12 | 400.14 |
| 274 | ethyl | 4-[3-(5-cyclopropyl-4H-[1,2,4]triazole-3-sulfonyl)-propoxy]-3,5-dimethyl-phenyl | 4-chloro-phenyl | LC18 | 4.44 | 623.29 |
| 275 | ethyl | 4-[3-(5-isopropyl-4H-[1,2,4]triazole-3-sulfonyl)-propoxy]-3,5-dimethyl-phenyl | 4-chloro-phenyl | LC18 | 4.47 | 625.31 |
| 276 | ethyl | 4-[3-(5-cyclopropyl-4H-[1,2,4]triazol-3-ylsulfanyl)-propoxy]-3,5-dimethyl-phenyl | 4-chloro-phenyl | LC18 | 4.54 | 591.25 |
| 277 | ethyl | 3-fluoro-4-methoxy-phenyl | 4-chloro-phenyl | LC18 | 4.55 | 414.18 |

TABLE 4-continued

Example compounds of the formula Iw

| Example | R¹ | R² | R³ | LC/MS | Rt [min] | m/z [M + H]⁺ |
|---|---|---|---|---|---|---|
| 278 | ethyl | 4-[3-(5-tert-butyl-4H-[1,2,4]triazole-3-sulfonyl)-propoxy]-3,5-dimethyl-phenyl | 4-chloro-phenyl | LC18 | 4.55 | 639.36 |
| 279 | ethyl | 3-fluoro-4-[(2-morpholin-4-yl-ethylcarbamoyl)-methoxy]-phenyl | 4-chloro-phenyl | LC19 | 1.66 | 570.01 |
| 280 | ethyl | 4-[2-hydroxy-3-(3-methanesulfonyl-amino-propyl-amino)-propoxy]-3,5-dimethyl-phenyl | 4-chloro-phenyl | LC19 | 1.72 | 618.18 |
| 281 | ethyl | 4-[3-(5-cyclo-propyl-4H-[1,2,4]triazol-3-ylsulfanyl)-2-hydroxy-propoxy]-3,5-dimethyl-phenyl | 4-chloro-phenyl | LC19 | 2.01 | 607.2 |
| 282 | ethyl | 4-[3-(5-tert-butyl-4H-[1,2,4]triazol-3-ylsulfanyl)-2-hydroxy-propoxy]-3,5-dimethyl-phenyl | 4-chloro-phenyl | LC19 | 2.08 | 623.21 |
| 283 | ethyl | 4-[3-(5-tert-butyl-4H-[1,2,4]triazole-3-sulfonyl)-2-hydroxy-propoxy]-3,5-dimethyl-phenyl | 4-chloro-phenyl | LC19 | 2.09 | 655.22 |
| 284 | ethyl | 3-methoxy-phenyl | 4-chloro-phenyl | LC19 | 2.19 | 396.11 |
| 285 | ethyl | 4-{3-[2-(5-hydroxy-4H-[1,2,4]triazol-3-yl)-ethylamino]-propoxy}-3,5-dimethyl-phenyl | 4-chloro-phenyl | LC20 | 1.6 | 578.18 |
| 286 | ethyl | 4-[2-hydroxy-3-(4H-[1,2,4]triazole-3-sulfinyl)-propoxy]-3,5-dimethyl-phenyl | 4-chloro-phenyl | LC20 | 1.75 | 583.16 |
| 287 | ethyl | 3,5-dimethyl-4-[(2-sulfamoyl-ethylcarbamoyl)-methoxy]-phenyl | 4-chloro-phenyl | LC20 | 1.78 | 574.22 |
| 288 | ethyl | 4-[(3-carboxy-propylcarbamoyl)-methoxy]-3,5-dimethyl-phenyl | 4-chloro-phenyl | LC20 | 1.8 | 553.25 |
| 289 | n-propyl | 4-[3-((S)-1-carboxy-2-phenyl-ethylamino)-propoxy]-3,5-dimethyl-phenyl | 4-chloro-phenyl | LC20 | 1.85 | 629.35 |
| 290 | ethyl | 4-[(2-methanesulfonylamino-ethyl-carbamoyl)-methoxy]-3,5-dimethyl-phenyl | 4-chloro-phenyl | LC20 | 1.85 | 588.18 |
| 291 | ethyl | 4-[2-hydroxy-3-(4H-[1,2,4]triazole-3-sulfonyl)-propoxy]-3,5-dimethyl-phenyl | 4-chloro-phenyl | LC20 | 1.85 | 599.21 |
| 292 | ethyl | 4-[3-(4H-[1,2,4]triazole-3-sulfinyl)-propoxy]-3,5-dimethyl-phenyl | 4-chloro-phenyl | LC20 | 1.85 | 567.18 |

TABLE 4-continued

Example compounds of the formula Iw

| Example | R¹ | R² | R³ | LC/MS | Rt [min] | m/z [M + H]⁺ |
|---|---|---|---|---|---|---|
| 293 | ethyl | 4-[2-hydroxy-3-(4H-[1,2,4]triazol-3-ylsulfanyl)-propoxy]-3,5-dimethyl-phenyl | 4-chloro-phenyl | LC20 | 1.86 | 567.26 |
| 294 | ethyl | 4-[(cyanomethyl-carbamoyl)-methoxy]-3,5-dimethyl-phenyl | 4-chloro-phenyl | LC20 | 1.94 | 506.16 |
| 295 | ethyl | 4-[3-(4H-[1,2,4]triazole-3-sulfonyl)-propoxy]-3,5-dimethyl-phenyl | 4-chloro-phenyl | LC20 | 1.96 | 583.18 |
| 296 | ethyl | 4-[3-(4H-[1,2,4]triazol-3-ylsulfanyl)-propoxy]-3,5-dimethyl-phenyl | 4-chloro-phenyl | LC20 | 2.02 | 551.13 |
| 297 | ethyl | 3-[((S)-1-carboxy-2-hydroxy-ethyl-carbamoyl)-methoxy]-phenyl | 4-chloro-phenyl | LC21 | 1.26 | 527.2 |
| 298 | ethyl | 3-[(2-carboxy-ethylcarbamoyl)-methoxy]-phenyl | 4-chloro-phenyl | LC21 | 1.29 | 511.24 |
| 299 | ethyl | 4-[(3-methanesulfonylamino-propylcarbamoyl)-methoxy]-3,5-dimethyl-phenyl | 4-chloro-phenyl | LC21 | 1.35 | 602.26 |
| 300 | ethyl | 4-[3-(5-cyclo-propyl-4H-[1,2,4]triazole-3-sulfonyl)-2-hydroxy-propoxy]-3,5-dimethyl-phenyl | 4-chloro-phenyl | LC21 | 1.35 | 639.2 |
| 301 | ethyl | 4-(3-hydroxymethyl-oxetan-3-ylmethoxy)-3,5-dimethyl-phenyl | 4-chloro-phenyl | LC21 | 1.39 | 510.26 |
| 302 | ethyl | 3-hydroxy-phenyl | 4-chloro-phenyl | LC22 | 2.56 | 382.23 |
| 303 | n-propyl | 3-fluoro-phenyl | (R)-3-fluoro-pyrrolidin-1-yl | LC5 | 1.44 | 375.21 |
| 304 | n-propyl | 3-fluoro-phenyl | 3-trifluoromethyl-piperidin-1-yl | LC5 | 1.79 | 439.2 |
| 305 | n-propyl | 4-{3-[(furan-2-carbonyl)-amino]-2-hydroxy-propoxy}-3,5-dimethyl-phenyl | 4-chloro-phenyl | LC6 | 4.35 | 591.08 |
| 306 | n-propyl | 3,5-dimethyl-4-(2-morpholin-4-yl-2-oxo-ethoxy)-phenyl | 4-chloro-phenyl | LC6 | 4.39 | 551.09 |
| 307 | n-propyl | 4-[2-((S)-2-tert-butoxycarbonyl-pyrrolidin-1-yl)-2-oxo-ethoxy]-3,5-dimethyl-phenyl | 4-chloro-phenyl | LC6 | 4.92 | 635.26 |
| 308 | n-propyl | 4-{2-hydroxy-3-[(1-hydroxy-cyclopropanecarbonyl)-amino]-propoxy}-3,5-dimethyl-phenyl | 4-chloro-phenyl | LC6 | 4.1 | 581.09 |
| 309 | ethyl | 3-methyl-phenyl | cyclohexyl | LC6 | 5.22 | 352.14 |
| 310 | ethyl | 3-carboxymethoxy-phenyl | 4-chloro-phenyl | LC9 | 4.9 | 440.14 |
| 311 | ethyl | 4-[2-((S)-2-carboxy-pyrrolidin-1-yl)-2-oxo-ethoxy]-3,5-dimethyl-phenyl | 4-chloro-phenyl | LC9 | 4.94 | 565.16 |

TABLE 4-continued

Example compounds of the formula Iw

| Example | R¹ | R² | R³ | LC/MS | Rt [min] | m/z [M + H]⁺ |
|---|---|---|---|---|---|---|
| 312 | ethyl | 4-(3-cyclohexyl-amino-2-hydroxy-propoxy)-3,5-dimethyl-phenyl | 4-chloro-phenyl | LC9 | 4.54 | 565.48 |
| 313 | n-propyl | 4-[2-hydroxy-3-(1-methyl-piperidin-4-ylamino)-propoxy]-3,5-dimethyl-phenyl | 4-chloro-phenyl | LC9 | 3.74 | 594.51 |
| 314 | ethyl | 4-[(2-carboxy-ethylcarbamoyl)-methoxy]-3,5-dimethyl-phenyl | 4-chloro-phenyl | LC9 | 4.86 | 537.05 (1) |
| 315 | n-propyl | 4-cyclopropylmethoxy-3,5-dimethyl-phenyl | 4-chloro-phenyl | LC9 | 6.1 | 478.2 |
| 316 | n-propyl | 3,5-dimethyl-4-(2-oxo-butoxy)-phenyl | 4-chloro-phenyl | LC9 | 5.4 | 494.06 |
| 317 | n-propyl | 3-methoxy-phenyl | phenyl | LC9 | 5.16 | 376.11 |
| 318 | ethyl | 4-[2-((1S,5R)-1-carboxy-2-azabi-cyclo[3.1.0]hex-2-yl)-2-oxo-ethoxy]-3,5-dimethyl-phenyl | 4-chloro-phenyl | LC9 | 4.94 | 577.18 |
| 319 | ethyl | 4-[2-((1R,2S,5S)-2-carboxy-3-azabi-cyclo[3.1.0]hex-3-yl)-2-oxo-ethoxy]-3,5-dimethyl-phenyl | 4-chloro-phenyl | LC21 | 1.36 | 577.2 |

(1) [M − H]⁻

Determination of the Pharmacological Activity

A) GTP-γ-S Assay Using Human Edg-1 Receptors

In order to determine the Edg-1 receptor activation by the compounds of the invention, a GTP-γ-S (guanosine 5'-[γ-thio]triphosphate) assay for G-protein coupled receptor binding based on the scintillation proximity assay principle was used, employing a cell membrane preparation from a CHO Flp-In cell line which constitutively overexpresses the human Edg-1 receptor.

(a) Cell Line Generation

The Flp-In™ expression system (Invitrogen, cat. no. K6010-01) allows the generation of stable mammalian cell lines into which the gene of interest has been integrated through homologous recombination at a specific genomic location called Flp Recombination Target (FRT) site by means of a Flp recombinase encoded by the pOG44 expression plasmid. The integration of the pcDNA5/FRT expression construct into the Flp-In host cell line genome results in the transcription of the gene of interest. The stably transfected cells become hygromycin-resistant.

One day prior to transfection, 200 000 Flp-In-CHO cells were seeded in Ham F-12 medium (Invitrogen, cat. no. 31765) supplemented with 10% fetal calf serum (FCS; Perbio Science, cat. no. SH30068.03) in a 6-well plate and incubated at 37° C./5% $CO_2$ overnight. Using the FuGENE® 6 transfection reagent (Roche, cat. no. 11988387001), cells were cotransfected with the Flp recombinase expression plasmid pOG44 and a modified plasmid additionally containing the edg-1 gene (accession no. NM_001400) termed as pcDNA5-FRT-TO_nFLAG_DEST-EDG-1 with a 9:1 ratio. To obtain the modified pcDNA5-FRT-TO_nFLAG_DEST plasmid, the Invitrogen plasmid pcDNA5/FRT/TO (Invitrogen, cat. no. V6520-20) was adapted to the Gateway® (Invitrogen) cloning system by inserting a Gateway cassette containing attR recombination sites flanking a ccdB gene and a chloramphenicol-resistance gene (Gateway conversion system, Invitrogen, cat. no. 11828-029). In addition a FLAG tag epitope was added before the 5' att recombination site to allow recombinant expression of N-terminally FLAG-tagged proteins.

For the transfection of one well, 1.08 μg of pOG44 and 0.12 μg of pcDNA5-FRT-TO_nFLAG_DEST-EDG-1 were mixed to 100 μl of serum-free Ham F-12 medium containing 6 μl of FuGENE® 6 transfection reagent. After 20 min of incubation, the transfection reagent/DNA complex was distributed dropwise on the cells. The cells were incubated for 24 h at 37° C. Then the cells from 3 wells each were transferred to a T75 flask (Greiner Cellstar®, cat. no. 658175) containing Ham F-12 medium supplemented with 10% of FCS but without antibiotic and were incubated another 24 h. 48 h after transfection, the medium was replaced by selection medium (Ham F-12 supplemented with 10% of FCS and 300 μg/ml of hygromycin B (Invitrogen, cat. no. 10687-010)). The medium was exchanged every 2 to 3 days until a resistant population of cells had grown. Cells were several times splitted and seeded into a new flask so that the cells did not reach more than 25% of confluency. After 2 weeks of selection, the cells were transferred into T175 flasks (Greiner Cellstar®, cat. no. 660175) and cultivated for batch production. Cells were harvested from the culture flasks by short treatment (2 to 5 min) with Accutase (PAA, cat. no. L11-007), resuspended in selection medium (see above) and centrifuged at 200×g for 5 min. Cells were resuspended in a mixture of 90% of FCS and 10% of dimethylsulfoxide and stored frozen in liquid nitrogen.

(b) Membrane Preparation

A membrane preparation was obtained by standard methods from the afore-described CHO Flp-In cell line constitutively overexpressing the human Edg-1 receptor. Briefly, the cryopreserved cells were taken in culture and grown until confluency in T175 cell culture flasks (Becton Dickinson, cat. no. 35 5001). Cell culture was stopped by washing with calcium-free phosphate-buffered saline (PBS; Gibco, cat. no. 14190), and cells were harvested with a rubber-policeman in 4° C. cold and calcium-free PBS supplemented with a protease inhibitor cocktail (complete protease inhibitor; Roche, cat. no. 1697498; 1 tablet per 50 ml) and subsequently centrifuged at 4° C. for 15 min at 1100×g (Heraeus Minifuge T). For cell lysis, the pellet was resuspended in a 4° C. cold hypotonic buffer consisting of 5 mM HEPES (Sigma-Aldrich, cat. no. H-0981), 1 mM EDTA (disodium salt; Merck, cat. No. 8418) supplemented with protease inhibitor cocktail (as above) in which cells were stored for another 15 min on ice. After lysis, cells were centrifuged at 4° C. for 10 min at 400×g (Heraeus Minifuge T). The pellet was disrupted in a Dounce homogenizer, diluted with the supernatant of the previous centrifugation and subsequently centrifuged at 4° C. for 10 min at 500×g (Heraeus Minifuge T) in order to separate nuclei and still intact cells from the membranes mainly present in the supernatant. The supernatant was then diluted in hypotonic buffer and centrifuged (Beckmann, Avanti J251) at approximately 18600×g for 2 h at 4° C. After centrifugation, the membrane pellet was resuspended in a storing buffer consisting of 20 mM HEPES; 150 mM NaCl (Merck, cat. no. 6400), 1 mM EDTA (as above) supplemented with protease inhibitor cocktail (as above). The membrane preparation was aliquoted and stored at −80° C. Protein concentration of the membrane preparation was determined in a sample by means of a commercial protein assay (Bio-Rad, DC Protein Assay, cat. nos. 500-0113, 500-0114, 500-0115).

(c) GTP-γ-S Assay

The Edg-1 membrane preparation obtained in (b) was employed in a commercially available scintillation proximity assay (SPA) kit for G-protein coupled receptor binding from Amersham Biosciences/GE Healthcare (code RPNQ0210), in which ligand-induced binding of $^{35}$S-radiolabled GTP-γ-S to the receptor-containing membrane, which is bound to scintillation beads, stimulates the emission of light and allows to quantify the in vitro activity of the Edg-1 agonistic compound. The assay was performed on a 96-well plate scale substantially according to the manufacturer's instructions. Before start of the experiments, scintillation beads were suspended in a reconstitution buffer consisting of Tris-HCl (pH 7.4) supplemented with 0.1% (w/v) sodium azide and subsequently diluted on ice with assay buffer (consisting of 20 mM HEPES, 100 mM NaCl, 1 mM EDTA (as above), 1 mM dithiothreitol (DTT), adjusted to pH 7.4) to a final bead concentration of 30 mg/ml.

Wells were charged with 10 µl of the specified assay buffer, 10 µl of a 100 µM guanosine diphosphate (GDP) solution, and 10 µl of a solution of the test compound in assay buffer/dimethylsulfoxide resulting in a final concentration of the test compound of 10 µM. For the high controls, 10 µl of a solution of sphingosine-1-phosphate (S1P; Sigma, cat. no. S-9666), resulting in a final S1P concentration of 10 µM, and for the low controls 10 µl of assay buffer, was added into respective wells instead of the solution of the test compound. All wells contained equivalent amounts of dimethylsulfoxide. Then 10 µl of a [$^{35}$S]GTP-γ-S solution (4 nM) and the Edg-1 membrane preparation obtained in (b) (15 µg membrane proteins in 100 µl of assay buffer) was added to each well. After incubation of the plates at room temperature for 5 min, 50 µl of the specified scintillation bead suspension (30 mg/ml) was added. After a further incubation period of 45 min at room temperature, plates were centrifuged for 10 min at 500×g. Quantification of [$^{35}$S]GTP-γ-S binding and thus receptor activation was measured by means of a beta counter (MicroBeta, Wallac) over 1 min. Values were background-corrected by subtraction of the respective low control. All measurements were made in triplicate. The receptor activation by the test compound is expressed in percent of the respective high control (10 µM S1P; regarded as 100% activation). In Table 5 activations observed with example compounds at 10 µM are listed.

TABLE 5

Edg-1 receptor activation by example compounds at 10 µM in percent of the activation by 10 µM S1P

| Example | % Activation |
| --- | --- |
| 1 | 117 |
| 2 | 80 |
| 3 | 113 |
| 4 | 105 |
| 5 | 98 |
| 6 | 60 |
| 7 | 23 |
| 8 | 51 |
| 9 | 37 |
| 10 | 66 |
| 11 | 39 |
| 12 | 65 |
| 13 | 119 |
| 14 | 97 |
| 15 | 104 |
| 16 | 106 |
| 17 | 74 |
| 18 | 128 |
| 19 | 102 |
| 20 | 299 |
| 21 | 71 |
| 22 | 95 |
| 23 | 97 |
| 24 | 115 |
| 25 | 117 |
| 26 | 123 |
| 27 | 124 |
| 28 | 102 |
| 29 | 118 |
| 30 | 114 |
| 31 | 59 |
| 32 | 42 |
| 33 | 93 |
| 34 | 90 |
| 35 | 119 |
| 36 | 127 |
| 37 | 116 |
| 38 | 114 |
| 39 | 82 |
| 40 | 123 |
| 41 | 116 |
| 42 | 92 |
| 43 | 122 |
| 44 | 78 |
| 45 | 69 |
| 46 | 35 |
| 47 | 85 |
| 48 | 81 |
| 49 | 48 |
| 50 | 102 |
| 51 | 24 |
| 52 | 35 |
| 53 | 69 |
| 54 | 30 |
| 55 | 22 |
| 56 | 44 |
| 57 | 99 |
| 58 | 35 |
| 59 | 30 |

TABLE 5-continued

Edg-1 receptor activation by example compounds at 10 µM in percent of the activation by 10 µM S1P

| Example | % Activation |
| --- | --- |
| 60 | 64 |
| 61 | 76 |
| 62 | 94 |
| 63 | 102 |
| 64 | 93 |
| 65 | 109 |
| 66 | 107 |
| 67 | 105 |
| 68 | 120 |
| 69 | 113 |
| 70 | 113 |
| 71 | 116 |
| 72 | 99 |
| 73 | 120 |
| 74 | 114 |
| 75 | 72 |
| 76 | 104 |
| 77 | 112 |
| 78 | 103 |
| 79 | 111 |
| 80 | 65 |
| 81 | 83 |
| 82 | 104 |
| 83 | 111 |
| 84 | 108 |
| 85 | 104 |
| 86 | 120 |
| 87 | 92 |
| 88 | 101 |
| 89 | 107 |
| 90 | 115 |
| 91 | 96 |
| 92 | 106 |
| 93 | 103 |
| 94 | 82 |
| 95 | 105 |
| 96 | 121 |
| 97 | 100 |
| 98 | 120 |
| 99 | 117 |
| 100 | 88 |
| 101 | 91 |
| 102 | 65 |
| 103 | 85 |
| 104 | 87 |
| 105 | 81 |
| 106 | 22 |
| 107 | 73 |
| 108 | 31 |
| 109 | 61 |
| 110 | 61 |
| 111 | 57 |
| 112 | 66 |
| 113 | 41 |
| 114 | 83 |
| 115 | 33 |
| 116 | 136 |
| 117 | 101 |
| 118 | 103 |
| 119 | 80 |
| 120 | 107 |
| 121 | 99 |
| 122 | 103 |
| 123 | 47 |
| 124 | 94 |
| 125 | 112 |
| 126 | 105 |
| 127 | 73 |
| 128 | 110 |
| 129 | 108 |
| 130 | 78 |
| 131 | 116 |
| 132 | 71 |
| 133 | 127 |
| 134 | 78 |
| 135 | 117 |
| 136 | 73 |
| 137 | 55 |
| 138 | 52 |
| 139 | 87 |
| 140 | 92 |
| 141 | 85 |
| 142 | 75 |
| 143 | 73 |
| 144 | 101 |
| 145 | 67 |
| 146 | 56 |
| 147 | 55 |
| 148 | 41 |
| 149 | 102 |
| 150 | 143 |
| 151 | 26 |
| 152 | 100 |
| 153 | 84 |
| 154 | 88 |
| 155 | 87 |
| 156 | 83 |
| 157 | 94 |
| 158 | 90 |
| 159 | 73 |
| 160 | 69 |
| 161 | 96 |
| 162 | 108 |
| 163 | 118 |
| 164 | 98 |
| 165 | 97 |
| 166 | 42 |
| 167 | 102 |
| 168 | 117 |
| 169 | 87 |
| 170 | 89 |
| 171 | 115 |
| 172 | 78 |
| 173 | 77 |
| 174 | 75 |
| 175 | 116 |
| 176 | 94 |
| 177 | 106 |
| 178 | 91 |
| 179 | 87 |
| 180 | 41 |
| 181 | 58 |
| 182 | 108 |
| 183 | 85 |
| 184 | 88 |
| 185 | 97 |
| 186 | 123 |
| 187 | 116 |
| 188 | 112 |
| 189 | 114 |
| 190 | 66 |
| 191 | 98 |
| 192 | 60 |
| 193 | 114 |
| 194 | 98 |
| 195 | 84 |
| 196 | 83 |
| 197 | 119 |
| 198 | 111 |
| 199 | 112 |
| 200 | 79 |
| 201 | 68 |
| 202 | 109 |
| 203 | 79 |
| 204 | 79 |
| 205 | 115 |
| 206 | 67 |
| 207 | 302 |
| 208 | 111 |
| 209 | 110 |

TABLE 5-continued

Edg-1 receptor activation by example compounds at 10 µM in percent of the activation by 10 µM S1P

| Example | % Activation |
|---|---|
| 210 | 94 |
| 211 | 112 |
| 212 | 78 |
| 213 | 101 |
| 214 | 106 |
| 215 | 96 |
| 216 | 105 |
| 217 | 78 |
| 218 | 42 |
| 219 | 107 |
| 220 | 69 |
| 221 | 84 |
| 222 | 71 |
| 223 | 92 |
| 224 | 113 |
| 225 | 100 |
| 226 | 98 |
| 227 | 142 |
| 228 | 107 |
| 229 | 70 |
| 230 | 101 |
| 231 | 104 |
| 232 | 125 |
| 233 | 79 |
| 234 | 106 |
| 235 | 59 |
| 236 | 102 |
| 237 | 115 |
| 238 | 71 |
| 239 | 86 |
| 240 | 123 |
| 241 | 128 |
| 242 | 106 |
| 243 | 106 |
| 244 | 97 |
| 245 | 144 |
| 246 | 111 |
| 247 | 110 |
| 248 | 89 |
| 249 | 104 |
| 250 | 72 |
| 251 | 112 |
| 252 | 102 |
| 253 | 79 |
| 254 | 86 |
| 255 | 74 |
| 256 | 69 |
| 257 | 122 |
| 258 | 97 |
| 259 | 66 |
| 260 | 95 |
| 261 | 86 |
| 262 | 43 |
| 263 | 138 |
| 264 | 55 |
| 265 | 132 |
| 266 | 52 |
| 267 | 72 |
| 268 | 100 |
| 269 | 69 |
| 270 | 104 |
| 271 | 53 |
| 272 | 105 |
| 273 | 106 |
| 274 | 120 |
| 275 | 88 |
| 276 | 54 |
| 277 | 49 |
| 278 | 105 |
| 279 | 77 |
| 280 | 53 |
| 281 | 79 |
| 282 | 108 |
| 283 | 92 |
| 284 | 103 |
| 285 | 146 |
| 286 | 114 |
| 287 | 112 |
| 288 | 113 |
| 289 | 80 |
| 290 | 114 |
| 291 | 116 |
| 292 | 86 |
| 293 | 99 |
| 294 | 83 |
| 295 | 100 |
| 296 | 52 |
| 297 | 99 |
| 298 | 92 |
| 299 | 94 |
| 300 | 89 |
| 301 | 97 |
| 302 | 103 |
| 303 | 104 |
| 304 | 102 |
| 305 | 103 |
| 306 | 81 |
| 307 | 10 |
| 308 | 107 |
| 309 | 104 |
| 310 | 87 |
| 311 | 78 |
| 313 | 143 |
| 314 | 96 |
| 315 | 79 |
| 316 | 70 |
| 317 | 105 |
| 318 | 101 |

The invention claimed is:

1. A compound selected from any of the following compounds:

2-(3-fluoro-phenyl)-5-morpholin-4-ylmethyl-7-propoxy-oxazolo[5,4-d]pyrimidine, 3-(5-morpholin-4-ylmethyl-7-propoxy-oxazolo[5,4-d]pyrimidin-2-yl)-phenol, 2-(2-chloro-5-fluoro-phenyl)-5-[1,4]oxazepan-4-ylmethyl-7-propoxy-oxazolo[5,4-d]pyrimidine, 2-(2-chloro-pyridin-4-yl)-5-morpholin-4-ylmethyl-7-propoxy-oxazolo[5,4-d]pyrimidine, 5-cyclohexylmethyl-7-propoxy-2-m-tolyl-oxazolo[5,4-d]pyrimidine, 5-(1-phenyl-ethyl)-7-propoxy-2-m-tolyl-oxazolo[5,4-d]pyrimidine, 3-{4-[5-(4-chloro-benzyl)-7-propoxy-oxazolo[5,4-d]pyrimidin-2-yl]-2,6-dimethyl-phenoxy}-propane-1,2-diol, 1-{4-[5-(4-chloro-benzyl)-7-ethoxy-oxazolo[5,4-d]pyrimidin-2-yl]-2,6-dimethyl-phenoxy}-3-diethylamino-propan-2-ol, 1-{4-[5-(4-chloro-benzyl)-7-ethoxy-oxazolo[5,4-d]pyrimidin-2-yl]-2,6-dimethyl-phenoxy}-3-morpholin-4-yl-propan-2-ol, 1-hydroxy-cyclopropanecarboxylic acid (3-{4-[5-(4-chloro-benzyl)-7-ethoxy-oxazolo[5,4-d]pyrimidin-2-yl]-2,6-dimethyl-phenoxy}-2-hydroxy-propyl)-amide, N-(3-{4-[5-(4-chloro-benzyl)-7-propoxy-oxazolo[5,4-d]pyrimidin-2-yl]-2,6-dimethyl-phenoxy}-2-hydroxy-propyl)-acetamide, 4-{4-[5-(4-chloro-benzyl)-7-propoxy-oxazolo[5,4-d]pyrimidin-2-yl]-2,6-dimethyl-phenoxy}-butyric acid, (2-{4-[5-(4-chloro-benzyl)-7-propoxy-oxazolo[5,4-d]pyrimidin-2-yl]-2,6-dimethyl-phenoxy}-acetylamino)-acetic acid, 3-(3-{4-[5-(4-chloro-benzyl)-7-propoxy-oxazolo[5,4-d]pyrimidin-2-yl]-2,6-dimethyl-phenoxy}-2-hydroxy-propylamino)-propionic acid, (S)-1-(2-{4-[5-(4-chloro-benzyl)-7-propoxy-oxazolo[5,4-d]pyrimidin-2-yl]-2,6-dimethyl-phenoxy}-acetyl)-pyrrolidine-2-carboxylic acid, 1-(5-tert-butyl-4H-[1,2,4]triazole-3-sulfonyl)-3-{4-[5-(4-chloro-benzyl)-7-ethoxy-oxazolo[5,4-d]pyrimidin-2-yl]-2,6-dimethyl-phenoxy}-propan-2-ol, and 4-[5-(4-chloro-benzyl)-7-ethoxy-oxazolo[5,4-d]pyrimidin-2-yl]-2-fluoro-phenol, including any stereoisomeric forms, any mixture of stereoisomeric forms in any ratio, or a physiologically acceptable salt thereof, or a physiologically acceptable solvate of any of them.

2. A pharmaceutical composition, comprising at least one compound of as claimed in claim 1, or a physiologically acceptable salt thereof, or a physiologically acceptable solvate of any of them, and a pharmaceutically acceptable carrier.

* * * * *